(12) United States Patent
Bloom et al.

(10) Patent No.: US 8,163,884 B2
(45) Date of Patent: Apr. 24, 2012

(54) INTERLEUKIN-21 RECEPTOR BINDING PROTEINS

(75) Inventors: Laird Bloom, Needham, MA (US); Davinder Gill, Andover, MA (US); Yulia Vugmeyster, North Reading, MA (US); Deborah A. Young, Melrose, MA (US); David Lowe, Cambridge (GB); Viia Valge-Archer, Cambridge (GB)

(73) Assignees: Wyeth LLC, Madison, NJ (US); MedImmune Limited, Cambridge (GB)

( * ) Notice: Subject to any disclaimer, the term of this patent is extended or adjusted under 35 U.S.C. 154(b) by 173 days.

(21) Appl. No.: 12/472,209

(22) Filed: May 26, 2009

(65) Prior Publication Data

US 2009/0298167 A1 Dec. 3, 2009

Related U.S. Application Data

(60) Provisional application No. 61/055,500, filed on May 23, 2008.

(51) Int. Cl.
*C07K 16/28* (2006.01)
*A61K 39/00* (2006.01)
*A61K 39/395* (2006.01)
*C12P 21/02* (2006.01)

(52) U.S. Cl. ............. 530/387.9; 530/388.23; 530/389.2; 530/391.3; 424/139.1; 424/143.1; 435/69.1; 536/23.5

(58) Field of Classification Search ........................ None
See application file for complete search history.

(56) References Cited

U.S. PATENT DOCUMENTS

| | | | |
|---|---|---|---|
| 6,057,128 A | 5/2000 | Donaldson et al. | 435/69.1 |
| 6,307,024 B1 | 10/2001 | Novak et al. | 530/351 |
| 6,576,744 B1 | 6/2003 | Presnell et al. | 530/351 |
| 6,777,539 B2 | 8/2004 | Sprecher et al. | 530/350 |
| 6,929,932 B2 | 8/2005 | Presnell et al. | 435/69.52 |
| 7,189,400 B2 | 3/2007 | Carter et al. | 424/185.1 |
| 7,198,789 B2 | 4/2007 | Carter et al. | 424/130.1 |
| 7,276,478 B2 | 10/2007 | Sivakumar et al. | 514/12 |
| 7,314,623 B2 | 1/2008 | Grusby et al. | 424/185.1 |
| 7,495,085 B2 | 2/2009 | Valge-Archer et al. | 530/387.9 |
| 7,705,123 B2 | 4/2010 | Donaldson et al. | 530/350 |
| 2004/0009150 A1 | 1/2004 | Nelson et al. | 424/85.2 |
| 2004/0016010 A1 | 1/2004 | Kasaian et al. | 800/18 |
| 2006/0024268 A1 | 2/2006 | Kasaian et al. | 424/85.2 |
| 2006/0039902 A1 | 2/2006 | Young et al. | 424/133.1 |
| 2006/0159655 A1 | 7/2006 | Collins et al. | 424/85.2 |
| 2006/0257403 A1 | 11/2006 | Young et al. | 424/144.1 |
| 2008/0241098 A1 | 10/2008 | Young et al. | 424/85.2 |

FOREIGN PATENT DOCUMENTS

| | | |
|---|---|---|
| WO | WO 00/53761 | 9/2000 |
| WO | WO 00/69880 | 11/2000 |
| WO | WO 01/85792 A2 | 11/2001 |
| WO | WO 2004/083249 A2 | 9/2004 |
| WO | WO 2004/084835 A2 | 10/2004 |
| WO | WO 2006/135385 A2 | 12/2006 |
| WO | WO 2008/081198 A1 | 7/2008 |

OTHER PUBLICATIONS

Paul, Fundamental Immunology, 3rd Edition, 1993, pp. 292-295, under the heading "Fv Structure and Diversity in Three Dimensions").*
Casset et al, Biochemical and Biophysical Research Communications, 2003; vol. 307, pp. 198-205.*
Asano et al. (2002), "Antitumor Activity of Interleukin-21 Prepared by Novel Refolding Procedure from Inclusion Bodies Expressed in *Escherichia coli*," *FEBS Lett.* 528:70-6.
Cosman, David (1993) "The Hematopoietin Receptor Superfamily," *Cytokine* 5:95-106.
Kasaian et al. (2002), "IL-21 Limits NK Cell Responses and Promotes Antigen-Specific T Cell Activation: A Mediator of the Transition from Innate to Adaptive Immunity", *Immunity* 16:559-69.
King et al. (2004), "Homeostatic Expansion of T Cells During Immune Insufficiency Generates Autoimmunity," *Cell* 117:265-77.
Leonard and Spolski (2005), "Interleukin-21: A Modulator of Lymphoid Proliferation, Apoptosis and Differentiation," *Nat. Rev. Immunol.* 5:688-98.
Liu et al. (2006), "Autoreactive T Cells Mediate NK Cell Degeneration in Autoimmune Disease," *J. Immunol.* 176:5247-54.
Livak and Schmittgen (2001), "Analysis of Relative Gene Expression Data Using Real-Time Quantitative PCR and the 2(-Delta Delta C(T)) Method," *Methods* 25:402-08.
Ozaki et al. (2000), "Cloning of a Type I Cytokine Receptor Most Related to the IL-2 Receptorβ Chain", *Proc. Natl. Acad. Sci. U.S.A.* 97:11439-44.
Ozaki et al. (2004), "Regulation of B Cell Differentiation and Plasma Cell Generation by IL-21, a Novel Inducer of Blimp-1 and Bcl-6", *J. Immunol.* 173:5361-71.
Parrish-Novak et al. (2000), "Interleukin 21 and Its Receptor Are Involved in NK Cell Expansion and Regulation of Lymphocyte Function", *Nature* 408:57-63.
Shang et al. (2006), "IgE isotype switch and IgE production are enhanced in IL-21-deficient but not IFN-γ-deficient mice in a Th2-biased response," *Cell. Immunol.* 241:66-74.
Sivakumar et al. (2004), "Interleukin-21 is a T-helper cytokine that regulates humoral immunity and cell-mediated anti-tumor responses," *Immunology* 112:177-82.
Stebbings et al. (2007), "'Cytokine Storm'" in the Phase I Trial of Monoclonal Antibody TGN1412: Better Understanding the Causes to Improve PreClinical Testing of Immunotherapeutics, *J. Immunol.* 179(5):3325-31.

(Continued)

*Primary Examiner* — Bridget E Bunner
*Assistant Examiner* — Fozia Hamud
(74) *Attorney, Agent, or Firm* — Fitzpatrick, Cella, Harper & Scinto

(57) ABSTRACT

The present invention provides binding proteins and antigen-binding fragments thereof that specifically bind to the human interleukin-21 receptor (IL-21R). The binding proteins can act as, e.g., antagonists of IL-21R activity, thereby modulating immune responses in general, and those mediated by IL-21R in particular. The disclosed compositions and methods may be used, e.g., in diagnosing and/or treating IL-21R-associated disorders, e.g., inflammatory disorders, autoimmune diseases, allergies, transplant rejection, cancer, and other immune system disorders.

21 Claims, 93 Drawing Sheets

OTHER PUBLICATIONS

Suntharalingam et al. (2006), "Cytokine Storm in a Phase 1 Trial of the Anti-CD28 Monoclonal Antibody TGN1412," *N. Engl. J. Med.* 355:1018-28.

Vollmer et al. (2005), "Differential Effects of IL-21 during Initiation and Progression of Autoimmunity against Neuroantigen," *J. Immunol.* 174:2696-2701.

Wing, et al. (1996), "Mechanism of First-Dose Cytokine-Release Syndrome by CAMPATH 1-H: involvement of CD16 (FcγRIII) and CD11A/CD18 (LFA-1) on NK Cells, "*J. Clin. Invest.* 98:2819-26.

Asao et al. (2001), "Cutting Edge: The Common γ-Chain is an Indispensable Subunit of the IL-21 Receptor Complex," *J. Immunol.*, 167:1-5.

Parrish-Novak et al. (2002), "Interleukin-21 and the IL-21 Receptor: Novel Effectors of NK and T Cell Responses" *J. Leukoc. Biol.* 72:856-63.

Muyldermans (2001), "Single Domain Camel Antibodies: Current Status," Rev. Mol. Biotechnol. 74:277-302.

International Preliminary Report on Patentability and Written Opinion of the International Searching Authority, with transmittal, issued in Applicants' corresponding International Application No. PCT/US2009/045182, mailed Dec. 2, 2010, 6 pp.

Communication Pursuant to Rules 161(1) and 162 EPC, issued in Applicants' corresponding EPO Application No. 09751751.0, dated Jan. 28, 2011, 2 pp.

Examination Report, issued in Applicants' corresponding New Zealand Application No. 589330, dated Apr. 11, 2011, 2 pp.

International Preliminary Report on Patentability and Written Opinion of the International Searching Authority, with transmittal, issued in Applicants' related International Application No. PCT/US2009/045188, mailed Dec. 2, 2010, 7 pp.

Communication Pursuant to Rules 161(1) and 162 EPC, issued in Applicants' related EPO Application No. 09751754.4, dated Jan. 28, 2011, 2 pp.

* cited by examiner

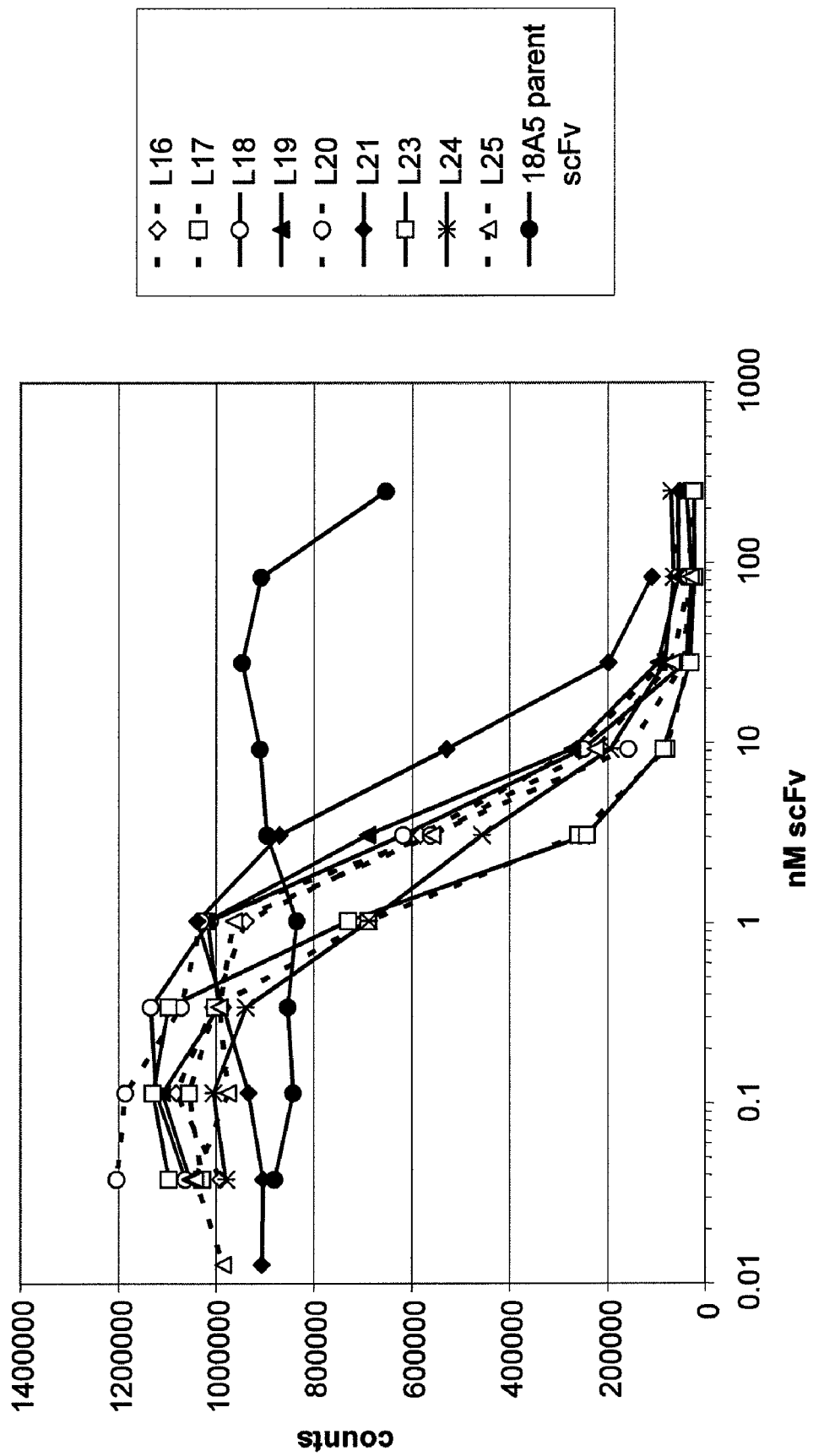

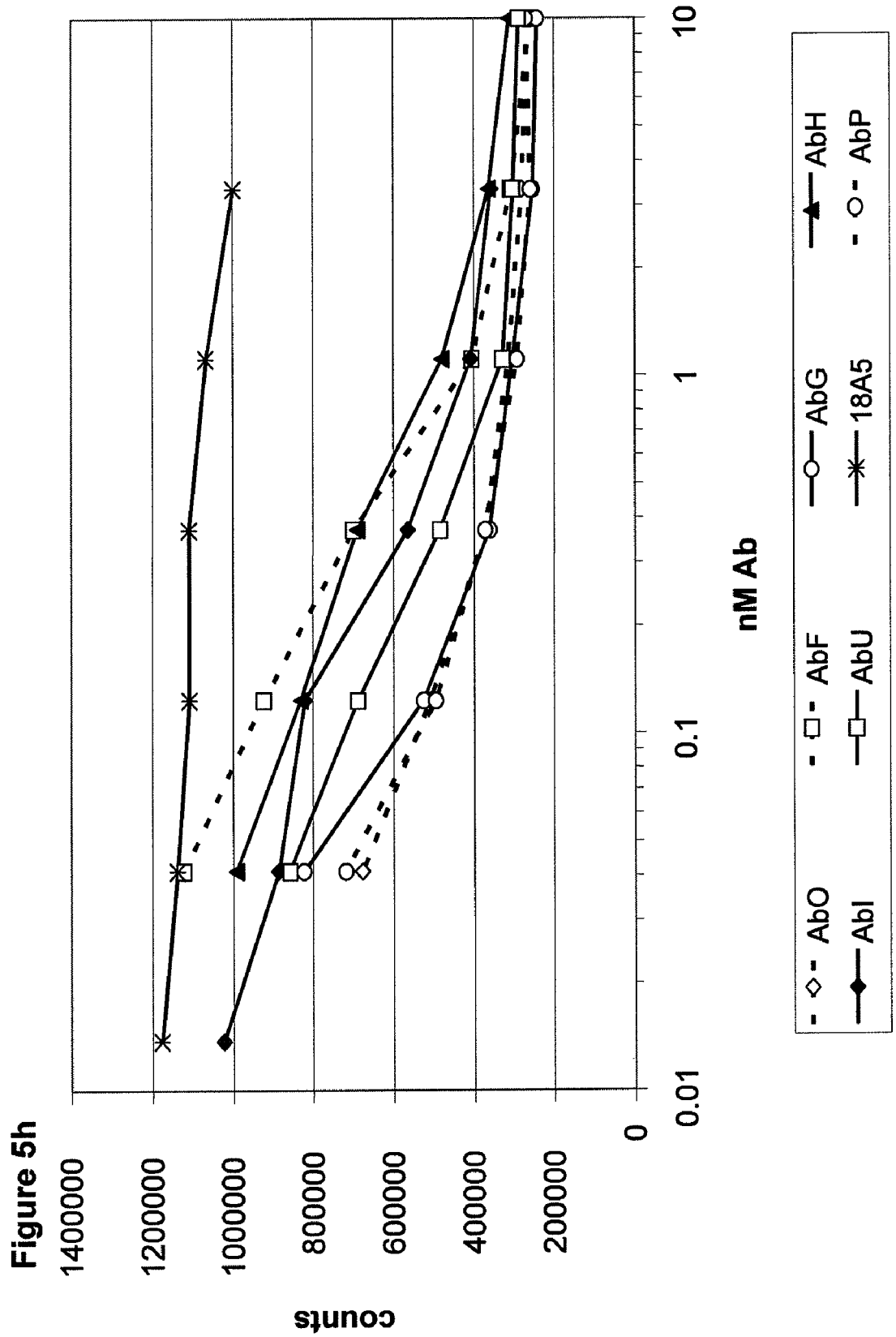

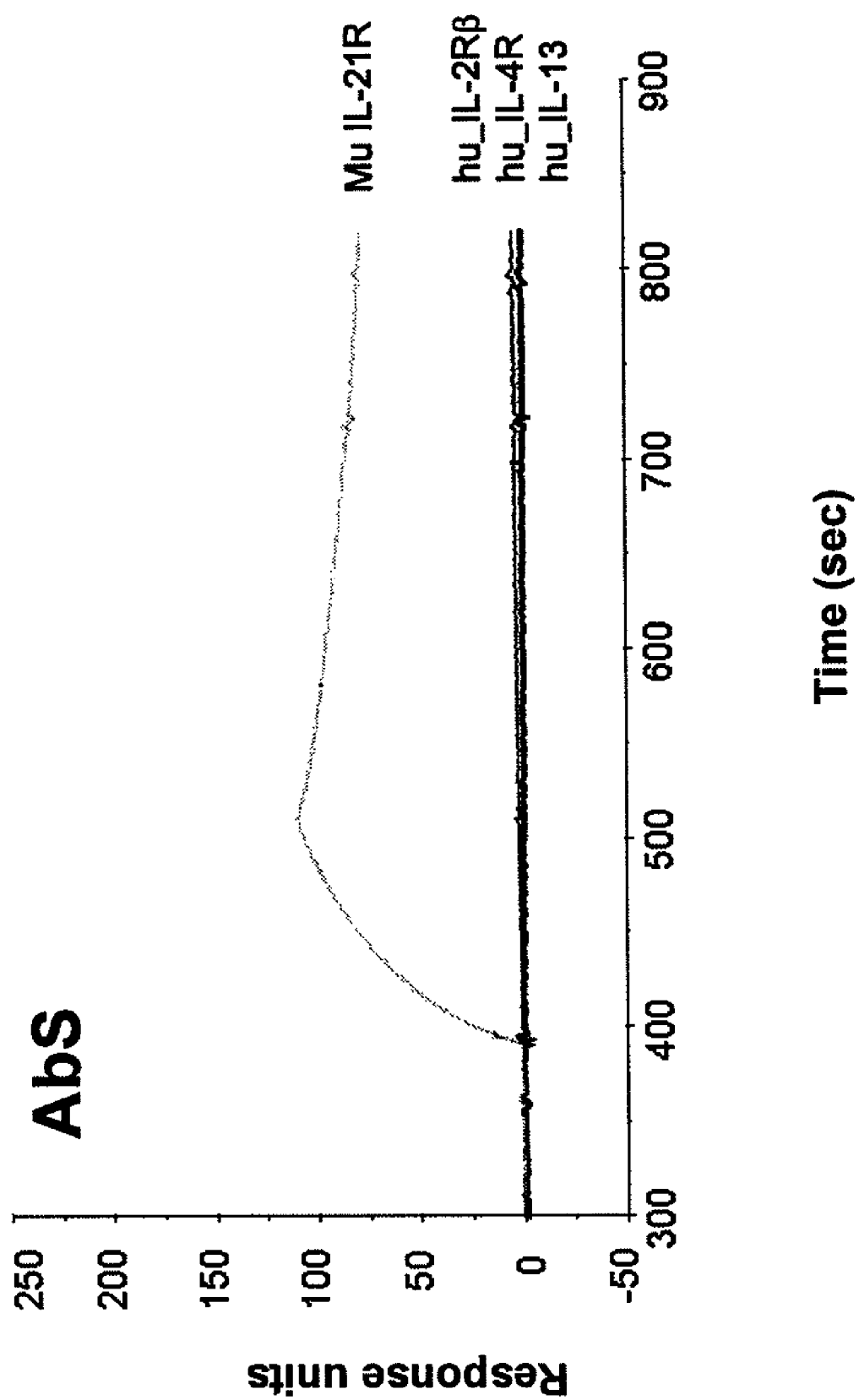

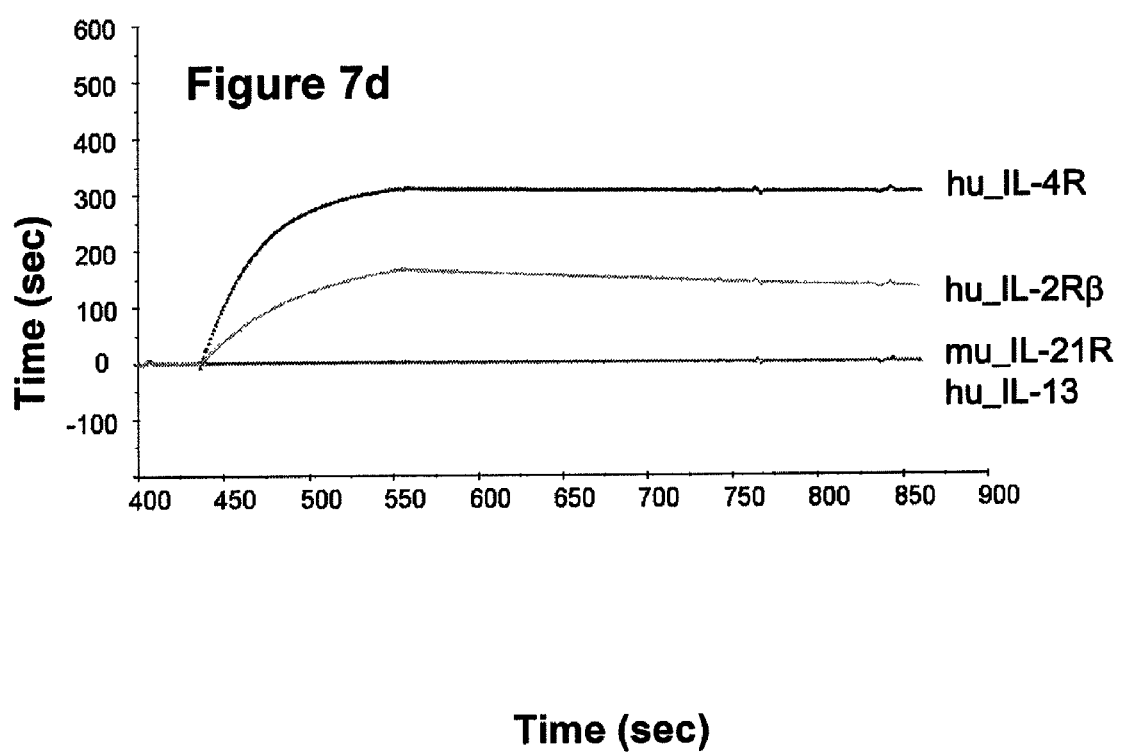

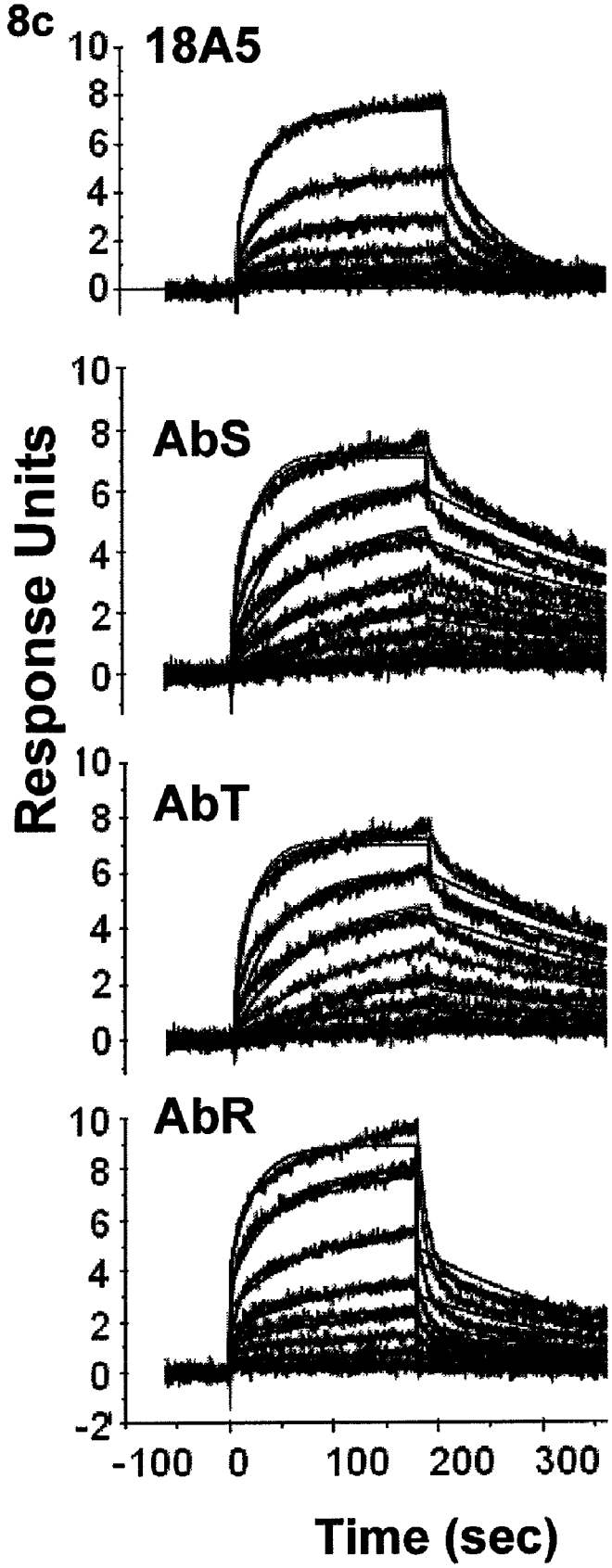

Figure 17a

AbQ:

Heavy chain for AbQ (SEQ ID NO:213), with CDRs H1, H2, and H3 underlined (SEQ ID NOs:163, 164, and 165, respectively). The heavy chain constant region is shown in lower case italics with the double mutation (L234A G237A) shown in bold lowercase underlined text (SEQ ID NO: 197).

QVQLQESGPGLVKPSETLSLTCAVSGYSISS<u>SGYYWG</u>WIRQPPGKGL
EWIGS<u>ISHTGNTYYNPPLKS</u>RVTISVDTSKNQFSLKLSSVTAADTA
VYYCAR<u>FMGFGRPEYWGQ</u>GTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papealgapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbQ (SEQ ID NO: 214), with CDRs L1, L2, and L3 underlined (SEQ ID NOs:194, 195, and 172, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IYGKHKRPSGIPDRFSGSSSGNTASLTITGAQAEDEADYYC<u>VARSV</u>
<u>VGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:213 is the full-length heavy chain for AbQ:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papealgapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 17b

SEQ ID NO:14 is the $V_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the $V_H$ portion of the full-length heavy chain:

SGYYWG

SEQ ID NO:164 is the CDR H2 portion of the $V_H$ portion of the full-length heavy chain:

SISHTGNTYYNPPLKS

SEQ ID NO:165 is the CDR H3 portion of the $V_H$ portion of the full-length heavy chain:

FMGFGRPEY

SEQ ID NO:197 is the heavy chain constant region with the double mutation (L234A G237A) shown in bold lowercase underlined text:

astkgpsvfplapsskstsggtaalgclvkdyfpepvtvswnsgal
tsgvhtfpavlqssglyslssvvtvpssslgtqtyicnvhkpsnt
kvdkkvepkscdkthtcppcpapealgapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk SEQ ID NO:214 is the full-length light chain for AbQ:

SSELTQDPAVSVALGQTVRITCQGDSLRTYYASWYQQKPGQAPVLV
IYGKHKRPSGIPDRFGSSSGNTASLTITGAQAEDEADYYCVARSV
VGNPHVLFGGGTQLTVLgqpkaapsvtlfppsseelqankatlvcl
isdfypgavtvawkadsspvkagvetttpskqsnnkyaassylslt
peqwkshrsyscqvthegstvektvaptecs

Figure 17c

SEQ ID NO:215 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:172 is the CDR L3 portion of the $V_L$ portion of the full-length light chain:

VARSVVGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 18a

AbR:

Heavy chain for AbR (SEQ ID NO:213), with CDRs H1, H2, and H3 underlined (SEQ ID NOs:163, 164, and 165, respectively). The heavy chain constant region is shown in lower case italics with the double mutation (L234A G237A) shown in bold lowercase underlined text (SEQ ID NO: 197).

QVQLQESGPGLVKPSETLSLTCAVSGYSIS<u>SGYYWG</u>WIRQPPGKGL
EWIGS<u>ISHTGNTYYNPPLKS</u>RVTISVDTSKNQFSLKLSSVTAADTA
VYYCAR<u>FMGFGRPEYW</u>GQGTLVTVS S *astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papealgapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbR (SEQ. ID NO:216), with CDRs L1, L2, and L3 underlined (SEQ. ID NOs:194, 195, and 187, respectively). The constant lambda light chain sequence is indicated by lower-case italics (SEQ. ID. NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VTRSV</u>
<u>KGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:213 is the full-length heavy chain for AbR:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVS S *astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papealgapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 18b

SEQ ID NO:14 is the V$_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the V$_H$ portion of the full-length heavy chain:

SGYYWG

SEQ ID NO:164 is the CDR H2 portion of the V$_H$ portion of the full-length heavy chain:

SISHTGNTYYNPPLKS

SEQ ID NO:165 is the CDR H3 portion of the V$_H$ portion of the full-length heavy chain:

FMGFGRPEY

SEQ ID NO:197 is the heavy chain constant region with the double mutation (L234A G237A) shown in bold lowercase underlined text:

astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapealgapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk SEQ ID NO:216 is the full-length light chain for AbR:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVLgqpkaapsvtlfppsseelqankatlvcl
isdfypgavtvawkadsspvkagvetttpskqsnnkyaassylslt
peqwkshrsyscqvthegstvektvaptecs

Figure 18c

SEQ ID NO:217 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:187 is the CDR L3 portion of the $V_L$ portion of the full-length light chain:

VTRSVKGNPHVL

SEQ ID NO:198 is the lambda light chain constant region gqpkaapsvtlfppsseelqankatlvclisdfypgavtvawkads
spvkagvetttpskqsnnkyaassylsltpeqwkshrsyscqvthe
gstvektvaptecs

Figure 19a

AbW:

Heavy chain for AbW (SEQ ID NO:218), with CDRs H1, H2, and H3 underlined (SEQ ID NOs:163, 164, and 165, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIG<u>SISHTGNTYYNPPLKSR</u>VTISVDTSKNQFSLKLSSVTAADTA
VYYCAR<u>FMGFGRPEYWGQ</u>GTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbW (SEQ ID NO:216), with CDRs L1, L2, and L3 underlined (SEQ ID NOs:194, 195, and 187, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VTRSV
KGNPHVL</u>FGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:218 is the full-length heavy chain for AbW:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 19b

SEQ ID NO:14 is the V<sub>H</sub> portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the V$_H$ portion of the full-length heavy chain:

SGYYWG

SEQ ID NO:164 is the CDR H2 portion of the V$_H$ portion of the full-length heavy chain:

SISHTGNTYYNPPLKS

SEQ ID NO:165 is the CDR H3 portion of the V$_H$ portion of the full-length heavy chain:

FMGFGRPEY

SEQ ID NO:196 is the heavy chain constant region with the triple mutation (L234A L235A G237A) shown in bold lowercase underlined text:

astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk SEQ ID NO:216 is the full-length light chain for AbW:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVLgqpkaapsvtlfppsseelqankatlvcl
isdfypgavtvawkadsspvkagvetttpskqsnnkyaassylslt
peqwkshrsyscqvthegstvektvaptecs

Figure 19c

SEQ ID NO:217 is V_L portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVL

SEQ ID NO:194 is the CDR L1 portion of the V_L portion of the full-length light chain:

QGDSLRTYYAS

SEQ ID NO:195 is the CDR L2 portion of the V_L portion of the full-length light chain:

GKHKRPS

SEQ ID NO:187 is the CDR L3 portion of the V_L portion of the full-length light chain:

VTRSVKGNPHVL

SEQ ID NO:198 is the lambda light chain constant region

*gqpkaapsvtlfppsseelqankatlvclisdfypgavtvawkads
spvkagvetttpskqsnnkyaassylsltpeqwkshrsyscqvthe
gstvektvaptecs*

Figure 20a

AbS:

Heavy chain for AbS (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSISS<u>SGYYWG</u>WIRQPPGKGL
EWIGS<u>ISHTGNTYYNPPLKSRVTISVDTSKNQFSLKLSSVTAADTA
VYYCAR<u>GGGISRPEYW</u>GQGTLVTVSS*astkgpsvfplapssktsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpdtlmisrtpevtcvvvdshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbS (SEQ ID NO:220), with CDRs L1, L2, and L3 underlined (SEQ ID NOs:194, 195, and 176, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>MSRSI
WGNPHV</u>LFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:219 is the full-length heavy chain for AbS:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS*astkgpsvfplapssktsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpdtlmisrtpevtcvvvdshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 20b

SEQ ID NO:6 is the $V_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS

SEQ ID NO:163 is the CDR H1 portion of the $V_H$ portion of the full-length heavy chain:

SGYYWG

SEQ ID NO:164 is the CDR H2 portion of the $V_H$ portion of the full-length heavy chain:

SISHTGNTYYNPPLKS

SEQ ID NO:169 is the CDR H3 portion of the $V_H$ portion of the full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:220 is the full-length light chain for AbS:

SSELTQDPAVSVALGQTVRITCQGDSLRTYYASWYQQKPGQAPVLV
IYGKHKRPSGIPDRFSGSSSGNTASLTITGAQAEDEADYYCMSRSI
WGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 20c

SEQ ID NO:221 is the V$_L$ portion of the full-length light chain:

SSELTQDPAVSVALGQTVRITCQGDSLRTYYASWYQQKPGQAPVLV
IYGKHKRPSGIPDRFGSSSGNTASLTITGAQAEDEADYYCMSRSI
WGNPHVLFGGGTQLTVL

SEQ ID NO:194 is the CDR L1 portion of the V$_L$ portion of the full-length light chain:

QGDSLRTYYAS

SEQ ID NO:195 is the CDR L2 portion of the V$_L$ portion of the full-length light chain:

GKHKRPS

SEQ ID NO:176 is the CDR L3 portion of the V$_L$ portion of the full-length light chain:

MSRSIWGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 21a

AbT:

Heavy chain for AbT (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSISS<u>GYYWG</u>WIRQPPGKGL
EWIGS<u>ISHTGNTYYNPPLKS</u>RVTISVDTSKNQFSLKLSSVTAADTA
VYYCAR<u>GGGISRPEYWGQ</u>GTLVTVSS*astkgpsvfplapssktsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflysklvtd
ksrwqqgnvfscsvmhealhnhytqkslslspgk*

Light chain for AbT (SEQ ID NO:222), with CDRs L1, L2, and L3 underlined (SEQ ID NOs:194, 195, and 178, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VARSN
KGNPHVL</u>FGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:219 is the full-length heavy chain for AbT:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS*astkgpsvfplapssktsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflysklvtd
ksrwqqgnvfscsvmhealhnhytqkslslspgk*

Figure 21b

SEQ ID NO:6 is the $V_H$ portion of full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS

SEQ ID NO:163 is the CDR H1 portion of the $V_H$ portion of full-length heavy chain:

SGYYWG

SEQ ID NO:164 is the CDR H2 portion of the $V_H$ portion of full-length heavy chain:

SISHTGNTYYNPPLKS

SEQ ID NO:169 is the CDR H3 portion of the $V_H$ portion of full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:222 is the full-length light chain for AbT:

SSELTQDPAVSVALGQTVRITCQGDSLRTYYASWYQQKPGQAPVLV
IYGKHKRPSGIPDRFSGSSSGNTASLTITGAQAEDEADYYCVARSN
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 21c

SEQ ID NO:223 is the V<sub>L</sub> portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVARSN
KGNPHVLFGGGTQLTVL

SEQ ID NO:194 is the CDR L1 portion of the V<sub>L</sub> portion of the full-length light chain:

QGDSLRTYYAS

SEQ ID NO:195 is the CDR L2 portion of the V<sub>L</sub> portion of the full-length light chain:

GKHKRPS

SEQ ID NO:178 is the CDR L3 portion of the V<sub>L</sub> portion of the full-length light chain:

VARSNKGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 22a

AbO:

Heavy chain for AbO (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIGS<u>ISHTGNTYYNPPLKSRVTISVDTSKNQFSLKLS</u>SVTAADTA
VYYCAR<u>GGGISRPEYWGQ</u>GTLVTVSS*astkgpsvfplapssksts g
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbO (SEQ ID NO:224), with CDRs L1, L2, and L3 underlined (SEQ ID NOs:194, 195, and 185, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VTRSA
KGNPHVL</u>FGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:219 is the full-length heavy chain for AbO:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS*astkgpsvfplapssksts g
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 22b

SEQ ID NO:6 is the V$_H$ portion of full-length heavy chain:

QVQLQESGPGLVKPSETLSLTCAVSGYSIS<u>SGYYWG</u>WIRQPPGKGL
EWIGS<u>ISHTGNTYYNPPLKS</u>RVTISVDTSKNQFSLKLSSVTAADTA
VYYCAR<u>GGGISRPEY</u>WGQGTLVTVSS

SEQ ID NO:163 is the CDR H1 portion of the V$_H$ portion of full-length heavy chain:

SGYYWG

SEQ ID NO:164 is the CDR H2 portion of the V$_H$ portion of full-length heavy chain:

SISHTGNTYYNPPLKS

SEQ ID NO:169 is the CDR H3 portion of the V$_H$ portion of full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaag<u>a</u>psvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:224 is the full-length light chain for AbO:

SSELTQDPAVSVALGQTVRITCQGDSLRTYYASWYQQKPGQAPVLV
IYGKHKRPSGIPDRFSGSSSGNTASLTITGAQAEDEADYYCVTRSA
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 22c

SEQ ID NO:225 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVTRSA
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:185 is the CDR L3 portion of the $V_L$ portion of the full-length light chain:

VTRSAKGNPHVL

SEQ ID NO:198 is the lambda light chain constant region:

*gqpkaapsvtlfppsseelqankatlvclisdfypgavtvawkads
spvkagvetttpskqsnnkyaassylsltpeqwkshrsyscqvthe
gstvektvaptecs*

Figure 23a

AbP:

Heavy chain for AbP (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIGS<u>ISHTGNTYYNPPLKSRVTISVDTSKNQFSLKLSSVTAADTA
VYYCARGGGISRPEY</u>WGQGTLVTVSS*astkgpsvfplapssktsg
gtaalgclvkdyfpepvtvswnsgaltsgvhtfpavlqssglysls
svvtvpssslgtqtyicnvnhkpsntkvdkkvepkscdkthtcppc
pape<u>aaga</u>psvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbP (SEQ ID NO:226), with CDRs L1, L2, and L3 underlined (SEQ ID NOs:194, 195, and 189, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IYGK<u>HKRPSGI</u>PDRFSGSSSGNTASLTITGAQAEDEADYYC<u>VSRSA
KGNPHVL</u>FGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:219 is the full-length heavy chain for AbP:

QVQLQESGPGLVKPSETLSLTCAVSGYSIS<u>SGYYWG</u>WIRQPPGKGL
EWIGS<u>ISHTGNTYYNPPLKSRVTISVDTSKNQFSLKLSSVTAADTA
VYYCARGGGISRPEY</u>WGQGTLVTVSS*astkgpsvfplapssktsg
gtaalgclvkdyfpepvtvswnsgaltsgvhtfpavlqssglysls
svvtvpssslgtqtyicnvnhkpsntkvdkkvepkscdkthtcppc
pape<u>aaga</u>psvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 23b

SEQ ID NO:6 is the V$_H$ portion of full-length heavy chain:

QVQLQESGPGLVKPSETLSLTCAVSGYSIS<u>SGYYWG</u>WIRQPPGKGL
EWIG<u>SISHTGNTYYNPPLKS</u>RVTISVDTSKNQFSLKLSSVTAADTA
VYYCAR<u>GGGISRPEY</u>WGQGTLVTVSS

SEQ ID NO:163 is the CDR H1 portion of the V$_H$ portion of full-length heavy chain:

SGYYWG

SEQ ID NO:164 is the CDR H2 portion of the V$_H$ portion of full-length heavy chain:

SISHTGNTYYNPPLKS

SEQ ID NO:169 is the CDR H3 portion of the V$_H$ portion of full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflysklrvdksrwqqgnvfscsvmhealhnhytqk
slslspgk*

SEQ ID NO:226 is the full-length light chain for AbP:

SSELTQDPAVSVALGQTVRITCQGDSLRTYYASWYQQKPGQAPVLV
IYGKHKRPSGIPDRFSGSSSGNTASLTITGAQAEDEADYYCVSRSA
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 23c

SEQ ID NO:227 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVSRSA
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:189 is the CDR L3 portion of the $V_L$ portion of the full-length light chain:

VSRSAKGNPHVL

SEQ ID NO:198 is the lambda light chain constant region:

*gqpkaapsvtlfppsseelqankatlvclisdfypgavtvawkads
spvkagvetttpskqsnnkyaassylsltpeqwkshrsyscqvthe
gstvektvaptecs*

Figure 24a

AbU:

Heavy chain for AbU (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIGS<u>ISHTGNTYYNPPLKSRVTISVDTSKNQFSLKLSSVTAADTA
VYYCAR<u>GGGISRPEY</u>WGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papеaag<u>a</u>psvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbU (SEQ ID NO:228), with CDRs L1, L2, and L3 underlined (SEQ ID NOs:194, 195, and 193, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>TTRSN
KGNPHVL</u>FGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:219 is the full-length heavy chain for AbU:

QVQLQESGPGLVKPSETLSLTCAVSGYSIS<u>SGYYWG</u>WIRQPPGKGL
EWIGS<u>ISHTGNTYYNPPLKSRVTISVDTSKNQFSLKLSSVTAADTA
VYYCAR<u>GGGISRPEY</u>WGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaag<u>a</u>psvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 24b

SEQ ID NO:6 is the $V_H$ portion of full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS

SEQ ID NO:163 is the CDR H1 portion of the $V_H$ portion of full-length heavy chain:

SGYYWG

SEQ ID NO:164 is the CDR H2 portion of the $V_H$ portion of full-length heavy chain:

SISHTGNTYYNPPLKS

SEQ ID NO:169 is the CDR H3 portion of the $V_H$ portion of full-length heavy chain:

GGGISRPEY

SEQ ID NO:196 is the heavy chain constant region with the triple mutation (L234A L235A G237A) shown in bold lowercase underlined text:

astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk SEQ ID NO:228 is the full-length light chain for AbU:

SSELTQDPAVSVALGQTVRITCQGDSLRTYYASWYQQKPGQAPVLV
IYGKHKRPSGIPDRFSGSSSGNTASLTITGAQAEDEADYYCTTRSN
KGNPHVLFGGGTQLTVLgqpkaapsvtlfppsseelqankatlvcl
isdfypgavtvawkadsspvkagvetttpskqsnnkyaassylslt
peqwkshrsyscqvthegstvektvaptecs

Figure 24c

SEQ ID NO:229 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCTTRSN
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:193 is the CDR L3 portion of the $V_L$ portion of the full-length light chain:

TTRSNKGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 25a

AbV:

Heavy chain for AbV (SEQ ID NO:218), with CDRs H1, H2, and H3 underlined (SEQ ID NOs:163, 164, and 165, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSISS<u>SGYYWG</u>WIRQPPGKGL
EWIGS<u>ISHTGNTYYNPPLKS</u>RVTISVDTSKNQFSLKLSSVTAADTA
VYYCAR<u>FMGFGRPEYW</u>GQGTLVTVSS*astkgpsvfplapssksts g
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgkk*

Light chain for AbV (SEQ ID NO:214), with CDRs L1, L2, and L3 underlined (SEQ ID NOs:194, 195, and 172, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VARSV
VGNPHV</u>LFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:218 is the full-length heavy chain for AbV:

QVQLQESGPGLVKPSETLSLTCAVSGYSISSSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapssksts g
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 25b

SEQ ID NO:14 is the V$_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the V$_H$ portion of the full-length heavy chain:

SGYYWG

SEQ ID NO:164 is the CDR H2 portion of the V$_H$ portion of the full-length heavy chain:

SISHTGNTYYNPPLKS

SEQ ID NO:165 is the CDR H3 portion of the V$_H$ portion of the full-length heavy chain:

FMGFGRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:214 is the full-length light chain for AbV:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 25c

SEQ ID NO:215 is the V_L portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL

SEQ ID NO:194 is the CDR L1 portion of the V_L portion of the full-length light chain:

QGDSLRTYYAS

SEQ ID NO:195 is the CDR L2 portion of the V_L portion of the full-length light chain:

GKHKRPS

SEQ ID NO:172 is the CDR L3 portion of the V_L portion of the full-length light chain:

VARSVVGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

INTERLEUKIN-21 RECEPTOR BINDING PROTEINS

RELATED APPLICATIONS

This application claims the benefit of priority from U.S. Provisional Patent Application No. 61/055,500, filed May 23, 2008, the content of which is hereby incorporated by reference herein in its entirety.

BACKGROUND OF THE INVENTION

1. Field of the Invention

The present invention relates to binding proteins and antigen-binding fragments thereof that bind interleukin-21 receptor (IL-21R), in particular, human IL-21R, and their use in regulating IL-21R-associated activities. The binding proteins disclosed herein are useful in treating and/or diagnosing IL-21R-associated disorders, e.g., inflammatory disorders, autoimmune diseases, allergies, transplant rejection, hyperproliferative disorders of the blood, and other immune system disorders.

2. Related Background Art

Antigens initiate immune responses and activate the two largest populations of lymphocytes: T cells and B cells. After encountering antigen, T cells proliferate and differentiate into effector cells, while B cells proliferate and differentiate into antibody-secreting plasma cells. These effector cells secrete and/or respond to cytokines, which are small proteins (less than about 30 kDa) secreted by lymphocytes and other cell types.

Human IL-21 is a cytokine that shows sequence homology to IL-2, IL-4 and IL-15 (Parrish-Novak et al. (2000) *Nature* 408:57-63). Despite low sequence homology among interleukin cytokines, cytokines share a common fold into a "four-helix-bundle" structure that is representative of the family. Most cytokines bind either class I or class II cytokine receptors. Class II cytokine receptors include the receptors for IL-10 and the interferons, whereas class I cytokine receptors include the receptors for IL-2 through IL-7, IL-9, IL-11, IL-12, IL-13, and IL-15, as well as hematopoietic growth factors, leptin, and growth hormone (Cosman (1993) *Cytokine* 5:95-106).

Human IL-21R is a class I cytokine receptor. The nucleotide and amino acid sequences encoding human IL-21 and its receptor (IL-21R) are described in International Application Publication Nos. WO 00/053761 and WO 01/085792; Parrish-Novak et al. (2000) supra; and Ozaki et al. (2000) *Proc. Natl. Acad. Sci. USA* 97:11439-44. IL-21R has the highest sequence homology to the IL-2 receptor β chain and the IL-4 receptor α chain (Ozaki et al. (2000) supra). Upon ligand binding, IL-21R associates with the common gamma cytokine receptor chain (γc) that is shared by receptor complexes for IL-2, IL-3, IL-4, IL-7, IL-9, IL-13 and IL-15 (Ozaki et al. (2000) supra; Asao et al. (2001) *J. Immunol.* 167:1-5).

IL-21R is expressed in lymphoid tissues, particularly on T cells, B cells, natural killer (NK) cells, dendritic cells (DC) and macrophages (Parrish-Novak et al. (2000) supra), which allows these cells to respond to IL-21 (Leonard and Spolski (2005) *Nat. Rev. Immunol.* 5:688-98). The widespread lymphoid distribution of IL-21R indicates that IL-21 plays an important role in immune regulation. In vitro studies have shown that IL-21 significantly modulates the function of B cells, CD4+ and CD8+ T cells, and NK cells (Parrish-Novak et al. (2000) supra; Kasaian et al. (2002) *Immunity* 16:559-69). Recent evidence suggests that IL-21-mediated signaling can have antitumor activity (Sivakumar et al. (2004) *Immunology* 112:177-82), and that IL-21 can prevent antigen-induced asthma in mice (Shang et al. (2006) *Cell. Immunol.* 241:66-74).

In autoimmunity, disruption of the IL-21 gene and injection of recombinant IL-21 have been shown to modulate the progression of experimental autoimmune myasthenia gravis (EAMG) and experimental autoimmune encephalomyelitis (EAE), respectively (King et al. (2004) *Cell* 117:265-77; Ozaki et al. (2004) *J. Immunol.* 173:5361-71; Vollmer et al. (2005) *J. Immunol.* 174:2696-2701; Liu et al. (2006) *J. Immunol.* 176:5247-54). In these experimental systems, it has been suggested that the manipulation of IL-21-mediated signaling directly altered the function of CD8+ cells, B cells, T helper cells, and NK cells.

SUMMARY OF THE INVENTION

The present invention describes the isolation and characterization of binding proteins, for example, human antibodies and fragments thereof, that specifically bind to the human and murine IL-21R. The binding proteins described herein are derived from antibody 18A5, which is disclosed in U.S. Pat. No. 7,495,085, the entirety of which is hereby incorporated by reference herein. The binding proteins of the present invention have a much greater degree of affinity to human and/or murine IL-21R than does the parental 18A5 antibody.

The invention provides, at least in part, IL-21R binding agents (such as binding proteins and antigen-binding fragments thereof) that bind to IL-21R, in particular, human IL-21R, with high affinity and specificity. The binding proteins, and antigen-binding fragments thereof, of the present invention are also referred to herein as "anti-IL-21R binding proteins" and "fragments thereof," respectively. In one embodiment, the binding protein or fragment thereof reduces, inhibits, or antagonizes IL-21R activity. Such binding proteins can be used to regulate immune responses or IL-21R-associated disorders by antagonizing IL-21R activity. In other embodiments, the anti-IL-21R binding protein can be used diagnostically, or as a targeting binding protein to deliver a therapeutic or cytotoxic agent to an IL-21R-expressing cell. Thus, the anti-IL-21R binding proteins of the invention are useful in diagnosing and treating IL-21R-associated disorders, e.g., inflammatory disorders, autoimmune diseases, allergies, transplant rejection, hyperproliferative disorders, and other immune system disorders.

Accordingly, in one aspect, the binding proteins of the invention feature an isolated binding protein (e.g., an isolated antibody) or antigen-binding fragment thereof that binds to IL-21R, in particular, human IL-21R. In certain embodiments, the anti-IL-21R binding protein (e.g., antibody) can have one or more of the following characteristics: (1) it is a monoclonal or single specificity binding protein; (2) it is a human binding protein; (3) it is an in vitro-generated binding protein; (4) it is an in vivo-generated (for example, a transgenic mouse system) binding protein; (5) it inhibits the binding of IL-21 to IL-21R; (6) it is an IgG1; (7) it binds to human IL-21R with an association constant of at least about $10^5$ $M^{-1}s^{-1}$; (8) it binds to murine IL-21R with an association constant of at least about $5 \times 10^4 M^{-1}s^{-1}$; (9) it binds to human IL-21R with a dissociation constant of about $10^{-3} s^{-1}$ or less; (10) it binds to murine IL-21R with a dissociation constant of about $10^{-2} s^{-1}$ or less; (11) it inhibits human IL-21R-mediated proliferation of human IL-21R-expressing BaF3 cells with an $IC_{50}$ of about 1.75 nM or less; (12) it inhibits murine IL-21R-mediated proliferation of murine IL-21R-expressing BaF3 cells with an $IC_{50}$ of about 0.5 nM or less; (13) it inhibits human IL-21R-mediated proliferation of human IL-21R-expressing TF1 cells with an IC$_{50}$ of about 14.0 nM or less; (14) it inhibits IL-21-mediated proliferation of human primary B cells with an IC$_{50}$ of about 1.9 nM or less; (15) it inhibits IL-21-mediated proliferation of human primary CD4$^+$ T cells with an IC$_{50}$ of about 1.5 nM or less; and (16) it inhibits IL-21-mediated proliferation of murine primary CD4$^+$ T cells with an IC$_{50}$ of about 5.0 nM or less.

Nonlimiting illustrative embodiments of the binding proteins of the invention (the term "binding proteins" also includes and refers to antigen-binding fragments thereof, as appropriate) are referred to herein as AbA-AbZ, and correlation of these terms with terms used in U.S. Provisional Patent Application No. 61/055,500 is presented in Table 2A. Other illustrative embodiments of the binding proteins of the present invention, i.e., scFv, are referred to herein as H3-H6, L1-L6, L8-L21, and L23-L25, as detailed in Table 2B.

One embodiment of the present invention is an isolated binding protein or antigen-binding fragment thereof that binds to IL-21R, wherein the binding protein or antigen-binding fragment thereof comprises at least one amino acid sequence that is at least about 95% identical to an amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248. The isolated binding protein or antigen-binding fragment can be, for example, an antibody, an scFv, a V$_H$, a V$_L$, or a CDR.

Another embodiment of the present invention is an isolated binding protein or antigen-binding fragment thereof that binds to IL-21R, wherein the binding protein or antigen-binding fragment thereof comprises at least one amino acid sequence encoded by a nucleotide sequence that is at least about 95% identical to a nucleotide sequence(s) selected from the group consisting of SEQ ID NOs:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247.

A further embodiment of the present invention is an isolated binding protein or antigen-binding fragment comprising at least one amino acid sequence selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

Yet another embodiment of the present invention is an isolated binding protein or antigen-binding fragment thereof that binds to IL-21R, wherein the binding protein or antigen-binding fragment thereof comprises at least one amino acid sequence that is at least about 95% identical to an amino acid sequence(s) selected from the group consisting of SEQ ID NOs:6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162-195, 213-229, 240, 242, 244, 246, and 248, and wherein, if the binding protein or antigen-binding fragment comprises at least one amino acid sequence that is at least about 95% identical to the sequence(s) selected from the group consisting of SEQ ID NOs:6, 8, 10, 12, 163, 164, 169, 170, 194, and 195, then the binding protein or antigen-binding fragment must also comprise at least one amino acid sequence that is at least about 95% identical to the amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

Yet another embodiment of the present invention is an isolated binding protein or antigen-binding fragment thereof that binds to IL-21R, wherein the binding protein or antigen-binding fragment thereof comprises at least one amino acid sequence encoded by a nucleotide sequence that is at least about 95% identical to a nucleotide sequence(s) selected from the group consisting of SEQ ID NOs:5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247, and wherein, if the binding protein or antigen-binding fragment comprises at least one amino acid sequence encoded by a nucleotide sequence that is at least about 95% identical to the sequence(s) selected from the group consisting of SEQ ID NOs:5, 7, 9, and 11, then the binding protein or antigen-binding fragment must also comprise at least one amino acid sequence encoded by a nucleotide sequence that is at least about 95% identical to the nucleotide sequence(s) selected from the group consisting of SEQ ID NOs:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247.

Yet a further embodiment of the present invention is an isolated binding protein or antigen-binding fragment comprising at least one amino acid sequence selected from the group consisting of SEQ ID NOs:6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162-195, 213-229, 240, 242, 244, 246, and 248, wherein, if the binding protein or antigen-binding fragment comprises at least one amino acid sequence that is at least about 95% identical to the sequence(s) selected from the group consisting of SEQ ID NOs:6, 8, 10, 12, 163, 164, 169, 170, 194, and 195, then the binding protein or antigen-binding fragment must also comprise at least one amino acid sequence that is at least about 95% identical to the amino acid sequence(s) selected from the group consisting of SEQ ID NOs: 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

Another embodiment of the present invention is an isolated binding protein or antigen-binding fragment thereof that binds to IL-21 R, wherein the binding protein or antigen-binding fragment thereof comprises a light chain and a heavy chain, and wherein the heavy chain comprises at least one amino acid sequence selected from the group consisting of SEQ ID NOs:14, 16, 18, 20, 68, 70, 72, 88, 90, 92, 94, 213, 218, 219, 240, and 242, or a sequence substantially identical thereto (e.g., a sequence substantially identical thereto includes a sequence at least about 85%, 90%, 95%, 96%, 97%, 98%, 99%, or more identical thereto), or a sequence substantially homologous thereto (e.g., a sequence substantially homologous thereto includes a sequence at least about 50%, 55%, 60%, 65%, 70%, 75%, 80%, 85%, 90%, 95%, 96%, 97%, 98%, 99%, or more identical thereto). In a further embodiment, the binding protein or antigen-binding fragment comprises a $V_L$ domain and a $V_H$ domain, and the $V_H$ domain comprises at least one amino acid sequence selected from the group consisting of SEQ ID NOs: 14, 16, 18, and 20, or a sequence substantially identical or homologous thereto. Another embodiment of the present invention is an isolated binding protein or antigen-binding fragment thereof that binds to IL-21R, wherein the binding protein or antigen-binding fragment thereof comprises a light chain and a heavy chain, and wherein the light chain comprises at least one amino acid sequence selected from the group consisting of SEQ ID NOs:22, 24, 26, 28, 30, 32, 34, 36, 38, 40, 42, 44, 46, 48, 50, 52, 54, 56, 58, 60, 62, 64, 66, 74, 76, 78, 80, 82, 84, 86, 96, 98, 100, 102, 104, 106, 108, 214-217, 220-229, 244, 246, and 248, or a sequence substantially identical or homologous thereto. In a further embodiment, the binding protein or antigen-binding fragment comprises a $V_L$ domain and a $V_H$ domain, and the $V_L$ domain comprises at least one amino acid sequence selected from the group consisting of SEQ ID NOs: 22, 24, 26, 28, 30, 32, 34, 36, 38, 40, 42, 44, 46, 48, 50, 52, 54, 56, 58, 60, 62, 64, 66, 215, 217, 221, 223, 225, 227, and 229, or a sequence substantially identical or homologous thereto. In yet another embodiment, the heavy chain comprises an amino acid sequence selected from the group consisting of SEQ ID NOs:88, 90, 92, 94, 213, 218, 219, 240, and 242, and the light chain comprises an amino acid sequence selected from the group consisting of SEQ ID NOs:96, 98, 100, 102, 104, 106, 108, 214, 216, 220, 222, 224, 226, 228, 244, 246, and 248, or a sequence substantially identical or homologous thereto.

The binding proteins of the present invention, e.g., antibodies, can be germlined or nongermlined. They may specifically bind to the same IL-21R epitope or a similar epitope (e.g., an overlapping epitope) to which AbA-AbZ, H3-H6, L1-L6, L8-L21, or L23-L25 bind. In other embodiments, the binding proteins specifically bind to a fragment of IL-21R, e.g., a fragment of at least 10, 20, 50, 75, 100, 150, or 200 amino acids contiguous to the amino acid sequence set forth in SEQ ID NOs:2 or 4, or a sequence that is at least 85%, 90%, 95%, 96%, 97%, 98%, 99% or more identical thereto.

Another embodiment of the present invention is an isolated binding protein or antigen-binding fragment thereof that binds to an IL-21R epitope that is recognized by a binding protein selected from the group consisting of AbA-AbZ, H3-H6, L1-L6, L8-L21, and L23-L25, wherein the binding protein or antigen-binding fragment competitively inhibits the binding of a binding protein selected from the group consisting of AbA-AbZ, H3-H6, L1-L6, L8-L21, and L23-L25 to human IL-21R. In another embodiment, the binding protein or antigen-binding fragment comprises a heavy chain, a light chain, or an $F_v$ fragment comprising an amino acid sequence selected from the group consisting of SEQ ID NOs: 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248, or a sequence substantially identical or homologous thereto. In yet another embodiment, the binding protein or antigen-binding fragment comprises a heavy chain, a light chain, or an $F_v$ fragment comprising an amino acid sequence encoded by a nucleotide sequence selected from the group consisting of SEQ ID NOs:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247, or a sequence substantially identical or homologous thereto.

In yet other embodiments, the binding protein comprises at least one complementarity determining region (CDR) of these $V_H$ and $V_L$ domains (e.g., one or more, two or more, three or more, four or more, or five or more of contiguous CDRs (e.g., two or more CDRs separated by framework regions (FR) or a linker) or noncontiguous CDRs (e.g., two or more CDRs separated by at least one other CDR and, e.g., FR(s)). For example, the binding protein can include one, two, three or more CDRs of the $V_H$ domain and/or the $V_L$ domain.

The disclosure provides nucleic acid sequences from the $V_H$ and $V_L$ domains of AbA-AbZ, H3-H6, L1-L6, L8-L21, and L23-L25. Also contemplated are nucleic acid sequences that comprise at least one CDR from AbA-AbZ, H3-H6, L1-L6, L8-L21, and L23-L25. The disclosure also provides vectors and host cells comprising such nucleic acids.

The binding proteins of the invention can be full-length (e.g., include at least one complete heavy chain and at least one complete light chain), or can include only an antigen-binding fragment (e.g., a Fab, a Fab', a F(ab')$_2$, an Fv, a single chain Fv fragment, an Fd fragment, a dAb fragment, a CDR, or other fragment of a full-length binding protein that retains the ability to specifically bind to an antigen). The binding protein can include a constant region, or a portion thereof, chosen from any of the kappa, lambda, alpha, gamma, delta, epsilon and mu constant region genes. For example, heavy chain constant regions of the various isotypes can be used, including: IgG1, IgG2, IgG3, IgG4, IgM, IgA1, IgA2, IgD, and IgE. The light chain constant region can be chosen from kappa or lambda. The binding protein may be an IgG, or it may also be IgG1$_\kappa$ or IgG1$\lambda$.

The anti-IL-21R binding protein described herein can be derivatized or linked to another functional molecule (such as another peptide or protein, e.g., a Fab fragment). For example, a binding protein of the invention can be functionally linked (e.g., by chemical coupling, genetic fusion, noncovalent association or otherwise) to at least one other molecular entity, such as another binding protein (e.g., a bispecific or a multispecific binding protein), toxin, radioisotope, cytotoxic or cytostatic agent, among others.

In one embodiment of the invention, the association constant of the binding protein or antigen-binding fragment for human IL-21R is at least about $10^5$ $M^{-1}s^{-1}$. In another embodiment, the binding protein or antigen-binding fragment inhibits IL-21-mediated proliferation of BaF3 cells with an IC$_{50}$ of about 1.75 nM or less, and the BaF3 cells comprise a human IL-21R. In another embodiment, the binding protein or antigen-binding fragment inhibits IL-21-mediated proliferation of TF1 cells with an IC$_{50}$ of about 14.0 nM or less, and the TF1 cells comprise a human IL-21R. In another embodiment, the binding protein or antigen-binding fragment inhibits IL-21-mediated proliferation of primary human B cells with an IC$_{50}$ of about 1.9 nM or less, and the B cells comprise a human IL-21R. In yet another embodiment, the binding protein or antigen-binding fragment inhibits IL-21-mediated proliferation of primary human CD4$^+$ cells with an IC$_{50}$ of about 1.5 nM or less, and the CD4$^+$ cells comprise a human IL-21R.

In one embodiment, the present invention provides a binding protein or antigen-binding fragment that specifically binds to an amino acid sequence that is at least about 95% identical to any sequence of at least 100 contiguous amino acids of SEQ ID NO:2. Another embodiment provides a binding protein or antigen-binding fragment that inhibits the binding of IL-21 to IL-21R. In at least one embodiment, the binding protein or antigen-binding fragment is IgG1. In at least one embodiment, the binding protein or antigen-binding fragment is human.

In another aspect, the invention features a pharmaceutical composition containing at least one anti-IL-21R binding protein and a pharmaceutically acceptable carrier. The pharmaceutical composition can further include a combination of at least one anti-IL-21R binding protein and at least one other therapeutic agent (e.g., cytokine and growth factor inhibitors, immunosuppressants, anti-inflammatory agents, metabolic inhibitors, enzyme inhibitors, cytotoxic agents, cytostatic agents, or combinations thereof, as described in more detail herein). Combinations of the anti-IL-21R binding protein and therapeutic agent(s) are also within the scope of the invention. The compositions and combinations of the invention can be used to regulate IL-21R-associated immune disorders, e.g., by modulating IL-21R signaling.

In one embodiment, the binding proteins of the invention are antibodies. In further embodiments, the antibodies are polyclonal, monoclonal, monospecific, polyspecific, nonspecific, humanized, human, single-chain, chimeric, synthetic, recombinant, hybrid, mutated, grafted, in vitro-generated and/or multispecific (e.g., bispecific antibodies formed from at least two intact antibodies).

Other embodiments of the invention include an isolated nucleic acid encoding an anti-IL-21R binding protein, an expression vector comprising the nucleic acid, and a host cell transformed with the vector. The host cell may be a bacteria, a mammalian cell, a yeast cell, a plant cell, or an insect cell.

The binding protein may be directly or indirectly labeled with a detectable substance to facilitate detection of the bound or unbound binding protein. Suitable detectable substances include, but are not limited to, various enzymes, prosthetic groups, fluorescent materials, luminescent materials, and radioactive materials.

In another aspect, the invention provides a method for delivering or targeting an agent, e.g., a therapeutic or a cytotoxic agent, to an IL-21R-expressing cell in vivo. The method includes administering an anti-IL-21R binding protein to a subject under conditions that allow for binding of the binding protein to IL-21R. The binding protein may be coupled to a second therapeutic moiety, e.g., a toxin.

In another embodiment, the invention provides a diagnostic kit comprising a binding protein or antigen-binding fragment of the present invention.

Additional aspects of the disclosure will be set forth in part in the description, and in part will be obvious from the description, or may be learned by practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve only to illustrate embodiments and not limit the invention.

BRIEF DESCRIPTION OF THE DRAWINGS

FIG. 7(a-c) depicts the binding specificity of particular anti-IL-21R antibodies (FIG. 7a, AbS; FIG. 7d shows that human IL-2Rβ and human soluble IL-4R are captured by specific anti-IL-2Rβ and anti-IL-4R antibodies, respectively (control).

FIG. 9 depicts the binding of anti-IL-21R antibodies to human and cynomolgus monkey IL-21R. Human anti-IL- 21R antibodies AbS and AbT were captured on anti-human IgG immobilized on a BIACORE™ chip. Varying concentrations of human and cynomolgus monkey IL-21R-His/FLAG were allowed to flow over the chip, and binding and dissociation were monitored.

FIG. 12 depicts the neutralization of IL-21-dependent proliferation of human primary B cells. The indicated antibodies were added to primary human B cells along with anti-CD40 antibodies and human IL-21. Incorporation of $^3$H-thymidine was measured after three days.

FIG. 17(a-c) depicts amino acid sequences for AbQ, including $V_H$ and $V_L$ domains, CDRs (H1, H2, H3, L1, L2, and L3), and constant regions.

FIG. 18(a-c) depicts amino acid sequences for AbR, including $V_H$ and $V_L$ domains, CDRs (H1, H2, H3, L1, L2, and L3), and constant regions.

FIG. 19(a-c) depicts amino acid sequences for AbW, including $V_H$ and $V_L$ domains, CDRs (H1, H2, H3, L1, L2, and L3), and constant regions.

FIG. 20(a-c) depicts amino acid sequences for AbS, including $V_H$ and $V_L$ domains, CDRs (H1, H2, H3, L1, L2, and L3), and constant regions.

FIG. 21(a-c) depicts amino acid sequences for AbT, including $V_H$ and $V_L$ domains, CDRs (H1, H2, H3, L1, L2, and L3), and constant regions.

FIG. 22(a-c) depicts amino acid sequences for AbO, including $V_H$ and $V_L$ domains, CDRs (H1, H2, H3, L1, L2, and L3), and constant regions.

FIG. 23(a-c) depicts amino acid sequences for AbP including $V_H$ and $V_L$ domains, CDRs (H1, H2, H3, L1, L2, and L3), and constant regions.

FIG. 24(a-c) depicts amino acid sequences for AbU, including $V_H$ and $V_L$ domains, CDRs (H1, H2, H3, L1, L2, and L3), and constant regions.

FIG. 25(a-c) depicts amino acid sequences for AbV, including $V_H$ and $V_L$ domains, CDRs (H1, H2, H3, L1, L2, and L3), and constant regions.

DETAILED DESCRIPTION OF THE INVENTION

Figure 1A:
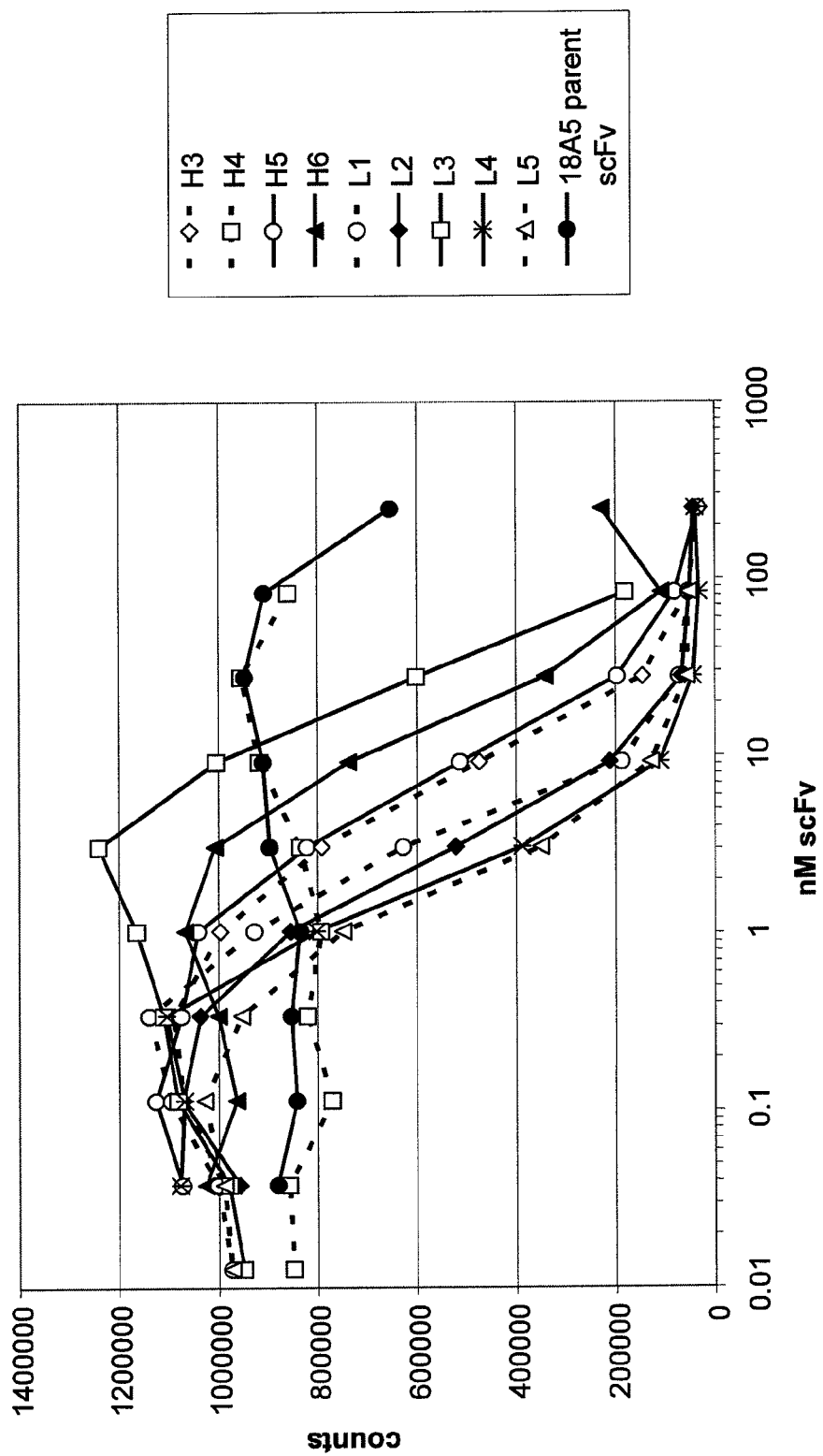
FIG. 1(a-c) depicts the neutralization of proliferation of human IL-21R-BaF3 cells by scFv. Cells were mixed with the indicated scFv and then incubated with 100 pg/ml of human IL-21. Proliferation was measured by CELLTITER-GLO® (Promega Corporation, Madison, Wis.) after 48 hours.

The binding proteins of the present invention were initially derived from parental antibody 18A5, but differ from 18A5 in the amino acid sequences of portions of the heavy chain and/or light chain complementarity determining region 3 (CDR3). Additionally, the present binding proteins show improved potency in binding to and neutralizing both human and murine IL-21R as compared to 18A5 in the equivalent format (e.g., scFv or IgG). High-potency neutralization of IL-21R from both species (human and mouse) by a single binding protein has not previously been reported. The present binding proteins having a greater neutralization potency than their parental antibody may translate into higher efficacy as compared to agents previously described. In addition, the amino acid sequence of the $V_H$ and $V_L$ framework regions has been altered to match sequences encoded by human genomic sequence, thereby reducing the potential for human anti-human antibody responses in patients treated with the present binding proteins.

DEFINITIONS

In order that the present invention may be more readily understood, certain terms are first defined. Additional definitions are set forth throughout the detailed description and elsewhere in the specification.

The term "binding protein" as used herein includes any naturally occurring, recombinant, synthetic, or genetically engineered protein, or a combination thereof, that binds an antigen, target protein, or peptide, or a fragment(s) thereof. Binding proteins of the invention can include antibodies, or be derived from at least one antibody fragment. The binding proteins can include naturally occurring proteins and/or proteins that are synthetically engineered. Binding proteins of the invention can bind to an antigen or a fragment thereof to form a complex and elicit a biological response (e.g., agonize or antagonize a particular biological activity). Binding proteins can include isolated antibody fragments, "Fv" fragments consisting of the variable regions of the heavy and light chains of an antibody, recombinant single-chain polypeptide molecules in which light and heavy chain variable regions are connected by a peptide linker ("scFv proteins"), and minimal recognition units consisting of the amino acid residues that mimic the hypervariable region. Binding protein fragments can also include functional fragments of an antibody, such as, for example, Fab, Fab', F(ab')$_2$, Fc, Fd, Fd', Fv, and a single variable domain of an antibody (dAb). The binding proteins can be double or single chain, and can comprise a single binding domain or multiple binding domains.

Binding proteins can also include binding domain-immunoglobulin fusion proteins, including a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain other than CH1, for example, the CH2 and CH3 regions of IgG and IgA, or the CH3 and CH4 regions of IgE (see, e.g., Ledbetter et al., U.S. Patent Publication 2005/0136049, for a more complete description). The binding domain-immunoglobulin fusion protein can further include a region that includes a native or engineered immunoglobulin heavy chain CH2 constant region polypeptide (or CH3 in the case of a construct derived in whole or in part from IgE) that is fused or otherwise connected to the hinge region polypeptide, and a native or engineered immunoglobulin heavy chain CH3 constant region polypeptide (or CH4 in the case of a construct derived in whole or in part from IgE) that is fused or otherwise connected to the CH2 constant region polypeptide (or CH3 in the case of a construct derived in whole or in part from IgE). Typically, such binding domain-immunoglobulin fusion proteins are capable of at least one immunological activity selected from the group consisting of antibody-dependent cell-mediated cytotoxicity, complement fixation, and/or binding to a target, for example, a target antigen. The binding proteins of the invention can be derived from any species including, but not limited to mouse, human, camel, llama, fish, shark, goat, rabbit, chicken, and bovine.

The term "antibody" as used herein refers to an immunoglobulin that is reactive to a designated protein or peptide or fragment thereof. Suitable antibodies include, but are not limited to, human antibodies, primatized antibodies, chimeric antibodies, monoclonal antibodies, monospecific antibodies, polyclonal antibodies, polyspecific antibodies, nonspecific antibodies, bispecific antibodies, multispecific antibodies, humanized antibodies, synthetic antibodies, recombinant antibodies, hybrid antibodies, mutated antibodies, grafted conjugated antibodies (i.e., antibodies conjugated or fused to other proteins, radiolabels, cytotoxins), and in vitro-generated antibodies. The antibody can be from any class of antibodies including, but not limited to, IgG, IgA, IgM, IgD, and IgE, and from any subclass (e.g., IgG1, IgG2, IgG3, and IgG4) of antibodies. The antibody can have a heavy chain constant region chosen from, e.g., IgG1, IgG2, IgG3, or IgG4. The antibody can also have a light chain chosen from, e.g., kappa (κ) or lambda (λ). The antibodies of the invention can be derived from any species including, but not limited to mouse, human, camel, llama, fish, shark, goat, rabbit, chicken, and bovine. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function). Typically, the antibody specifically binds to a predetermined antigen, e.g., an antigen associated with a disorder, e.g., an inflammatory, immune, autoimmune, neurodegenerative, metabolic, and/or malignant disorder.

The term "single domain binding protein" as used herein includes any single domain binding scaffold that binds to an antigen, protein, or polypeptide. Single domain binding proteins can include any natural, recombinant, synthetic, or genetically engineered protein scaffold, or a combination thereof, that binds an antigen or fragment thereof to form a complex and elicit a biological response (e.g., agonize or antagonize a particular biological activity). Single domain binding proteins may be derived from naturally occurring proteins or antibodies, or they can be synthetically engineered or produced by recombinant technology. Single domain binding proteins may be any in the art or any future single domain binding proteins, and may be derived from any species including, but not limited to mouse, human, camel, llama, fish, shark, goat, rabbit, chicken, and bovine. In some embodiments of the invention, a single domain binding protein scaffold can be derived from a variable region of the immunoglobulin found in fish, such as, for example, that which is derived from the immunoglobulin isotype known as Novel Antigen Receptor (NAR) found in the serum of shark. Methods of producing single domain binding scaffolds derived from a variable region of NAR ("IgNARs") are described in International Application Publication No. WO 03/014161 and Streltsov (2005) *Protein Sci.* 14(11):2901-09.

In other embodiments, a single domain binding protein is a naturally occurring single domain binding protein which has been described in the art as a heavy chain antibody devoid of light chains. Such single domain binding proteins are disclosed in, e.g., International Application Publication No. WO 94/004678. For clarity reasons, a variable domain binding protein that is derived from a heavy chain antibody naturally devoid of light chain is known herein as a VHH or "nanobody" to distinguish it from the conventional $V_H$ of four-chain immunoglobulins. Such a VHH molecule can be derived from antibodies raised in Camelidae species, for example in camel, llama, dromedary, alpaca, and guanaco. Other families besides Camelidae may also be used to produce heavy chain binding proteins naturally devoid of light chains. VHH molecules are approximately ten times smaller than traditional IgG molecules. They are single polypeptides and are very stable, resisting extreme pH and temperature conditions. Moreover, they are resistant to the action of proteases, which is not the case for conventional antibodies. Furthermore, in vitro expression of VHHs can produce high-yield, properly folded functional VHHs. In addition, binding proteins generated in Camelids can recognize epitopes other than those recognized by antibodies generated in vitro via antibody libraries or via immunization of mammals other than Camelids (see, e.g., International Application Publication Nos. WO 97/049805 and WO 94/004678, both hereby incorporated by reference herein).

The terms "antigen-binding domain" and "antigen-binding fragment" refer to a part of a binding protein that comprises amino acids responsible for the specific binding between the binding protein and an antigen. The part of the antigen that is specifically recognized and bound by the binding protein is referred to as the "epitope." An antigen-binding domain may comprise a light chain variable region ($V_L$) and a heavy chain variable region ($V_H$) of an antibody; however, it does not have to comprise both. Fd fragments, for example, have two $V_H$ regions and often retain antigen-binding function of the intact antigen-binding domain. Examples of antigen-binding fragments of a binding protein include, but are not limited to: (1) a Fab fragment, a monovalent fragment having $V_L$, $V_H$, $C_L$ and $C_H1$ domains; (2) a F(ab')$_2$ fragment, a bivalent fragment having two Fab fragments linked by a disulfide bridge at the hinge region; (3) an Fd fragment, having two $V_H$ and one $C_H1$ domains; (4) an Fv fragment, having the $V_L$ and $V_H$ domains of a single arm of an antibody; (5) a dAb fragment (see, e.g., Ward et al. (1989) *Nature* 341:544-46), having a $V_H$ domain; (6) an isolated CDR; and (7) a single chain variable fragment (scFv). Although the two domains of an Fv fragment, $V_L$ and $V_H$ are coded for by separate genes, they can be joined, using recombinant methods, by a synthetic linker that enables them to be made as a single protein chain in which the $V_L$ and $V_H$ regions pair to form monovalent molecules (known as scFv) (see, e.g., Bird et al. (1988) *Science* 242:423-26; Huston et al. (1988) *Proc. Natl. Acad. Sci. USA* 85:5879-83). These binding domain fragments can be obtained using conventional techniques known to those with skill in the art, and the fragments are evaluated for function in the same manner as are intact binding proteins such as, for example, antibodies.

The term "neutralizing" refers to a binding protein or antigen-binding fragment thereof (for example, an antibody) that reduces or blocks the activity of a signaling pathway or an antigen, e.g., IL-21/IL-21R signaling pathway or IL-21R antigen.

The term "effective amount" refers to a dosage or amount that is sufficient to regulate IL-21R activity to ameliorate or lessen the severity of clinical symptoms or achieve a desired biological outcome, e.g., decreased T cell and/or B cell activity, suppression of autoimmunity, suppression of transplant rejection.

The term "human binding protein" includes binding proteins having variable and constant regions corresponding substantially to human germline immunoglobulin sequences known in the art, including, for example, those described by Kabat et al. (5th ed. 1991) *Sequences of Proteins of Immunological Interest*, U.S. Department of Health and Human Services, NIH Publication No. 91-3242. The human antibodies of the invention may include amino acid residues not encoded by human germline immunoglobulin sequences (e.g., mutations introduced by random or site-specific mutagenesis in vitro or by somatic mutation in vivo), for example, in the CDRs, and in particular, CDR3. The human antibody can have at least one, two, three, four, five, or more positions replaced with an amino acid residue that is not encoded by the human germline immunoglobulin sequence.

The phrases "inhibit," "antagonize," "block," or "neutralize" IL-21R activity and its cognates refer to a reduction, inhibition, or otherwise diminution of at least one activity of IL-21R due to binding an anti-IL-21R antibody, wherein the reduction is relative to the activity of IL-21R in the absence of the same antibody. The IL-21R activity can be measured using any technique known in the art. Inhibition or antagonism does not necessarily indicate a total elimination of the IL-21R biological activity. A reduction in activity may be about 10%, 20%, 30%, 40%, 50%, 60%, 70%, 80%, 90%, 95%, or more.

The terms "interleukin-21 receptor" or "IL-21R" or the like refer to a class I cytokine family receptor, also known as MU-1 (see, e.g., U.S. patent application Ser. No. 09/569,384 and U.S. Application Publication Nos. 2004/0265960; 2006/0159655; 2006/0024268; and 2008/0241098), NILR or zalpha 11 (see, e.g., International Application Publication No. WO 01/085792; Parrish-Novak et al. (2000) supra; Ozaki et al. (2000) supra), that binds to an IL-21 ligand. IL-21R is homologous to the shared β chain of the IL-2 and IL-15 receptors, and IL-4α (Ozaki et al. (2000) supra). Upon ligand binding, IL-21R is capable of interacting with a common gamma cytokine receptor chain (γc) and inducing the phosphorylation of STAT1 and STAT3 (Asao et al. (2001) supra) or STAT5 (Ozaki et al. (2000) supra). IL-21R shows widespread lymphoid tissue distribution. The terms "interleukin-21 receptor" or "IL-21R" or the like also refer to a polypeptide (preferably of mammalian origin, e.g., murine or human IL-21R) or, as context requires, a polynucleotide encoding such a polypeptide, that is capable of interacting with IL-21 (preferably IL-21 of mammalian origin, e.g., murine or human IL-21) and has at least one of the following features: (1) an amino acid sequence of a naturally occurring mammalian IL-21R polypeptide or a fragment thereof, e.g., an amino acid sequence set forth in SEQ ID NO:2 (human—corresponding to GENBANK® (U.S. Dept. of Health and Human Services, Bethesda, Md.) Accession No. NP_068570) or SEQ ID NO:4 (murine—corresponding to GENBANK® Acc. No. NP_068687), or a fragment thereof; (2) an amino acid sequence substantially homologous to, e.g., at least 85%, 90%, 95%, 98%, or 99% homologous to, an amino acid sequence set forth in SEQ ID NO:2 or SEQ ID NO:4, or a fragment thereof; (3) an amino acid sequence that is encoded by a naturally occurring mammalian IL-21R nucleotide sequence or fragment thereof (e.g., SEQ ID NO:1 (human—which comprises an open reading frame corresponding to the open reading frame of GENBANK® Accession No. NM_021798) or SEQ ID NO:3 (murine—which comprises an open reading frame corresponding to the open reading frame of GENBANK® Acc. No. NM_021887), or a fragment thereof); (4) an amino acid sequence encoded by a nucleotide sequence which is substantially homologous to, e.g., at least 85%, 90%, 95%, 98%, or 99% homologous to, a nucleotide sequence set forth in SEQ ID NO:1 or SEQ ID NO:3 or a fragment thereof; (5) an amino acid sequence encoded by a nucleotide sequence degenerate to a naturally occurring IL-21R nucleotide sequence or a fragment thereof, e.g., SEQ ID NO:1 or SEQ ID NO:3, or a fragment thereof; or (6) a nucleotide sequence that hybridizes to one of the foregoing nucleotide sequences under stringent conditions, e.g., highly stringent conditions. In addition, other nonhuman and nonmammalian IL-21Rs are contemplated as useful in the disclosed methods.

The term "interleukin-21" or "IL-21" refers to a cytokine that shows sequence homology to IL-2, IL-4 and IL-15 (Parrish-Novak et al. (2000) supra), and binds to an IL-21R. Such cytokines share a common fold into a "four-helix-bundle" structure that is representative of the family. IL-21 is expressed primarily in activated CD4$^+$ T cells, and has been reported to have effects on NK, B and T cells (Parrish-Novak et al. (2000) supra; Kasaian et al. (2002) supra). Upon IL-21 binding to IL-21R, activation of IL-21R leads to, e.g., STAT5 or STAT3 signaling (Ozaki et al. (2000) supra). The term "interleukin-21" or "IL-21" also refers to a polypeptide (preferably of mammalian origin, e.g., murine or human IL-21), or as context requires, a polynucleotide encoding such a polypeptide, that is capable of interacting with IL-21R (preferably of mammalian origin, e.g., murine or human IL-21R) and has at least one of the following features: (1) an amino acid sequence of a naturally occurring mammalian IL-21 or a fragment thereof, e.g., an amino acid sequence set forth in SEQ ID NO:212 (human), or a fragment thereof; (2) an amino acid sequence substantially homologous to, e.g., at least 85%, 90%, 95%, 98%, or 99% homologous to, an amino acid sequence set forth in SEQ ID NO:212, or a fragment thereof; (3) an amino acid sequence which is encoded by a naturally occurring mammalian IL-21 nucleotide sequence or a fragment thereof (e.g., SEQ ID NO:211 (human), or a fragment thereof); (4) an amino acid sequence encoded by a nucleotide sequence which is substantially homologous to, e.g., at least 85%, 90%, 95%, 98%, or 99% homologous to, a nucleotide sequence set forth in SEQ ID NO:211 or a fragment thereof; (5) an amino acid sequence encoded by a nucleotide sequence degenerate to a naturally occurring IL-21 nucleotide sequence or a fragment thereof; or (6) a nucleotide sequence that hybridizes to one of the foregoing nucleotide sequences under stringent conditions, e.g., highly stringent conditions.

The terms "IL-21R activity" and the like (e.g., "activity of IL-21R," "IL-21/IL-21R activity") refer to at least one cellular process initiated or interrupted as a result of IL-21R binding. IL-21R activities include, but are not limited to: (1) interacting with, e.g., binding to, a ligand, e.g., an IL-21 polypeptide; (2) associating with or activating signal transduction (also called "signaling," which refers to the intracellular cascade occurring in response to a particular stimuli) and signal transduction molecules (e.g., gamma chain (γc) and JAK1), and/or stimulating the phosphorylation and/or activation of STAT proteins, e.g., STAT5 and/or STAT3; and (3) modulating the proliferation, differentiation, effector cell function, cytolytic activity, cytokine secretion, and/or survival of immune cells, e.g., T cells, NK cells, B cells, macrophages, regulatory T cells (Tregs) and megakaryocytes.

As used herein, "in vitro-generated antibody" refers to an antibody where all or part of the variable region (e.g., at least one CDR) is generated in a nonimmune cell selection (e.g., an in vitro phage display, protein chip, or any other method in which candidate sequences can be tested for their ability to bind to an antigen).

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions, or is at least 70-80% (w/w) pure, at least 80-90% (w/w) pure, at least 90-95% (w/w) pure, or at least 95%, 96%, 97%, 98%, 99%, or 100% (w/w) pure.

The phrase "percent identical" or "percent identity" refers to the similarity between at least two different sequences. This percent identity can be determined by standard alignment algorithms, for example, the Basic Local Alignment Search Tool (BLAST) described by Altshul et al. ((1990) *J. Mol. Biol.* 215:403-10); the algorithm of Needleman et al. ((1970) *J. Mol. Biol.* 48:444-53); or the algorithm of Meyers et al. ((1988) *Comput. Appl. Biosci.* 4:11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) *CABIOS* 4:11-17), which has been incorporated into the ALIGN program (version 2.0), using a PAM120 weight residue table, a gap length penalty of 12, and a gap penalty of 4. The percent identity is usually calculated by comparing sequences of similar length.

The term "repertoire" refers to at least one nucleotide sequence derived wholly or partially from at least one sequence encoding at least one immunoglobulin.

The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, or other methods (see, e.g., U.S. Pat. No. 5,565,332). A repertoire may include only one sequence or may include a plurality of sequences, including ones in a genetically diverse collection.

The terms "specific binding," "specifically binds," and the like refer to two molecules forming a complex that is relatively stable under physiologic conditions. Specific binding is characterized by a high affinity and a low-to-moderate capacity as distinguished from nonspecific binding, which usually has a low affinity with a moderate-to-high capacity. Typically, binding is considered specific when the association constant Ka is higher than about $10^6$ $M^{-1}s^{-1}$. If necessary, nonspecific binding can be reduced without substantially affecting specific binding by varying the binding conditions. The appropriate binding conditions, such as concentration of binding protein, ionic strength of the solution, temperature, time allowed for binding, concentration of a blocking agent (e.g., serum albumin or milk casein), etc., can be improved by a skilled artisan using routine techniques. Illustrative conditions are set forth herein, but other conditions known to the person of ordinary skill in the art fall within the scope of this invention.

As used herein, the terms "stringent," "stringency," and the like describe conditions for hybridization and washing. The isolated polynucleotides of the present invention can be used as hybridization probes and primers to identify and isolate nucleic acids having sequences identical to or similar to those encoding the disclosed polynucleotides. Therefore, polynucleotides isolated in this fashion may be used to produce binding proteins against IL-21R or to identify cells expressing such binding proteins. Hybridization methods for identifying and isolating nucleic acids include polymerase chain reaction (PCR), Southern hybridizations, in situ hybridization and Northern hybridization, and are well known to those skilled in the art.

Hybridization reactions can be performed under conditions of different stringencies. The stringency of a hybridization reaction includes the difficulty with which any two nucleic acid molecules will hybridize to one another and the conditions under which they will remain hybridized. Preferably, each hybridizing polynucleotide hybridizes to its corresponding polynucleotide under reduced stringency conditions, more preferably stringent conditions, and most preferably highly stringent conditions. Stringent conditions are known to those skilled in the art and can be found in, e.g., *Current Protocols in Molecular Biology*, John Wiley & Sons, N.Y. (1989) 6.3.1-6.3.6. Both aqueous and nonaqueous methods are described in this reference, and either can be used. One example of stringent hybridization conditions is hybridization in 6× sodium chloride/sodium citrate (SSC) at about 45° C., followed by at least one wash in 0.2×SSC/0.1% SDS at 50° C. Stringent hybridization conditions are also accomplished with wash(es) in, e.g., 0.2×SSC/0.1% SDS at 55° C., 60° C., or 65° C. Highly stringent conditions include, e.g., hybridization in 0.5 M sodium phosphate/7% SDS at 65° C., followed by at least one wash at 0.2×SSC/1% SDS at 65° C. Further examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

Hybridization Conditions

| Condition | Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1X SSC -or- 42° C.; 1X SSC, 50% formamide | 65° C.; 0.3X SSC |
| B | DNA:DNA | <50 | $T_B$*; 1X SSC | $T_B$*; 1X SSC |
| C | DNA:RNA | >50 | 67° C.; 1X SSC -or- 45° C.; 1X SSC, 50% formamide | 67° C.; 0.3X SSC |
| D | DNA:RNA | <50 | $T_D$*; 1X SSC | $T_D$*; 1X SSC |
| E | RNA:RNA | >50 | 70° C.; 1X SSC -or- 50° C.; 1X SSC, 50% formamide | 70° C.; 0.3X SSC |
| F | RNA:RNA | <50 | $T_F$*; 1X SSC | $T_F$*; 1X SSC |
| G | DNA:DNA | >50 | 65° C.; 4X SSC -or- 42° C.; 4X SSC, 50% formamide | 65° C.; 1X SSC |
| H | DNA:DNA | <50 | $T_H$*; 4X SSC | $T_H$*; 4X SSC |
| I | DNA:RNA | >50 | 67° C.; 4X SSC -or- 45° C.; 4X SSC, 50% formamide | 67° C.; 1X SSC |
| J | DNA:RNA | <50 | $T_J$*; 4X SSC | $T_J$*; 4X SSC |
| K | RNA:RNA | >50 | 70° C.; 4X SSC -or- 50° C.; 4X SSC, 50% formamide | 67° C.; 1X SSC |
| L | RNA:RNA | <50 | $T_L$*; 2X SSC | $T_L$*; 2X SSC |
| M | DNA:DNA | >50 | 50° C.; 4X SSC -or- 40° C.; 6X SSC, 50% formamide | 50° C.; 2X SSC |
| N | DNA:DNA | <50 | $T_N$*; 6X SSC | $T_N$*; 6X SSC |
| O | DNA:RNA | >50 | 55° C.; 4X SSC -or- 42° C.; 6X SSC, 50% formamide | 55° C.; 2X SSC |
| P | DNA:RNA | <50 | $T_P$*; 6X SSC | $T_P$*; 6X SSC |
| Q | RNA:RNA | >50 | 60° C.; 4X SSC -or- 45° C.; 6X SSC, 50% formamide | 60° C.; 2X SSC |
| R | RNA:RNA | <50 | $T_R$*; 4X SSC | $T_R$*; 4X SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2]SSPE (1xSSPE is 0.15M NaCl, 10 mM NaH$_2$PO$_4$, and 1.25 mM EDTA, pH 7.4) can be substituted for SSC (1xSSC is 0.15M NaCl and 15 mM sodium citrate) in the hybridization and wash buffers; washes are performed for 15 min after hybridization is complete.
$T_B$*-$T_R$*: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$ (° C.) = 81.5 + 16.6(log$_{10}$Na$^+$) + 0.41(% G + C) − (600/N), where N is the number of bases in the hybrid, and Na$^+$ is the concentration of sodium ions in the hybridization buffer (Na$^+$ for 1X SSC = 0.165 M).
Additional examples of stringency conditions for polynucleotide hybridization are provided in Sambrook et al., Molecular Cloning: A Laboratory Manual, Chs. 9 & 11, Cold Spring Harbor Laboratory Press, Cold Spring Harbor, NY (1989), and Ausubel et al. eds., Current Protocols in Molecular Biology, Sects. 2.10 & 6.3-6.4, John Wiley & Sons, Inc. (1995), herein incorporated by reference.

The isolated polynucleotides of the present invention may be used as hybridization probes and primers to identify and isolate DNAs having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least about 90% sequence identity (more preferably, at least about 95% identity; most preferably, at least about 99% identity) with the disclosed polynucleotides. The isolated polynucleotides of the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least about 50% sequence identity (more preferably, at least about 75% identity; most preferably, at least about 90% identity) with the disclosed polynucleotides, whereas polypeptide homologs have at least about 30% sequence identity (more preferably, at least about 45% identity; most preferably, at least about 60% identity) with the disclosed binding proteins/polypeptides. Preferably, homologs of the disclosed polynucleotides and polypeptides are those isolated from mammalian species. The isolated polynucleotides of the present invention may additionally be used as hybridization probes and primers to identify cells and tissues that express the binding proteins of the present invention and the conditions under which they are expressed.

The phrases "substantially as set out," "substantially identical," and "substantially homologous" mean that the relevant amino acid or nucleotide sequence (e.g., CDR(s), $V_H$, or $V_L$ domain(s)) will be identical to or have insubstantial differences (e.g., through conserved amino acid substitutions) in comparison to the sequences which are set out. Insubstantial differences include minor amino acid changes, such as one or two substitutions in a five amino acid sequence of a specified region. In the case of antibodies, the second antibody has the same specificity and has at least about 50% of the affinity of the first antibody.

Sequences substantially identical or homologous to the sequences disclosed herein are also part of this application. In some embodiments, the sequence identity can be about 85%, 90%, 95%, 96%, 97%, 98%, 99%, or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

The term "therapeutic agent" or the like is a substance that treats or assists in treating a medical disorder or symptoms thereof. Therapeutic agents may include, but are not limited to, substances that modulate immune cells or immune responses in a manner that complements the use of anti-IL-21R binding proteins. In one embodiment of the invention, a therapeutic agent is a therapeutic antibody, e.g., an anti-IL-21R antibody. In another embodiment of the invention, a therapeutic agent is a therapeutic binding protein, e.g., an anti-IL-21R nanobody. Nonlimiting examples and uses of therapeutic agents are described herein.

As used herein, a "therapeutically effective amount" of an anti-IL-21R binding protein (e.g., an antibody) refers to an amount of the binding protein that is effective, upon single or multiple dose administration to a subject (such as a human patient) for treating, preventing, curing, delaying, reducing the severity of, and/or ameliorating at least one symptom of a disorder or a recurring disorder, or prolonging the survival of the subject beyond that expected in the absence of such treatment.

Anti-IL-21R Binding Proteins

The disclosure of the present application provides novel anti-IL-21R binding proteins that comprise novel antigen-binding fragments. Numerous methods known to those skilled in the art are available for obtaining binding proteins or antigen-binding fragments thereof. For example, anti-IL-21R binding proteins that comprise antibodies can be produced using recombinant DNA methods (see, e.g., U.S. Pat. No. 4,816,567). Monoclonal antibodies may also be produced by generation of hybridomas in accordance with known methods (see, e.g., Kohler and Milstein (1975) *Nature* 256:495-99). Hybridomas formed in this manner are then screened using standard methods, such as enzyme-linked immunosorbent assays (ELISA) and surface plasmon resonance (BIACORE™) analysis, to identify one or more hybridomas that produce an antibody that specifically binds with a particular antigen. Any form of the specified antigen may be used as the immunogen, e.g., recombinant antigen, naturally occurring forms, any variants or fragments thereof, and antigenic peptides thereof.

One exemplary method of making binding proteins that comprise antibodies includes screening protein expression libraries, e.g., phage or ribosome display libraries. Phage display is described, for example, in U.S. Pat. No. 5,223,409; Smith (1985) *Science* 228:1315-17; Clackson et al. (1991) *Nature* 352:624-28; Marks et al. (1991) *J. Mol. Biol.* 222:581-97; and International Application Publication Nos. WO 92/018619; WO 91/017271; WO 92/020791; WO 92/015679; WO 93/001288; WO 92/001047; WO 92/009690; and WO 90/002809.

In addition to the use of display libraries, the specified antigen can be used to immunize a nonhuman animal, e.g., a cynomolgus monkey, a chicken, or a rodent (e.g., a mouse, hamster, or rat). In one embodiment, the nonhuman animal includes at least a part of a human immunoglobulin gene. For example, it is possible to engineer mouse strains deficient in mouse antibody production with large fragments of the human Ig loci. Using the hybridoma technology, antigen-specific monoclonal binding proteins, such as antibodies, derived from the genes with the desired specificity may be produced and selected (see, e.g., XENOMOUSE™ (Amgen Inc., Thousand Oaks, Calif.); Green et al. (1994) *Nat. Genet.* 7:13-21; U.S. Pat. No. 7,064,244; and International Application Publication Nos. WO 96/034096 and WO 96/033735).

In one embodiment of the invention, the binding proteins is a monoclonal antibody that is obtained from a nonhuman animal, and then modified (e.g., humanized, deimmunized, or chimeric) using recombinant DNA techniques known in the art. A variety of approaches for making chimeric antibodies have been described (see, e.g., Morrison et al. (1985) *Proc. Natl. Acad. Sci. USA* 81(21):6851-55; Takeda et al. (1985) *Nature* 314(6010):452-54; U.S. Pat. Nos. 4,816,567 and 4,816,397; European Application Publication Nos. EP 0 171 496 and EP 0 173 494; and United Kingdom Patent No. GB 2 177 096). Humanized binding proteins may also be produced, for example, using transgenic mice that express human heavy and light chain genes, but are incapable of expressing the endogenous mouse immunoglobulin heavy and light chain genes. Winter (U.S. Pat. No. 5,225,539) describes an exemplary CDR-grafting method that may be used to prepare the humanized binding proteins described herein. All of the CDRs of a particular human binding protein may be replaced with at least a portion of a nonhuman CDR, or only some of the CDRs may be replaced with nonhuman CDRs. It is only necessary to replace the number of CDRs required for binding of the humanized binding protein to a predetermined antigen.

Humanized binding proteins or fragments thereof can be generated by replacing sequences of the Fv variable domain that are not directly involved in antigen binding with equivalent sequences from human Fv variable domains. Exemplary methods for generating humanized binding proteins or fragments thereof are provided by, e.g., Morrison (1985) *Science* 229:1202-07; Oi et al. (1986) *BioTechniques* 4:214; and U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized binding protein is improved by the introduction of conservative substitutions, consensus sequence substitutions, germline substitutions and/or backmutations. Such altered immunoglobulin molecules can be made by any of several techniques known in the art, (see, e.g., Teng et al. (1983) *Proc. Natl. Acad. Sci. USA* 80:7308-73; Kozbor et al. (1983) *Immunol. Today* 4:7279; Olsson et al. (1982) *Meth. Enzymol.* 92:3-16); International Application Publication No. WO 92/006193; and European Patent No. EP 0 239 400).

A binding protein or fragment thereof may also be modified by specific deletion of human T cell epitopes or "deimmunization" by the methods disclosed in, e.g., International Application Publication Nos. WO 98/052976 and WO 00/034317. Briefly, the heavy and light chain variable domains of a binding protein (such as, for example, a binding protein derived from an antibody) can be analyzed for peptides that bind to MHC Class II; these peptides represent potential T cell epitopes (as defined in, e.g., International Application Publication Nos. WO 98/052976 and WO 00/034317). For detection of potential T cell epitopes, a computer modeling approach termed "peptide threading" can be applied, and in addition a database of human MHC class II binding peptides can be searched for motifs present in the $V_H$ and $V_L$ sequences, as described in International Application Publication Nos. WO 98/052976 and WO 00/034317. These motifs bind to any of the 18 major MHC Class II DR allotypes and thus, constitute potential T cell epitopes. Potential T cell epitopes detected can be eliminated by substituting small numbers of amino acid residues in the variable domains or by single amino acid substitutions. Typically, conservative substitutions are made. Often, but not exclusively, an amino acid common to a position in human germline antibody sequences may be used. Human germline sequences are disclosed in, e.g., Tomlinson et al. (1992) *J. Mol. Biol.* 227:776-98; Cook et al. (1995) *Immunol. Today* 16(5):237-42; Chothia et al. (1992) *J. Mol. Biol.* 227:799-817; and Tomlinson et al. (1995) *EMBO J.* 14:4628-38. The V BASE directory provides a comprehensive directory of human immunoglobulin variable region sequences (compiled by Tomlinson et al., MRC Centre for Protein Engineering, Cambridge, UK). These sequences can be used as a source of human sequence, e.g., for framework regions and CDRs. Consensus human framework regions can also be used, as described in, e.g., U.S. Pat. No. 6,300,064.

In certain embodiments, a binding protein can contain an altered immunoglobulin constant or Fc region. For example, binding proteins produced in accordance with the teachings herein may bind more strongly or with more specificity to effector molecules such as complement and/or Fc receptors, which can control several immune functions of the binding protein such as effector cell activity, lysis, complement-mediated activity, binding protein clearance, and binding protein half-life. Typical Fc receptors that bind to an Fc region of a binding protein (e.g., an IgG antibody) include, but are not limited to, receptors of the FcγRI, FcγRII, and FcRn subclasses, including allelic variants and alternatively spliced forms of these receptors. Fc receptors are reviewed in, e.g., Ravetch and Kinet (1991) *Annu. Rev. Immunol.* 9:457-92; Capel et al. (1994) *Immunomethods* 4:25-34; and de Haas et al. (1995) *J. Lab. Clin. Med.* 126:330-41. For additional binding protein/antibody production techniques, see, e.g., Antibodies: A Laboratory Manual (1988) Harlow et al. eds., Cold Spring Harbor Laboratory. The present invention is not necessarily limited to any particular source, method of production, or other special characteristic of a binding protein or an antibody.

Binding proteins comprising antibodies (immunoglobulins) are typically tetrameric glycosylated proteins composed of two light (L) chains of approximately 25 kDa each and two heavy (H) chains of approximately 50 kDa each. Two types of light chains, termed lambda (λ) and kappa (κ), may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2. Each light chain includes an N-terminal variable (V) domain ($V_L$) and a constant (C) domain ($C_L$). Each heavy chain includes an N-terminal V domain ($V_H$), three or four C domains ($C_H$s), and a hinge region. The $C_H$ domain most proximal to $V_H$ is designated as $C_H1$. The $V_H$ and $V_L$ domains consist of four regions of relatively conserved sequences called framework regions (FR1, FR2, FR3, and FR4) that form a scaffold for three regions of hypervariable sequences, called CDRs. The CDRs contain most of the residues responsible for specific interactions of the antibody with the antigen. CDRs are referred to as CDR1, CDR2, and CDR3. CDR constituents on the heavy chain are referred to as H1, H2, and H3 (also referred to herein as CDR H1, CDR H2, and CDR H3, respectively), while CDR constituents on the light chain are referred to as L1, L2, and L3 (also referred to herein as CDR L1, CDR L2, and CDR L3, respectively).

CDR3 is typically the greatest source of molecular diversity within the antigen-binding site. CDR H3, for example, can be as short as two amino acid residues or greater than 26 amino acids. The subunit structures and three-dimensional configurations of different classes of immunoglobulins are well known in the art. For a review of antibody structure, see, e.g., Harlow et al. (1988) supra. One of skill in the art will recognize that each subunit structure, e.g., a $C_H$, $V_H$, $C_L$, $V_L$, CDR, and/or FR structure, comprises active fragments, e.g., the portion of the $V_H$, $V_L$, or CDR subunit that binds to the antigen, i.e., the antigen-binding fragment, or, e.g., the portion of the $C_H$ subunit that binds to and/or activates, e.g., an Fc receptor and/or complement. The CDRs typically refer to the Kabat CDRs (as described in Kabat et al. (1991) supra). Another standard for characterizing the antigen binding site is to refer to the hypervariable loops as described in, e.g., Chothia et al. (1992) supra and Tomlinson et al. (1995) supra. Still another standard is the "AbM" definition used by Oxford Molecular's AbM antibody modeling software (see, generally, e.g., *Protein Sequence and Structure Analysis of Antibody Variable Domains* in: *Antibody Engineering* (2001) Duebel and Kontermann eds., Springer-Verlag, Heidelberg). Embodiments described with respect to Kabat CDRs can alternatively be implemented using similar described relationships with respect to Chothia hypervariable loops or to the AbM-defined loops.

The Fab fragment consists of $V_H$-$C_H1$ and $V_L$-$C_L$ domains covalently linked by a disulfide bond between the constant regions. The $F_v$ fragment is smaller and consists of $V_H$ and $V_L$ domains noncovalently linked. To overcome the tendency of noncovalently linked domains to dissociate, an scFv can be constructed. The scFv contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide, for example, may be used as a linker, but other linkers are known in the art.

The sequence of antibody genes after assembly and somatic mutation is highly varied, and these varied genes are estimated to encode $10^{10}$ different antibody molecules (*Immunoglobulin Genes* (2nd ed. 1995) Jonio et al. eds., Academic Press, San Diego, Calif.).

In certain embodiments of the invention, the binding protein is a single domain binding protein. Single domain binding proteins include binding proteins wherein the CDRs are part of a single domain polypeptide. Examples include, but are not limited to, heavy chain binding proteins, binding proteins that are naturally devoid of light chains, single domain binding proteins derived from conventional four-chain antibodies, engineered binding proteins, and single domain protein scaffolds other than those derived from antibodies. Single domain binding proteins include any known in the art, as well as any future-determined or -learned single domain binding proteins.

Single domain binding proteins may be derived from any species including, but not limited to, mouse, human, camel, llama, fish, shark, goat, rabbit, chicken, and bovine. In one aspect of the invention, the single domain binding protein can be derived from a variable region of the immunoglobulin found in fish, such as, for example, that which is derived from the immunoglobulin isotype known as Novel Antigen Receptor (NAR) found in the serum of shark. Methods of producing single domain binding proteins derived from a variable region of NAR (IgNARs) are described in, e.g., International Application Publication No. WO 03/014161 and Streltsov (2005) *Protein Sci.* 14:2901-09. Single domain binding proteins also include naturally occurring single domain binding proteins known in the art as heavy chain antibodies devoid of light chains. This variable domain derived from a heavy chain antibody naturally devoid of a light chain is known herein as a VHH, or a nanobody, to distinguish it from the conventional $V_H$ of four-chain immunoglobulins. Such a VHH molecule can be derived from antibodies raised in Camelidae species, for example, in camel, llama, dromedary, alpaca, and guanaco, and is sometimes called a camelid or camelized variable domain (see, e.g., Muyldermans (2001) *J. Biotechnol.* 74(4): 277-302, incorporated herein by reference). Other species besides those in the family Camelidae may also produce heavy chain binding proteins naturally devoid of light chains. VHH molecules are about ten times smaller than IgG molecules. They are single polypeptides and are very stable, resisting extreme pH and temperature conditions. Moreover, they are resistant to the actions of proteases, which is not the case for conventional antibodies. Furthermore, in vitro expression of VHHs can produce high-yield, properly folded functional VHHs. In addition, binding proteins generated in camelids will recognize epitopes other than those recognized by antibodies generated in vitro via antibody libraries or via immunization of mammals other than camelids (see, e.g., International Application Publication Nos. WO 97/049805 and WO 94/004678, which are incorporated herein by reference).

A "bispecific" or "bifunctional" binding protein is an artificial hybrid binding protein having two different heavy/light chain pairs and two different binding sites. Bispecific binding proteins can be produced by a variety of methods including fusion of hybridomas or linking of Fab' fragments (see, e.g., Songsivilai and Lachmann (1990) *Clin. Exp. Immunol.* 79:315-21; Kostelny et al. (1992) *J. Immunol.* 148:1547-53). In one embodiment, the bispecific binding protein comprises a first binding domain polypeptide, such as a Fab' fragment, linked via an immunoglobulin constant region to a second binding domain polypeptide.

Another binding protein according to the invention can comprise, for example, a binding domain-immunoglobulin fusion protein that includes a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain, other than $C_H1$, for example, the $C_H2$ and $C_H3$ regions of IgG and IgA1 or the $C_H3$ and $C_H4$ regions of IgE (see, e.g., U.S. Application Publication No. 2005/0136049, which is incorporated by reference herein, for a more complete description). The binding domain-immunoglobulin fusion protein can further include a region that includes a native or engineered immunoglobulin heavy chain $C_H2$ constant region polypeptide (or $C_H3$ in the case of a construct derived in whole or in part from IgE) that is fused or otherwise connected to the hinge region polypeptide and a native or engineered immunoglobulin heavy chain $C_H3$ constant region polypeptide (or $C_H4$ in the case of a construct derived in whole or in part from IgE) that is fused or otherwise connected to the $C_H2$ constant region polypeptide (or $C_H3$ in the case of a construct derived in whole or in part from IgE). Typically, such binding domain-immunoglobulin fusion proteins are capable of at least one immunological activity selected from the group consisting of antibody-dependent cell-mediated cytotoxicity (ADCC), complement fixation, and/or binding to a target, for example, a target antigen, such as human IL-21R.

Binding proteins of the invention can also comprise peptide mimetics. Peptide mimetics are peptide-containing molecules that mimic elements of protein secondary structure (see, for example, Johnson et al., *Peptide Turn Mimetics* in *Biotechnology and Pharmacy* (1993) Pezzuto et al. eds., Chapman and Hall, New York, incorporated by reference herein in its entirety). The underlying rationale behind the use of peptide mimetics is that the peptide backbone of proteins exists chiefly to orient amino acid side chains in such a way as to facilitate molecular interactions, such as those between antibody and antigen. A peptide mimetic is expected to permit molecular interactions similar to the natural molecule. These principles may be used to engineer second generation molecules having many of the natural properties of the targeting peptides disclosed herein, but with altered and potentially improved characteristics.

Other embodiments of binding proteins useful for practicing the invention include fusion proteins. These molecules generally have all or a substantial portion of a targeting peptide, for example, IL-21R or an anti IL-21R antibody, linked at the N- or C-terminus, to all or a portion of a second polypeptide or protein. For example, fusion proteins may employ leader (or signal) sequences from other species to permit the recombinant expression of a protein in a heterologous host. For example, amino acid sequences, or nucleic acid sequences encoding amino acid sequences, of the binding proteins and antigen-binding fragments thereof of the present invention comprising a leader (or signal) sequence may be selected from SEQ ID NOs:87-109 and 239-248. Another useful fusion includes the addition of an immunologically active domain, such as a binding protein epitope, to facilitate purification of the fusion protein. Inclusion of a cleavage site at or near the fusion junction will facilitate removal of the extraneous polypeptide after purification. Other useful fusions include the linking of functional domains, such as active sites from enzymes, glycosylation domains, cellular targeting signals, or transmembrane regions. Examples of proteins or peptides that may be incorporated into a fusion protein include, but are not limited to, cytostatic proteins, cytocidal proteins, pro-apoptosis agents, anti-angiogenic agents, hormones, cytokines, growth factors, peptide drugs, antibodies, Fab fragments of antibodies, antigens, receptor proteins, enzymes, lectins, MHC proteins, cell adhesion proteins, and binding proteins. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

In one embodiment, the targeting peptide, for example, IL-21R, is fused with an immunoglobulin heavy chain constant region, such as an Fc fragment, which contains two constant region domains and a hinge region, but lacks the variable region (see, e.g., U.S. Pat. Nos. 6,018,026 and 5,750,375, incorporated by reference herein). The Fc region may be a naturally occurring Fc region, or may be altered to improve certain qualities, e.g., therapeutic qualities, circulation time, reduced aggregation. Peptides and proteins fused to an Fc region typically exhibit a greater half-life in vivo than the unfused counterpart does. In addition, a fusion to an Fc region permits dimerization/multimerization of the fusion polypeptide.

One aspect of the present invention comprises binding proteins and antigen-binding fragments thereof that bind IL-21R. The disclosure provides novel CDRs that have been derived from human immunoglobulin gene libraries. The protein structure that is generally used to carry a CDR is an antibody heavy or light chain or a portion thereof, wherein the CDR is localized to a region associated with a naturally occurring CDR. The structures and locations of variable domains may be determined as described in Kabat et al. ((1991) supra).

Illustrative embodiments of the binding proteins (and antigen-binding fragments thereof) of the invention are identified as AbA-AbZ, H3-H6, L1-L6, L8-L21, and L23-L25. DNA and amino acid sequences of the nonlimiting illustrative embodiments of the anti-IL-21R binding proteins of the invention are set forth in SEQ ID NOs:5-195, 213-229, and 239-248. DNA and amino acid sequences of some illustrative embodiments of the anti-IL-21R binding proteins of the invention, including their scFv fragments, $V_H$ and $V_L$ domains, and CDRs, as well as their present codes and previous designations, are set forth in FIGS. 17-25, and Tables 2A and 2B.

TABLE 2A

Correlation of Present Antibody Codes and Previous Designations

| Present Code | Previous Designation |
| --- | --- |
| AbA | VHP/VL2 |
| AbB | VHP/VL3 |
| AbC | VHP/VL11 |
| AbD | VHP/VL13 |
| AbE | VHP/VL14 |
| AbF | VHP/VL17 |
| AbG | VHP/VL18 |
| AbH | VHP/VL19 |
| AbI | VHP/VL24 |
| AbJ | VH3/VLP |
| AbK | VH3/VL3 |
| AbL | VH3/VL13 |
| AbM | VH6/VL13 |
| AbN | VH6/VL24 |
| AbO | VHP/VL16; VHPTM/VL16 |
| AbP | VHP/VL20; VHPTM/VL20 |
| AbQ | VH3/VL2; VH3DM/VL2 |
| AbR | VH3/VL18; VH3DM/VL18 |
| AbS | VHP/VL6; VHPTM/VL6; VL6 |
| AbT | VHP/VL9; VHPTM/VL9; VL9 |
| AbU | VHP/VL25; VHPTM/VL25 |
| AbV | VH3TM/VL2 |
| AbW | VH3TM/VL18 |
| AbX | VHPDM/VL9 |
| AbY | VHPg4/VL9 |
| AbZ | VHPWT/VL9 |

TABLE 2B

Amino Acid and Nucleotide Sequences of $V_H$ and $V_L$ Domains, scFv, and CDRs of Illustrative Binding Proteins of the Invention

| REGION | TYPE | H3 SEQ ID | H4 SEQ ID | H5 SEQ ID | H6 SEQ ID | L1 SEQ ID |
| --- | --- | --- | --- | --- | --- | --- |
| $V_H$ | AA | NO: 14 | NO: 16 | NO: 18 | NO: 20 | NO: 6 |
| $V_L$ | AA | NO: 10 | NO: 10 | NO: 10 | NO: 10 | NO: 22 |
| scFv | AA | NO: 110 | NO: 112 | NO: 114 | NO: 116 | NO: 118 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 165 | NO: 166 | NO: 167 | NO: 168 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 170 | NO: 170 | NO: 170 | NO: 170 | NO: 171 |
| $V_H$ | DNA | NO: 13 | NO: 15 | NO: 17 | NO: 19 | NO: 5 |
| $V_L$ | DNA | NO: 9 | NO: 9 | NO: 9 | NO: 9 | NO: 21 |
| scFv | DNA | NO: 109 | NO: 111 | NO: 113 | NO: 115 | NO: 117 |

| REGION | TYPE | L2 SEQ ID | L3 SEQ ID | L4 SEQ ID | L5 SEQ ID | L6 SEQ ID |
| --- | --- | --- | --- | --- | --- | --- |
| $V_H$ | AA | NO: 6 | NO: 6 | NO: 6 | NO: 6 | NO: 6 |
| $V_L$ | AA | NO: 24 | NO: 26 | NO: 28 | NO: 30 | NO: 32 |
| scFv | AA | NO: 120 | NO: 122 | NO: 124 | NO: 126 | NO: 128 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 172 | NO: 173 | NO: 174 | NO: 175 | NO: 176 |
| $V_H$ | DNA | NO: 5 | NO: 5 | NO: 5 | NO: 5 | NO: 5 |
| $V_L$ | DNA | NO: 23 | NO: 25 | NO: 27 | NO: 29 | NO: 31 |
| scFv | DNA | NO: 119 | NO: 121 | NO: 123 | NO: 125 | NO: 127 |

| REGION | TYPE | L8 SEQ ID | L9 SEQ ID | L10 SEQ ID | L11 SEQ ID | L12 SEQ ID |
| --- | --- | --- | --- | --- | --- | --- |
| $V_H$ | AA | NO: 6 | NO: 6 | NO 6 | NO: 6 | NO: 6 |
| $V_L$ | AA | NO: 34 | NO: 36 | NO: 38 | NO: 40 | NO: 42 |
| scFv | AA | NO: 130 | NO: 132 | NO: 134 | NO: 136 | NO: 138 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 177 | NO: 178 | NO: 179 | NO: 180 | NO: 181 |
| $V_H$ | DNA | NO: 5 | NO: 5 | NO: 5 | NO: 5 | NO: 5 |
| $V_L$ | DNA | NO: 33 | NO: 35 | NO: 37 | NO: 39 | NO: 41 |
| scFv | DNA | NO: 129 | NO: 131 | NO: 133 | NO: 135 | NO: 137 |

TABLE 2B-continued

Amino Acid and Nucleotide Sequences of $V_H$ and $V_L$ Domains, scFv, and CDRs of Illustrative Binding Proteins of the Invention

| REGION | TYPE | L13 SEQ ID | L14 SEQ ID | L15 SEQ ID | L16 SEQ ID | L17 SEQ ID |
|---|---|---|---|---|---|---|
| $V_H$ | AA | NO: 6 | NO: 6 | NO: 6 | NO: 6 | NO: 6 |
| $V_L$ | AA | NO: 44 | NO: 46 | NO: 48 | NO: 50 | NO: 52 |
| scFv | AA | NO: 140 | NO: 142 | NO: 144 | NO: 146 | NO: 148 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 182 | NO: 183 | NO: 184 | NO: 185 | NO: 186 |
| $V_H$ | DNA | NO: 5 | NO: 5 | NO: 5 | NO: 5 | NO: 5 |
| $V_L$ | DNA | NO: 43 | NO: 45 | NO: 47 | NO: 49 | NO: 51 |
| scFv | DNA | NO: 139 | NO: 141 | NO: 143 | NO: 145 | NO: 147 |

| REGION | TYPE | L18 SEQ ID | L19 SEQ ID | L20 SEQ ID | L21 SEQ ID | L23 SEQ ID |
|---|---|---|---|---|---|---|
| $V_H$ | AA | NO: 6 | NO: 6 | NO: 6 | NO: 6 | NO: 6 |
| $V_L$ | AA | NO: 54 | NO: 56 | NO: 58 | NO: 60 | NO: 62 |
| scFv | AA | NO: 150 | NO: 152 | NO: 154 | NO: 156 | NO: 158 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 187 | NO: 188 | NO: 189 | NO: 190 | NO: 191 |
| $V_H$ | DNA | NO: 5 | NO: 5 | NO: 5 | NO: 5 | NO: 5 |
| $V_L$ | DNA | NO: 53 | NO: 55 | NO: 57 | NO: 59 | NO: 61 |
| scFv | DNA | NO: 149 | NO: 151 | NO: 153 | NO: 155 | NO: 157 |

| REGION | TYPE | L24 SEQ ID | L25 SEQ ID |
|---|---|---|---|
| $V_H$ | AA | NO: 6 | NO: 6 |
| $V_L$ | AA | NO: 64 | NO: 66 |
| scFv | AA | NO: 160 | NO: 162 |
| CDR H1 | AA | NO: 163 | NO: 163 |
| CDR H2 | AA | NO: 164 | NO: 164 |
| CDR H3 | AA | NO: 169 | NO: 169 |
| CDR L1 | AA | NO: 194 | NO: 194 |
| CDR L2 | AA | NO: 195 | NO: 195 |
| CDR L3 | AA | NO: 192 | NO: 193 |
| $V_H$ | DNA | NO: 5 | NO: 5 |
| $V_L$ | DNA | NO: 63 | NO: 65 |
| scFv | DNA | NO: 159 | NO: 161 |

Anti-IL-21R binding proteins of the present invention may comprise antibody constant regions or parts thereof. For example, a $V_L$ domain may be attached at its C-terminal end to a light chain constant domain like Cκ or Cλ. Similarly, a $V_H$ domain, or portion thereof, may be attached to all or part of a heavy chain like IgA, IgD, IgE, IgG, and IgM, and any isotype subclass. Constant regions are known in the art (see, e.g., Kabat et al. (1991) supra). Therefore, binding proteins within the scope of this invention include $V_H$ and $V_L$ domains, or portions thereof, combined with constant regions known in the art.

Certain embodiments comprise a $V_H$ domain, a $V_L$ domain, or a combination thereof, of the Fv fragment from AbA-AbZ, H3-H6, L1-L6, L8-L21, and/or L23-L25. Further embodiments comprise one, two, three, four, five or six CDRs from the $V_H$ and $V_L$ domains. Binding proteins whose CDR sequence(s) are the same as, or similar to (i.e., differ insubstantially from), one or more CDR sequence(s) present within the sequences set forth in SEQ ID NOs:5-195, 213-229, and 239-248 are encompassed within the scope of the invention.

In certain embodiments, the $V_H$ and/or $V_L$ domains may be germlined, i.e., the FR of these domains are mutated using conventional molecular biology techniques to match those produced by the germline cells. In other embodiments, the FR sequences remain diverged from the consensus germline sequences.

In one embodiment, mutagenesis is used to make a binding protein more similar to one or more germline sequences. This may be desirable when mutations are introduced into the FR of a binding protein (e.g., an antibody) through somatic mutagenesis or through error prone PCR. Germline sequences for the $V_H$ and $V_L$ domains can be identified by performing amino acid and nucleic acid sequence alignments against the VBASE database (MRC Center for Protein Engineering, UK). VBASE is a comprehensive directory of all human germline variable region sequences compiled from over a thousand published sequences, including those in the current releases of the GENBANK® and EMBL data libraries. In some embodiments, the FRs of scFvs are mutated in conformity with the closest matches in the VBASE database and the CDR portions are kept intact.

In certain embodiments, binding proteins of the invention specifically react with an epitope that is the same as the epitope recognized by AbA-AbZ, H3-H6, L1-L6, L8-L21, or L23-L25, such that they competitively inhibit the binding of AbA-AbZ, H3-H6, L1-L6, L8-L21, or L23-L25 to human IL-21R. Such binding proteins can be determined in competitive binding assays. In one embodiment, the association constant ($K_A$) of these binding proteins for human IL-21R is at least $10^5$ $M^{-1}s^{-1}$. The binding affinity may be determined using techniques known in the art, such as ELISA, biosensor technology (such as biospecific interaction analysis) or other techniques, including those described in this application.

It is contemplated that binding proteins of the invention may bind other proteins, such as, for example, recombinant proteins comprising all or a portion of IL-21R.

One of ordinary skill in the art will recognize that the disclosed binding proteins may be used to detect, measure, and/or inhibit proteins that differ somewhat from IL-21R. For example, these proteins may be homologs of IL-21R. Anti-IL-21R binding proteins are expected to bind proteins that comprise a sequence which is at least about 60%, 70%, 80%, 90%, 95%, or more identical to any sequence of at least 100, 80, 60, 40, or 20 contiguous amino acids in the sequence set forth SEQ ID NOs:2 or 4.

In addition to sequence homology analyses, epitope mapping (see, e.g., *Epitope Mapping Protocols* (1996) Morris ed., Humana Press), and secondary and tertiary structure analyses can be carried out to identify specific 3D structures assumed by the presently disclosed binding proteins and their complexes with antigens. Such methods include, but are not limited to, x-ray crystallography (Engstom (1974) *Biochem. Exp. Biol.* 11:7-13) and computer modeling of virtual representations of the present binding proteins (Fletterick et al. (1986) *Computer Graphics and Molecular Modeling, in Current Communications in Molecular Biology*, Cold Spring Harbor Laboratory, Cold Spring Harbor, N.Y.).

The disclosure provides a method for obtaining anti-IL-21R binding proteins. The method comprises creating binding proteins with $V_H$ and/or $V_L$ sequence(s) that are altered from those sequences disclosed herein. Such binding proteins may be derived by a skilled artisan using techniques known in the art. For example, amino acid substitutions, deletions, or additions can be introduced in FR and/or CDR regions. FR changes are usually designed to improve the stability and immunogenicity of the binding protein, while CDR changes are typically designed to increase a binding protein's affinity for its antigen. The changes that increase affinity may be tested by altering one or more CDR sequences and measuring the affinity of the binding protein for its target (see, e.g., *Antibody Engineering* (2nd ed. 1995) Borrebaeck ed., Oxford University Press).

Binding proteins whose CDR sequences differ insubstantially from those set forth in or included within the sequences of SEQ ID NOs:5-195, 213-229, and 239-248 are encompassed within the scope of this invention. Typically, such an insubstantial difference(s) involves substitution of an amino acid with an amino acid having similar charge, hydrophobicity, or stereochemical characteristics. More drastic substitutions in FR regions, in contrast to CDR regions, may also be made as long as they do not adversely affect (e.g., reduce affinity by more than 50% as compared to the unsubstituted binding protein) the binding properties of the binding protein. Substitutions may also be made to germline the binding protein or stabilize its antigen binding site.

Conservative modifications will produce molecules having functional and chemical characteristics similar to those of the molecule from which such modifications are made. In contrast, substantial modifications in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, and/or (3) the size of the molecule.

For example, a "conservative amino acid substitution" may involve a substitution of a native amino acid residue with a normative residue such that there is little or no effect on the polarity or charge of the amino acid residue at that position (see, e.g., MacLennan et al. (1998) *Acta Physiol. Scand. Suppl.* 643:55-67; Sasaki et al. (1998) *Adv. Biophys.* 35:1-24).

Desired amino acid substitutions (whether conservative or nonconservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions include, but are not limited to, those set forth in Table 3.

TABLE 3

Exemplary Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-diamino-butyric acid, Gln, Asn | Arg |
| Met (M) | Leu, Phe, Ile | Leu |
| Phe (F) | Leu, Val, Ile, Ala, Tyr | Leu |
| Pro (P) | Ala, Gly | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass nonnaturally occurring amino acid residues that are typically incorporated by chemical peptide synthesis rather than by synthesis in biological systems.

In one embodiment, the method for making a variant $V_H$ domain comprises adding, deleting, or substituting at least one amino acid in the disclosed $V_H$ domains, or combining the disclosed $V_H$ domains with at least one $V_L$ domain, and testing the variant $V_H$ domain for IL-21R binding or modulation of IL-21R/IL-21 activity.

An analogous method for making a variant $V_L$ domain comprises adding, deleting, or substituting at least one amino acid in the disclosed $V_L$ domains, or combining the disclosed $V_L$ domains with at least one $V_H$ domain, and testing the variant $V_L$ domain for IL-21R binding or modulation of IL-21R activity.

In some alternative embodiments, the anti-IL-21R binding proteins can be linked to a protein (e.g., albumin) by chemical cross-linking or recombinant methods. The disclosed binding proteins may also be linked to a variety of nonproteinaceous polymers (e.g., polyethylene glycol, polypropylene glycol, or polyoxyalkylenes) in manners set forth in U.S. Pat. Nos. 4,640,835; 4,496,689; 4,301,144; 4,670,417; 4,791,192; and 4,179,337. The binding proteins can be chemically modified by covalent conjugation to a polymer, for example, to increase their half-life in blood circulation. Exemplary polymers and attachment methods are shown in U.S. Pat. Nos. 4,766,106; 4,179,337; 4,495,285; and 4,609,546.

The disclosed binding proteins can be modified to alter their glycosylation; that is, at least one carbohydrate moiety can be deleted or added to the binding protein. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the binding protein, e.g., antibody (see, e.g., International Application Publication No. WO 87/05330 and Aplin et al. (1981) *CRC Crit. Rev. Biochem.* 22:259-306). Removal of carbohydrate moieties can also be accomplished chemically or enzymatically (see, e.g., Hakimuddin et al. (1987) *Arch. Biochem. Biophys.* 259:52; Edge et al. (1981) *Anal. Biochem.* 118:131; and Thotakura et al. (1987) *Meth. Enzymol.* 138: 350). Modification of carbohydrate structures may be preferable as amino acid changes in the Fc domain may enhance immunogenicity of a pharmaceutical composition (see, e.g., International Application Publication No. WO 2008/052030). For immunoglobulin molecules it has been demonstrated that attachment of N-linked carbohydrate to Asn-297 of the CH2 domain is critical for ADCC activity. Its removal enzymatically or through mutation of the N-linked consensus site results in little to no ADCC activity. In glycoproteins, carbohydrates may attach to the amide nitrogen atom in the side chain of an asparagine in a tripeptide motif Asn-X-Thr/Ser. This type of glycosylation, termed N-linked glycosylation, commences in the endoplasmic reticulum (ER) with the addition of multiple monosaccharides to a dolichol phosphate to form a 14-residue branched carbohydrate complex. This carbohydrate complex is then transferred to the protein by the oligosaccharyltransferase (OST) complex. Before the glycoprotein leaves the lumen of the ER, three glucose molecules are removed from the 14-residue oligosaccharide. The enzymes ER glucosidase I, ER glucosidase II and ER mannosidase are involved in ER processing. Subsequently, the polypeptides are transported to the Golgi complex, where the N-linked sugar chains are modified in many different ways. In the cis and medial compartments of the Golgi complex, the original 14-saccharide N-linked complex may be trimmed through removal of mannose (Man) residues and elongated through addition of N-acetylglucosamine (GlcNac) and/or fucose (Fuc) residues. The various forms of N-linked carbohydrates generally have in common a pentasaccharide core consisting of three mannose and two N-acetylglucosamine residues. Finally, in the trans Golgi, other GlcNac residues can be added, followed by galactose (Gal) and a terminal sialic acid (Sial). Carbohydrate processing in the Golgi complex is called "terminal glycosylation" to distinguish it from "core glycosylation," which takes place in the ER. The final complex carbohydrate units can take on many forms and structures, some of which have two, three or four branches (termed biantennary, triantennary or tetraantennary). A number of enzymes are involved in Golgi processing, including Golgi mannosidases IA, IB and IC, GlcNAc-transferase I, Golgi mannosidase II, GlcNAc-transferase II, galactosyl transferase and sialyl transferase.

Methods for altering the constant region of a binding protein (such as, for example, the constant region of an antibody) are known in the art. Binding proteins with altered function (e.g., altered affinity for an effector ligand such as FcR on a cell or the C1 component of complement) can be produced by replacing at least one amino acid residue in the constant portion with a different residue (see, e.g., European Application Publication No. EP 0 388 151 and U.S. Pat. Nos. 5,624, 821 and 5,648,260). Similar types of alterations could be described that, if applied to a murine or other species of binding protein, would reduce or eliminate similar functions.

For example, it is possible to alter the affinity of an Fc region of a binding protein (e.g., an IgG, such as a human IgG) for FcR (e.g., Fc gamma R1) or C1q. The affinity may be altered by replacing at least one specified residue with at least one residue having an appropriate functionality on its side chain, or by introducing a charged functional group, such as glutamate or aspartate, or perhaps an aromatic nonpolar residue such as phenylalanine, tyrosine, tryptophan or alanine (see, e.g., U.S. Pat. No. 5,624,821).

For example, replacing residue 297 (asparagine) with alanine in the IgG constant region significantly inhibits recruitment of effector cells, while only slightly reducing (about three-fold weaker) affinity for C1q (see, e.g., U.S. Pat. No. 5,624,821). The numbering of the residues in the heavy chain is that of the EU index (see Kabat et al. (1991) supra). This alteration destroys the glycosylation site, and it is believed that the presence of carbohydrate is required for Fc receptor binding. Any other substitution at this site that destroys the glycosylation site is believed to cause a similar decrease in lytic activity. Other amino acid substitutions, e.g., changing any one of residues 318 (Glu), 320 (Lys) and 322 (Lys), to Ala, are also known to abolish C1q binding to the Fc region of IgG antibodies (see, e.g., U.S. Pat. No. 5,624,821).

Modified binding proteins can be produced which have a reduced interaction with an Fc receptor. For example, it has been shown that in human $IgG_3$, which binds to the human Fc gamma R1 receptor, changing Leu 235 to Glu destroys its interaction with the receptor. Mutations on adjacent or close sites in the hinge link region of a binding protein (e.g., replacing residues 234, 235 and 237 with Ala) can also be used to affect binding protein affinity for the Fc gamma R1 receptor. The numbering of the residues in the heavy chain is based on the EU index (see Kabat et al. (1991) supra). Thus, in some embodiments of the invention, the Fc region of the binding proteins of the invention contains at least one constant region mutation, such as, for example, changing Leu to Ala at position 234 (L234A), changing Leu to Ala at position 235 (L235A), and/or changing Gly to Ala at position 237 (G237A). In one embodiment, the Fc region of the binding protein contains two constant region mutations, L234A and G237A (i.e., "double-mutant" or "DM"). In another embodiment, the Fc region of the binding protein contains three constant region mutations, L234A, L235A, and G237A (i.e., "triple-mutant" or "TM"). For example, a human IgG constant region triple-mutant is set forth in SEQ ID NO: 196.

Additional methods for altering the lytic activity of a binding protein, for example, by altering at least one amino acid in the N-terminal region of the CH2 domain, are described in International Application Publication No. WO 94/029351 and U.S. Pat. No. 5,624,821.

The binding proteins of the invention can be tagged with a detectable or functional label. These labels include radiolabels (e.g., $^{131}I$ and $^{99}Tc$), enzymatic labels (e.g., horseradish peroxidase and alkaline phosphatase), and other chemical moieties (e.g., biotin).

The invention may also feature an isolated binding protein or antigen-binding fragment thereof that binds to IL-21R, in particular, human IL-21R. In certain embodiments, the anti- IL-21R binding protein may have at least one of the following characteristics: (1) it is a monoclonal or single specificity binding protein; (2) it is a human binding protein; (3) it is an in vitro generated binding protein; (4) it is an in vivo generated binding protein (e.g., transgenic mouse system); (5) it inhibits the binding of IL-21 to IL-21R; (6) it is an IgG1; (7) it binds to human IL-21R with an association constant of at least about $10^5$ $M^{-1}s^{-1}$; (8) it binds to murine IL-21R with an association constant of at least about $5\times10^4$ $M^{-1}s^{-1}$; (9) it binds to human IL-21R with a dissociation constant of about $10^{-3}$ (1/s) or less; (10) it binds to murine IL-21R with a dissociation constant of about $10^{-2}$ (1/s) or less; (11) it inhibits human IL-21R-mediated proliferation of human IL-21R-expressing BaF3 cells with an $IC_{50}$ of about 1.75 nM or less; (12) it inhibits murine IL-21R-mediated proliferation of murine IL-21R-expressing BaF3 cells with an $IC_{50}$ of about 0.5 nM or less; (13) it inhibits human IL-21R-mediated proliferation of human IL-21R-expressing TF1 cells with an $IC_{50}$ of about 14.0 nM or less; (14) it inhibits IL-21-mediated proliferation of human primary B cells with an $IC_{50}$ of about 1.9 nM or less; (15) it inhibits IL-21-mediated proliferation of human primary $CD4^+$ T cells with an $IC_{50}$ of about 1.5 nM or less; and (16) it inhibits IL-21-mediated proliferation of murine primary $CD4^+$ T cells with an $IC_{50}$ of about 5.0 nM or less.

One of skill in the art will appreciate that the modifications described above are not exhaustive, and that many other modifications will be obvious to a skilled artisan in light of the teachings of the present disclosure.

Nucleic Acids, Cloning and Expression Systems

The disclosure provides isolated nucleic acids encoding the disclosed binding proteins. The nucleic acids may comprise DNA or RNA, and they may be synthetic (completely or partially) or recombinant (completely or partially). Reference to a nucleotide sequence as set out herein encompasses a DNA molecule with the specified sequence, and encompasses an RNA molecule with the specified sequence in which U is substituted for T.

Also contemplated are nucleic acids that comprise a coding sequence for one, two, or three CDRs, a $V_H$ domain, a $V_L$ domain, or combinations thereof, as disclosed herein, or a sequence substantially identical thereto (e.g., a sequence at least 50%, 60%, 70%, 80%, 85%, 90%, 95%, 96%, 97%, 98%, 99% or higher identical thereto, or which is capable of hybridizing under stringent conditions to the sequences).

In one embodiment, the isolated nucleic acids have nucleotide sequences encoding heavy chain and light chain variable regions of an anti-IL-21R binding protein comprising at least one CDR chosen from the amino acid sequences of SEQ ID NOs: 163-195, or a sequence encoding a CDR which differs by one or two or three or four amino acids from the sequences described herein.

The nucleic acid can encode only the light chain or the heavy chain variable region, or can encode a binding protein light or heavy chain constant region, operatively linked to the corresponding variable region. In one embodiment, the light chain variable region is linked to a constant region chosen from a kappa or a lambda constant region. The light chain constant region may also be a human kappa or lambda type. In another embodiment, the heavy chain variable region is linked to a heavy chain constant region of a binding protein isotype chosen from IgG (e.g., IgG1, IgG2, IgG3, and IgG4), IgM, IgA1, IgA2, IgD, and IgE. The heavy chain constant region may be an IgG (e.g., an IgG1) isotype.

The nucleic acid compositions of the present invention, while often in the native sequence (of cDNA or genomic DNA or mixtures thereof), except for modified restriction sites and the like, can be mutated in accordance with standard techniques to provide gene sequences. For coding sequences, these mutations, may affect amino acid sequences as desired. In particular, nucleotide sequences substantially identical to or derived from native V, D, J, constant, switches and other such sequences described herein are contemplated (where "derived" indicates that a sequence is identical to or modified from another sequence).

In one embodiment, the nucleic acid differs (e.g., differs by substitution, insertion, or deletion) from that of the sequences provided (e.g., by at least one but less than 10, 20, 30, or 40 nucleotides; at least one but less than 1%, 5%, 10% or 20% of the nucleotides in the subject nucleic acid). If necessary for this analysis the sequences should be aligned for maximum homology. "Looped" out sequences from deletions or insertions, or mismatches, are considered differences. The difference may be at a nucleotide(s) encoding a nonessential residue(s), or the difference may be a conservative substitution(s).

The disclosure also provides nucleic acid constructs in the form of plasmids, vectors, and transcription or expression cassettes, which comprise at least one nucleic acid as described herein.

The disclosure further provides a host cell that comprises at least one nucleic acid construct described herein.

Also provided is a method of making an encoded protein(s) from a nucleic acid(s) comprising the sequence(s) described herein. The method comprises culturing host cells under appropriate conditions so they express the protein from the nucleic acid. Following expression and production, the $V_H$ or $V_L$ domain, or specific binding member, may be isolated and/or purified using any suitable technique, and then used as appropriate. The method can also include the steps of fusing a nucleic acid encoding an scFv with nucleic acids encoding an Fc portion of a binding protein, and expressing the fused nucleic acid in a cell. The method can also include a step of germlining.

Antigen-binding fragments, $V_H$ and/or $V_L$ domains, and encoding nucleic acid molecules and vectors may be isolated and/or purified from their natural environment, in substantially pure or homogenous form, or, in the case of nucleic acids, free or substantially free of nucleic acids or genes of origin other than the sequence encoding a polypeptide with the require function.

Systems for cloning and expressing polypeptides in a variety of host cells are known in the art. Cells suitable for producing binding proteins are described in, for example, Fernandez et al. (1999) *Gene Expression Systems*, Academic Press. In brief, suitable host cells include mammalian cells, insect cells, plant cells, yeast cells, or prokaryotic cells, e.g., *E. coli*. Mammalian cells available in the art for heterologous polypeptide expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cells. In other embodiments, the nucleic acids encoding the binding proteins of the invention are placed under the control of a tissue-specific promoter (e.g., a mammary-specific promoter) and the binding proteins are produced in transgenic animals. For example, the binding proteins are secreted into the milk of the transgenic animal, such as a transgenic cow, pig, horse, sheep, goat, or rodent.

Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone. For details, see, e.g., Sambrook et al., *Molecular Cloning: A Laboratory Manual* (2nd ed. 1989) Cold Spring Harbor Laboratory Press. Many established techniques used with vectors, including the manipulation, preparation, mutagenesis, sequencing, and transfection of DNA, are described, e.g., in Current Protocols in Molecular Biology (2nd ed. 1992) Ausubel et al. eds., John Wiley & Sons.

A further aspect of the disclosure provides a method of introducing the nucleic acid into a host cell. For eukaryotic cells, suitable transfection techniques may include calcium phosphate, DEAE-Dextran, electroporation, liposome-mediated transfection, and transduction using a retrovirus or other virus(es), e.g., vaccinia or baculovirus. For bacterial cells, suitable techniques may include calcium chloride transformation, electroporation, and transfection using bacteriophage. DNA introduction may be followed by a selection method (e.g., drug resistance) to select cells that contain the nucleic acid.

Uses of Anti-IL-21R Binding Proteins

Anti-IL-21R binding proteins that act as antagonists to IL-21R can be used to regulate at least one IL-21R-mediated immune response, such as one or more of cell proliferation, cytokine expression or secretion, chemokine secretion, and cytolytic activity, of T cells, B cells, NK cells, macrophages, or synovial cells. Accordingly, the binding proteins of the invention can be used to inhibit the activity (e.g., proliferation, differentiation, and/or survival) of an immune or hematopoietic cell (e.g., a cell of myeloid, lymphoid, or erythroid lineage, or precursor cells thereof), and, thus, can be used to treat a variety of immune disorders and hyperproliferative disorders of the blood. Examples of immune disorders that can be treated include, but are not limited to, transplant rejection, graft-versus-host disease (GVHD), allergies (for example, atopic allergy), and autoimmune diseases. Autoimmune diseases include diabetes mellitus, arthritic disorders (including rheumatoid arthritis, juvenile rheumatoid arthritis, osteoarthritis, psoriatic arthritis, and ankylosing spondylitis), spondyloarthropathy, multiple sclerosis, encephalomyelitis, myasthenia gravis, systemic lupus erythematosus, cutaneous lupus erythematosus, autoimmune thyroiditis, dermatitis (including atopic dermatitis and eczematous dermatitis), psoriasis, Sjögren's syndrome, IBD (including Crohn's disease and ulcerative colitis), asthma (including intrinsic asthma and allergic asthma), scleroderma and vasculitis.

Combination Therapy

In one embodiment, a pharmaceutical composition comprising at least one anti-IL-21R binding protein and at least one therapeutic agent is administered in combination therapy. The therapy is useful for treating pathological conditions or disorders, such as immune and inflammatory disorders. The term "in combination" in this context means that the binding protein composition and the therapeutic agent are given substantially contemporaneously, either simultaneously or sequentially. If given sequentially, at the onset of administration of the second compound, the first of the two compounds may still be detectable at effective concentrations at the site of treatment.

For example, the combination therapy can include at least one anti-IL-21R binding protein, such as, for example, an anti-IL-21R antibody, coformulated with, and/or coadministered with, at least one additional therapeutic agent. The additional agents may include at least one cytokine inhibitor, growth factor inhibitor, immunosuppressant, anti-inflammatory agent, metabolic inhibitor, enzyme inhibitor, cytotoxic agent, and/or cytostatic agent. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-21/IL-21R pathway, and thus are expected to enhance and/or synergize with the effects of the anti-IL-21R binding proteins.

Another aspect of the present invention relates to kits for carrying out the combined administration of anti-IL-21R binding proteins with other therapeutic agents. In one embodiment, the kit comprises at least one anti-IL-21R binding protein formulated in a pharmaceutical carrier, and at least one therapeutic agent, formulated as appropriate in one or more separate pharmaceutical preparations.

Diagnostic Uses

The binding proteins of the invention may also be used to detect the presence of IL-21R in biological samples. By correlating the presence or level of these proteins with a medical condition, one of skill in the art can diagnose the associated medical condition. For example, stimulated T cells increase their expression of IL-21R, and an unusually high concentration of IL-21R expressing T cells in joints may indicate joint inflammation and possible arthritis. Illustrative medical conditions that may be diagnosed by the binding proteins of this invention include, but are not limited to, multiple sclerosis, rheumatoid arthritis, and transplant rejection.

Binding protein-based detection methods, such as those commonly used for antibodies, are well known in the art, and include ELISA, radioimmunoassays, immunoblots, Western blots, flow cytometry, immunofluorescence, immunoprecipitation, and other related techniques. The binding proteins may be provided in a diagnostic kit that incorporates at least one of these procedures to detect IL-21R. The kit may contain other components, packaging, instructions, reagents and/or other material to aid the detection of the protein and use of the kit.

Binding proteins may be modified with detectable markers, including ligand groups (e.g., biotin), fluorophores, chromophores, radioisotopes, electron-dense reagents, or enzymes. Enzymes are detected by their activity. For example, horseradish peroxidase is detected by its ability to convert tetramethylbenzidine (TMB) to a blue pigment, quantifiable with a spectrophotometer. Other suitable binding partners include biotin and avidin, IgG and protein A, and other receptor-ligand pairs known in the art.

Binding proteins can also be functionally linked (e.g., by chemical coupling, genetic fusion, noncovalent association, or otherwise) to at least one other molecular entity, such as another binding protein (e.g., a bispecific or a multispecific binding protein), toxins, radioisotopes, cytotoxic or cytostatic agents, among others. Other permutations and possibilities are apparent to those of ordinary skill in the art, and they are considered equivalents within the scope of this invention.

Pharmaceutical Compositions and Methods of Administration

Certain embodiments of the invention include compositions comprising the disclosed binding proteins. The compositions may be suitable for pharmaceutical use and administration to patients. The compositions comprise a binding protein of the present invention and a pharmaceutical excipient. As used herein, "pharmaceutical excipient" includes solvents, dispersion media, coatings, antibacterial and antifungal agents, isotonic and absorption delaying agents, etc., that are compatible with pharmaceutical administration. Use of these agents for pharmaceutically active substances is well known in the art. The compositions may also contain other active compounds providing supplemental, additional, or enhanced therapeutic functions. The pharmaceutical compositions may also be included in a container, pack, or dispenser, together with instructions for administration.

A pharmaceutical composition of the invention is formulated to be compatible with its intended route of administration. Methods to accomplish the administration are known to those of ordinary skill in the art. Pharmaceutical compositions may be topically or orally administered, or capable of transmission across mucous membranes. Examples of administration of a pharmaceutical composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases by methods known in the art. Such preparations may be enclosed in ampoules, disposable syringes, or multiple dose vials.

Solutions or suspensions used for intravenous administration include a carrier such as physiological saline, bacteriostatic water, CREMOPHOR EL® (BASF Corp., Ludwigshafen, Germany), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (e.g., mannitol and sorbitol), or sodium chloride may be included in the composition. Prolonged absorption of the composition can be accomplished by adding an agent that delays absorption, e.g., aluminum monostearate or gelatin.

Oral compositions include an inert diluent or edible carrier. For the purpose of oral administration, the binding proteins can be incorporated with excipients and placed, e.g., in tablets, troches, capsules, or gelatin. Pharmaceutically compatible binding agents or adjuvant materials can be included in the composition. The compositions may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; and/or (6) a sweetening or flavoring agent.

The composition may also be administered by a transmucosal or transdermal route. For example, binding proteins that comprise an Fc portion (for example, an antibody) may be capable of crossing mucous membranes in the intestine, mouth, or lungs (via Fc receptors). Transmucosal administration can be accomplished by lozenges, nasal sprays, inhalers, or suppositories. Transdermal administration can be accomplished with a composition containing ointments, salves, gels, or creams known in the art. For transmucosal or transdermal administration, penetrants appropriate to the barrier to be permeated are used. For administration by inhalation, the binding proteins may be delivered in an aerosol spray from a pressured container or dispenser, which contains a propellant (e.g., liquid or gas), or a nebulizer.

In certain embodiments, the binding proteins of this invention are prepared with carriers to protect the binding proteins against rapid elimination from the body. Biodegradable polymers (e.g., ethylene vinyl acetate, polyanhydrides, polyglycolic acid, collagen, polyorthoesters, and polylactic acid) are often used. Methods for the preparation of such formulations are known by those skilled in the art. Liposomal suspensions can be used as pharmaceutically acceptable carriers also. The liposomes can be prepared according to established methods known in the art (see, e.g., U.S. Pat. No. 4,522,811).

The binding proteins or binding protein compositions of the invention are administered in therapeutically effective amounts as described. Therapeutically effective amounts may vary with the subject's age, condition, sex, and severity of medical condition. Appropriate dosages can be determined by a physician based upon clinical indications. The binding proteins or compositions may be given as a bolus dose to maximize the circulating levels of binding proteins for the greatest length of time. Continuous infusion may also be used.

As used herein, the term "subject" is intended to include human and nonhuman animals. Subjects may include a human patient having a disorder characterized by cells that express IL-21R, e.g., a cancer cell or an immune cell. The term "nonhuman animals" of the invention includes all vertebrates, such as nonhuman primates, sheep, dogs, cows, chickens, amphibians, reptiles, etc.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of binding protein calculated to produce a therapeutic effect in association with the carrier. The dosage unit depends on the characteristics of the binding protein and the particular therapeutic effect to be achieved.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Binding proteins that exhibit large therapeutic indices may be less toxic and/or more therapeutically effective.

The data obtained from the cell culture assays and animal studies can be used to formulate a dosage range in humans. The dosage of these compounds may lie within the range of circulating binding protein concentrations in the blood, which includes an $ED_{50}$ with little or no toxicity. The dosage may vary within this range depending upon the dosage composition form employed and the route of administration. For any binding protein used in the present invention, the therapeutically effective dose can be estimated initially using cell culture assays. A dose may be formulated in animal models to achieve a circulating plasma concentration range that includes the $IC_{50}$ (i.e., the concentration of binding protein that achieves a half-maximal inhibition of symptoms). The effects of any particular dosage can be monitored by a suitable bioassay. Examples of suitable bioassays include DNA replication assays, transcription-based assays, gene expression assays, IL-21/IL-21R binding assays, and other immunological assays.

The entire contents of all references, patent applications, and patents cited throughout this application are hereby incorporated by reference herein.

EXAMPLES

The invention will be further illustrated in the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art.

Example 1

Generation of Binding Proteins by Phage Display

The scFv parental clone 18A5, described in U.S. Pat. No. 7,495,085 (incorporated by reference herein), was obtained from the CS human scFv library by standard phage display methods, using BaF3 cells expressing human IL-21R as a target in rounds 1 and 3 and biotinylated IL-21R-Fc fusion protein as a target in round 2.

Example 2

Library Construction

Phage display libraries were based upon the parental 18A5 scFv, using a pCANTAB6 vector in which the scFv was fused at its 3' end to the intact gene III. Various CDR3 sequences were derived using techniques well known in the art.

Two overlapping blocks of six consecutive codons were randomized in the CDR3 of the $V_H$ and the $V_L$, producing a total of four libraries: H3B1, H3B2, L3B1, and L3B2. The following identify nucleotide and amino acid sequences, respectively: IL-21R: 18A5 $V_H$CDR3 [SEQ ID NOs:199 and 200]; H3B1 (library size $1.40\times10^9$) [SEQ ID NOs:201 and 202]; H3B2 (library size $1.00\times10^9$) [SEQ ID NOs:203 and 204]; IL-21R: 18A5 $V_L$CDR3 [SEQ ID NOs:205 and 206]; L3B1 (library size $9.00\times10^9$) [SEQ ID NOs:207 and 208]; L3B2 (library size $6.40\times10^9$) [SEQ ID NOs:209 and 210].

Example 3

Phage Selection

All derivatives of 18A5 were isolated from the scFv libraries above by selection of phage able to bind in solution phase to biotinylated human IL-21R extracellular domain His-Flag fusion proteins ("biotin-hIL-21R-H/F") and biotinylated murine IL-21R extracellular domain His-Flag fusion proteins ("biotin-mIL-21R-H/F"); all procedures and techniques related to selection are well known to one of skill in the art. A total of twenty-seven anti-IL-21R scFv were isolated by phage selection procedures.

Example 4

Library Screening

Resulting binding proteins in scFv format were chosen based on their ability to compete with parental 18A5 in human IgG1 format for binding to biotin-hIL-21R-H/F and biotin-mIL-21R-H/F, to prevent the hIL-21-dependent proliferation of genetically engineered cell lines expressing human IL-21R and the mIL-21-dependent proliferation of genetically engineered cell lines expressing murine IL-21R.

Example 4.1

Preparation of Crude Periplasmic Material ("Peri-Preps") for Use in Screening Assays Depending on the growth conditions used, scFv can be expressed in solution in the bacterial periplasmic space. To induce release of scFv into the periplasm, 96-deep-well plates containing 990 µl 2×TY media with 0.1% glucose/100 µg/ml ampicillin were inoculated from thawed glycerol stocks (one clone per well) using the QPix2 Colony picker (Genetix, New Milton, England) and grown at 37° C. (999 rpm) for about 4 hr. Cultures were induced with IPTG at a final concentration of 0.02 mM and grown overnight at 30° C. (999 rpm). The contents of the bacterial periplasm (peri-preps) were released by osmotic shock. Briefly, plates were centrifuged and pellets were resuspended in 150 µl TES periplasmic buffer (50 mM Tris/HCl (pH 8.0)/1 mM EDTA (pH 8.0)/20% Sucrose), followed by the addition of 150 µl 1:5 TES:water, and incubated on ice for 30 min. Plates were centrifuged and the scFv-containing supernatant was harvested.

Example 4.2

Epitope Competition Assay for Library Screening

Those scFv able to compete with the parental 18A5 antibody for binding to human or murine IL-21R were identified from selected phage by a homogeneous time-resolved fluorescence (HTRF®) assay. Purified parental 18A5 antibody was covalently modified with cryptate, a derivative of europium, according to the instructions in an HTRF® Cryptate Labeling Kit (Cisbio, Bedford, Mass.). Peri-preps of scFv were prepared as described above and diluted to 0.25% in PBS/0.4 M potassium fluoride/0.1% BSA (HTRF® buffer); then 10 µl of the mixture was transferred to the wells of black 384-shallow-well plates (Nunc, Rochester, N.Y.). Five µl of cryptate-conjugated 18A5 antibody was then added to each well, followed by 5 µl of a mixture of a 1:800 dilution of streptavidin-XL665 conjugate (Cisbio), and either 4.8 nM biotin-hIL-21R-H/F or 40 nM biotin-mIL-21R-H/F. The mixture was incubated for 2 hr at RT, and time-resolved fluorescence measurements were made (340 nm excitation, 615 nm and 665 nm emission). Competition with 18A5 antibody was indicated by a reduction in the background-corrected ratio of emission at 665 nm to emission at 615 nm.

A total of 8280 independently isolated scFv were screened in the HTRF® assay using human IL-21R-H/F, and 376 clones able to compete with the parental 18A5 antibody for binding to biotin-hIL-21R-H/F were chosen for further analysis.

Example 5

DNA Sequence Analysis of Library-Derived scFv-PCR Amplification of scFv Regions for Sequencing Analysis The sequences of 287 18A5-derived scFv variants with improved IL-21R binding over that of the parent 18A5 scFv molecule were determined, and the frequencies of amino acids found at each position were determined. Among the $V_H$ clones, only two (1.7%) were derived from a library which mutated the last six amino acids of, e.g., SEQ ID NO: 169 (at the C-terminus of $V_H$ CDR3), while the remainder were derived from a library which mutated the first six amino acids of, e.g., SEQ ID NO: 169. Among the $V_L$ clones, only one clone (0.6%) was derived from a library in which the last six amino acids of, e.g., SEQ ID NO: 170 (at the C-terminus of $V_L$ CDR3) were mutated, while the majority were derived from alterations in the first six amino acids of, e.g., SEQ ID NO: 170 (at the N-terminus of $V_L$ CDR3).

PCR amplification of scFvs was carried out using VENT® DNA Polymerase (New England Biolabs, Ispwich, Mass.) in HN buffer (Epicentre Biotechnologies, Madison, Wis.) according to the manufacturer's instructions. Five µl of a 1:10 dilution of a stationary phase bacterial culture was used as the template for a final reaction volume of 20 µl. The cycling conditions used were a 2-min hot start at 94° C., 30 cycles of denaturation at 94° C. (1 min), primer annealing at 55° C. (2 min) and extension at 72° C. (1 min), followed by a final extension at 72° C. (5 min). PCR products were verified by agarose gel electrophoresis and cleaned up with ExoI/SAP (shrimp alkaline phosphatase) prior to sequencing with the M13 rev primer.

The SEQ ID NOs for the CDR3 sequences of twenty-seven scFv are listed in Table 4. These scFv were chosen for further analysis based on assays described in Example 6.

TABLE 4

CDR3 SEQ ID NOs of Improved 18A5-derived scFv

| scFv | Heavy CDR3 | Light CDR3 |
| --- | --- | --- |
| H3  | 165 | 170 |
| H4  | 166 | 170 |
| H5  | 167 | 170 |
| H6  | 168 | 170 |
| L1  | 169 | 171 |
| L2  | 169 | 172 |
| L3  | 169 | 173 |
| L4  | 169 | 174 |
| L5  | 169 | 175 |
| L6  | 169 | 176 |
| L8  | 169 | 177 |
| L9  | 169 | 178 |
| L10 | 169 | 179 |
| L11 | 169 | 180 |
| L12 | 169 | 181 |
| L13 | 169 | 182 |
| L14 | 169 | 183 |
| L15 | 169 | 184 |
| L16 | 169 | 185 |
| L17 | 169 | 186 |
| L18 | 169 | 187 |
| L19 | 169 | 188 |
| L20 | 169 | 189 |
| L21 | 169 | 190 |
| L23 | 169 | 191 |
| L24 | 169 | 192 |
| L25 | 169 | 193 |

Example 6

Characterization of Library-Derived scFv

Example 6.1

Preparation of Purified scFv for Quantitative Analysis

Individual scFv clones were purified on a small scale by Ni-NTA purification on PHYTIP® columns (PhyNexus, Inc., San Jose, Calif.). Single colonies were grown in 20 ml 2×TY medium with 0.1% glucose/100 µg/ml ampicillin in 50-ml conical tubes to mid-logarithmic phase at 37° C. with shaking at 250 rpm. Expression of scFv was induced with IPTG at a final concentration of 0.02 mM, and cultures were grown overnight at 30° C. Cells were harvested by centrifugation and resuspended in 1 ml TES periplasmic buffer, followed by the addition of 1 ml 1:5 TES:water and incubation on ice for 30 min. Lysates were centrifuged at 3200 rpm for 10 min at 4° C., and supernatants were brought to 2 mM $MgCl_2$. scFv were captured on Ni-NTA PHYTIPs® (PhyNexus) by repeated passage of the supernatant over the PHYTIPs® on a Perkin Elmer (Waltham, Mass.) MINITRAK™ IX liquid handling robot, followed by washing in IMAC wash buffer and elution with 200 mM imidazole, 50 mM Tris, 300 mM NaCl (pH 8.0). The buffer was exchanged to PBS by three cycles of dilution 1:10 into PBS, followed by concentration on a 10,000 molecular weight cutoff filter plate (Millipore MULTI-SCREEN ULTRACEL™ 96-well ultrafiltration plate, Millipore, Billerica, Mass.). Samples were quantitated using a Micro BCA™ kit (Thermo Fisher Scientific Inc., Rockford, Ill.) using the manufacturer's bovine serum albumin standard.

Example 6.2

Assays for IL-21-Dependent Proliferation of Cells Overexpressing Human or Murine IL-21R Inhibition assays were performed with 18A5-derived binding proteins (scFv and IgG) to measure their blockade of IL-21-dependent proliferation of cell lines transfected with human or murine IL-21R. BaF3 cells, a murine pre-B cell line, and TF1 cells, a human erythroid cell line, were retrovirally transduced with IL-21R and green fluorescent protein (GFP). Cells were routinely grown in RPMI 1640 with 10% FBS, 2 mM L-glutamine, 100 U/ml penicillin, 100 µg/ml streptomycin, and 0.00036% β-mercaptoethanol. Human IL-21R-BaF3 cell cultures were supplemented with 50 ng/ml of human IL-21; murine IL-21R-BaF3 cell cultures were supplemented with 10 U/ml of IL-3; TF1 cell cultures were supplemented with 50 ng/ml of GM-CSF. Prior to assay, cells were washed 3× in assay medium lacking supplemental growth factors, resuspended in assay medium, and incubated at 37° C./5% $CO_2$ for 6 hr. To prepare assay plates, 5000 cells were added to the central 60 wells of a 96-well flat-bottomed white tissue culture plate (Thermo Scientific, Waltham, Mass.) in a volume of 55 µl/well. Test scFv or IgG samples were prepared by diluting the stock sample in assay medium and diluting serially three-fold. Twenty-five µl of the binding protein samples were added to the cells and incubated for 30 min at 37° C./5% $CO_2$. Twenty µl of assay medium containing 100-400 pg/ml of human or murine IL-21 was added to each well, and the cells were incubated for an additional 48 hr. Proliferation was measured by bringing plates to RT, adding 15 µl/well CELLTITER-GLO®, incubating for 10 min at RT, and measuring luminescence with a Perkin Elmer ENVISION™ plate reader. After purification with PhyNexus IMAC tips, 108 scFv were tested for neutralization of IL-21-dependent proliferation of all three cell lines. All showed neutralization of human IL-21R-BaF3 cells, with $IC_{50}$s lower than or equal to that of the parental 18A5 scFv. A subset showed strong neutralization of proliferation of murine IL-21R-BaF3 cells and human IL-21R-TF1 cells. Data from the 27 most potent clones are shown in FIGS. 1-3, and are summarized in Table 5.

Figure 1B:
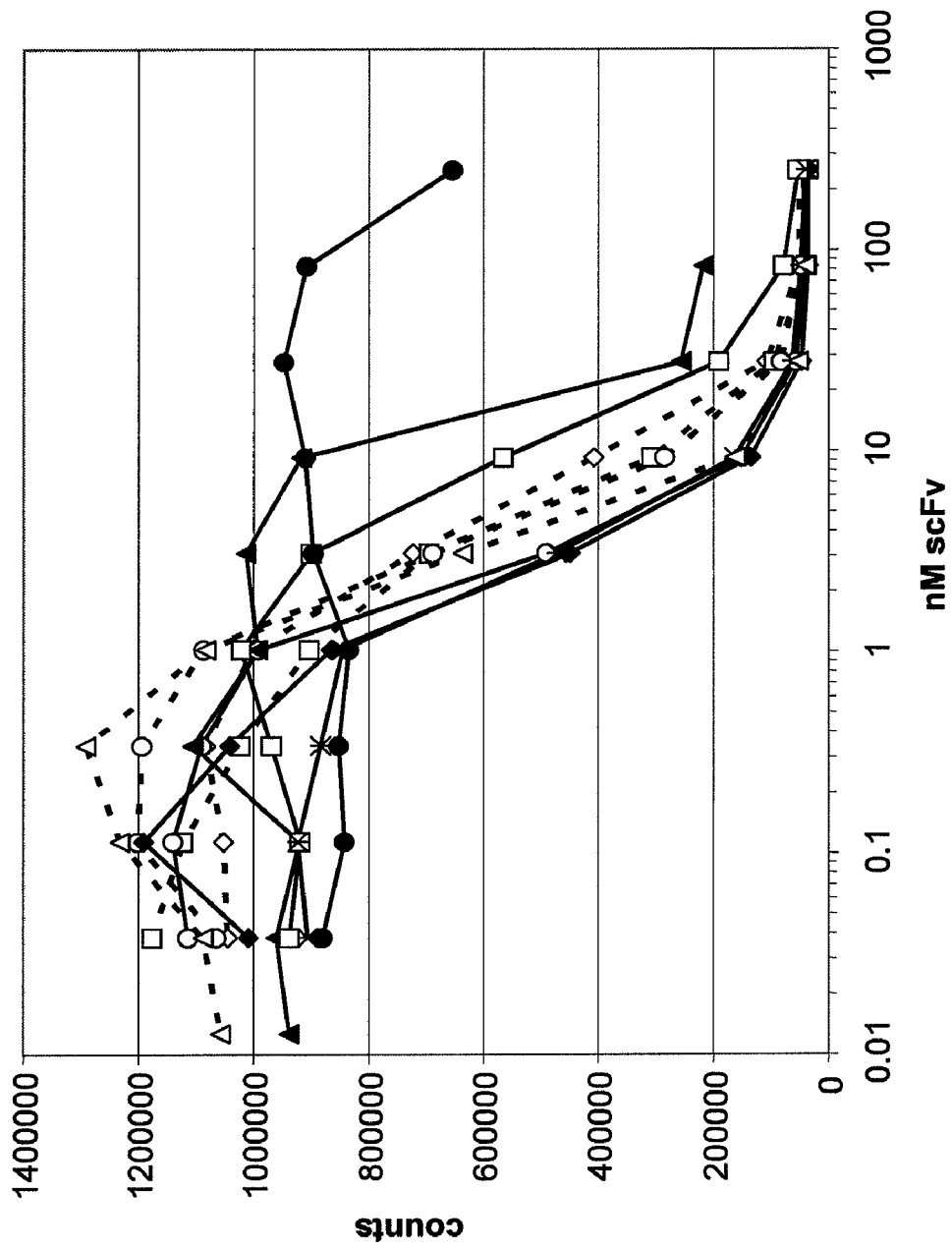
Figure 2A:
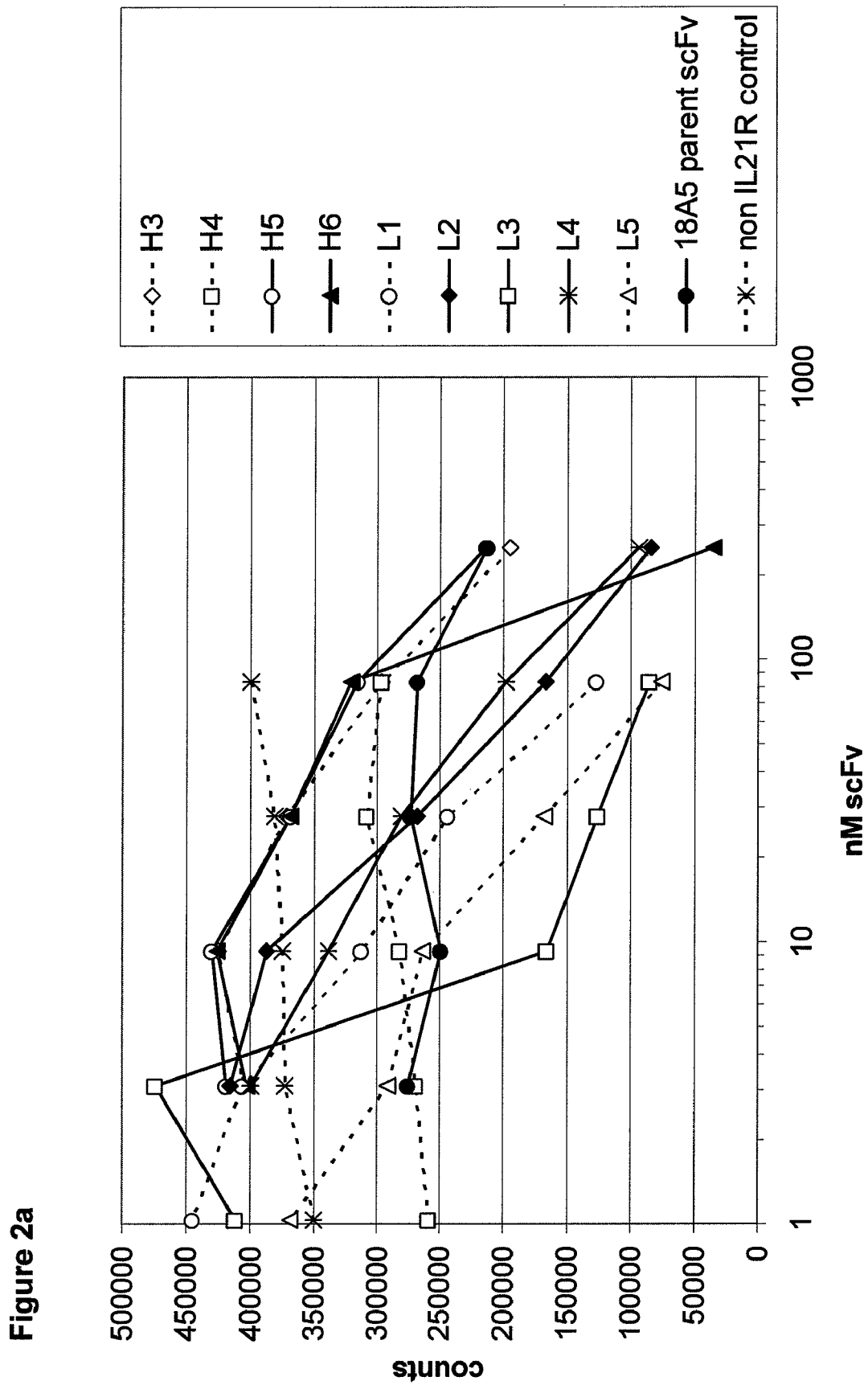
FIG. 2(a-c) depicts the neutralization of proliferation of human IL-21R-TF1 cells by scFv. Cells were mixed with the indicated scFv and then incubated with 100 pg/ml of human IL-21. Proliferation was measured by CELLTITER-GLO® after 48 hours.
Figure 2B:
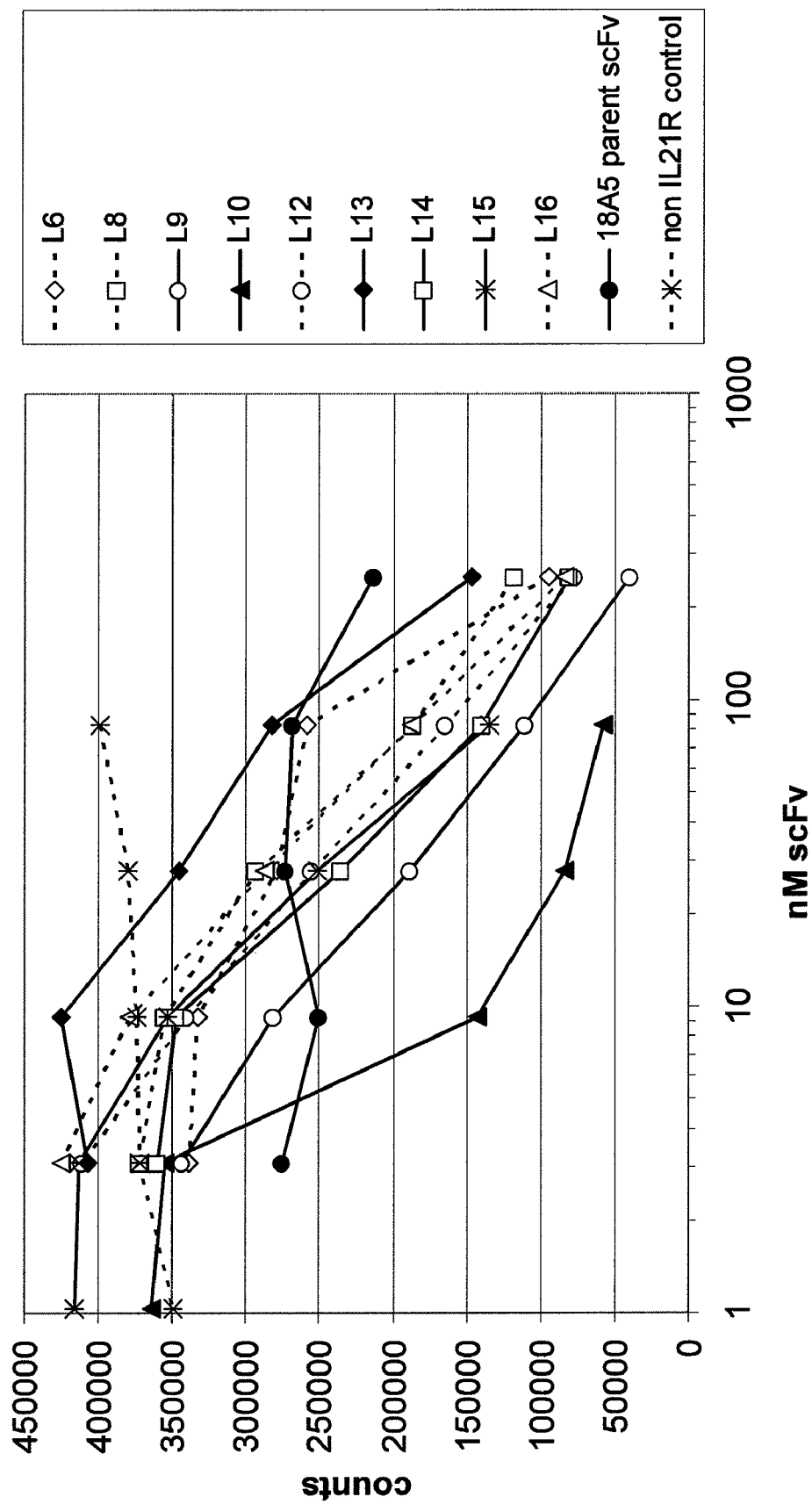
Figure 2C:
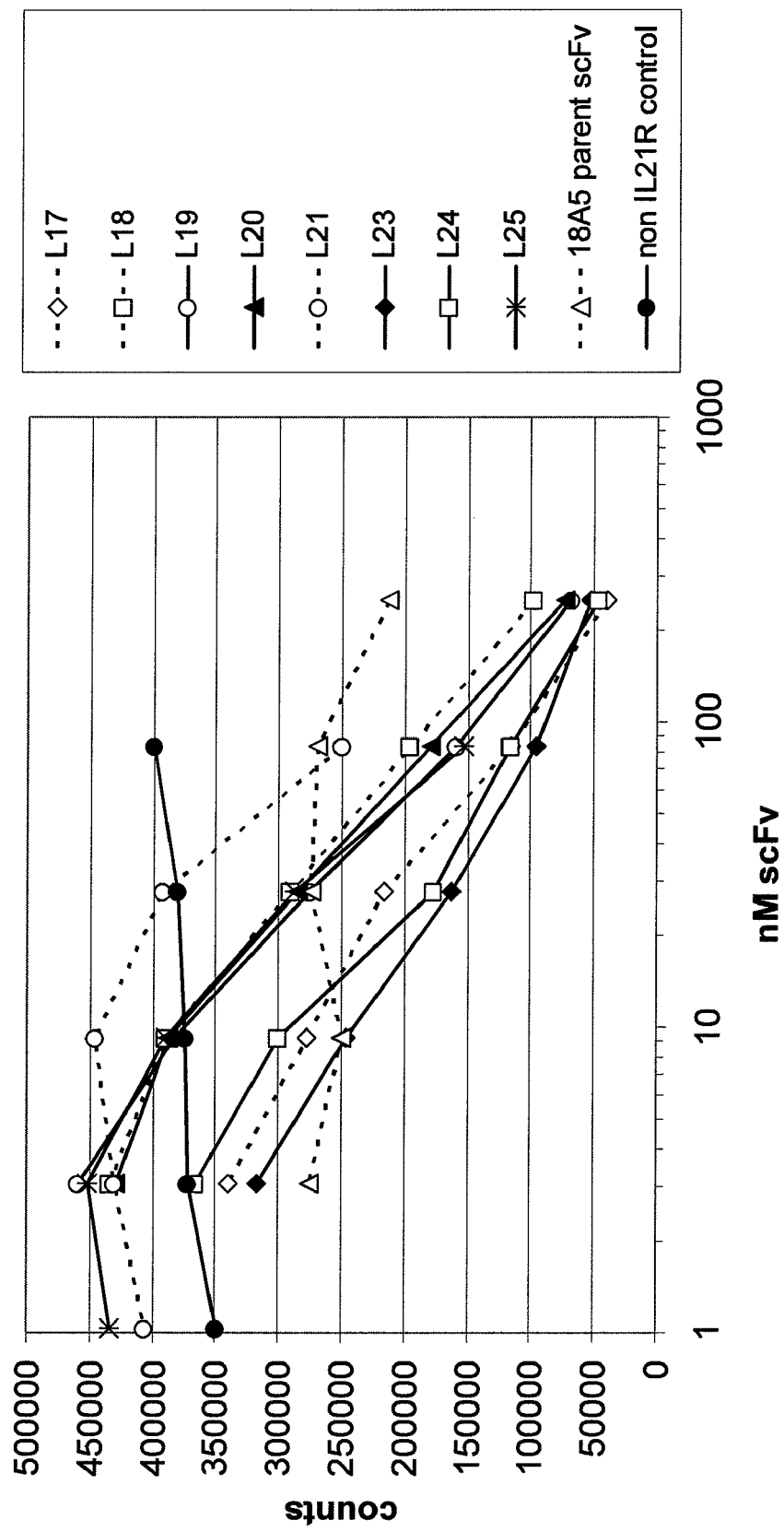
Figure 3A:
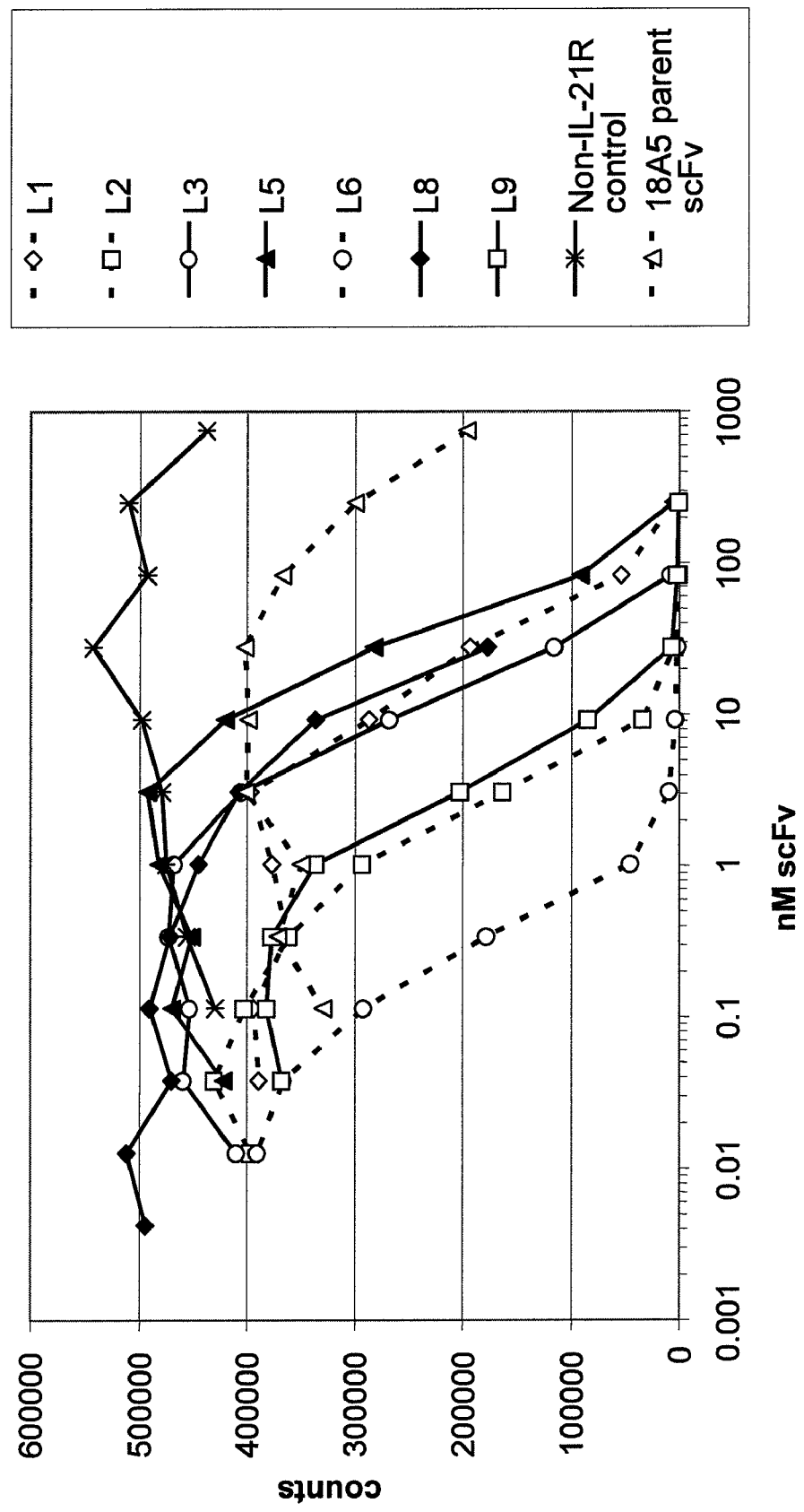
FIG. 3(a-c) depicts the neutralization of proliferation of murine IL-21R-BaF3 cells by scFv. Cells were mixed with the indicated scFv and then incubated with 400 pg/ml of murine IL-21. Proliferation was measured by CELLTITER-GLO® after 48 hours.
Figure 3B:
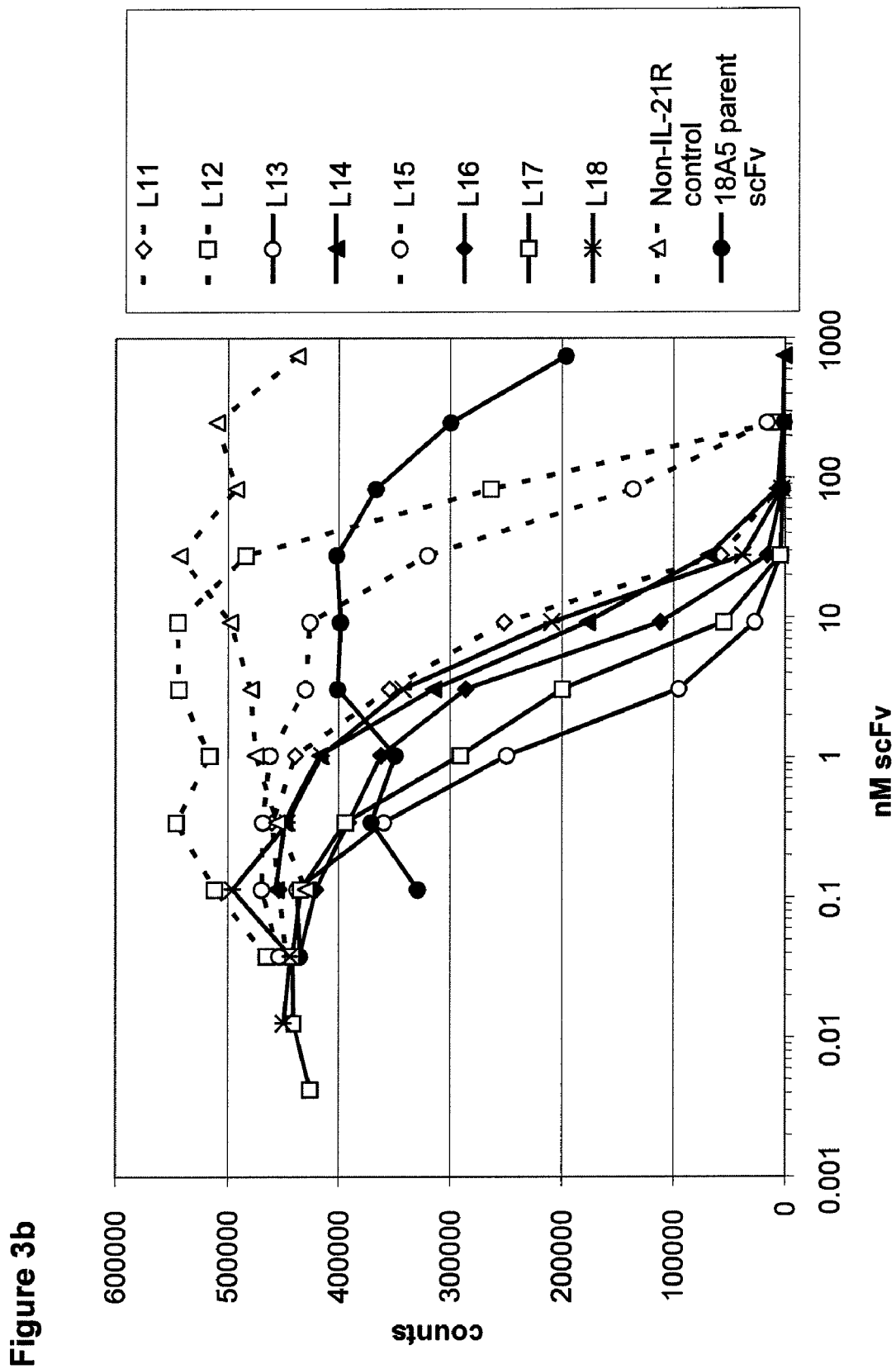
Figure 3C:
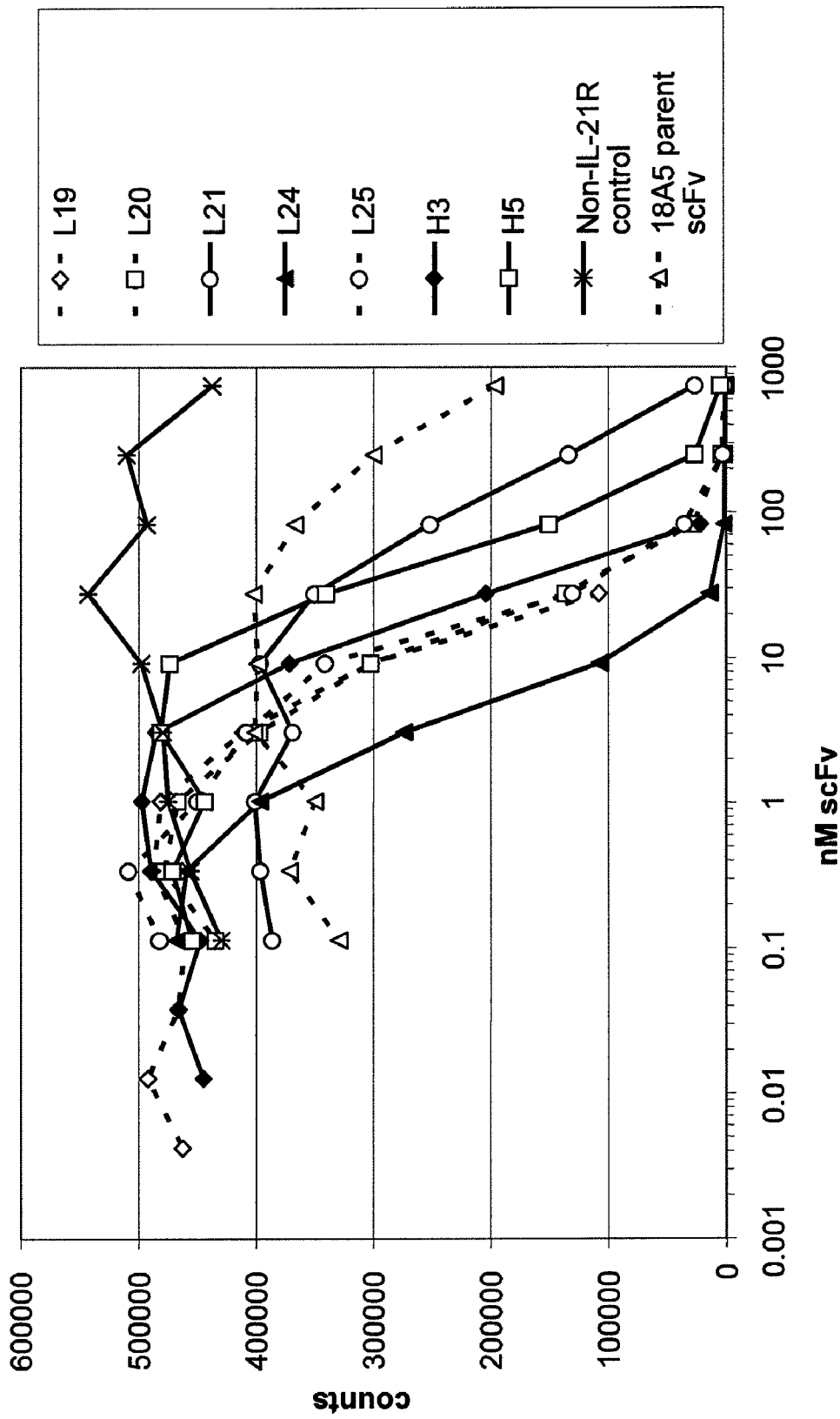

FIGS. 1-3 show the neutralization of proliferation by scFv of human IL-21R-BaF3 cells (FIGS. 1a-c); human IL-21R-TF1 cells (FIGS. 2a-c); and murine IL-21R-BaF3 cells (FIGS. 3a-c). Cells were mixed with the indicated scFv and incubated with 100 pg/ml (FIGS. 1-2) or 400 pg/ml (FIG. 3) of human IL-21.

Example 6.3

Quantitative Epitope Competition Assay

Figure 4A:
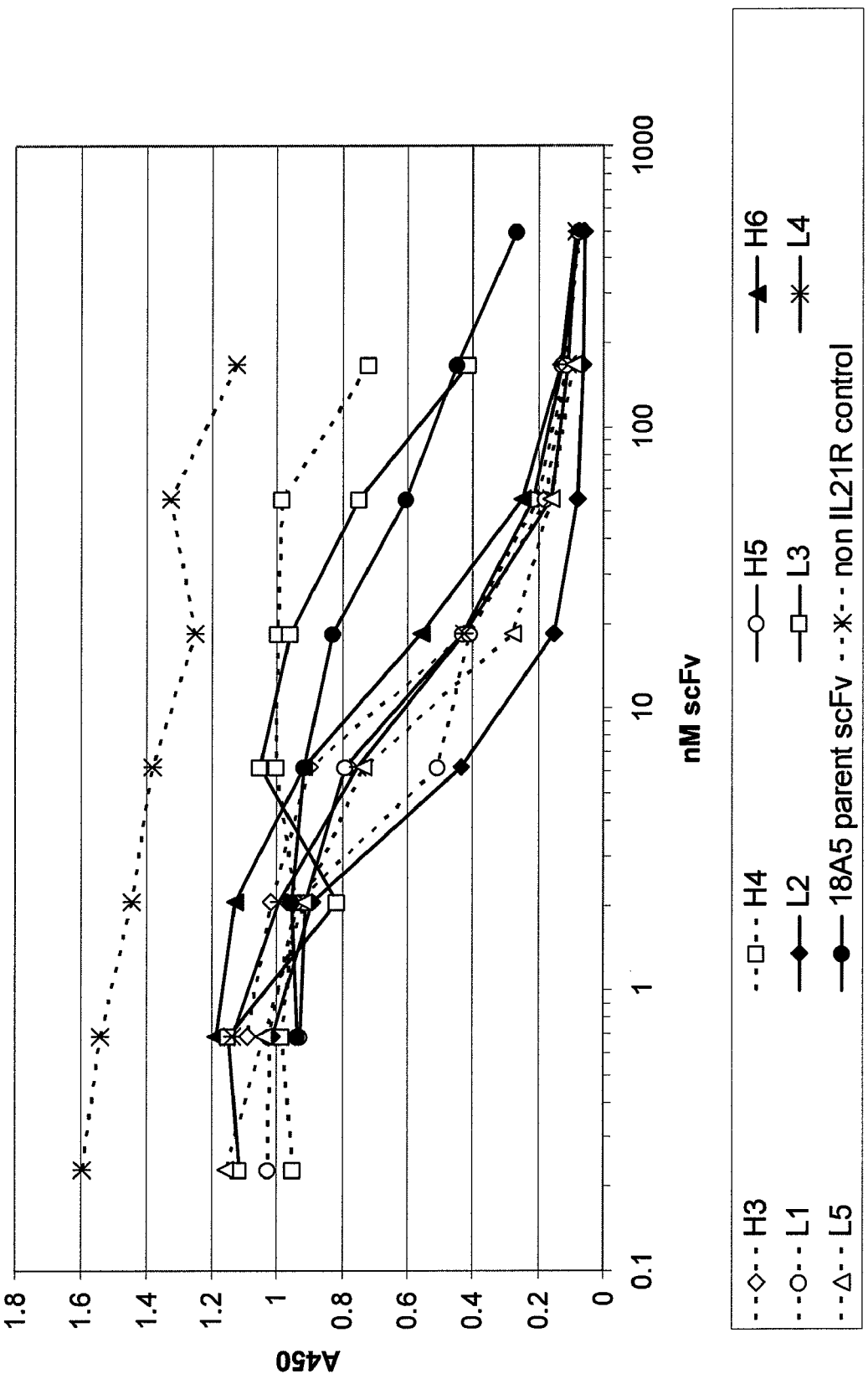
FIG. 4(a-c) depicts scFv competition with parental antibody 18A5 IgG for binding to murine IL-21R. The scFv were mixed with biotinylated-murine IL-21R-H/F, and the mixtures were added to antibody 18A5 immobilized on an ELISA plate. Capture of mIL-21R was detected with HRP-streptavidin, and competition for binding to mIL-21R was indicated by a reduction in the A450 signal.
Figure 4B:
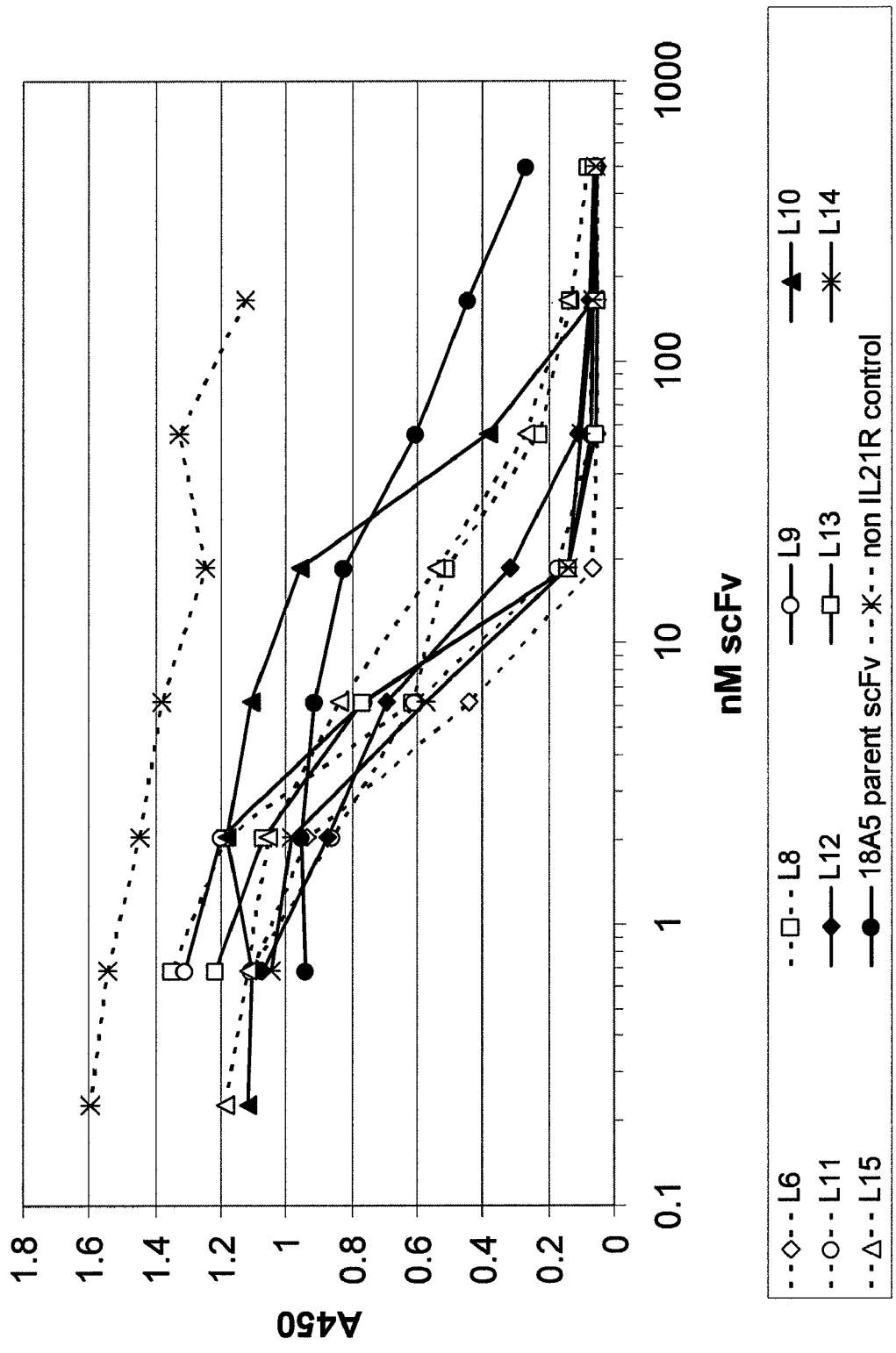
Figure 4C:
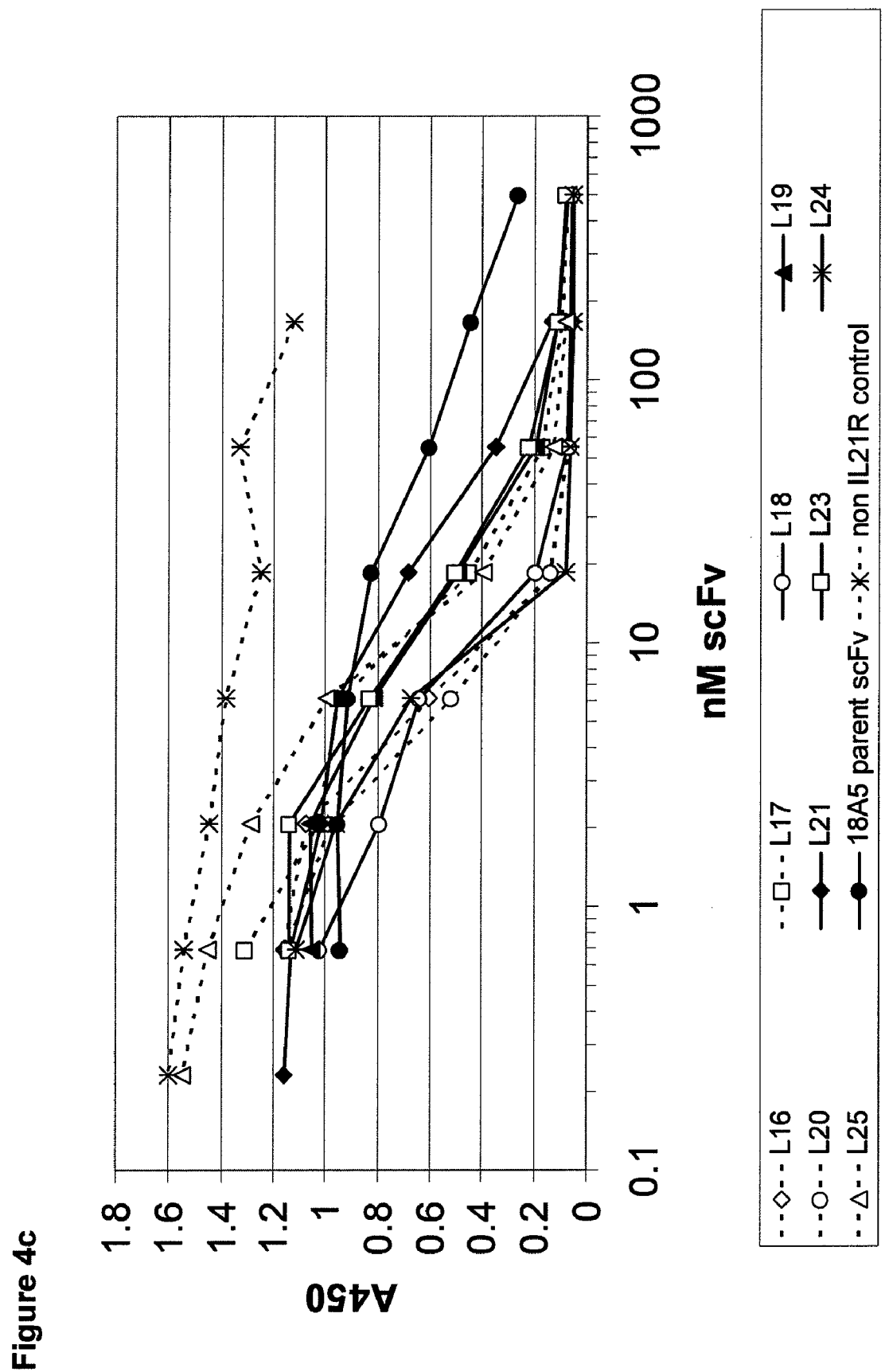

Purified scFv were analyzed quantitatively for their ability to compete with the parental 18A5 antibody for binding to murine IL-21R in an enzyme-linked immunosorbent assay (ELISA). Parental 18A5 antibody was coated overnight at 4° C. on 96-well Nunc MAXISORP® plates at a concentration of 0.75 µg/ml in PBS. Plates were washed 3× using PBS, and then blocked for 3 hr at RT in PBS/1% BSA/0.05% Tween-20. scFv were mixed with 36 nM biotinylated mIL-21R-H/F and incubated for 10 min at RT. Blocked plates were washed 3× with PBS, and 50 µl/well of scFv/IL-21R mixtures were transferred to the appropriate plates and incubated for 1 hr at RT. Plates were washed 5× with PBS prior to the addition of a 1:6000 dilution of horseradish peroxidase-conjugated streptavidin (Southern Biotech, Birmingham, Ala.) secondary antibody to detect bound biotinylated mIL-21R-H/F. Plates were then incubated for 1 hr at RT and washed 7× with PBS. Signal was developed using 3,3',5,5'-tetramethylbenzidine (TMB), the reaction stopped with $H_2SO_4$, and the absorbance read at 450 nm on an ENVISION™ plate reader (Perkin Elmer). 108 scFv purified by PhyNexus IMAC tips were tested in this assay, and most competed with the parental 18A5 antibody for binding to biotinylated murine IL-21R-H/F with $IC_{50}$s lower than that of the parental 18A5 scFv. Epitope competition data for the 27 clones with the highest potencies in cell-based neutralization assays are shown in FIGS. 4a-c and summarized in Table 5.

TABLE 5

Neutralization of Human and Murine IL-21R in Cell-based Assays and Competition with 18A5 Antibody for Murine IL-21R Binding

|  | $IC_{50}$ (nM) in Human IL-21R-BaF3 Neutralization Assay | $IC_{50}$ (nM) in Human IL-21R-TF1 Neutralization Assay | $IC_{50}$ (nM) in Murine IL-21R-BaF3 Neutralization Assay | $IC_{50}$ (nM) in Murine IL-21R Epitope Competition ELISA |
|---|---|---|---|---|
| H3 | 7.7 | 98.1 | 25.68 | 14 |
| H4 | 3.8 | 9.3 | nd | nd |
| H5 | 7.9 | 178.5 | 53.66 | 17 |
| H6 | 13.8 | 150 (estimated) | nd | 13 |
| L1 | 3.7 | 55 (estimated) | 28.77 | 7 |
| L2 | 3.1 | 37.5 | 2.41 | 5 |
| L3 | 27.6 | 7 (estimated) | 13.78 | 100 |
| L4 | 2.1 | 60 (estimated) | nd | 8 |
| L5 | 2.1 | 20 (estimated) | 38.52 | 7 |
| L6 | 5.9 | 150 (estimated) | 0.29 | 4 |
| L8 | 4.1 | 51.3 | 715.27 | 7 |
| L9 | 2.8 | 27.7 | 3.61 | 7 |
| L10 | 15.1 | 7 | nd | 40 |
| L11 | 4.2 | 38.3 | 10.03 | 6 |
| L12 | 2.6 | 54.9 | 87.77 | 8 |
| L13 | 11.0 | 257.4 | 1.25 | 7 |
| L14 | 3.2 | 33.5 | 6.49 | 6 |
| L15 | 3.3 | 30.3 | 53.49 | 14 |
| L16 | 3.7 | 67.4 | 4.71 | 6 |
| L17 | 1.6 | 60.3 | 2.66 | 12 |
| L18 | 3.7 | 54.4 | 8.34 | 8 |
| L19 | 4.5 | 35.3 | 13.59 | 15 |
| L20 | 3.1 | 57.5 | 15.39 | 5 |
| L21 | 9.4 | 100 (estimated) | 162.27 | 28 |
| L23 | 1.5 | 15.3 | nd | 12 |
| L24 | 2.4 | 18.7 | 3.73 | 6 |
| L25 | 3.7 | 33.1 | 15.55 | 9 |

Example 7

Conversion of Parental 18A5 IgG to Germline Sequence

The following fifteen scFv with modified $V_L$ regions, along with the germlined parental 18A5 $V_L$ (see below), were chosen for conversion to full-length human IgG lambda: L2, L3, L6, L9, L11, L13, L14, L16, L17, L18, L19, L20, L23, L24, and L25. Four scFv with modified $V_H$ regions, H3, H4, H5, and H6, along with the germlined parental 18A5 $V_H$ (see below) were chosen for conversion to full-length human IgG1.

The $V_H$ and $V_L$ amino sequences of the parental 18A5 antibody were modified so that the sequences outside the CDR regions matched the closest human germline sequences: DP67/$V_H$4B+ (VBASE_AA:WAP00CEAZ_1) and JH1/JH4/JH5 in the case of the $V_H$, and DPL16/$V_L$3.1 (VBASE_AA:WAP00CEMI_1) in the case of the $V_L$. Modifications were done by a combination of gene synthesis at GENEART (Regensburg, Germany) and site-directed changes introduced by PCR. In addition, the sequences were codon-optimized for expression in mammalian cells by GENEART using their proprietary methods. An alignment of the parental 18A5 sequences and the germline-corrected 18A5 sequences is shown below:

18A5 Heavy Chain Comparison

```
Parental 18A5 V_H
                                         (SEQ ID NO: 5)
CAGGTGCAGCTGCAGGAGTCGGGCCCAGGACTGGTGAAGACTTCGGAGAC
CCTGTCCCTCACCTGCGCTGTCTCTGGTTACTCCATCAGCAGTGGTTACT
ACTGGGGCTGGATCCGGCAGCCCCCAGGGAAGGGGTTGGAGTGGATTGGG
AGTATCTCTCATACTGGGAACACCTACTACAACCCGCCCCTCAAGAGTCG
CGTCACCATATCAGTAGACACGTCCAAGAACCAGTTCTCCCTGAAACTGA
GCTCTGTGACCGCCGCAGACACGGCCGTGTATTACTGTGCGCGAGGTGGG
GGAATTAGCAGGCCGGAGTACTGGGGCAAAGGCACCCTGGTCACCGTCTC
GAGT Germlined 18A5 V_H
                                         (SEQ ID NO: 7)
CAGGTGCAGCTGCAGGAGTCTGGCCCTGGCCTGGTGAAGCCTTCCGAGAC
CCTGTCTCTGACCTGTGCCGTGTCCGGCTACTCCATCTCCTCCGGCTACT
ACTGGGGCTGGATCAGACAGCCTCCTGGCAAGGGCCTGGAGTGGATCGGC
TCCATCTCTCACACCGGCAACACCTACTACAACCCCCCTCTGAAGTCCAG
AGTGACCATCTCCGTGGACACCTCCAAGAACCAGTTCTCCCTGAAGCTGT
CCTCTGTGACCGCTGCCGATACCGCCGTGTACTACTGTGCCAGAGGCGGC
GGAATCTCCAGACCTGAGTACTGGGGCCAGGGCACCCTGGTGACCGTGTC
CTCT
```

Germlined 18A5 V_H x Parental 18A5 V_H

```
  1 CAGGTGCAGCTGCAGGAGTCTGGCCCTGGCCTGGTGAAGCCTTCCGAGAC  50
    ||||||||||||||||||||| |||| || ||||||||| |||  |||||
  1 CAGGTGCAGCTGCAGGAGTCGGGCCCAGGACTGGTGAAGACTTCGGAGAC  50

51 CCTGTCTCTGACCTGTGCCGTGTCCGGCTACTCCATCTCCTCCGGCTACT 100
    |||||| || ||||| || || |||||| |||||||||    || ||||
 51 CCTGTCCCTCACcTGCGCTGTCTCTGGTTACTCCATCAGCAGTGGTTACT 100

101 ACTGGGGCTGGATCAGACAGCCTCCTGGCAAGGGCCTGGAGTGGATCGGC 150
    |||||||||||||| ||  |||||    |||||| ||||||||||  ||
101 ACTGGGGCTGGATCCGGCAGCCCCCAGGGAAGGGGTTGGAGTGGATTGGG 150

151 TCCATCTCTCACACCGGCAACACCTACTACAACCCCCCTCTGAAGTCCAG 200
    |||||||| || || ||||||||||||||||||| || ||| |
151 AGTATCTCTCATACTGGGAACACCTACTACAACCCGCCCCTCAAGAGTCG 200

201 AGTGACCATCTCCGTGGACACCTCCAAGAACCAGTTCTCCCTGAAGCTGT 250
    || |||||| ||  ||||| ||||||||||||||||||||||||   |||
201 CGTCACCATATCAGTAGACACGTCCAAGAACCAGTTCTCCCTGAAACTGA 250

251 CCTCTGTGACCGCTGCCGATACCGCCGTGTACTACTGTGCCAGAGGCGGC 300
    ||||||||||||  ||  || ||||||| |||||||||   |||| ||
251 GCTCTGTGACCGCCGCAGACACGGCCGTGTATTACTGTGCGCGAGGTGGG 300

301 GGAATCTCCAGACCTGAGTACTGGGGCCAGGGCACCCTGGTGACCGTGTC 350
    |||||   |||  || ||||||||||||   |||||||||||| ||  ||
301 GGAATTAGCAGGCCGGAGTACTGGGGCAAAGGCACCCTGGTCACCGTCTC 350

351 CTCT 354 (SEQ ID NO:7)
    |
351 GAGT 354 (SEQ ID NO:5)
```

18A5 Light Chain Comparison

Parental 18A5 V_L
(SEQ ID NO: 9)
```
TCTTCTGAGCTGACTCAGGACCCTCCTGTGTCTGTGGCCTTGGGACAGAC
AGTCACGCTCACATGCCAAGGAGACAGCCTCAGAACCTATTATGCAAGCT
GGTACCAGCAGAAGTCAGGACAGGCCCCTATACTTCTCCTCTATGGTAAA
CACAAACGGCCCTCAGGGATCCCAGACCGCTTCTCTGGCTCCACCTCAGG
AGACACAGCTTCCTTGACCATCACTGGGGCTCAGGCGGAAGACGAGGCTG
ACTATTACTGTAACTCCCGGGACTCCAGTGGCAACCCCCATGTTCTGTTC
GGCGGAGGGACCCAGCTCACCGTTTTA
```

Germlined 18A5 V_L
(SEQ ID NO: 11)
```
TCCTCTGAGCTGACCCAGGATCCTGCTGTGTCTGTGGCCCTGGGCCAGAC
CGTCAGGATCACCTGCCAGGGCGATAGCCTGAGAACCTACTACGCCTCCT
GGTATCAGCAGAAGCCTGGACAGGCCCCTGTGCTGGTGATCTACGGCAAG
CACAAGAGGCCATCCGGCATCCCTGACAGATTCTCCGGCTCCTCCTCTGG
CAATACCGCCTCCCTGACCATCACCGGCGCTCAGGCCGAGGACGAGGCCG
ACTACTACTGTAACTCCCGGGACTCTTCCGGCAACCCTCACGTGCTGTTT
GGCGGCGGAACCCAGCTGACCGTGCTA
```

Germlined 18A5 V_L x Parental 18A5 V_L

```
  1 TCCTCTGAGCTGACCCAGGATCCTGCTGTGTCTGTGGCCCTGGGCCAGAC  50
    || |||||||||||| ||||||||||||||||||||||||  |||  |||
  1 TCTTCTGAGCTGACTCAGGACCCTCCTGTGTCTGTGGCCTTGGGACAGAC  50

51 CGTCAGGATCACCTGCCAGGGCGATAGCCTGAGAACCTACTACGCCTCCT 100
    |||| | |||| ||||||||||| |||||||| |||||| || || || |
 51 AGTCACGCTCACATGCCAAGGAGACAGCCTCAGAACCTATTATGCAAGCT 100

101 GGTATCAGCAGAAGCCTGGACAGGCCCCTGTGCTGGTGATCTACGGCAAG 150
    |||| |||||||||| ||||||||||||| ||  |   ||||  || ||
101 GGTACCAGCAGAAGTCAGGACAGGCCCCTATACTTCTCCTCTATGGTAAA 150

151 CACAAGAGGCCATCCGGCATCCCTGACAGATTCTCCGGCTCCTCCTCTGG 200
    |||||  |||| || ||  |||||||| ||||| |||||||||  || ||
151 CACAAACGGCCCTCAGGGATCCCAGACCGCTTCTCTGGCTCCACCTCAGG 200

201 CAATACCGCCTCCCTGACCATCACCGGCGCTCAGGCCGAGGACGAGGCCG 250
    | || || ||  |||||||||||||| || ||||||||||||||||||||  |
201 AGACACAGCTTCCTTGACCATCACTGGGGCTCAGGCGGAAGACGAGGCTG 250

251 ACTACTACTGTAACTCCCGGGACTCTTCCGGCAACCCTCACGTGCTGTTT 300
    |||| ||||||||||||||||||||  |||||||||| || ||  |||||
251 ACTATTACTGTAACTCCCGGGACTCCAGTGGCAACCCCCATGTTCTGTTC 300

301 GGCGGCGGAACCCAGCTGACCGTGCTA 327 (SEQ ID NO:11)
    ||||| || ||||||||| ||  ||
301 GGCGGAGGGACCCAGCTCACCGTTTTA 327 (SEQ ID NO:9)
```

Germline-Corrected $V_H$ Sequence (Changes from Parental Sequence are Bold and Underlined):

```
Parental
                                              (SEQ ID NO: 6)
QVQLQESGPGLVKTSETLSLTCAVSGYSISSGYYWGWIRQPPGKG
Germlined
                                              (SEQ ID NO: 8)
QVQLQESGPGLVKPSETLSLTCAVSGYSISSGYYWGWIRQPPGKG Parental
LEWIGSISHTGNTYYNPPLKSRVTISVDTSKNQFSLKLSSVTAADTAVYY
CARGGGISRP
Germlined
LEWIGSISHTGNTYYNPPLKSRVTISVDTSKNQFSLKLSSVTAADTAVYY
CARGGGISRP Parental
EYWGKGTLVTVSS
Germlined
EYWGQGTLVTVSS
```

Germline-Corrected $V_L$ Sequence (Changes from Parental Sequence are Bold and Underlined):

```
Parental
                                             (SEQ ID NO: 10)
SSELTQDPPVSVALGQTVTLTCQGDSLRTYYASWYQQKSGQAPIL
Germlined
                                             (SEQ ID NO: 12)
SSELTQDPAVSVALGQTVRITCQGDSLRTYYASWYQQKPGQAPVL Parental
LLYGKHKRPSGIPDRFSGSTSGDTASLTITGAQAEDEADYYCNSRDSSGN
PHVLFGGGTQ
Germlined
VIYGKHKRPSGIPDRFSGSSSGNTASLTITGAQAEDEADYYCNSRDSSGN
PHVLFGGGTQ Parental
LTVL
Germlines
LTVL
```

Example 8

Conversion of Library-Derived scFv to IgG

The CDR3 regions of the $V_L$ and $V_H$ domains of improved 18A5 scFv derivatives were amplified by PCR and subcloned into the germline-corrected $V_L$ and $V_H$ frameworks of the parental 18A5 by the following method. A PCR fragment encompassing the 5' portion of the germlined 18A5 $V_H$ gene was generated by amplification of the plasmid pSMED2_OP18A5G_huIgG1 with primers BssHII_II_$V_H$_F (5'-GCTTGGCGCGCACTCTCAGGTGCAGCT-GCAGGAG-3') [SEQ ID NO:230] and G$V_H$_R_for_BssHII (5'-TCAGGGAGAACTGGTTCTTGG-3') [SEQ ID NO:231]. A PCR fragment encompassing the 3' portion of the $V_H$ gene from the improved scFv clone $V_H$3 was amplified with the following primers: G_$V_H$_F_for_SalI (5'-TCCAA-GAACCAGTTCTCCCTG-3') [SEQ ID NO:232] and scFv_SalI_IV$_H$_R (5'-GCGACGTCGACAGGACTCAC-CACTCGAGACGGTGACCAGGGTGCC-3') [SEQ ID NO:233]. Fragments were gel-purified, and then the two were mixed and amplified with the outside primer sets BssHI-I_G_$V_H$_F and SalI_$V_H$_R to generate a complete $V_H$ gene fragment. This was digested with BssHII and SalI and ligated into a vector containing the constant regions of human IgG1 with a triple-mutant hinge region. The insert was reamplified with BssHII_II_$V_H$_F and a new primer (Sa1_$V_H$_R_RJ (5'-GCGACGTCGACAGGACTCACCACTCGAGACGG-3')) [SEQ ID NO:234] in order to alter the coding sequence of the $V_H$ J segment to conform to the JH1 germline sequence, and ligated into a human IgG 1-triple-mutant constant region vector.

The $V_L$ genes from improved scFv were subcloned by a similar method. A PCR fragment encompassing the 5' portion of the 18A5 $V_L$ gene was generated by amplification of the plasmid pSMEN2_OP18A5G_hu Lambda with primers BssHII_II_$V_L$_F (5'-GCTTGGCGCGCACTCTTCCTCT-GAGCTGACCCAG-3') [SEQ ID NO:235] and scFv_$V_L$_R_for_BssII (5'-GCCTGAGCCCCAGTGATGGTCA-3') [SEQ ID NO:236]. PCR fragments encompassing the 3' portions of the $V_L$ genes from improved scFv clones were amplified with the primers G$V_L$_F_for_XbaI (5'-ACCGCCTC-CCTGACCATCAC-3') [SEQ ID NO:237] and scFv_XbaI_$V_L$_R (5'-GCGCCGTCTAGAGTTATTCTACT-CACCTAAAACGGTGAGCTGGGTCCC TC-3') [SEQ ID NO:238]. Fragments were gel-purified, and then fragments corresponding to the 5' and 3' portions of each gene were mixed and amplified with the outside primer set BssHII_II_$V_L$_F and scFv_XbaI_$V_L$_R to generate complete $V_L$ gene fragments. These were digested with BssHII and XbaI, and ligated into a vector containing the constant regions of the human lambda gene.

Example 9

Characterization of Improved IgG In Vitro

Example 9.1

Transient Small-Scale Expression of Binding Proteins

Clones were tested for function in full IgG format following transient expression in cos-7 cells. Each light chain in the set of sixteen test sequences (germlined parental 18A5 $V_L$ and L2, L3, L6, L9, L11, L13, L14, L16, L17, L18, L19, L20, L23, L24 and L25) was paired with each heavy chain in the set of five test sequences (H3, H4, H5, and H6, along with $V_H$_P, the germlined parental 18A5 $V_H$ domain). Each plasmid in the pair (1.4 µg) was combined with the TRANSIT® transfection reagent (Mirus, Madison, Wis.) according to the manufacturer's instructions, and DNA:TRANSIT® reagent complexes were added to monolayers of cos-7 cells growing in Dulbecco's Modified Eagle's medium (DMEM)/10% heat-inactivated fetal bovine serum/penicillin/streptomycin/2 mM L-glutamine in 6-well tissue culture plates. After 24 hr, the medium was changed to a serum-free medium (R1CD1), and was then collected 48 hr later. Binding proteins, now comprising full-length antibodies, were quantitated by anti-human IgG ELISA.

Example 9.2

Activity of Anti-IL-21R IgG in Neutralization of Cell Proliferation

The 80 transiently expressed IgGs in serum-free conditioned medium were tested for activity in IL-21-dependent proliferation assays in three cell lines as described above: (1) human IL-21R-BaF3 cells, (2) murine IL-21R-BaF3 cells, and (3) human IL-21R-TF1 cells. All 80 pairs showed neutralization of proliferation of human IL-21R-expressing BaF3 cells, and all pairs except those involving $V_H$4 showed neutralization of human IL-21R-expressing TF1 cells (data not shown). All 80 pairs also showed neutralization of proliferation of murine IL-21R-expressing BaF3 cells, with the strongest neutralization generally associated with light chains paired with the parental heavy chain and the weakest neutralization generally associated with the V$_H$4 heavy chain (data not shown). Neutralization data from the most potent 21 IgG combinations (AbA-AbU) are shown in FIG. 5, and IC$_{50}$ data are summarized in Table 6.

Figure 5A:
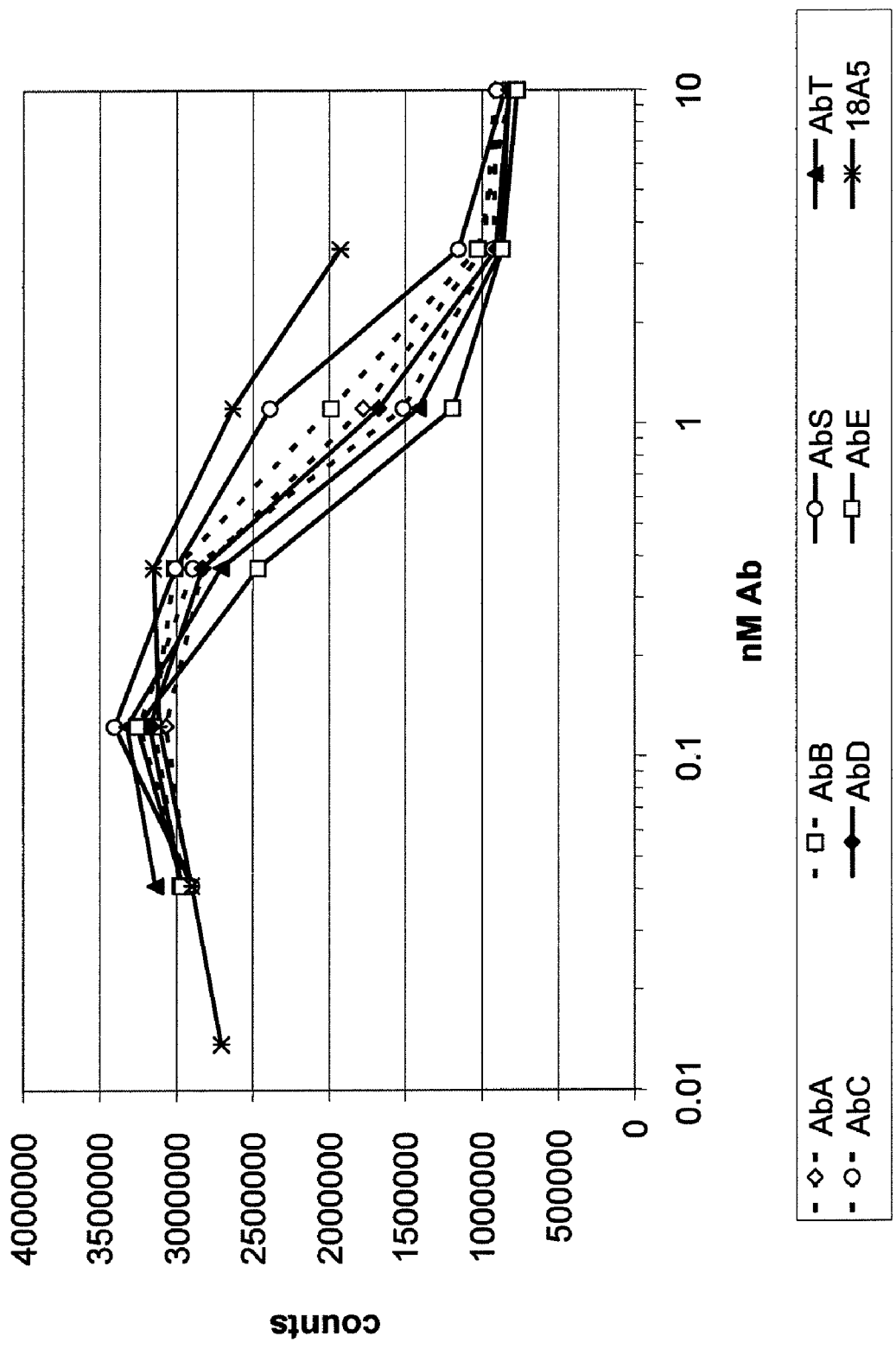
FIG. 5 depicts the neutralization of IL-21-dependent proliferation by 21 heavy chain/light chain pairs. Antibodies, as indicated in the figure, were added to cells. IL-21 was subsequently added, and proliferation measured with CELLTITER-GLO® after 48 hours. Assays were conducted on human IL-21R-BaF3 cells with 100 pg/ml of human IL-21 (FIGS. 5a-c), human IL-21R-TF1 cells with 100 pg/ml of human IL-21 (FIGS. 5d-f), or murine IL-21R-BaF3 cells with 400 pg/ml of murine IL-21 (FIGS. 5g-i).
Figure 5B:
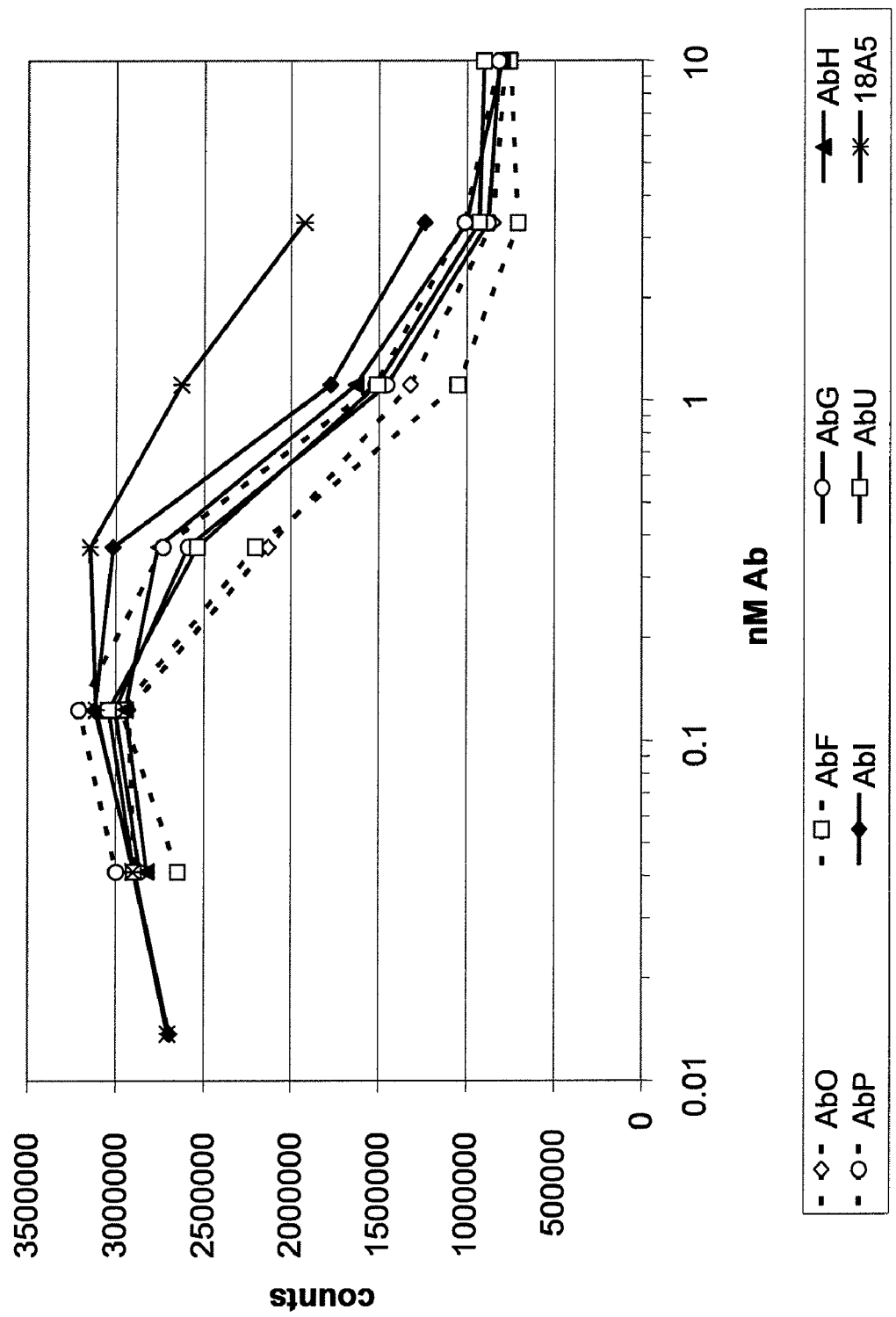
Figure 5C:
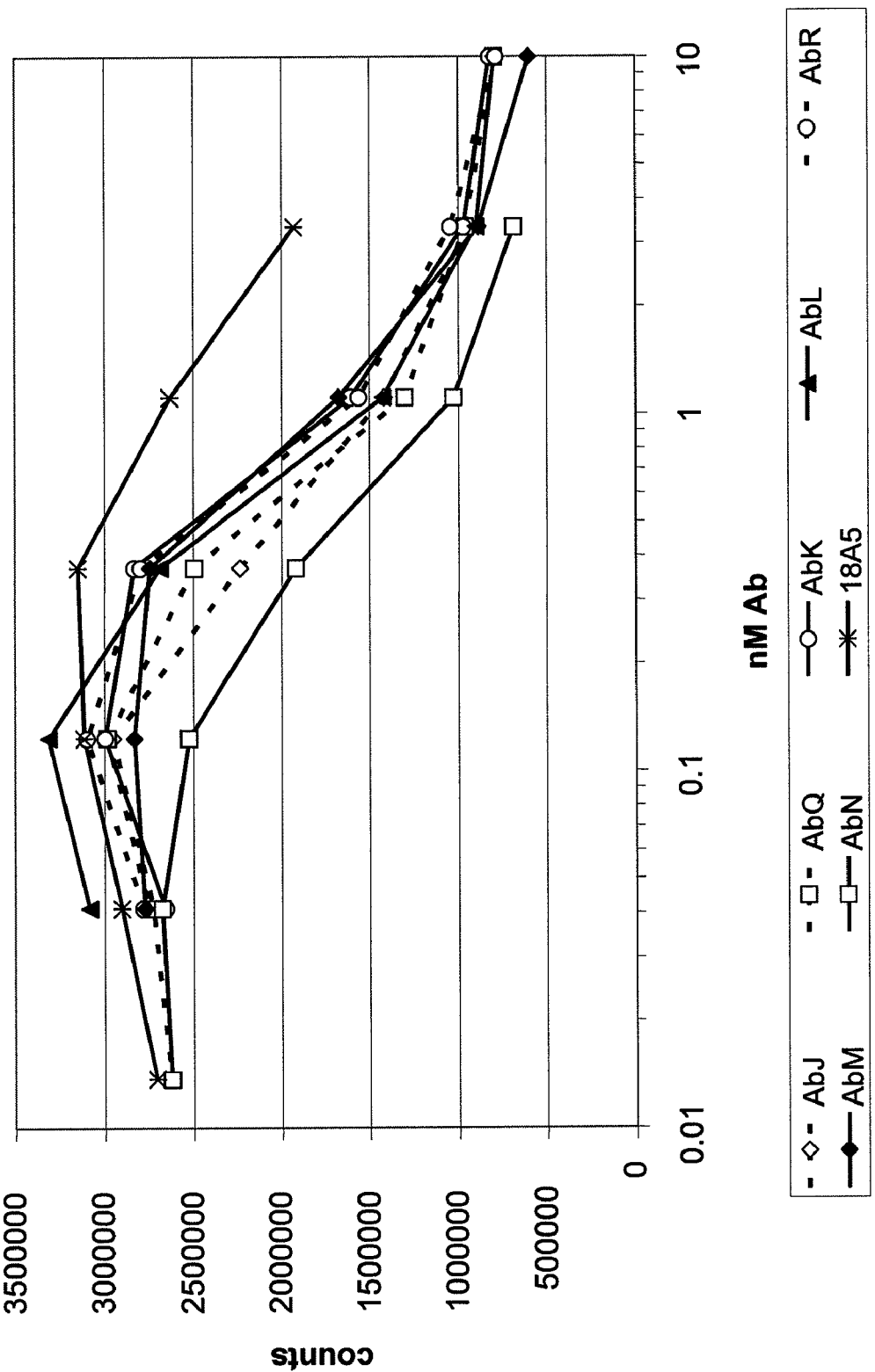
Figure 5D:
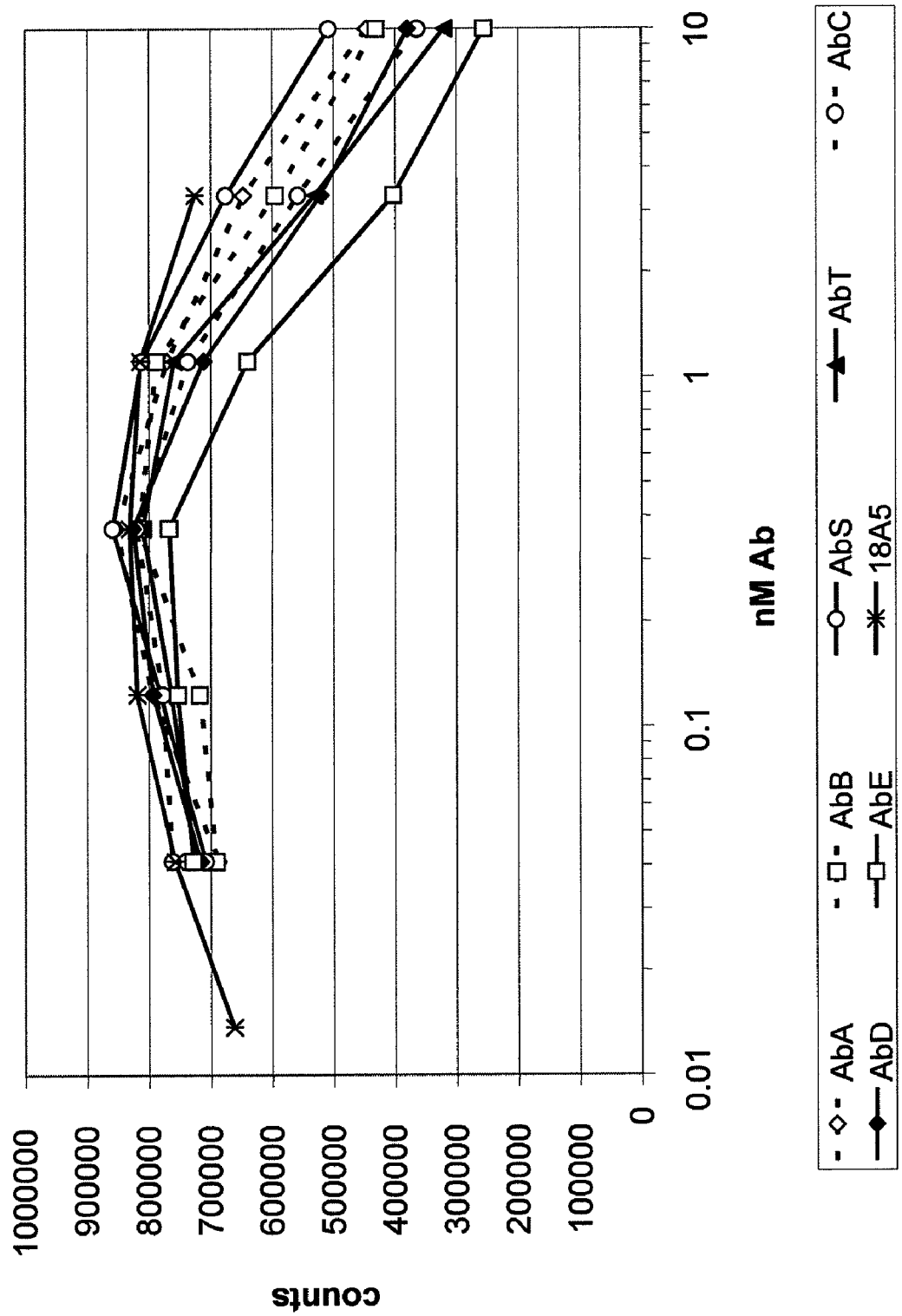
Figure 5E:
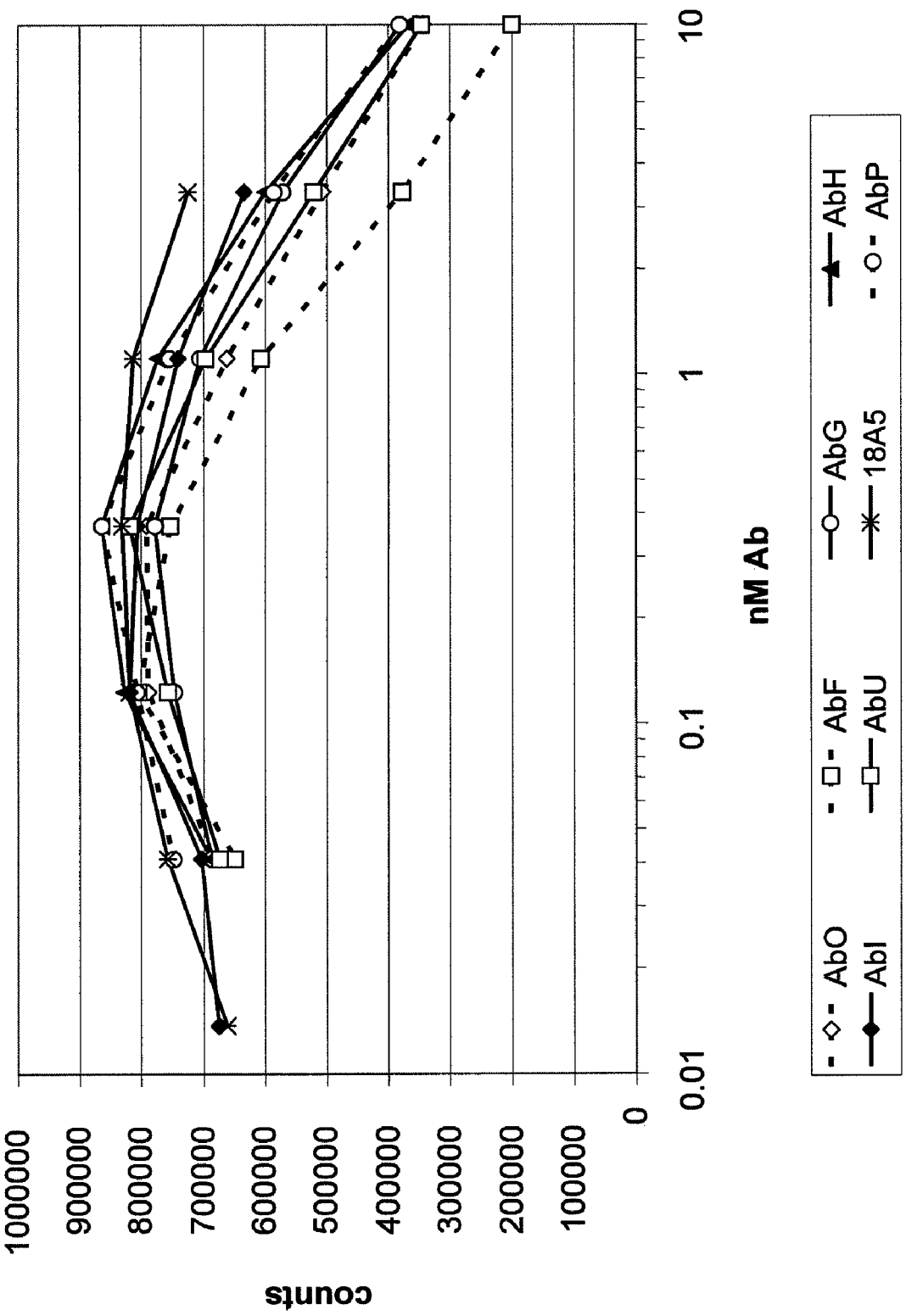
Figure 5F:
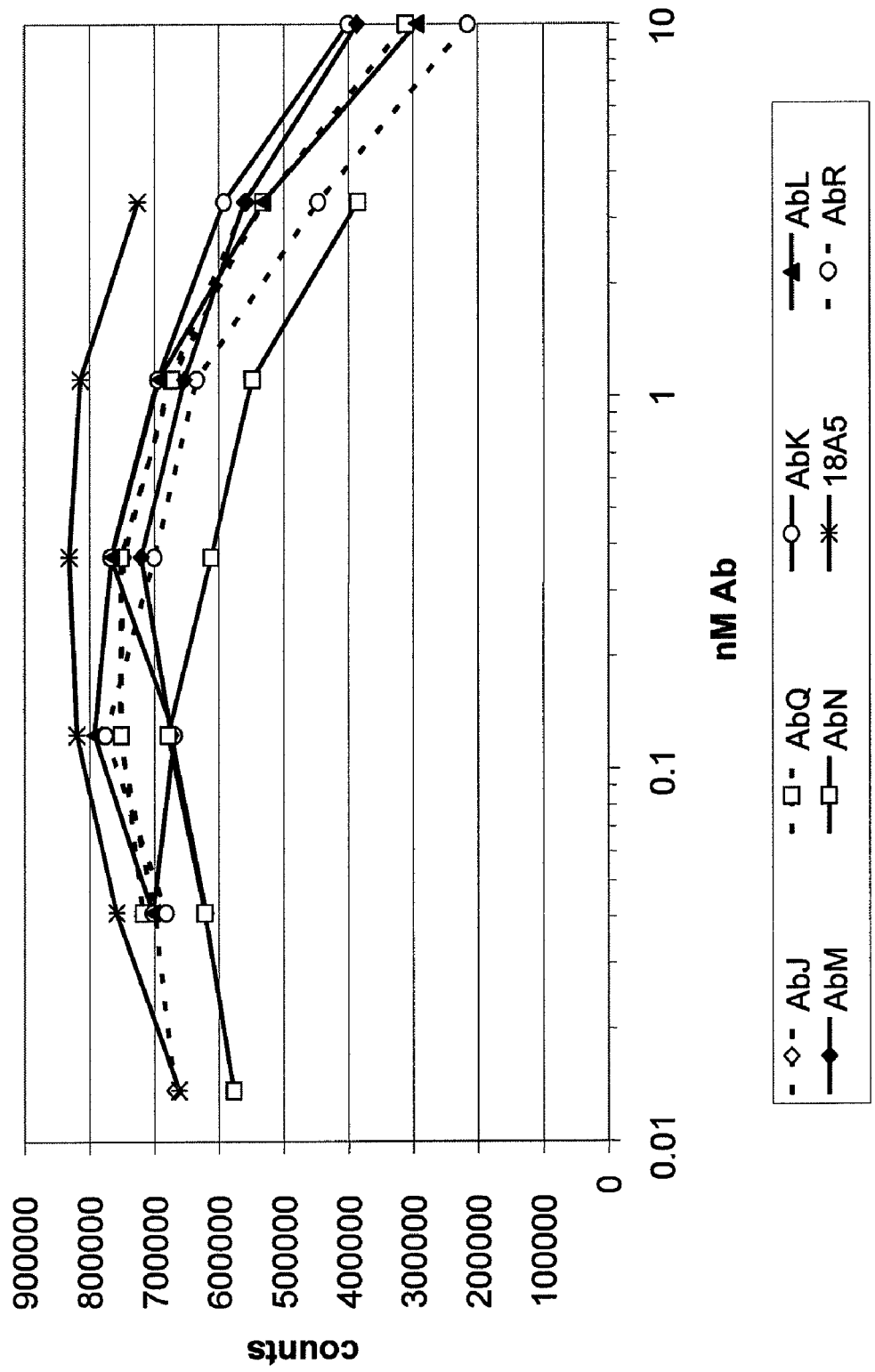
Figure 5G:
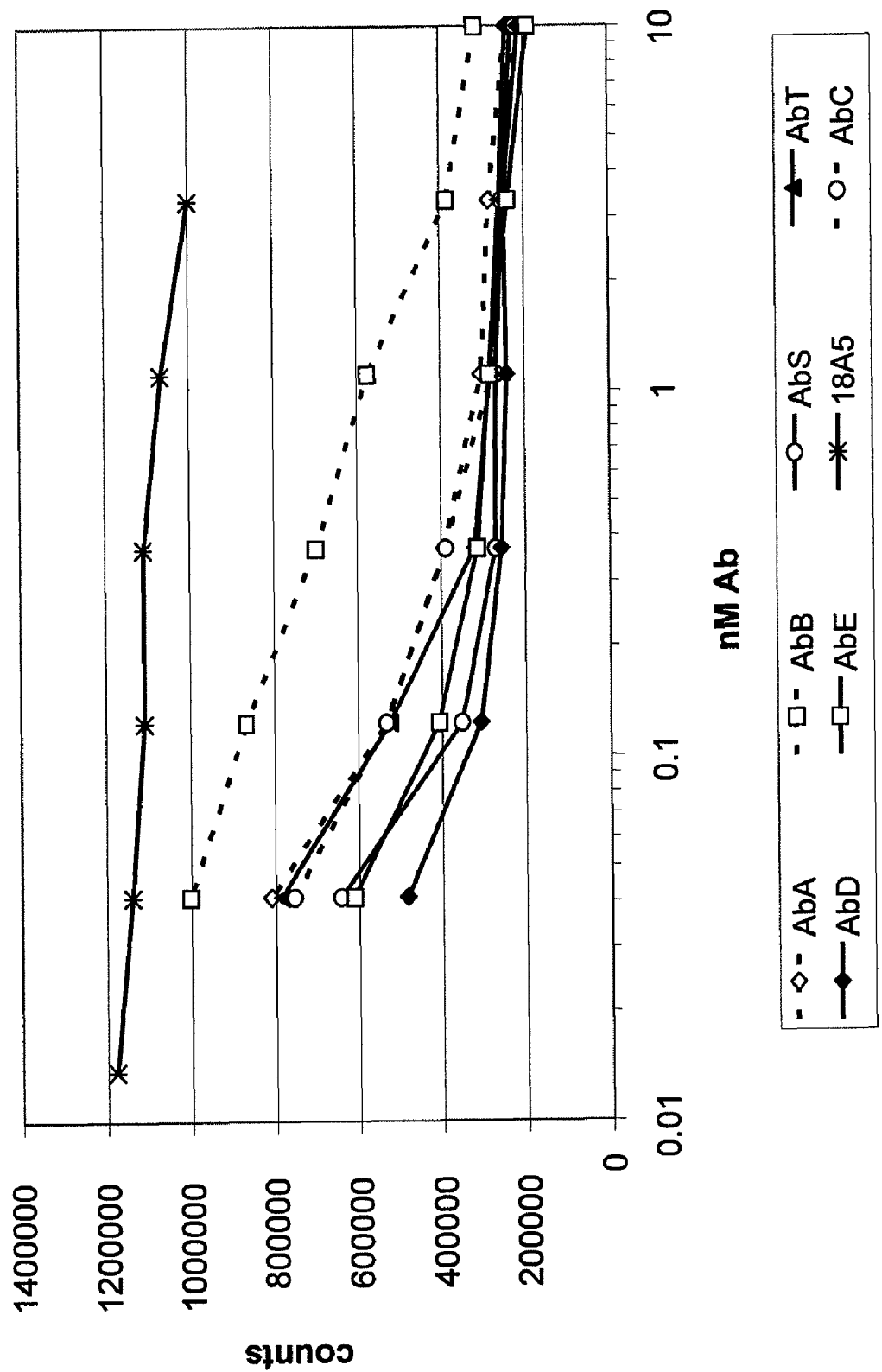
Figure 5I:
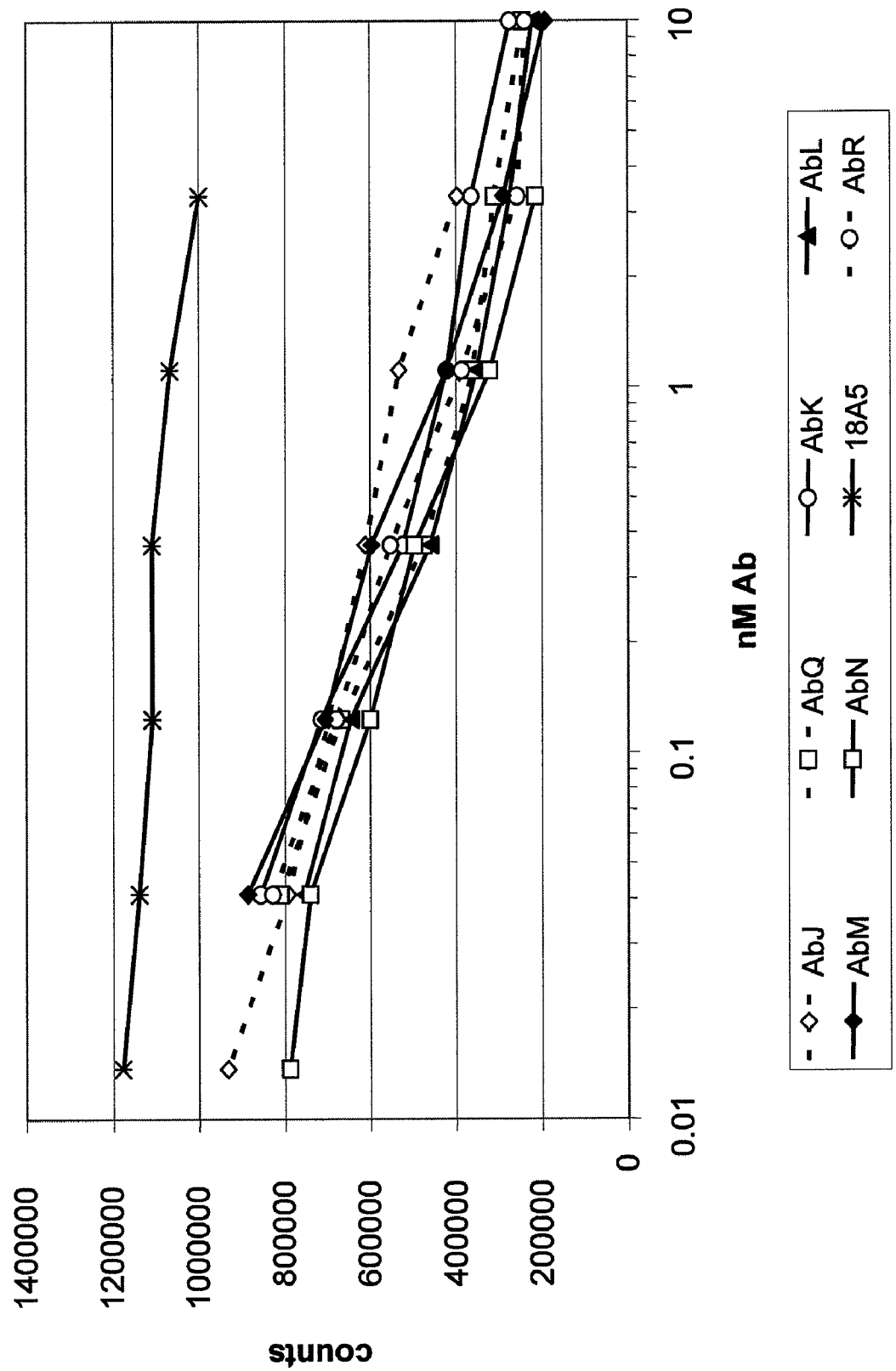
Figure 26A:
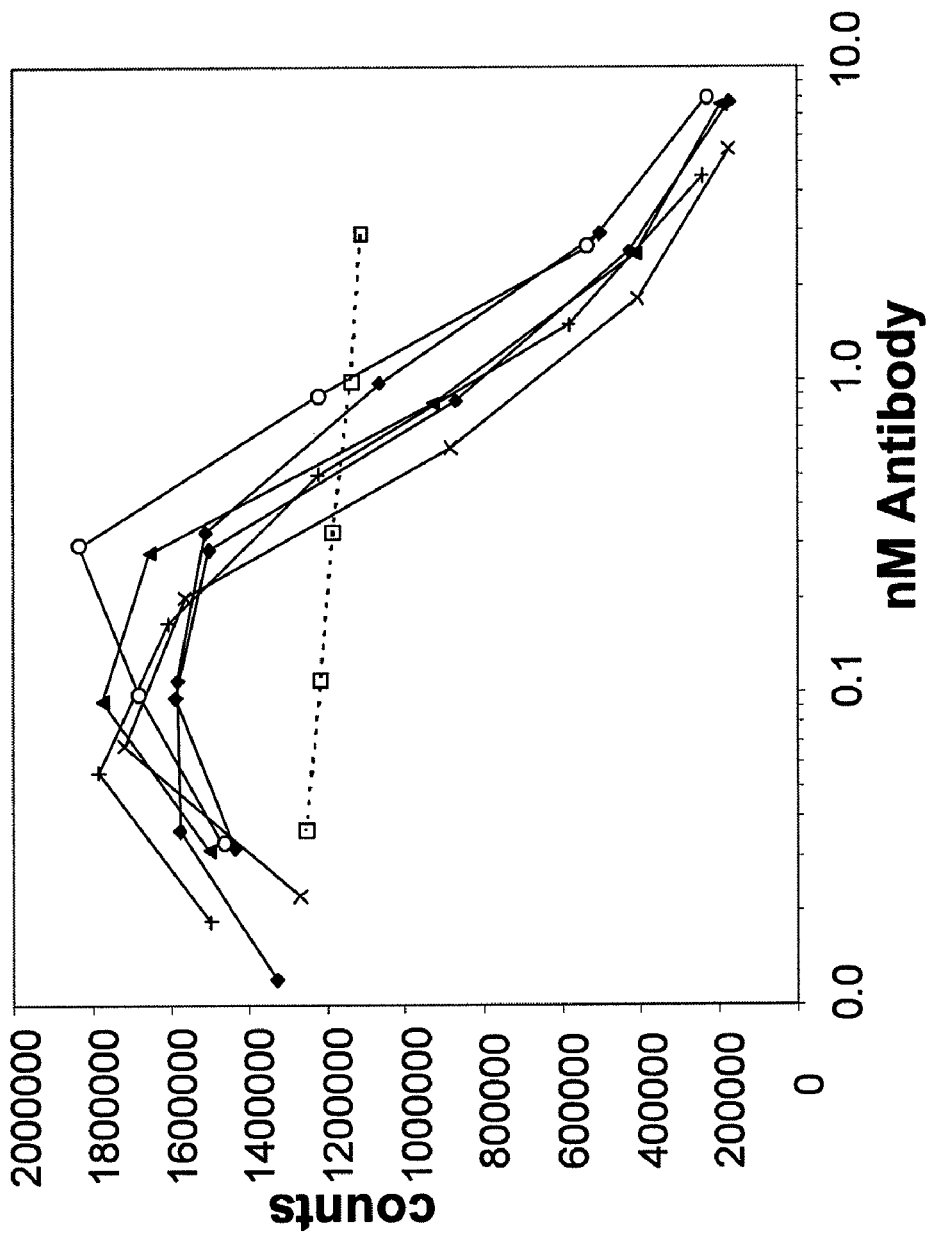
FIG. 26(a-g) depicts results generated from additional studies that were performed similarly to those performed to generate the results shown in FIGS. 5, 11, 12, 13, and 14 (described above).
Figure 26B:
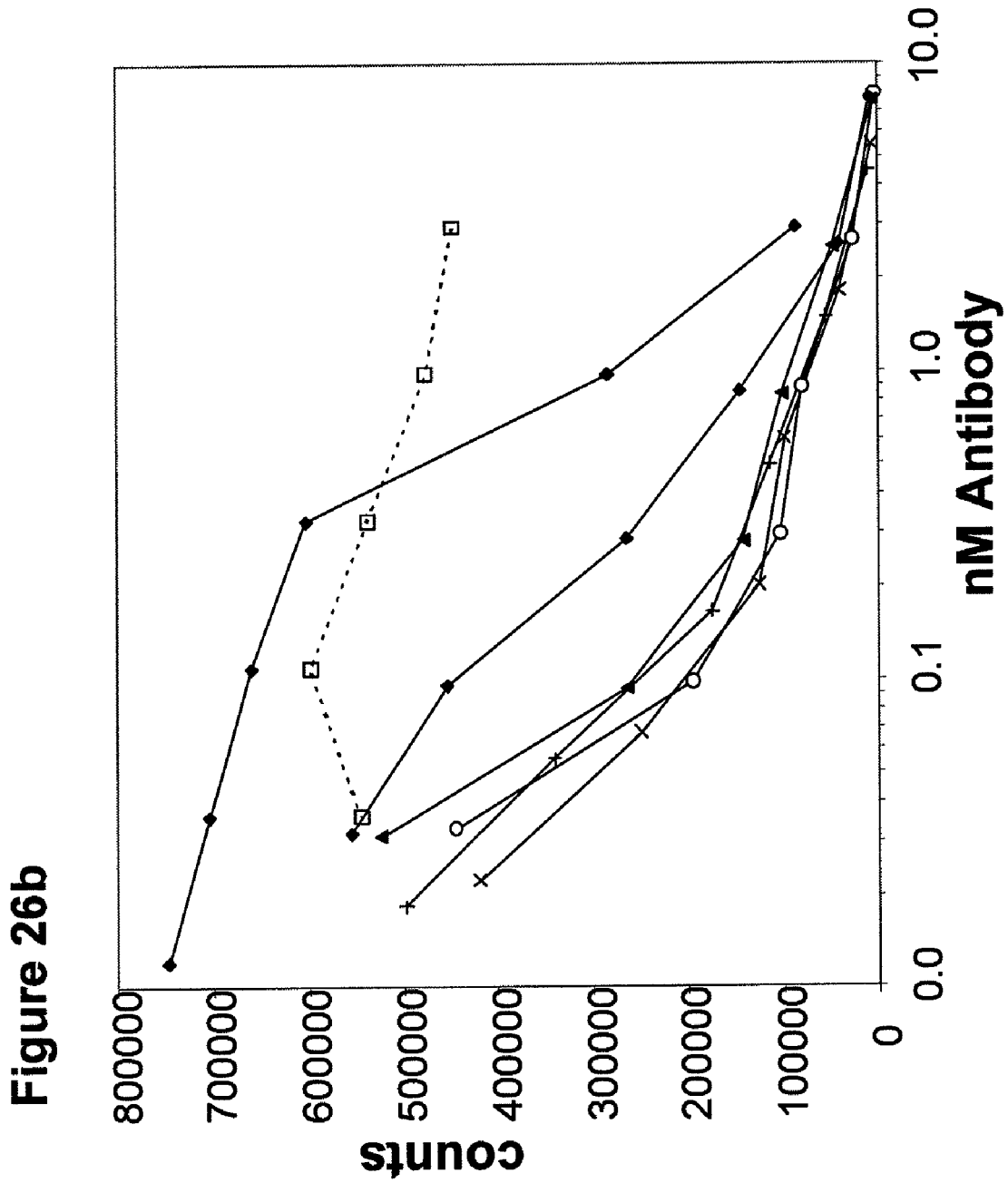
Figure 26C:
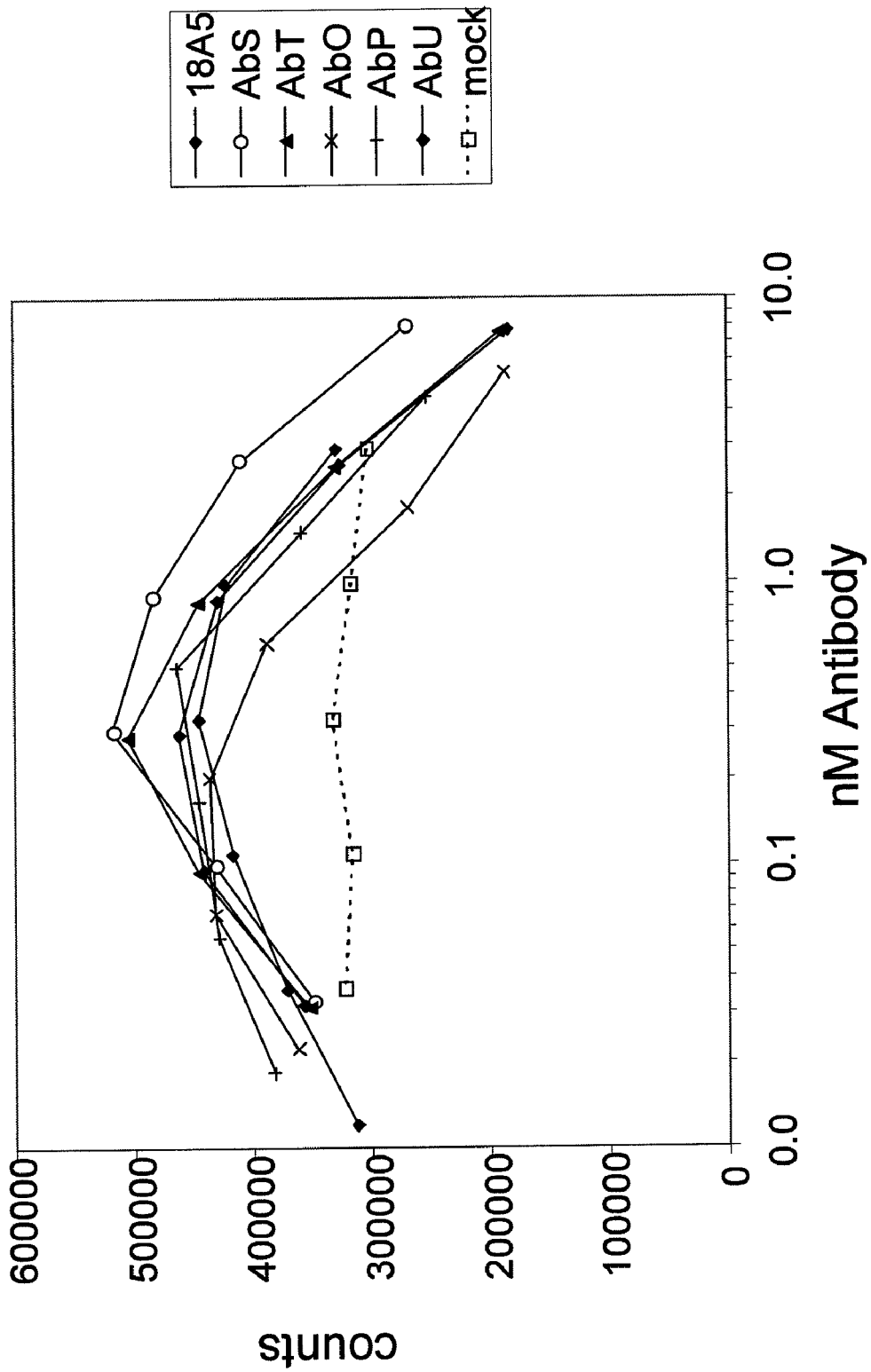

Assays were conducted on human IL-21R-BaF3 cells with 100 pg/ml of human IL-21 (FIGS. 5a-c), human IL-21R-TF1 cells with 100 pg/ml of human IL-21 (FIGS. 5d-f), or murine IL-21R-BaF3 cells with 400 pg/ml of murine IL-21 (FIGS. 5g-i). IL-21 was added to the cells after the indicated antibodies; proliferation was measured with CELLTITER-GLO® after 48 hr. FIGS. 26a-c show additional studies demonstrating similar inhibition in the same three cell lines.

buffer was removed. Cells were incubated with 100 µl TMB until the color reaction reached saturation, stopped with 100 µl of 0.18 M H$_2$SO$_4$, and read at A450 on a Perkin Elmer ENVISION™ plate reader.

Figure 6A:
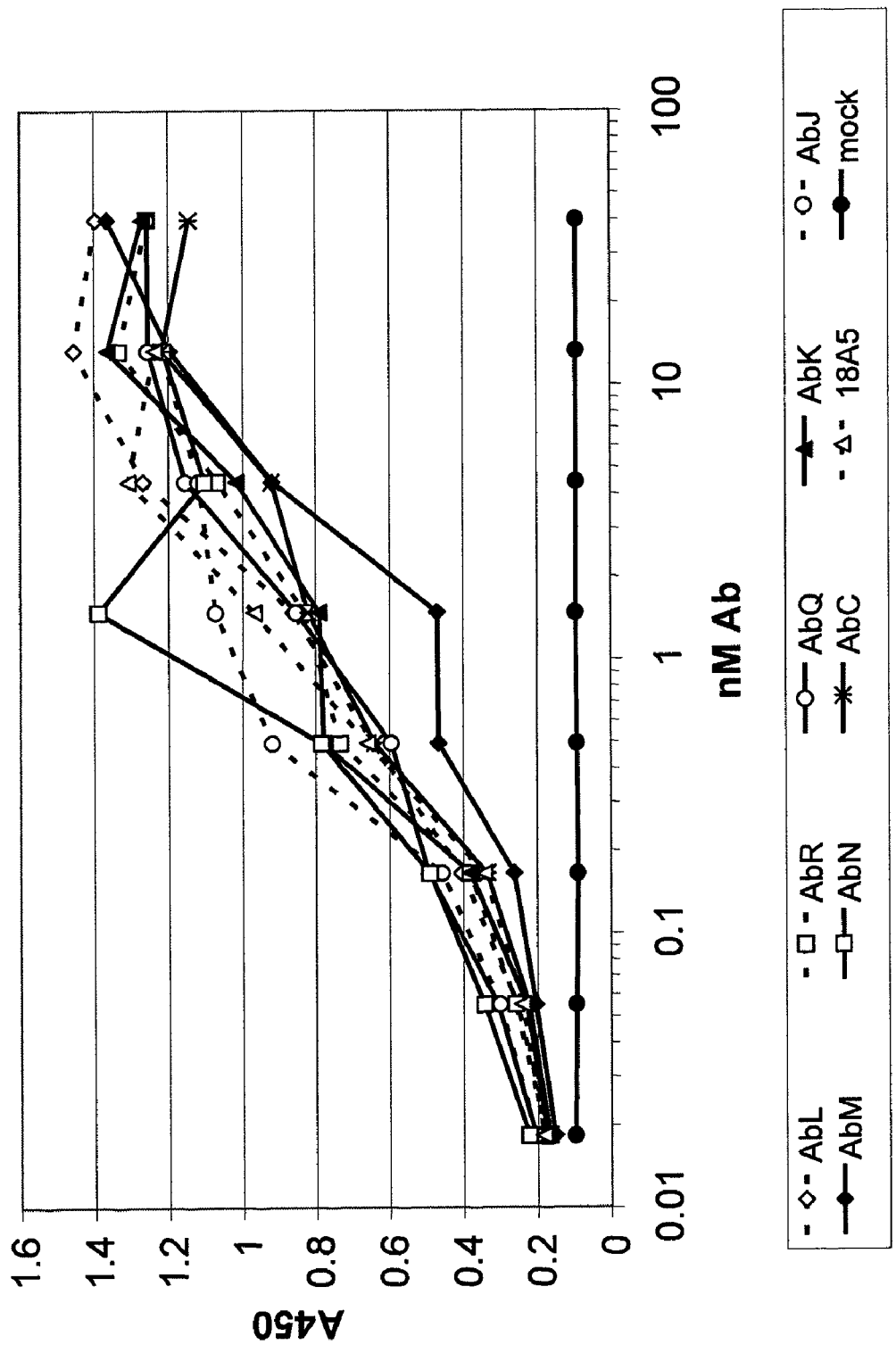
FIG. 6 depicts the binding of 21 anti-IL-21R IgGs to CHO cells transiently expressing human IL-21R (FIGS. 6a-c), rat IL-21R (FIGS. 6d-f), cynomolgus monkey IL-21R (FIGS. 6g-i), and human gamma common chain (FIGS. 6j-l). CHO cells were transiently transfected with IL-21R or the control gamma common chain, and binding was detected with HRP-conjugated anti-human IgG in a cell-based ELISA.
Figure 6B:
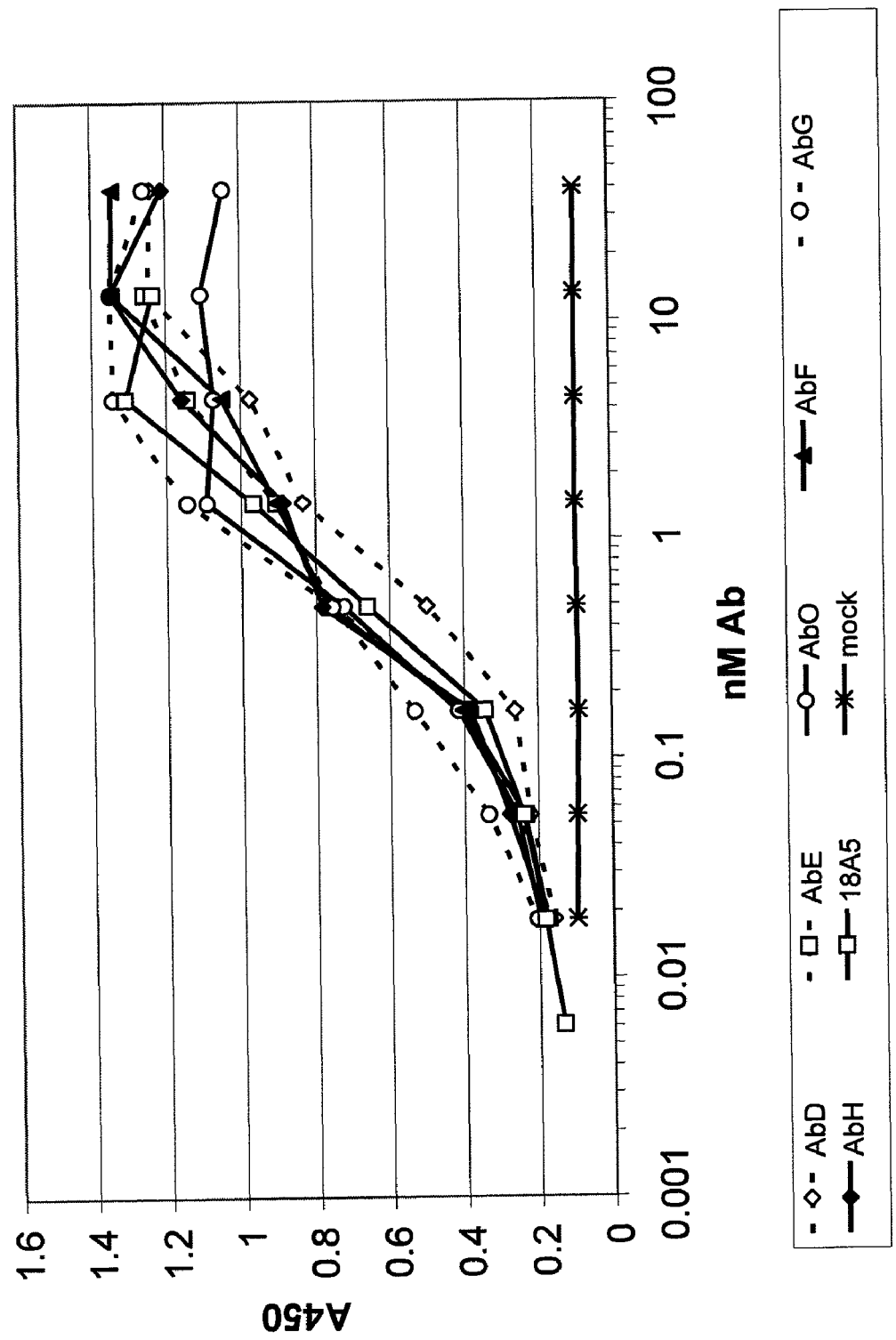
Figure 6C:
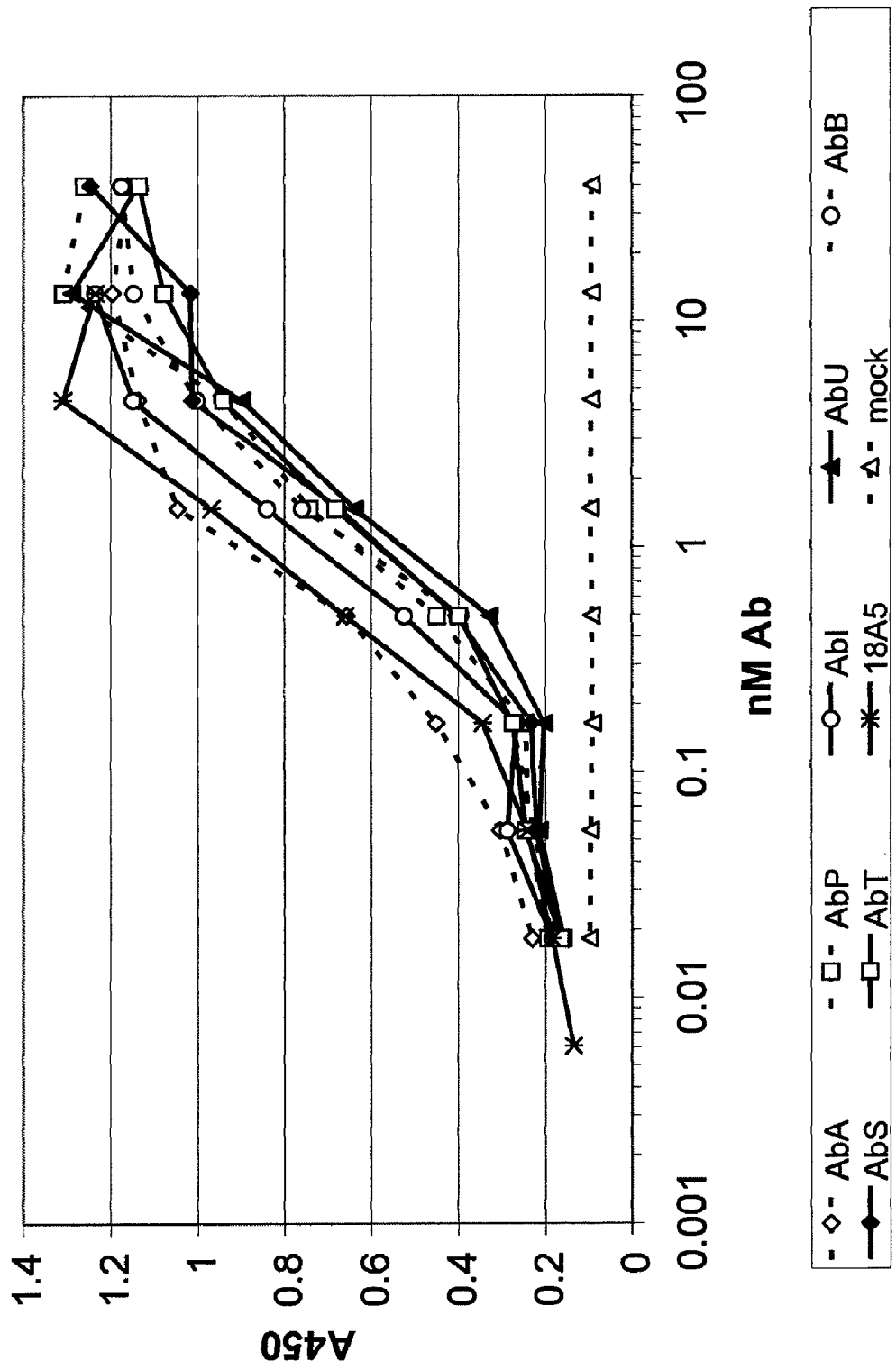
Figure 6D:
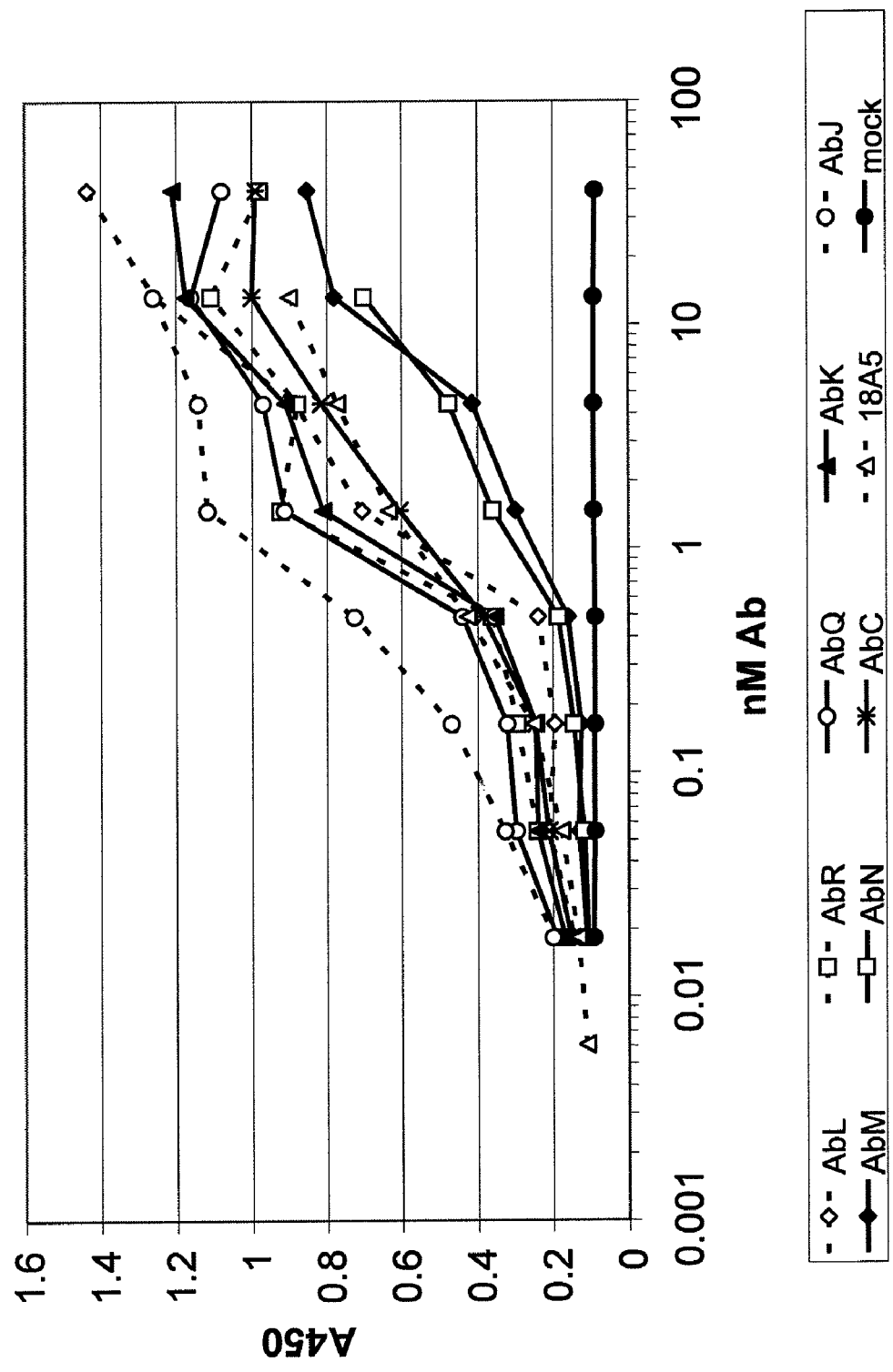
Figure 6E:
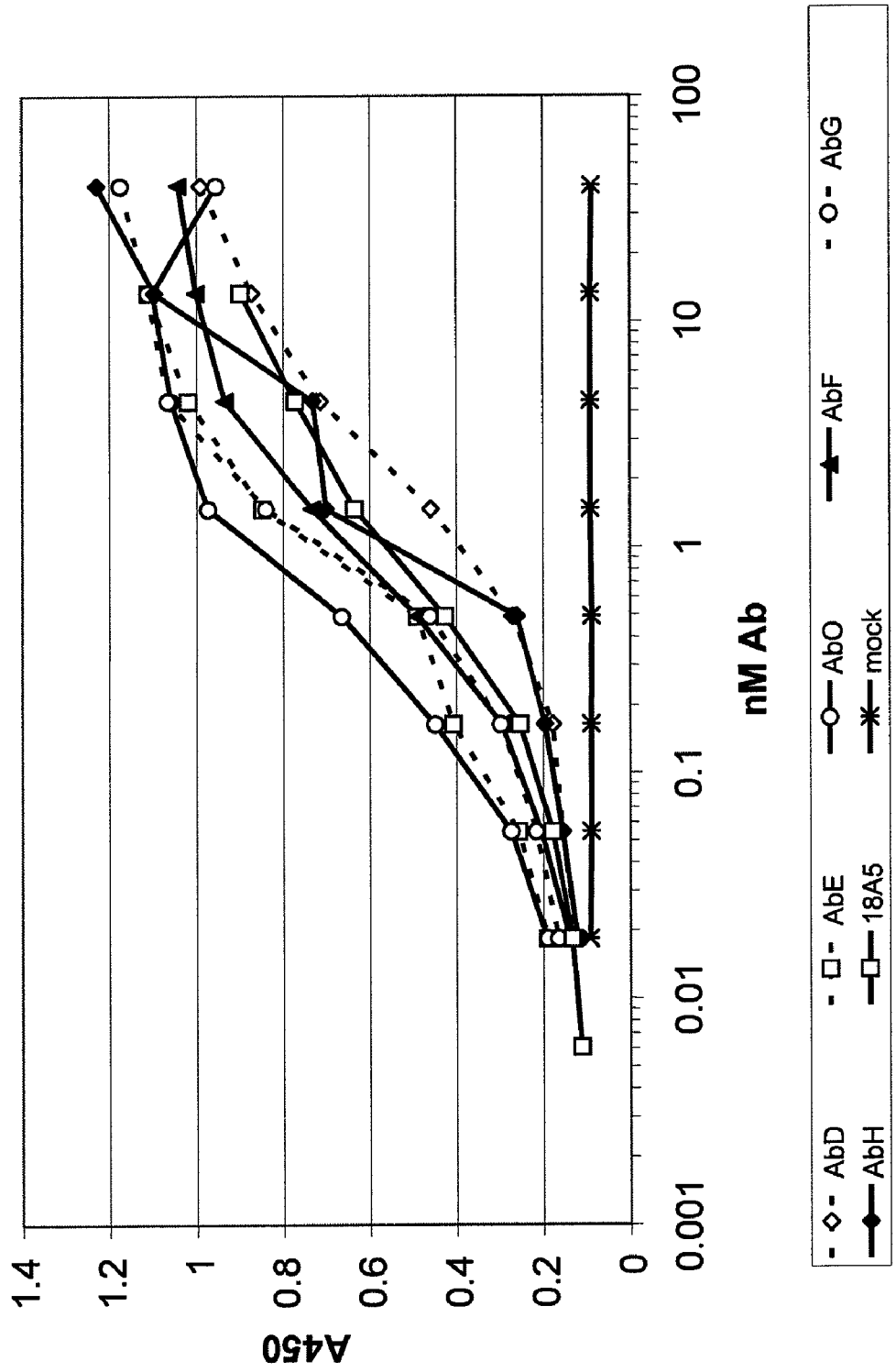
Figure 6F:
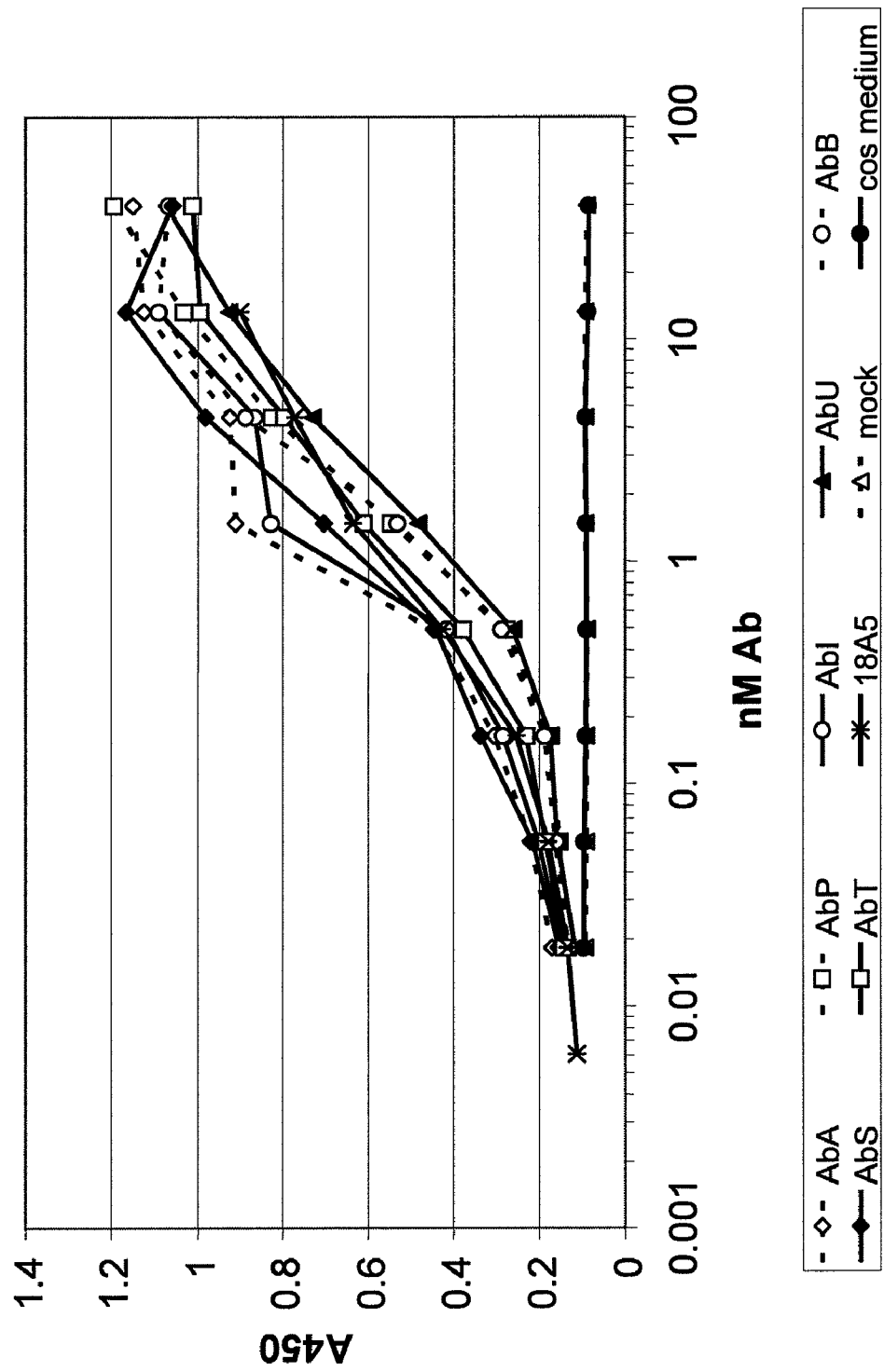
Figure 6G:
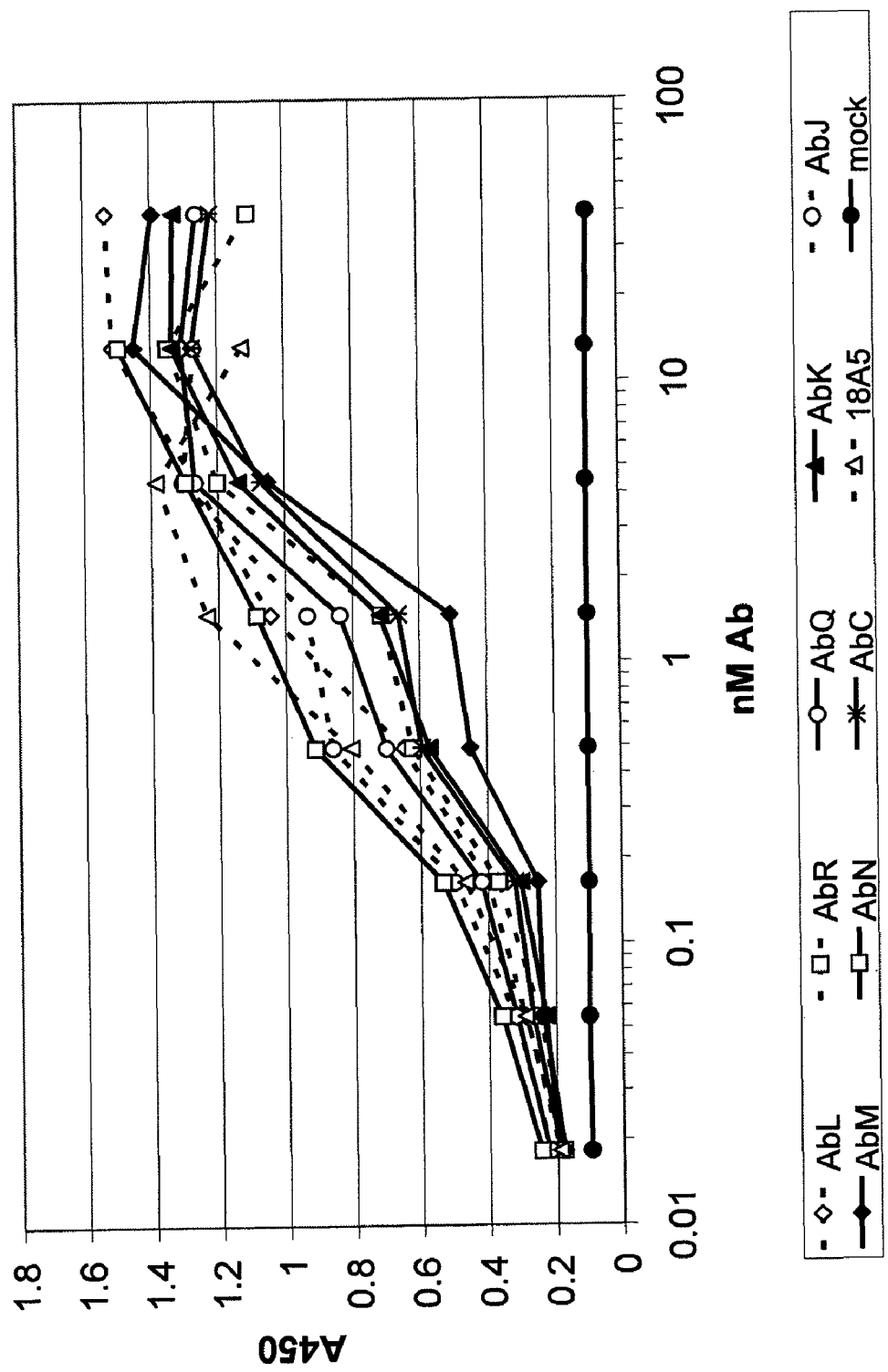
Figure 6H:
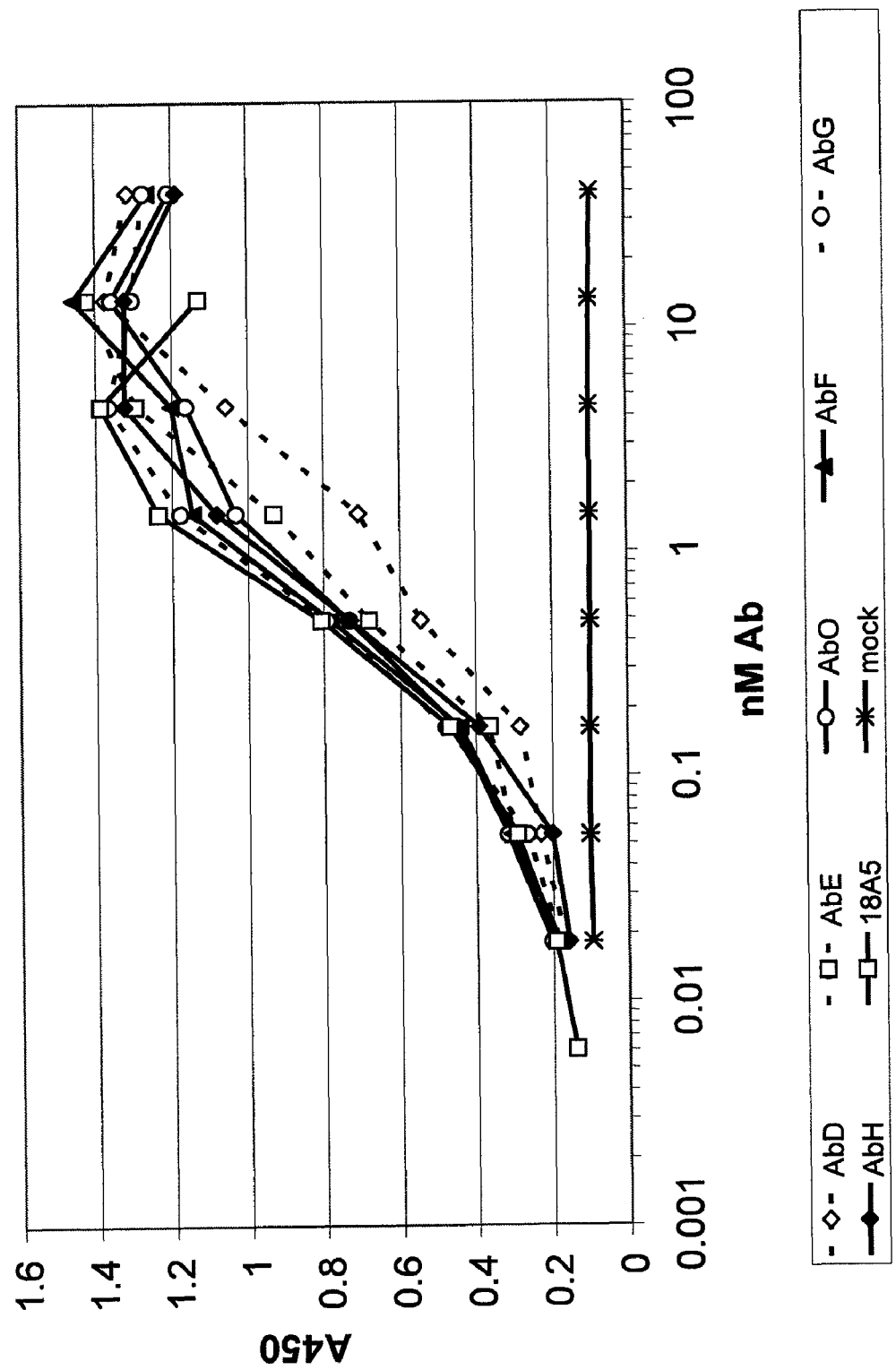
Figure 6I:
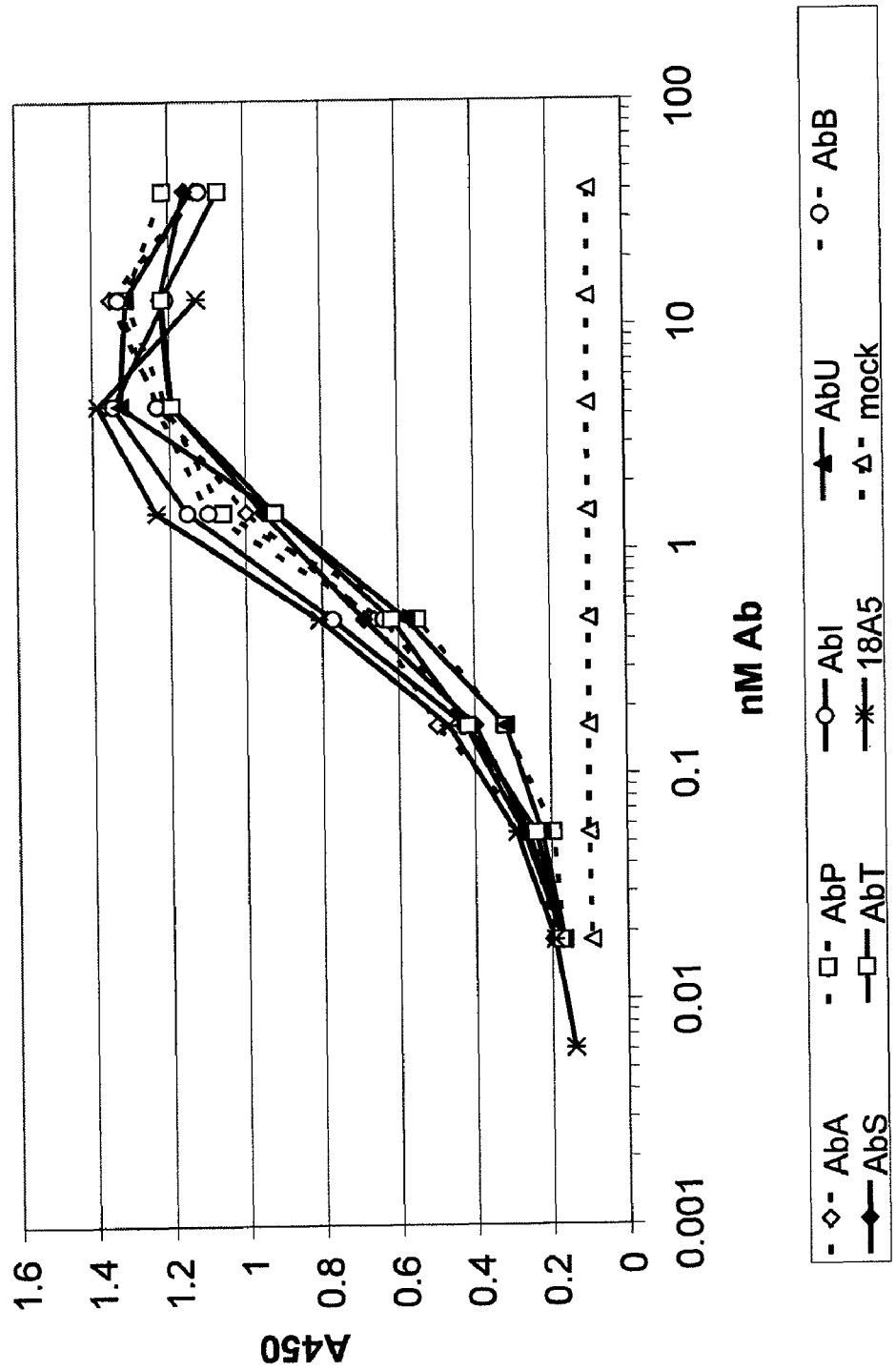
Figure 6J:
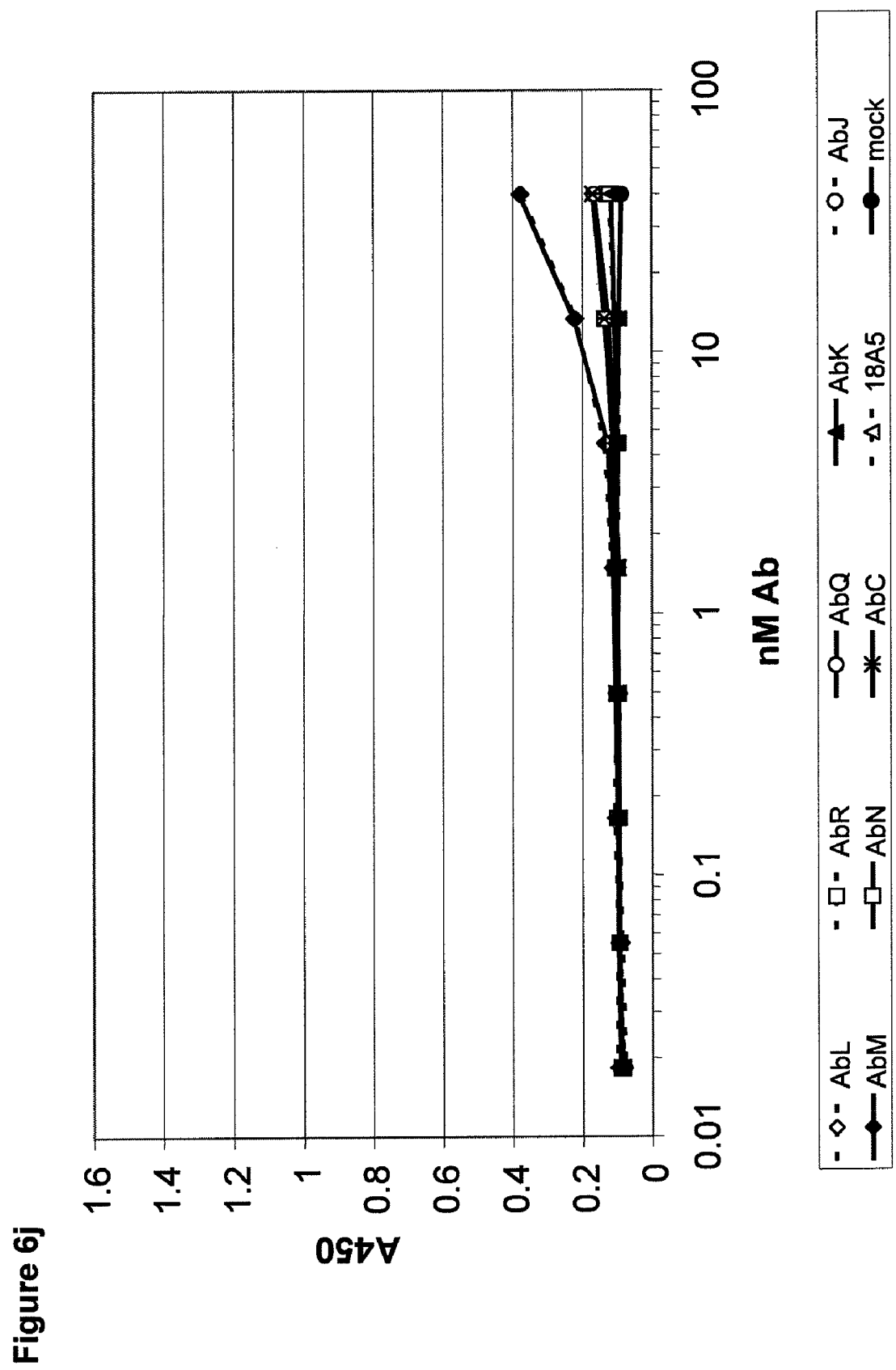
Figure 6K:
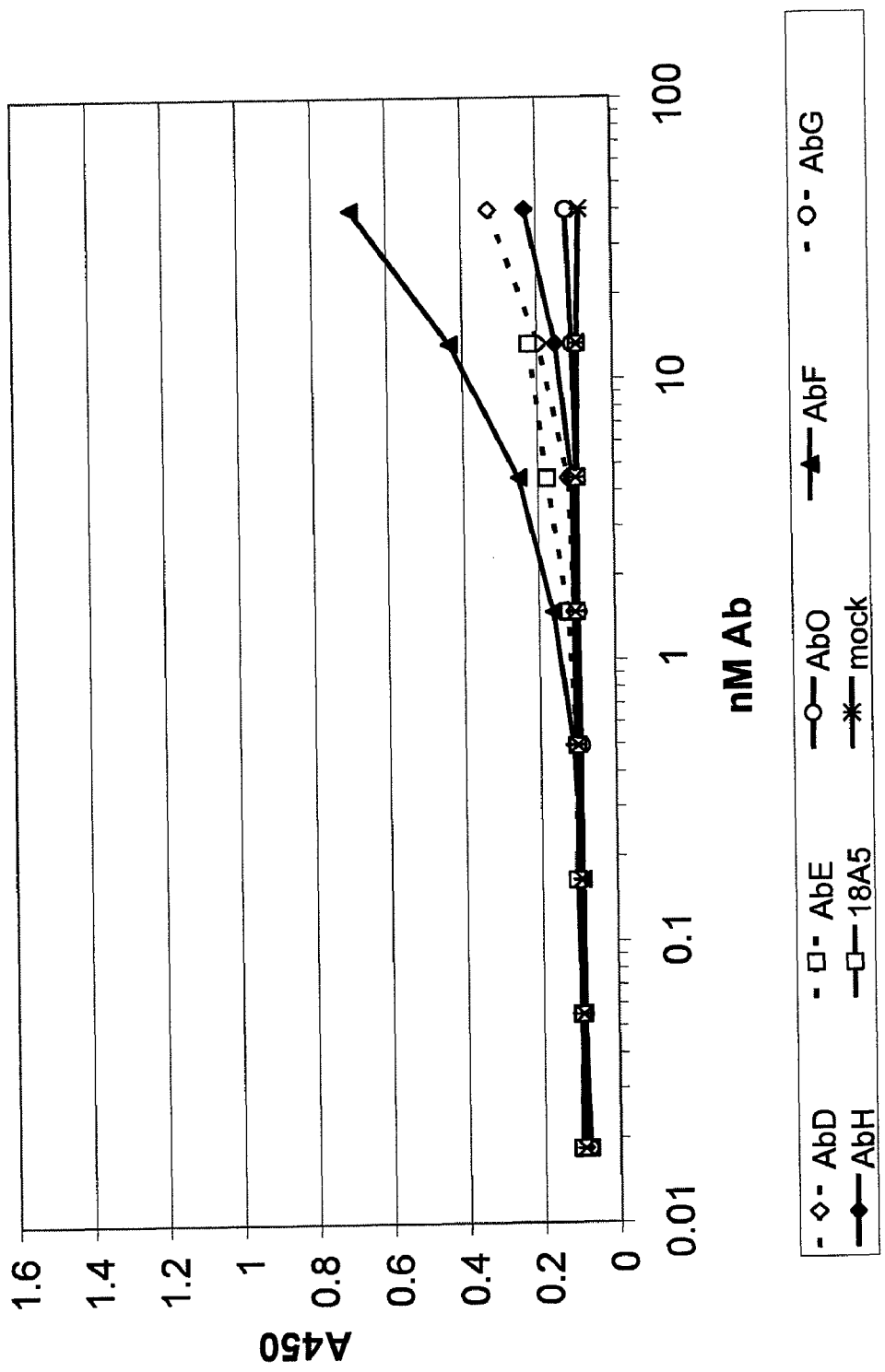
Figure 6I:
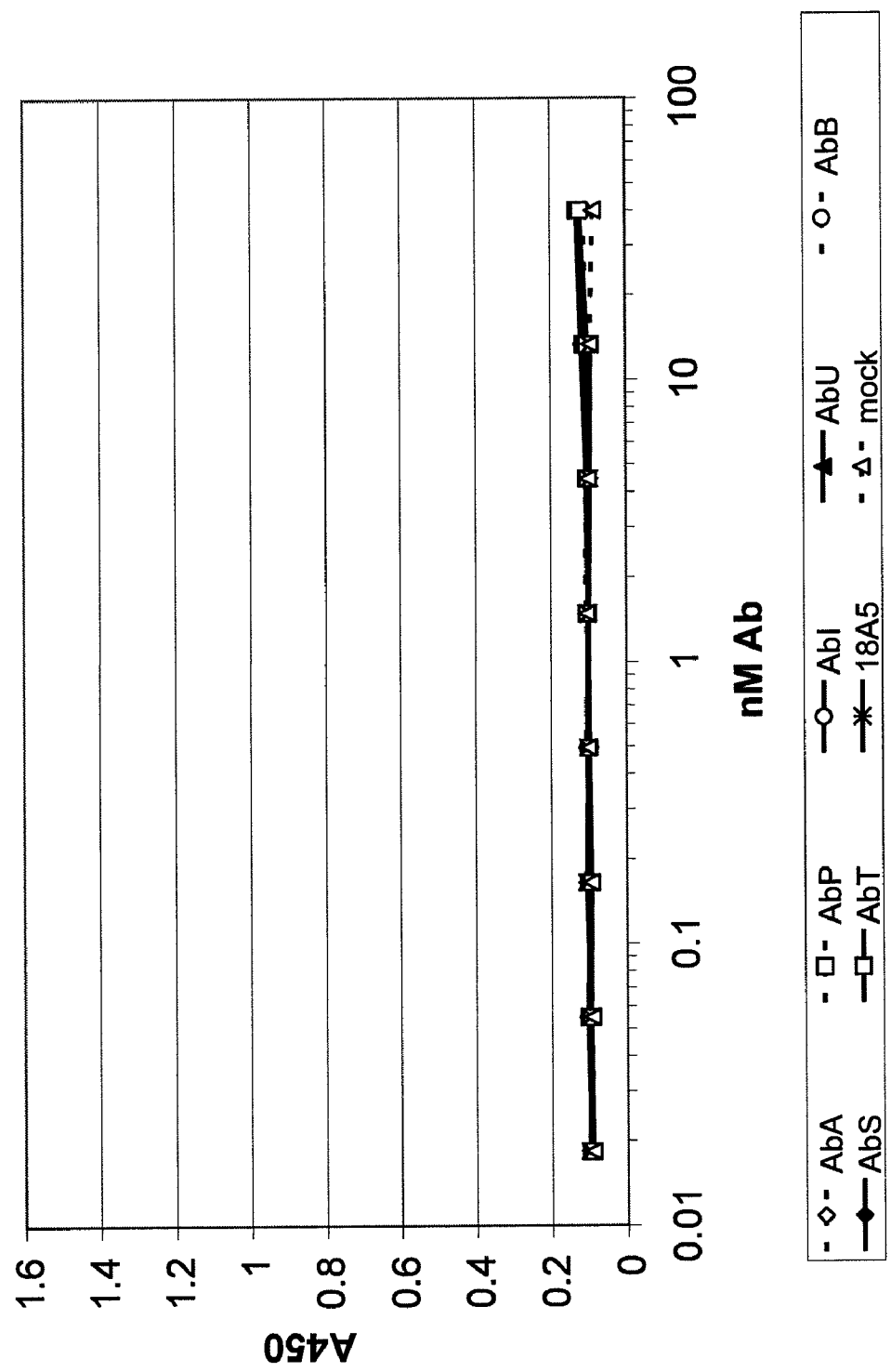

All of the twenty-one IgGs bound to CHO cells transiently expressing human (FIGS. 6a-c), rat (FIGS. 6d-f), or cynomolgus monkey (FIGS. 6g-i) IL-21R. Most showed no binding above background to a control protein (human gamma (γ) common chain) transiently expressed on CHO cells, but a subset of IgGs (AbD, AbE, AbF, AbH, AbL, and AbM) bound above background at 13 nM or greater (FIGS. 6j-1). Data are summarized in Table 6.

TABLE 6

Summary of Neutralization of Human and Murine IL-21R Activity in Cell-proliferation Assays and Binding to Human, Rat, and Cynomolgus Monkey IL-21R Expressed on CHO Cells

| Binding Protein | Human IL-21R-BaF3 Proliferation IC$_{50}$ (nM) | Human IL-21R-TF1 Proliferation IC$_{50}$ (nM) | Murine IL-21R-BaF3 Proliferation IC$_{50}$ (nM) | Human IL-21R Binding (13 nM Ab in Cell ELISA; A450) | Rat IL-21R Binding (13 nM Ab in Cell ELISA; A450) | Cynomolgus Monkey IL-21R Binding (13 nM Ab in Cell ELISA; A450) | Human Gamma Common Binding (13 nM Ab in Cell ELISA; A450) |
|---|---|---|---|---|---|---|---|
| AbA | 0.97 | 3.80 | 0.08 | 1.196 | 1.124 | 1.352 | 0.111 |
| AbB | 1.14 | 3.34 | 0.421 | 1.147 | 1.09 | 1.333 | 0.107 |
| AbC | 0.82 | 3.36 | 0.03 | 1.218 | 0.999 | 1.277 | 0.137 |
| AbD | 0.91 | 2.67 | 0.01 | 1.247 | 0.874 | 1.375 | 0.197 |
| AbE | 0.56 | 2.28 | 0.04 | 1.257 | 1.111 | 1.423 | 0.223 |
| AbF | 0.54 | 2.41 | 0.304 | 1.347 | 1.001 | 1.458 | 0.433 |
| AbG | 0.77 | 3.84 | 0.07 | 1.35 | 1.112 | 1.304 | 0.108 |
| AbH | 0.94 | 3.64 | 0.327 | 1.35 | 1.097 | 1.324 | 0.152 |
| AbI | 1.00 | 3.80 | 0.224 | 1.237 | 1.088 | 1.209 | 0.107 |
| AbJ | 0.65 | 4.60 | 0.4 | 1.217 | 1.261 | 1.273 | 0.126 |
| AbK | 0.98 | 4.00 | 0.079 | 1.364 | 1.175 | 1.338 | 0.108 |
| AbL | 0.68 | 4.25 | 0.227 | 1.454 | 1.257 | 1.514 | 0.219 |
| AbM | 1.08 | 4.22 | 0.125 | 1.197 | 0.78 | 1.45 | 0.224 |
| AbN | 0.50 | 1.59 | 0.435 | 1.214 | 0.702 | 1.497 | 0.136 |
| AbO | 0.52 | 2.91 | 0.065 | 1.107 | 1.101 | 1.358 | 0.108 |
| AbP | 0.75 | 3.48 | 0.03 | 1.308 | 1.03 | 1.313 | 0.112 |
| AbQ | 0.68 | 4.62 | 0.153 | 1.255 | 1.161 | 1.31 | 0.125 |
| AbR | 0.87 | 3.94 | 0.302 | 1.334 | 1.108 | 1.35 | 0.109 |
| AbS | 1.53 | 5.00 | 0.04 | 1.017 | 1.166 | 1.224 | 0.118 |
| AbT | 0.67 | 3.26 | 0.093 | 1.078 | 0.994 | 1.219 | 0.102 |
| AbU | 0.73 | 3.13 | 0.184 | 1.289 | 0.927 | 1.314 | 0.104 |

Example 9.3

Anti-IL-21R IgG Binding to Transiently Expressed Rat and Cynomolgus Monkey IL-21R A subset of binding proteins was tested for binding to rat, cynomolgus monkey, human IL-21R, or human IL-2R-γ common subunit expressed transiently on the surfaces of CHO-PA-Dukx cells. Cells were transfected 48 hr prior to the assay. On the day of the assay, cells were washed gently 5× in PBS containing 0.9 mM CaCl$_2$ and 0.45 mM MgCl$_2$ (PBS/CaMg) on an automated plate washer (Titertek, Huntsville, Ala.), and blocked for 1 hr at RT in PBS/CaMg/5% nonfat dry milk. Conditioned media from transiently expressed anti-IL-21R IgGs were serially diluted in blocking buffer and added to the cells in the blocked plates for 1 hr at RT. Cells were washed 5× with PBS/CaMg and then incubated with horseradish peroxidase-conjugated anti-human IgG for 1 hr at RT. Cells were then washed 10× in PBS/CaMg and all of the wash Example 9.4

BIACORE™ Analysis of Selectivity of Anti-IL-21R IgG Binding to Human IL-21R

The specificity of binding of a subset of transiently expressed anti-IL-21R binding proteins (here antibodies) was tested on a BIACORE™ 2000 surface plasmon resonance instrument. Anti-human-IgG, anti-murine immunoglobulin antibodies, and murine IL-21R-H/F were immobilized onto a research-grade carboxymethyl-dextran chip (CM5) using standard amine coupling. The sensor chip surface was activated with EDC/NHS for 7 min at a flow rate of 20 µl/min. The first flow cell was used as reference surface to correct for bulk refractive index, matrix effects, and nonspecific binding. Capture antibodies (7,150 resonance units (RU) of anti-human-Fc antibody (Invitrogen Corporation, Carlsbad, Calif.) on flow cell 2 and 7,500 RU of anti-murine-Fc antibody on flow cell 3) were diluted to 10 µg/ml in sodium acetate buffer (pH 5.0) and injected over the activated surface. Remaining activated groups were blocked with 1.0 M ethanolamine (pH 8.0). The molecular weights of the anti-human IgG and the anti-murine IgG were both 150 kD, and the molecular weight of the IL-21R monomer was 27 kD.

Conditioned media containing anti-IL-21R antibodies and antibody controls (murine anti-human IL-2Rβ and murine anti-human IL-4R(R&D Systems, Minneapolis, Minn.); human anti-human IL-13 (Wyeth, Cambridge, Mass.)) were diluted in HBS/EP buffer supplemented with 0.2% bovine serum and injected onto all four flow cells of the BIACORE™ chip, capturing 500-700 (RU) of antibody on the species-appropriate capture antibody. Following a 5 sec washing period, 50 nM solutions of a positive control protein (murine IL-21R-H/F), two human proteins related to IL-21R (human IL-2Rβ and human sIL-4R(R&D Systems)), or an unrelated His/FLAG-tagged protein (human IL-13-H/F), were injected over the captured antibodies on the chip. The association and dissociation phases were monitored for 120 and 180 sec, respectively, followed by two 5 μl injections of glycine (pH 1.5) to regenerate a fully active capturing surface. All binding experiments were done at 25° C. in HBS/EP buffer. Blank and buffer effects were subtracted for each sensorgram using double referencing.

Figure 7B:
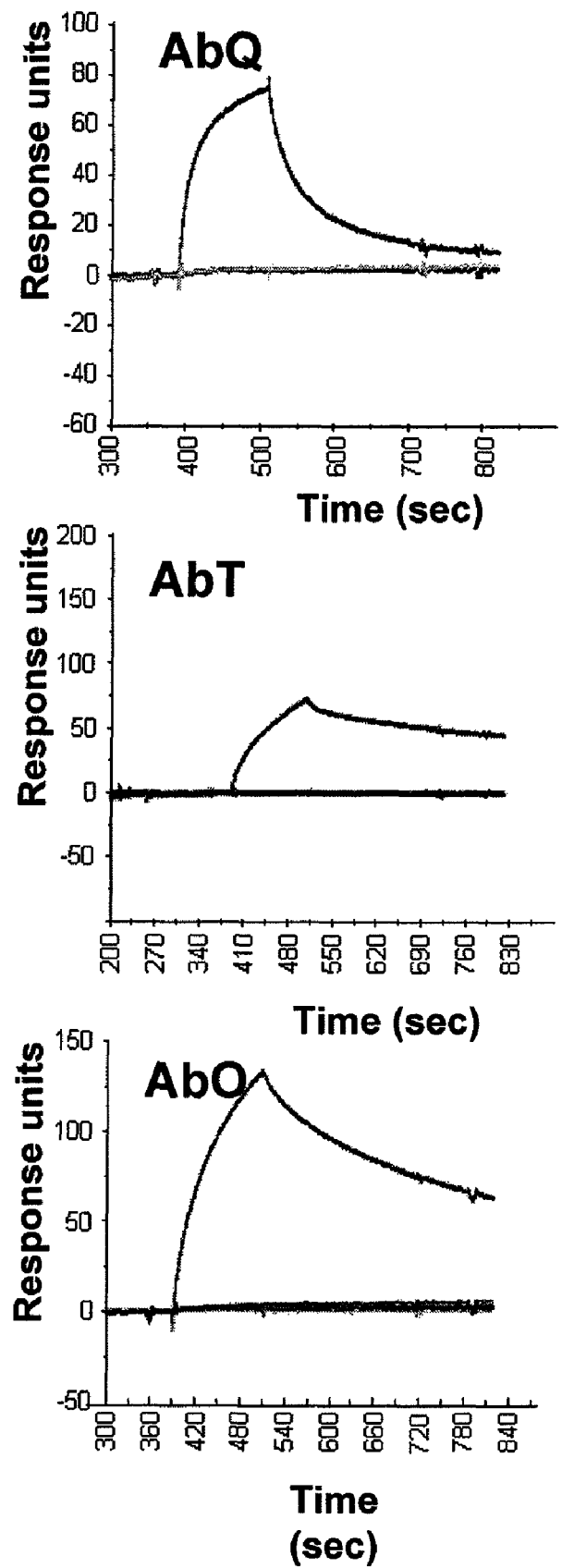
FIG. 7b, AbQ, AbT, AbO.
Figure 7C:
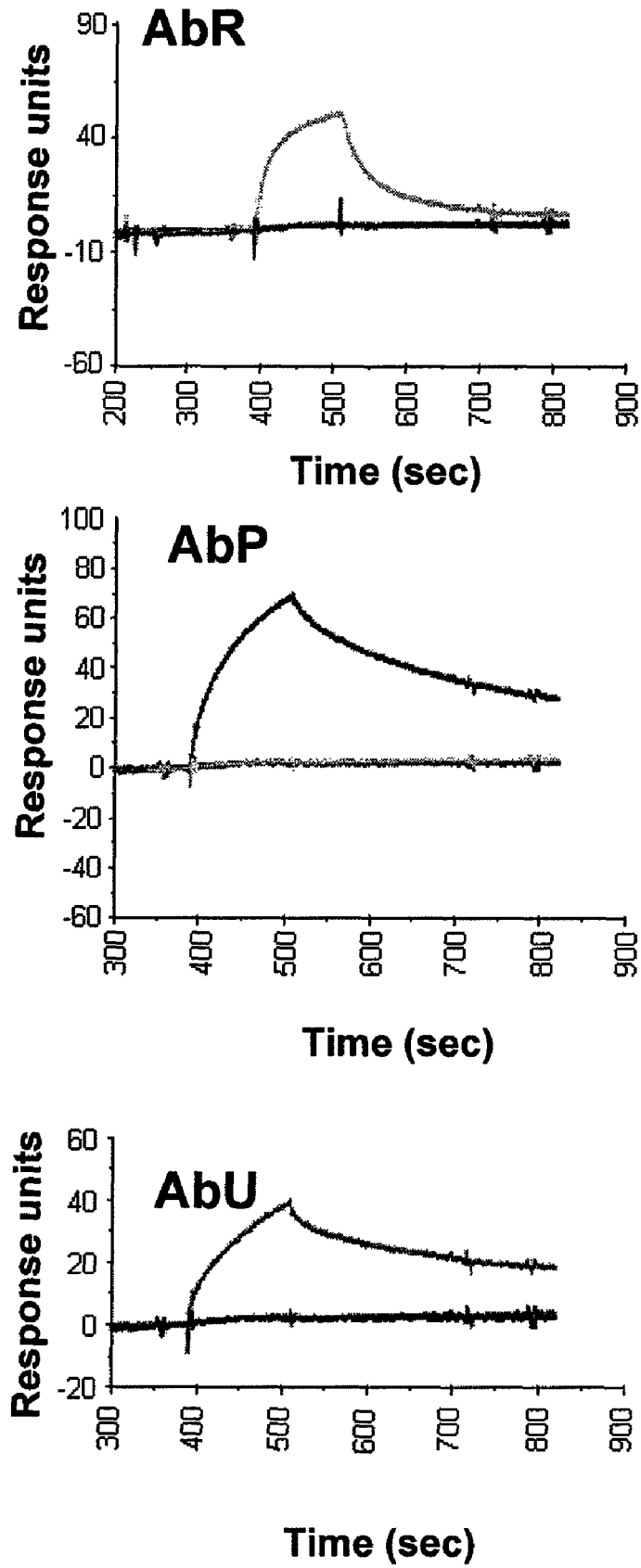
FIG. 7c, AbR, AbP, and AbU), measured by surface plasmon resonance. The anti-IL-21R antibodies were captured on anti-human IgG, and subsequent binding to either murine IL-21R-H/F, human IL-13-H/F, human IL-2Rβ, or human soluble IL-4R was measured in a BIACORE™ (GE Healthcare, Piscataway, N.J.) instrument.

All of the anti-IL-21R antibodies tested (18A5 antibody and AbA-AbU) showed clear binding to murine IL-21R, but no binding to the IL-21R-related proteins human IL-2Rβ and human soluble IL-4R, or to the unrelated His/FLAG-tagged protein human IL-13-His/FLAG (FIGS. 7a-c). Controls indicated that IL-2Rβ and human soluble IL-4R could be captured by specific anti-IL-2Rβ and anti-IL-4R antibodies (FIG. 7d).

Example 9.5

Purification of Transiently Expressed Antibodies

Seven antibodies (human IgG1 triple-mutant versions: AbS, AbT, AbO, AbP, and AbU; and double-mutant versions: AbQ and AbR) were transiently expressed in cos-7 cells and purified for further analysis. In addition, three versions of AbT with human IgG tails expected to have different levels of Fc receptor binding (wild-type IgG1, IgG4, and IgG1 double-mutants) were also prepared. The TRANSIT® protocol described above was followed, except that 25 μg of each plasmid was used to transfect cells in each of eight T-175 flasks. Following the first harvest of conditioned medium, fresh R1CD1 was added and then collected after an additional 72 hr. Conditioned media were pooled and filtered on a 0.22 μm filter. Antibodies were loaded onto protein A resin, eluted with 20 mM citric acid/150 mM sodium chloride (pH 2.5), neutralized with Tris (pH 8.5), and dialyzed into PBS.

Example 9.6

BIACORE™ Analysis of Antibody Binding to Human and Murine IL-21R

The kinetics of binding of anti-IL-21R antibodies to human and murine IL-21R-H/F was tested on a BIACORE™ surface plasmon resonance instrument. Anti-human IgG antibodies (Invitrogen Corporation) were immobilized onto a research-grade carboxy-methyl-dextran chip (CM5) using standard amine coupling. The surface was activated with EDC/NHS for 7 min at a flow of 20 μl/min. The first flow cell was used as a reference surface to correct for bulk refractive index, matrix effects, and nonspecific binding. The anti-human-Fc antibody was diluted to 20 μg/ml in 10 mM sodium acetate buffer (pH 5.0), and 2950-3405 resonance units (RU) were captured on each of the four flow cells. Remaining activated groups were blocked with 1.0 M ethanolamine-HCl (pH 8.5).

Figure 8A:
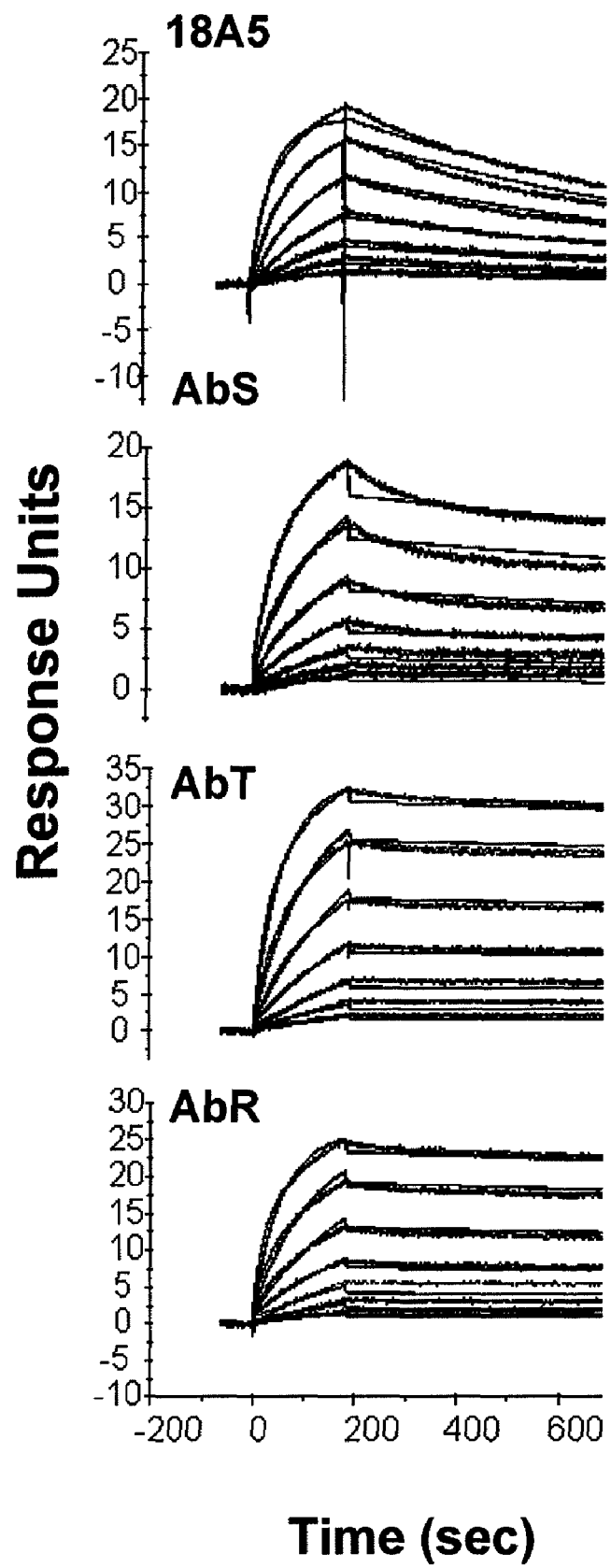
FIG. 8(a-d) depicts the binding of anti-IL-21R antibodies to human and murine IL-21R. The indicated human anti-IL-21R antibodies were captured on anti-human IgG immobilized on a BIACORE™ chip. Varying concentrations of human IL-21R-His/FLAG (FIGS. 8a-b) and murine IL-21R-His/FLAG (FIGS. 8c-d) were allowed to flow over the chip, and binding and dissociation were monitored.
Figure 8B:
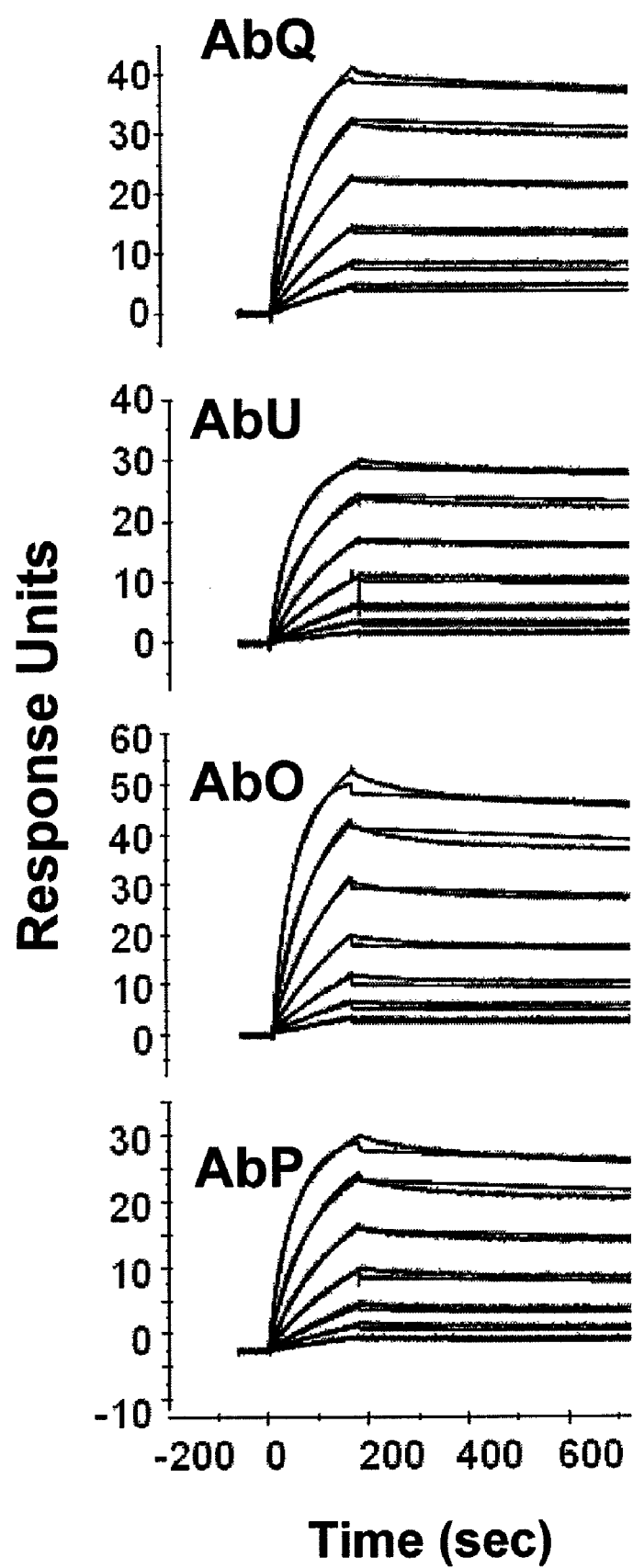
Figure 8D:
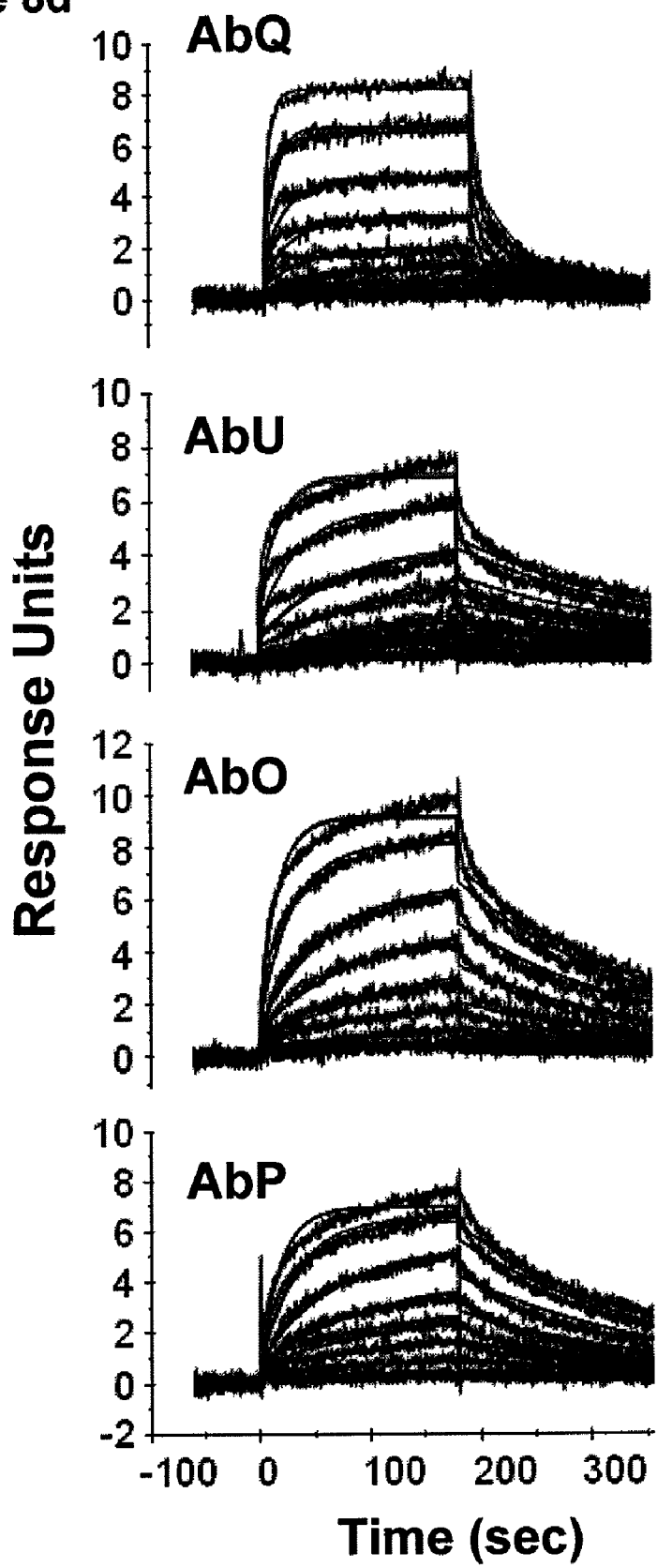
Figure 9A:
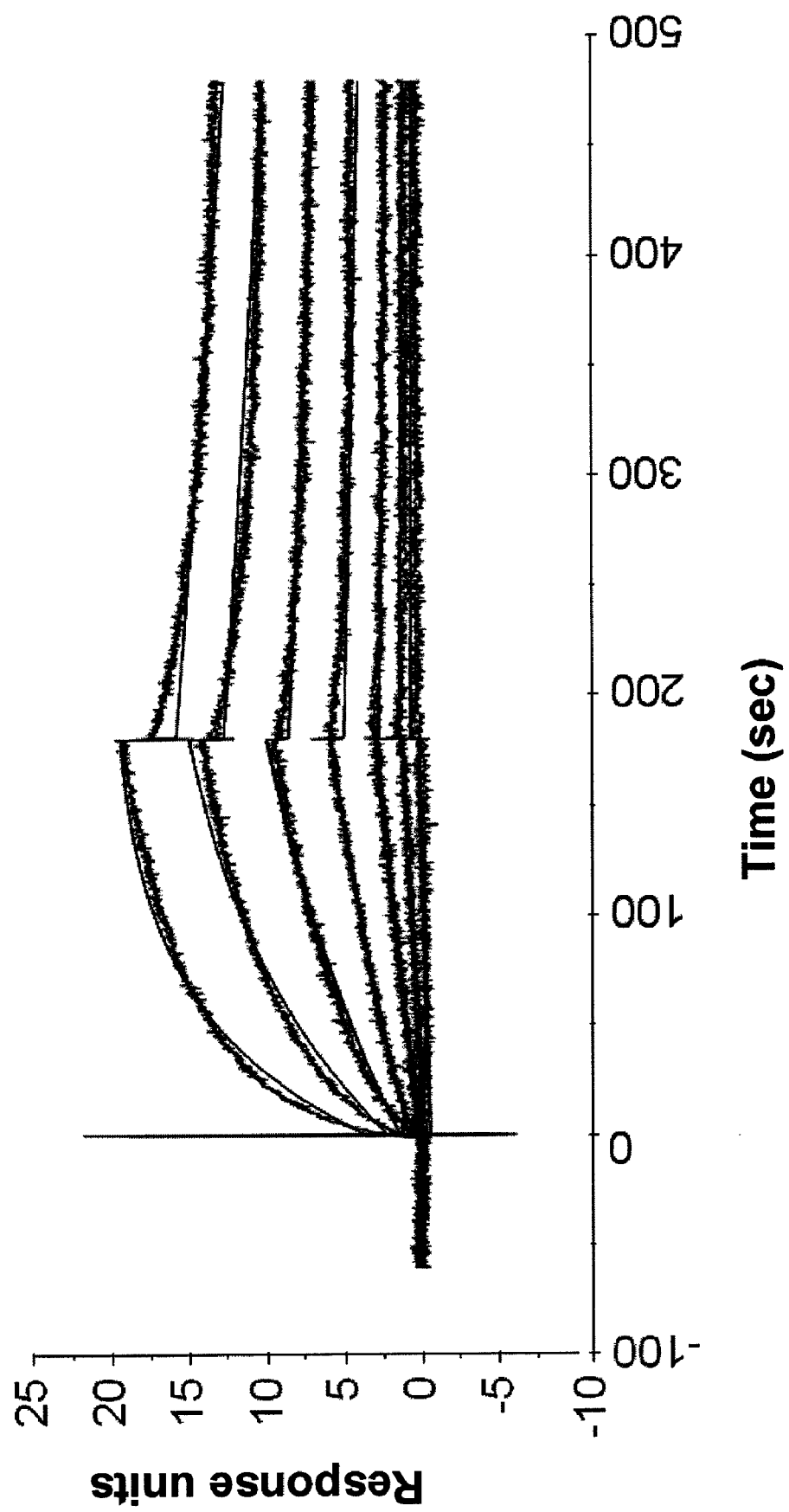
FIG. 9a shows cynomolgus monkey IL-21R-His/FLAG binding to AbS.
Figure 9B:
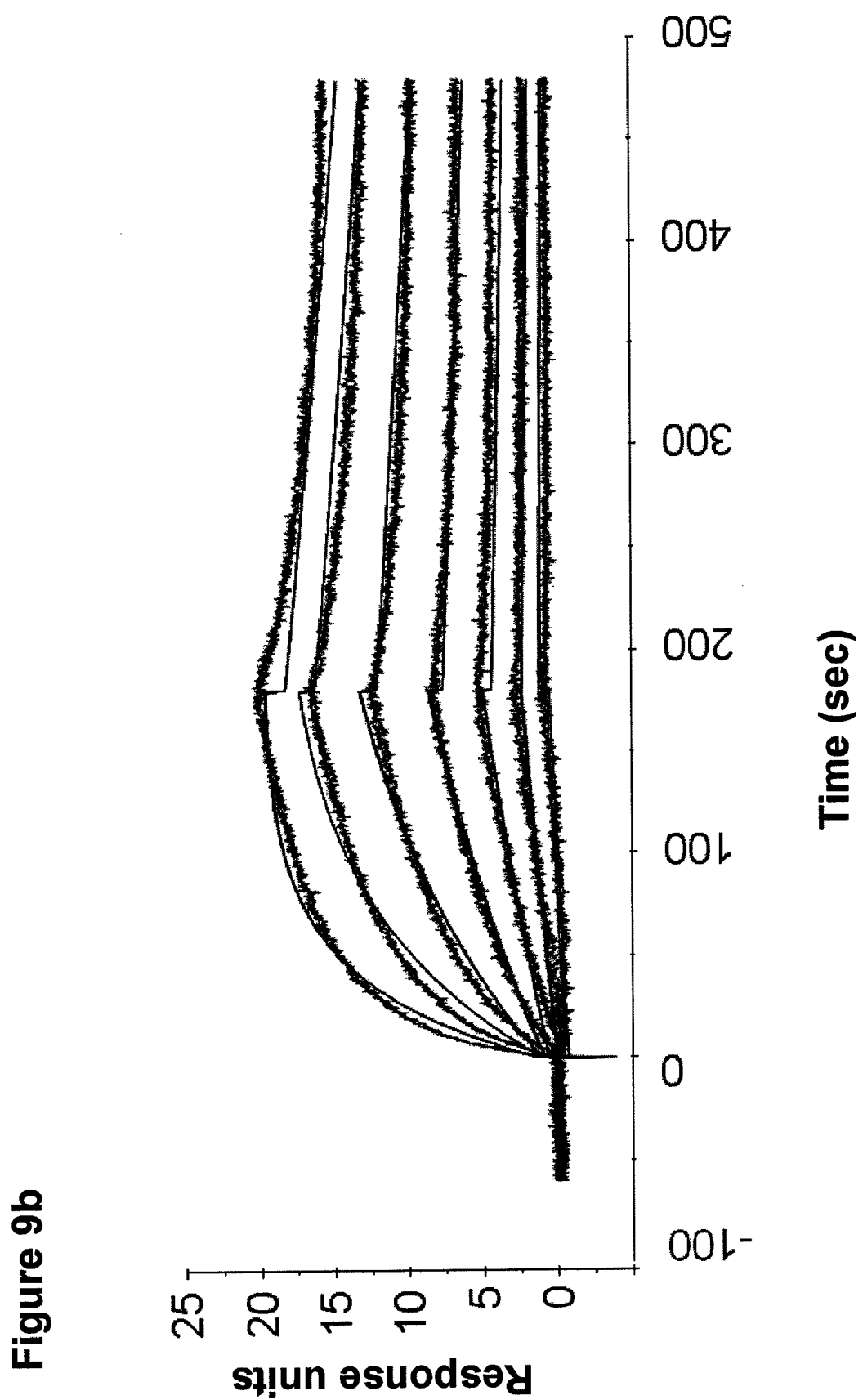
FIG. 9b shows human IL-21R-His/FLAG binding to AbS.
Figure 9C:
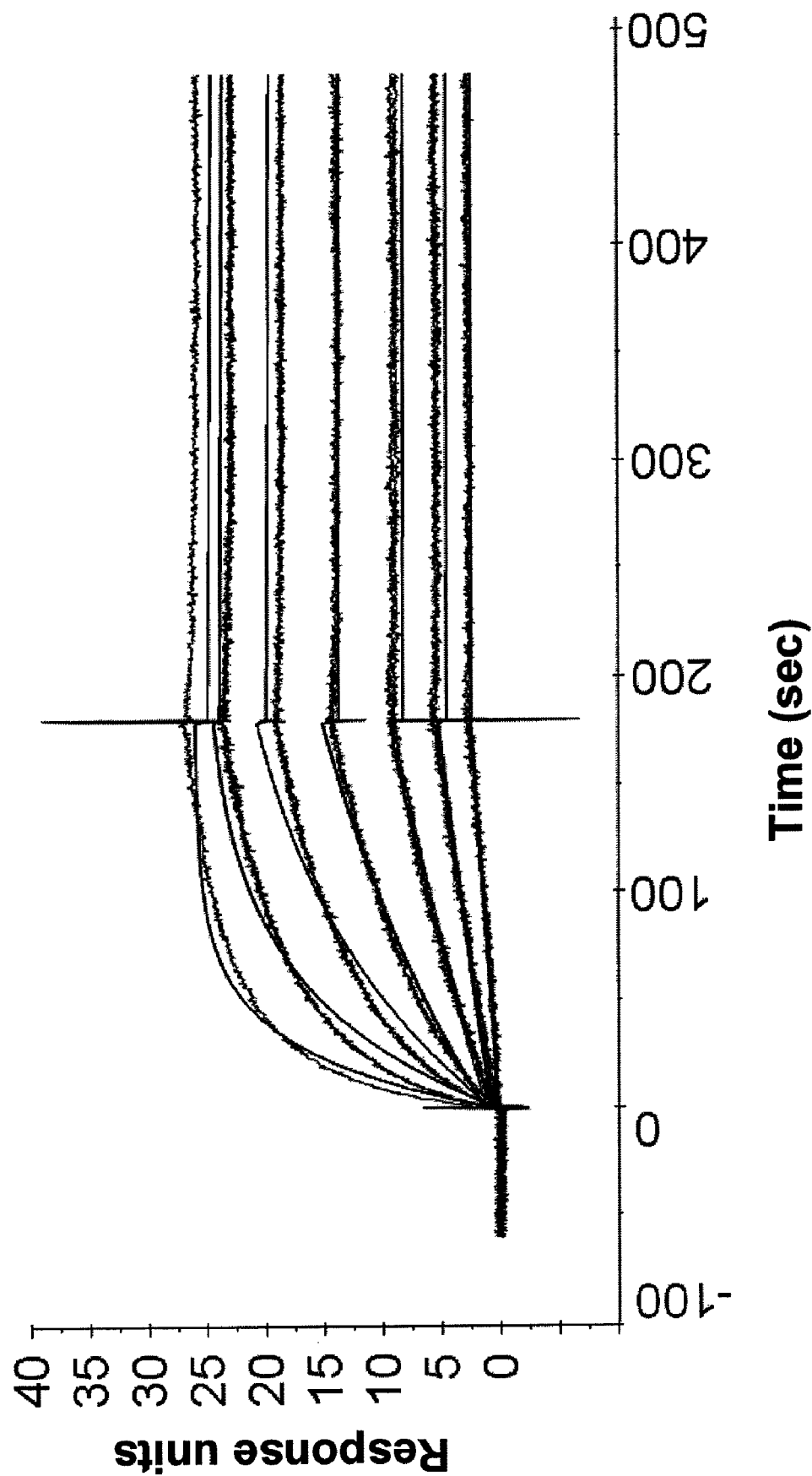
FIG. 9c shows cynomolgus monkey IL-21R-His/FLAG binding to AbT.
Figure 9D:
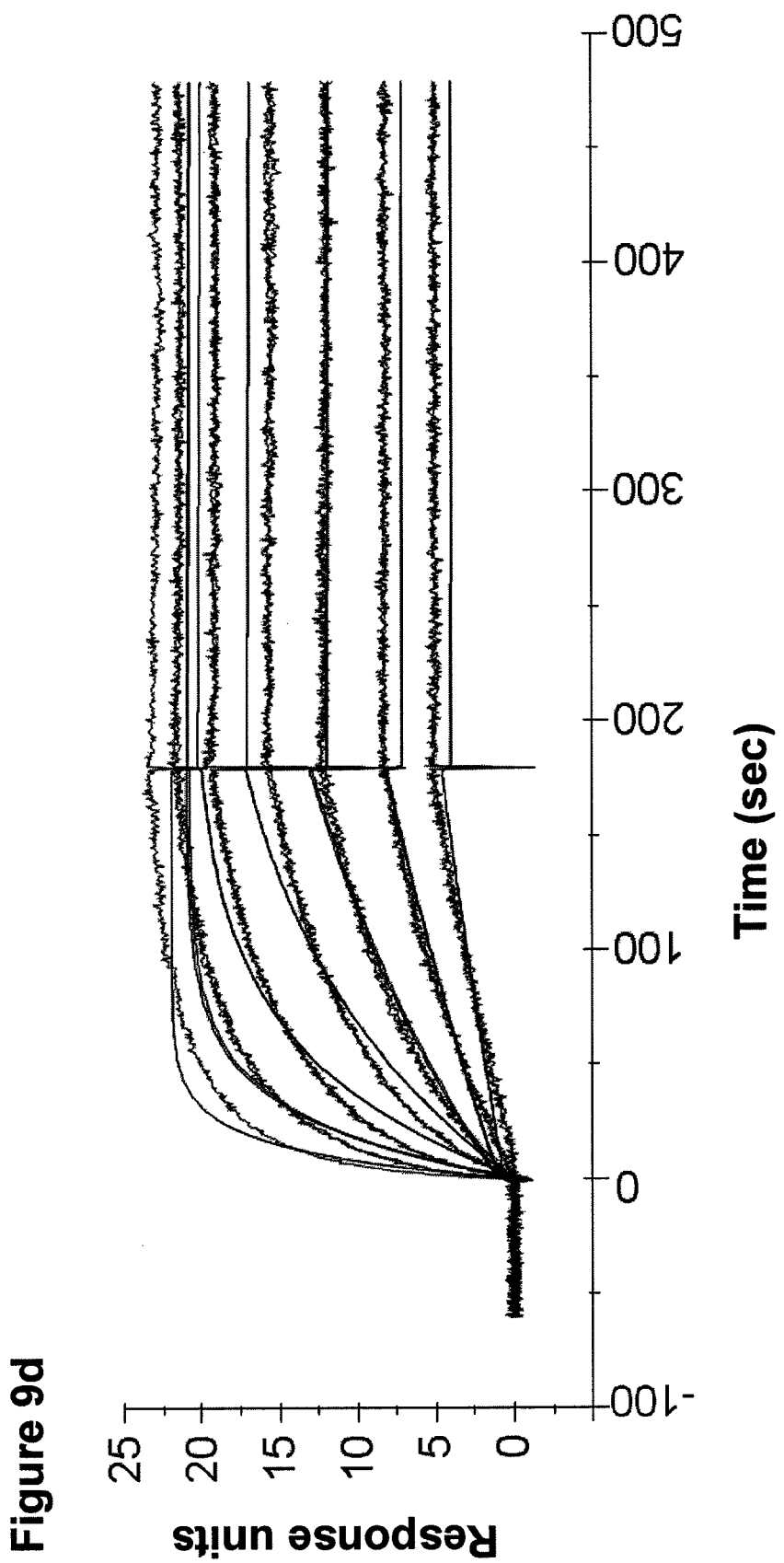
FIG. 9d shows human IL-21R-His/FLAG binding to AbT.

Anti-IL-21R antibodies were diluted to 0.1-0.2 μg/ml in HBS/EP buffer supplemented with 0.2% bovine serum albumin and loaded onto the BIACORE™ chip. Following a brief washing period, solutions of 0-100 nM human IL-21R-H/F or 10-500 nM murine IL-21R-H/F were injected over the chip at a flow rate of 50 μl/min. The association phase was run for 3 min for human and murine IL-21R kinetics, and the dissociation phase was monitored for 15 min for hIL-21R and for 5 min for mIL-21R, followed by two 10 μl injections and one 30 μl injection of glycine (pH 1.5), to regenerate a fully active capturing surface. All binding experiments were done at 25° C. in HBS/EP buffer, and the sample rack was kept at 15° C. Blank and buffer effects were subtracted for each sensorgram using double referencing. Sensorgrams are shown in FIGS. 8a-b (human IL-21R-His/FLAG) and 8c-d (murine IL-21R-His/FLAG). Binding kinetic parameters are shown in Table 7A, and additional kinetic data from a replicate experiment are shown in Table 7B.

In addition, AbS and AbT were tested for binding kinetics to cynomolgus monkey IL-21R-His/FLAG by the above-described protocol. Binding profiles to human and cynomolgus monkey IL-21R-H/F were similar for both AbS and AbT (FIG. 9). FIG. 9 shows cynomolgus monkey IL-21R-His/FLAG binding to AbS (9a); and to AbT (9c); and human IL-21R-His/FLAG binding to AbS (9b); and AbT (9d).

TABLE 7A

Kinetic Parameters of Anti-IL-21R Antibody Binding Human and Murine IL-21R-His/FLAG

| | Human IL-21R | | | Murine IL-21R | | |
| --- | --- | --- | --- | --- | --- | --- |
| Antibody | ka (1/Ms) | kd (1/s) | KD (M) | ka (1/Ms) | kd (1/s) | KD (M) |
| 18A5 | 2.43E+05 | 1.08E−03 | 4.43E−09 | 2.12E+05 | 1.53E−02 | 7.20E−08 |
| AbO | 2.41E+05 | 1.14E−04 | 4.75E−10 | 1.12E+05 | 5.49E−03 | 4.92E−08 |
| AbP | 1.94E+05 | 1.19E−04 | 6.15E−10 | 9.99E+04 | 5.08E−03 | 5.08E−08 |
| AbQ | 4.39E+05 | 9.34E−05 | 2.13E−10 | 3.01E+05 | 2.07E−02 | 6.88E−08 |
| AbR | 1.70E+05 | 9.61E−05 | 5.67E−10 | 7.65E+04 | 4.93E−03 | 6.45E−08 |
| AbS | 1.44E+05 | 2.91E−04 | 2.02E−09 | 1.99E+05 | 3.32E−03 | 1.67E−08 |
| AbT | 1.79E+05 | 6.78E−05 | 3.79E−10 | 2.11E+05 | 3.31E−03 | 1.57E−08 |
| AbU | 1.86E+05 | 8.18E−05 | 4.40E−10 | 9.81E+04 | 4.34E−03 | 4.42E−08 |

TABLE 7B

Kinetic Parameters of Anti-IL-21R Antibody Binding Human IL-21R-His/FLAG

| Antibody | Human IL-21R | | |
|---|---|---|---|
| | ka (1/Ms) | kd (1/s) | KD (M) |
| 18A5 | 3.04E+05 | 1.34E−03 | 4.40E−09 |
| AbP | 2.33E+05 | 1.02E−04 | 4.36E−10 |
| AbQ | 4.39E+05 | 9.34E−05 | 2.13E−10 |
| AbR | 2.48E+05 | 9.76E−05 | 3.94E−10 |
| AbS | 2.02E+05 | 3.05E−04 | 1.51E−09 |
| AbT | 2.73E+05 | 7.42E−05 | 2.72E−10 |
| AbU | 2.38E+05 | 7.83E−05 | 3.29E−10 |

Example 9.7

BIACORE™ Epitope Competition Assay

Figure 10A:
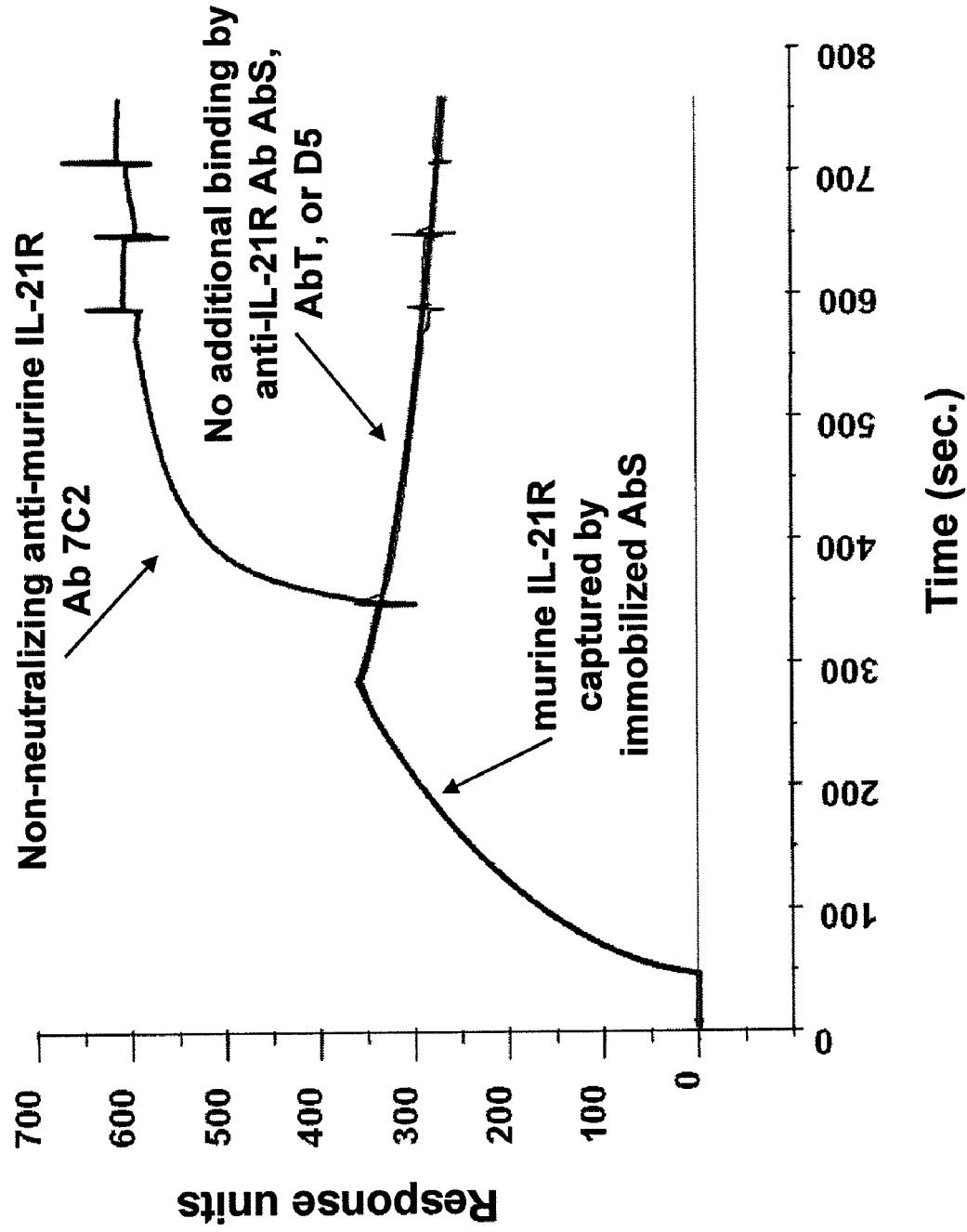
FIG. 10 depicts an epitope assessment of IL-21R antibodies. In the experiment depicted in FIG. 10a (see also illustration at left of Y-axis), murine IL-21R-H/F (His-Flag fusion protein) was captured by anti-IL-21R antibody AbS immobilized on a BIACORE™ chip. Additional anti-IL-21R antibodies (AbS, AbT, D5 (D5-20, a neutralizing anti-murine IL-21R antibody), and 7C2 (a nonneutralizing anti-murine IL-21R control antibody)) were flowed over the chip and their binding to the captured IL-21R-H/F was monitored. In the experiment depicted in FIG. 10b, human IL-21R-H/F was captured by anti-IL-21R antibody AbS immobilized on a BIACORE™ chip. Additional anti-IL-21R antibodies (AbS, AbT, and 9D2 (a nonneutralizing anti-human IL-21R control antibody)) were flowed over the chip and their binding to the captured IL-21R-H/F was monitored.

Antibodies AbS and AbT and the parental antibody 18A5 were immobilized directly onto a CM5 BIACORE™ chip. Murine IL-21R-H/F (100 nM) was allowed to flow over the chip for 300 sec, followed by a wash (100 sec), and then a 5 µg/ml solution of either AbS, AbT, D5, or a nonneutralizing anti-mIL-21R antibody (7C2) was allowed to flow over the surface. No additional binding was observed with AbS, AbT, and D5, indicating that their binding site on mIL-21R-H/F was blocked by concurrent binding to AbS, AbT, or 18A5 antibody (FIG. 10a). In contrast, the nonneutralizing control anti-IL-21R antibody 7C2 was able to bind to mIL-21R-H/F captured on AbS, AbT, or 18A5 antibody, indicating that this control antibody bound at a different epitope from the one bound by the capture antibodies.

Figure 10B:
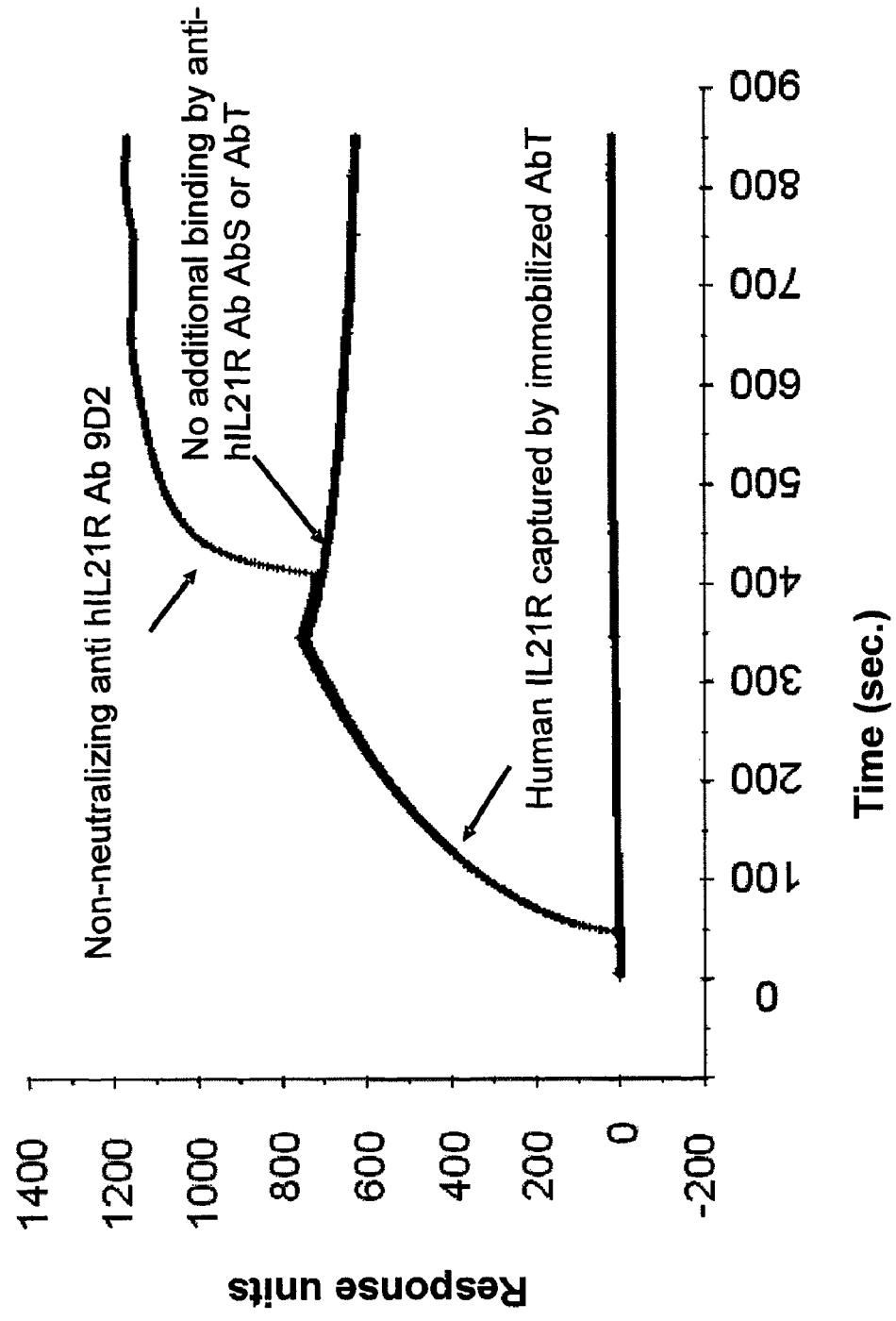

Similarly, AbS and AbT did not bind to human IL-21R-H/F captured by AbS or AbT immobilized on a CM5 BIACORE™ chip, while the control anti-human IL-21R antibody (9D2) was able to bind human IL-21R-H/F captured by AbS or AbT (FIG. 10b). This observation suggested that the binding site for AbS is blocked by concurrent binding by AbT, and vice versa.

Example 9.8

Cell-based Proliferation Assays

Figure 11A:
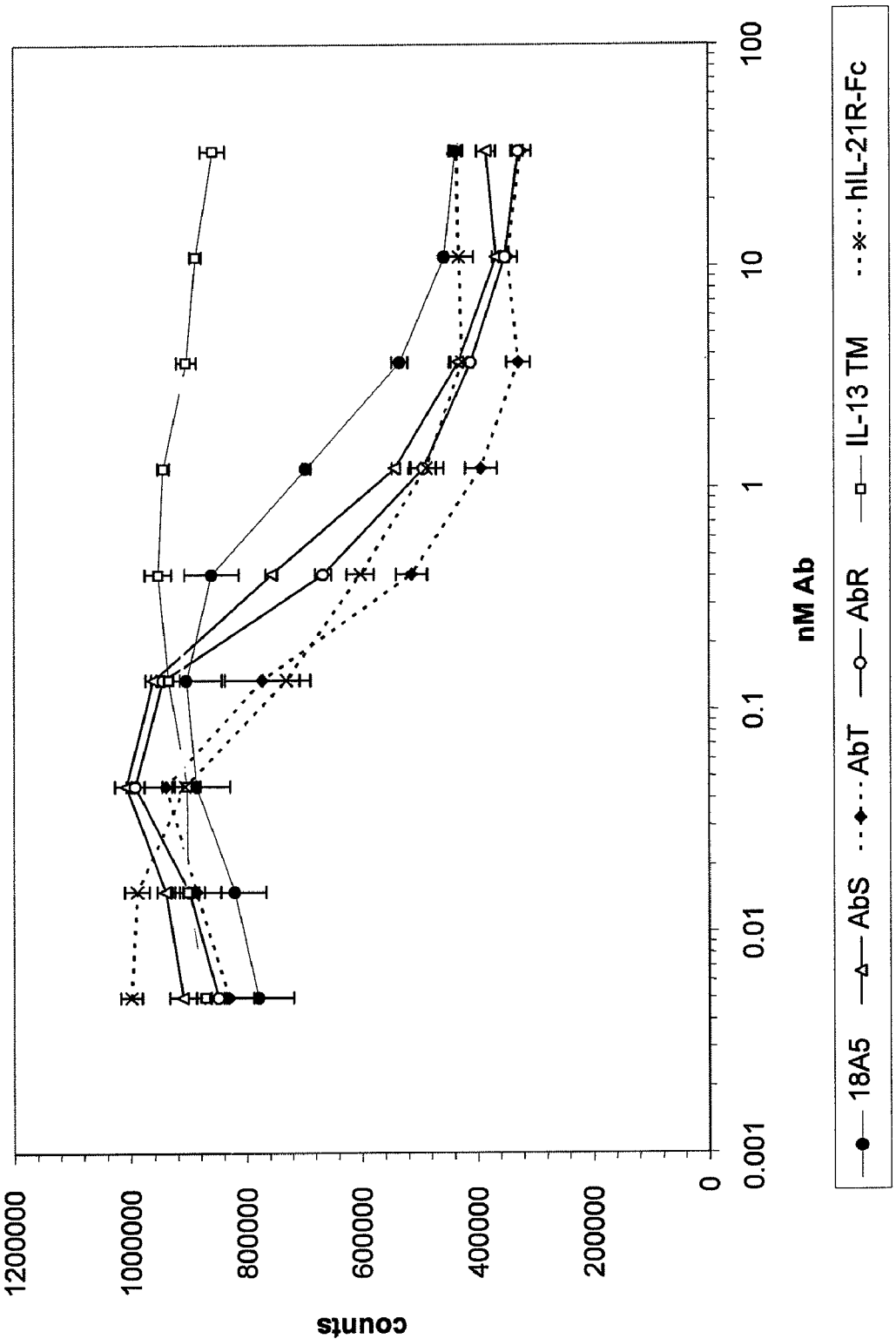
FIG. 11 depicts the neutralization of proliferation of human IL-21R-BaF3 cells and murine IL-21R-BaF3 cells by the indicated antibodies. Antibodies were added to cells. IL-21 was subsequently added and proliferation measured with CELLTITER-GLO® after 48 hours. Assays were conducted on human IL-21R-BaF3 cells with 100 pg/ml of human IL-21 (FIG. 11a), murine IL-21R-BaF3 cells with 200 pg/ml of murine IL-21 (FIG. 11b), and human IL-21R-TF1 cells with 100 pg/ml of human IL-21 (FIG. 11c).
Figure 11B:
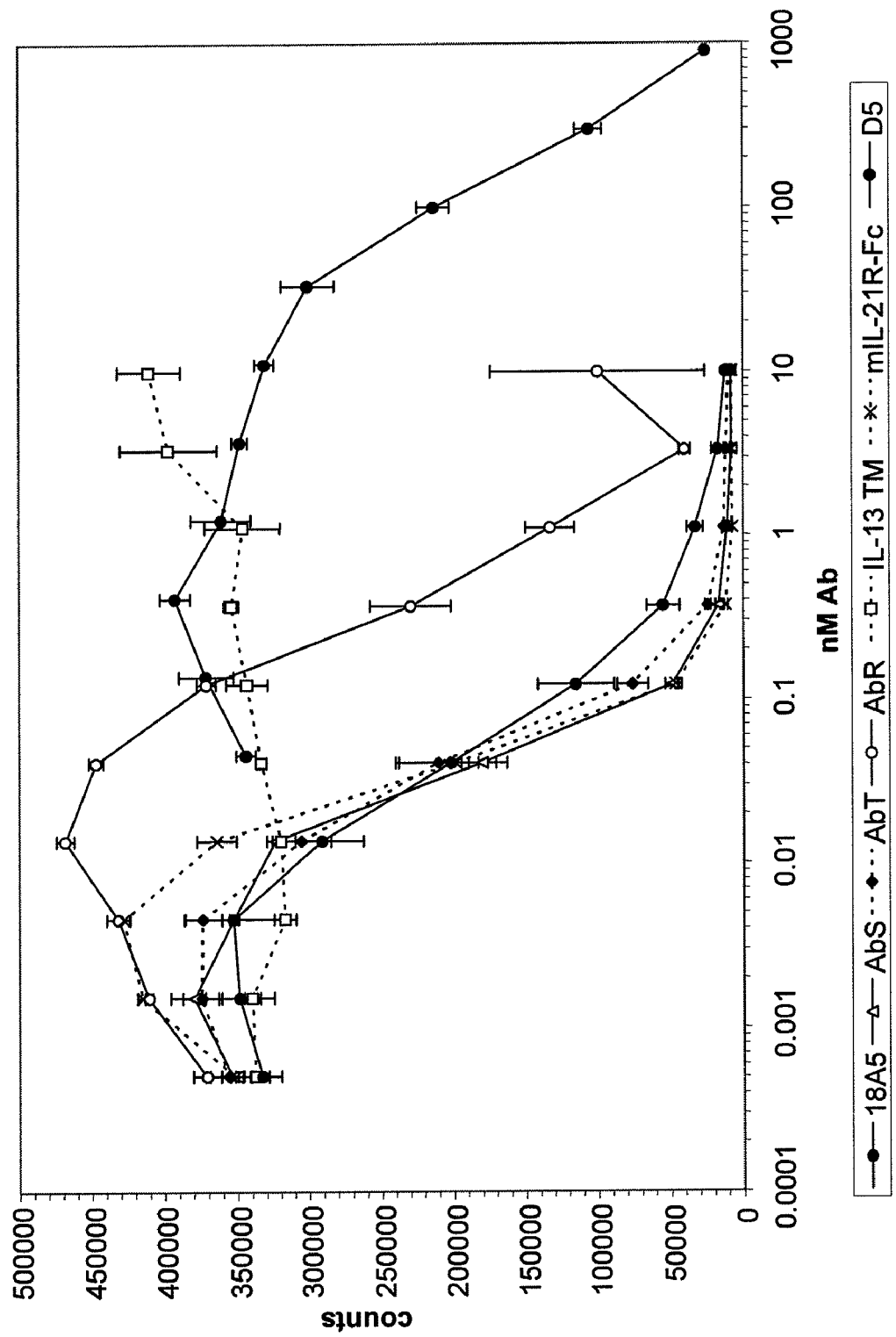
Figure 11C:
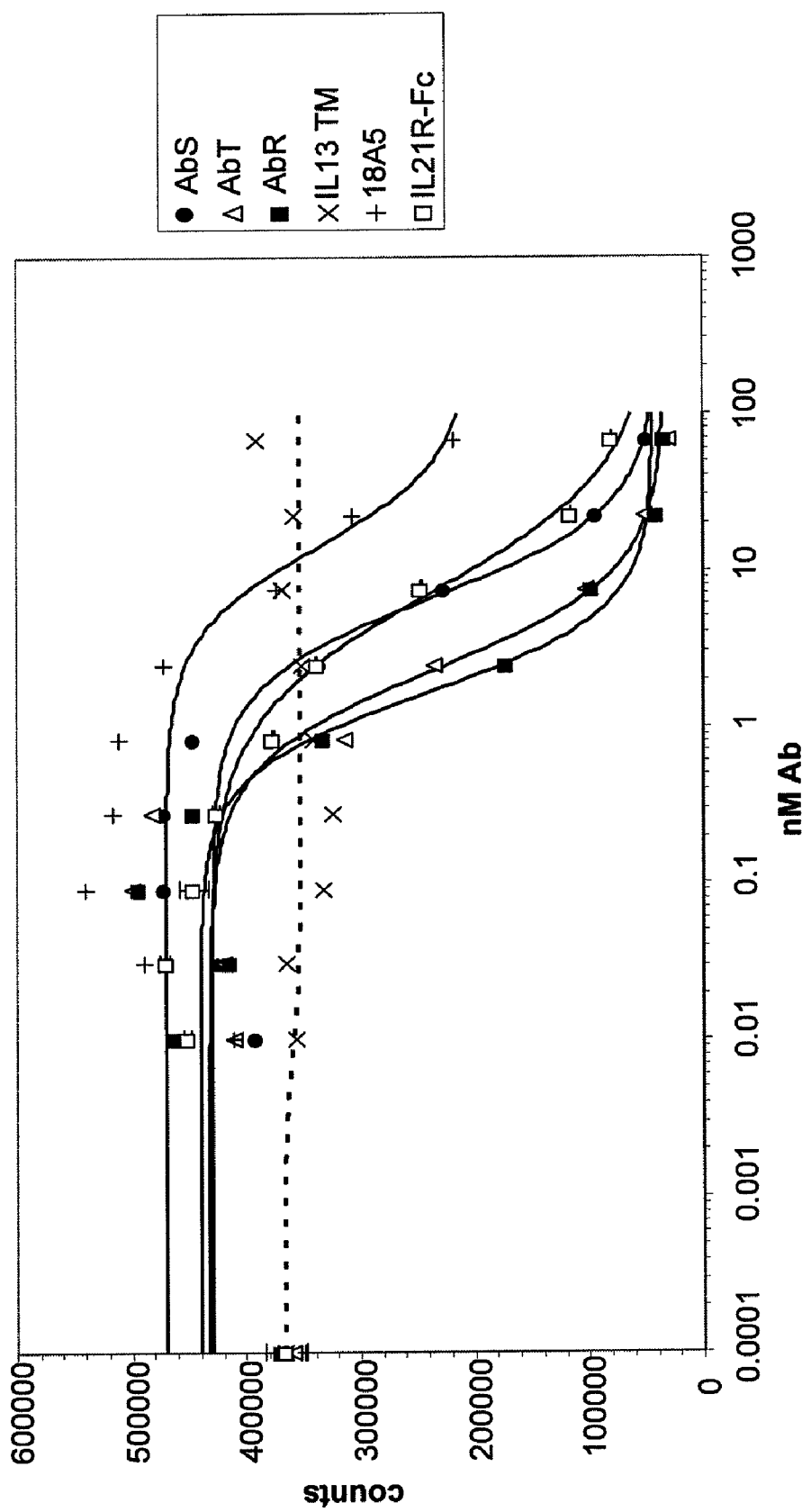
Figure 26D:
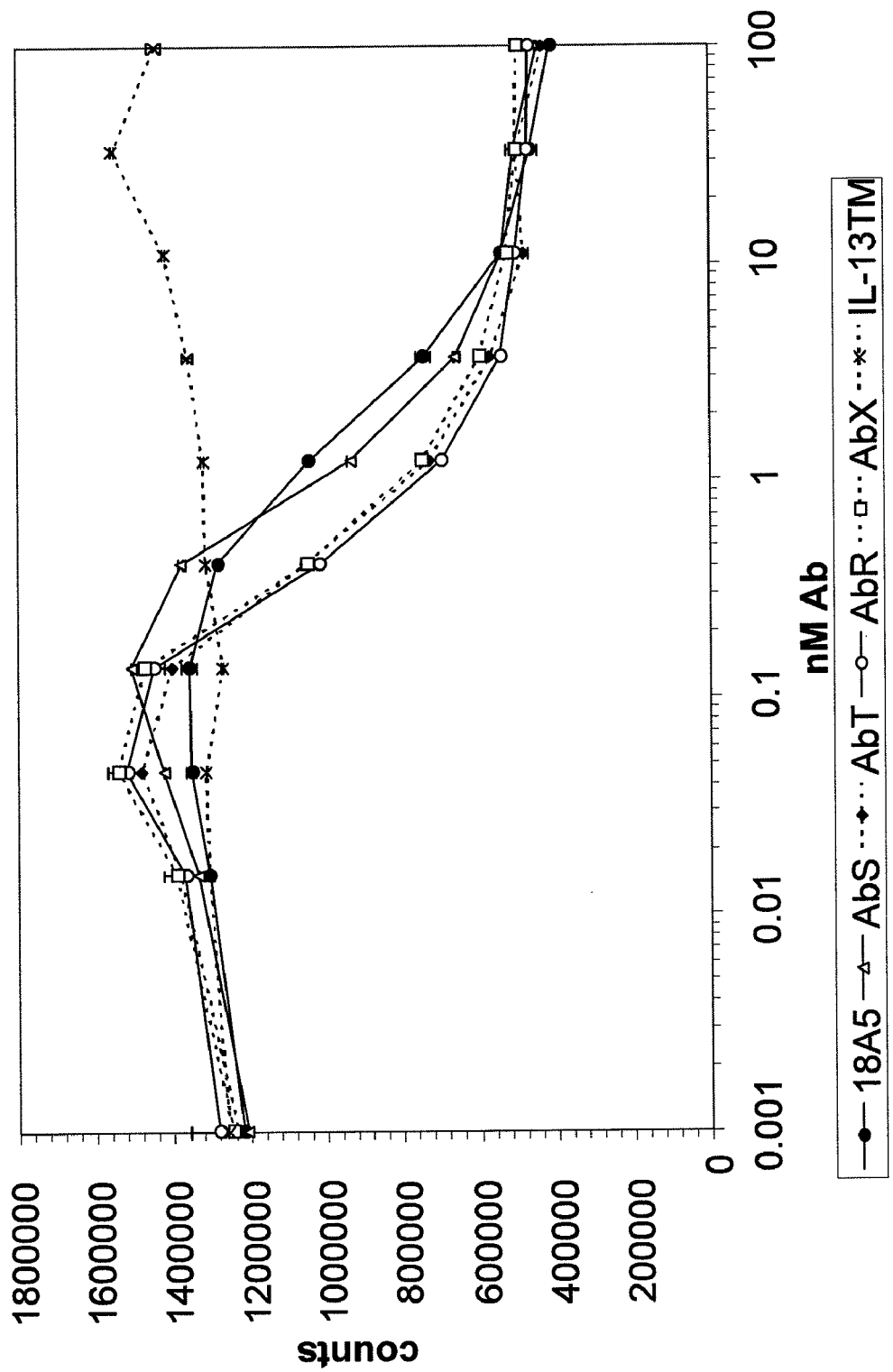

Purified IgGs were tested for activity in IL-21-dependent proliferation assays in three cell lines as described above: human IL-21R-BaF3 cells, murine IL-21R-BaF3 cells, and human IL-21R-TF-1 cells. All showed strong inhibition of both human and murine IL-21R-dependent proliferation with greater potency than that of the parental 18A5 IgG (FIG. 11, Table 8). Assays were conducted on human IL-21R-BaF3 cells with 100 pg/ml of human IL-21 (FIG. 11a), murine IL-21R-BaF3 cells with 200 pg/ml of murine IL-21 (FIG. 11b), and human IL-21R-TF-1 cells with 100 pg/ml of human IL-21 (FIG. 11c). FIG. 26d depicts the results of an additional study of the effects of these antibodies on human IL-21R-BaF3 cells.

TABLE 8

Neutralization of Proliferation of Human IL-21R-BaF3 Cells, Murine IL-21R-BaF3 Cells, and Human IL-21R-TF-1 Cells

| Antibody | Human IL-21R-BaF3 Neutralization $IC_{50}$ (nM) | Murine IL-21R-BaF3 Neutralization $IC_{50}$ (nM) | Human IL-21R-TF1 Neutralization $IC_{50}$ (nM) |
|---|---|---|---|
| 18A5 antibody | 1.71 | 177.23 | 13.99 |
| AbR | 0.56 | 0.34 | 1.63 |
| AbS | 0.68 | 0.04 | 6.67 |
| AbT | 0.30 | 0.05 | 2.32 |
| AbX | 0.54 | nd | nd |
| IL21R-Fc | 0.20 (human IL-21R-Fc) | 0.04 (mouse IL-21R-Fc) | 7.22 (human IL-21R-Fc) |

Example 9.9

Primary Human B cell Proliferation Assays

Figure 12A:
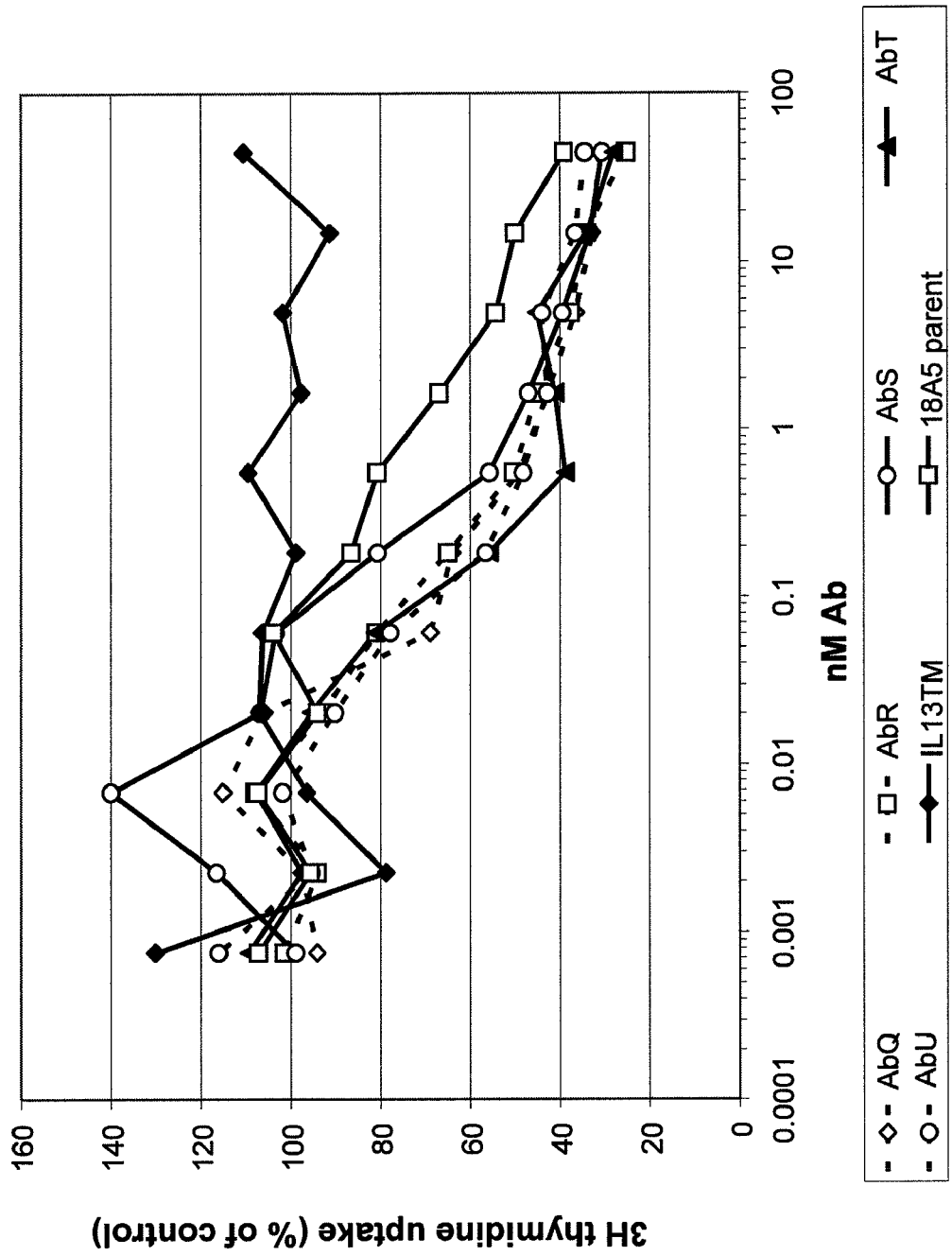
FIG. 12a depicts the comparison between AbQ, AbR, AbS, AbT, AbU, IL-13 triple-mutant, and 18A5 parental antibody.
Figure 12B:
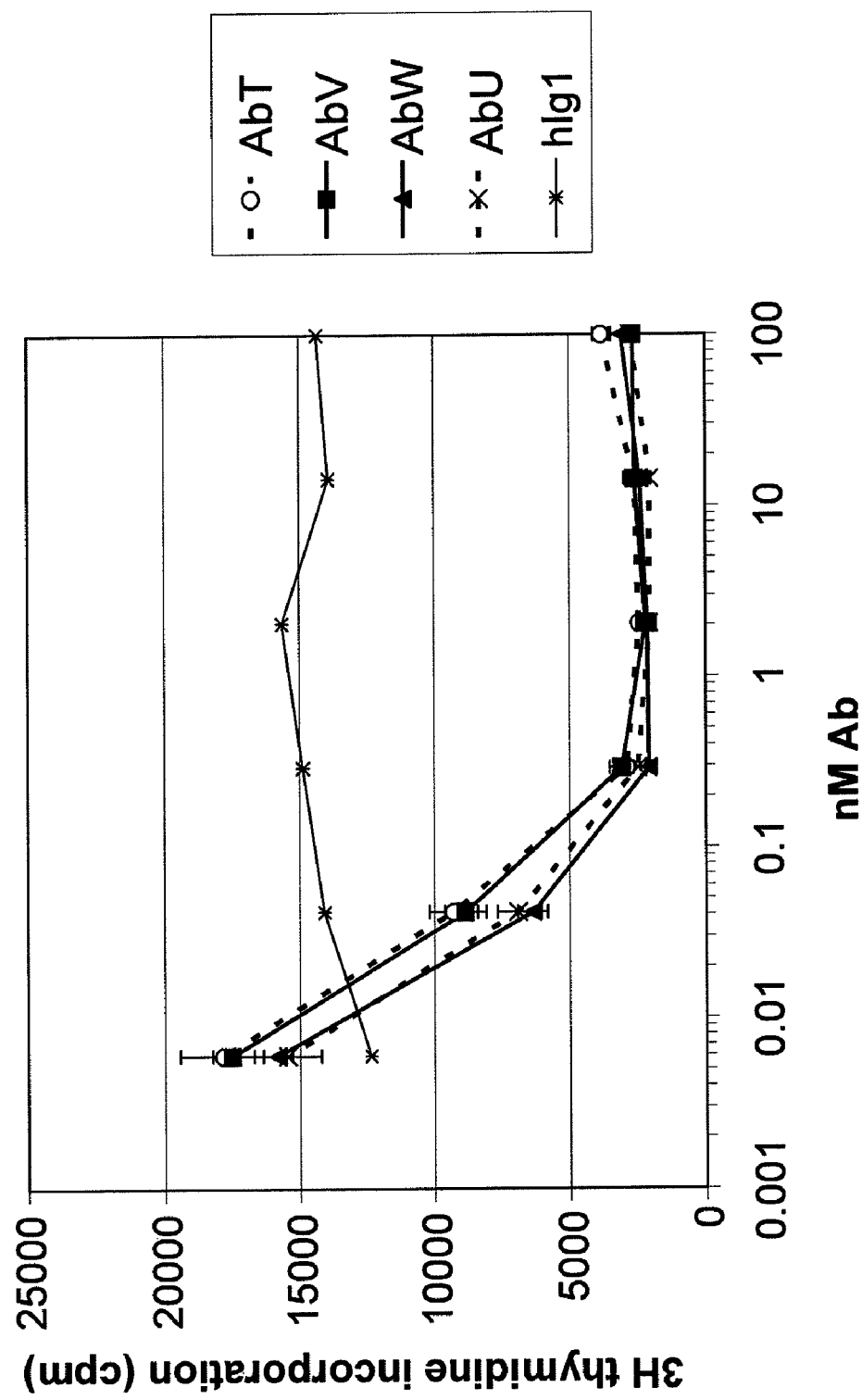
FIG. 12b depicts the comparison between AbT, AbV, AbW, AbU, and human IgG1 control (hIg1).
Figure 26E:
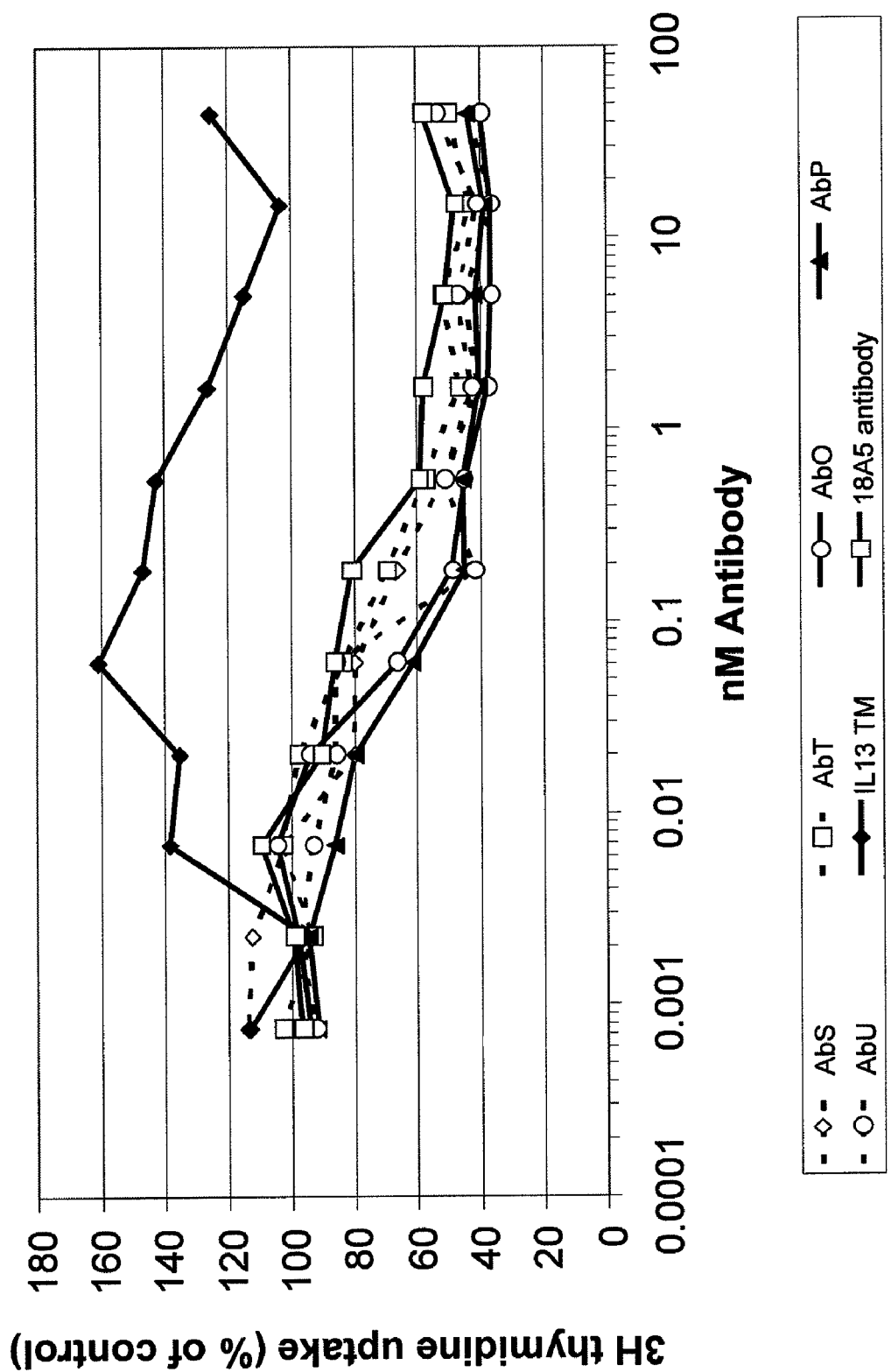

Anti-IL-21R antibodies were tested for their ability to inhibit IL-21-dependent proliferation of primary human B cells. Buffy coat cells from healthy human donors were obtained from Massachusetts General Hospital (Boston, Mass.). The cells were incubated with a ROSETTESEP™ B cell enrichment cocktail (StemCell Technologies, Vancouver, Canada), and B cells isolated according to the manufacturer's instructions. The resulting population (60-80% $CD19^+$ B cells) were cultured in RPMI containing 10% FBS, 50 U/ml penicillin, 50 µg/ml streptomycin, and 2 mM L-glutamine at $1\times10^5$/well in 96-well flat-bottom plates. B cells were pretreated with serially diluted anti-human IL-21R antibodies in a 37° C. incubator adjusted to 5% $CO_2$ for 30 min. The treated B cells were then stimulated with 0.5 µg/ml anti-CD40 mAb (BD Biosciences, San Jose, Calif.) and 10 ng/ml IL-21 cytokine for 3 days in a 37° C. incubator adjusted to 5% $CO_2$. On day 3, cultures were pulsed with 0.5 µCi/well $^3$H-thymidine (Perkin Elmer (NEN)) and harvested 5 hr later onto glass fiber filter mats. $^3$H-thymidine incorporation was determined by liquid scintillation counting. All of the improved antibodies neutralized IL-21-dependent proliferation with greater potency than the parental 18A5 antibody (FIGS. 12a-b, Table 9; also see FIG. 26e).

TABLE 9

Neutralization of Human Primary B Cell Proliferation

| Antibody | Neutralization of B cell proliferation $IC_{50}$ (nM) |
|---|---|
| AbQ | 0.16 |
| AbR | 0.22 |
| AbS | 0.44 |
| AbT | 0.14 |
| AbU | 0.13 |
| 18A5 antibody | 1.86 |

Example 9.10

Primary Human T cell Proliferation Assays

Figure 13:
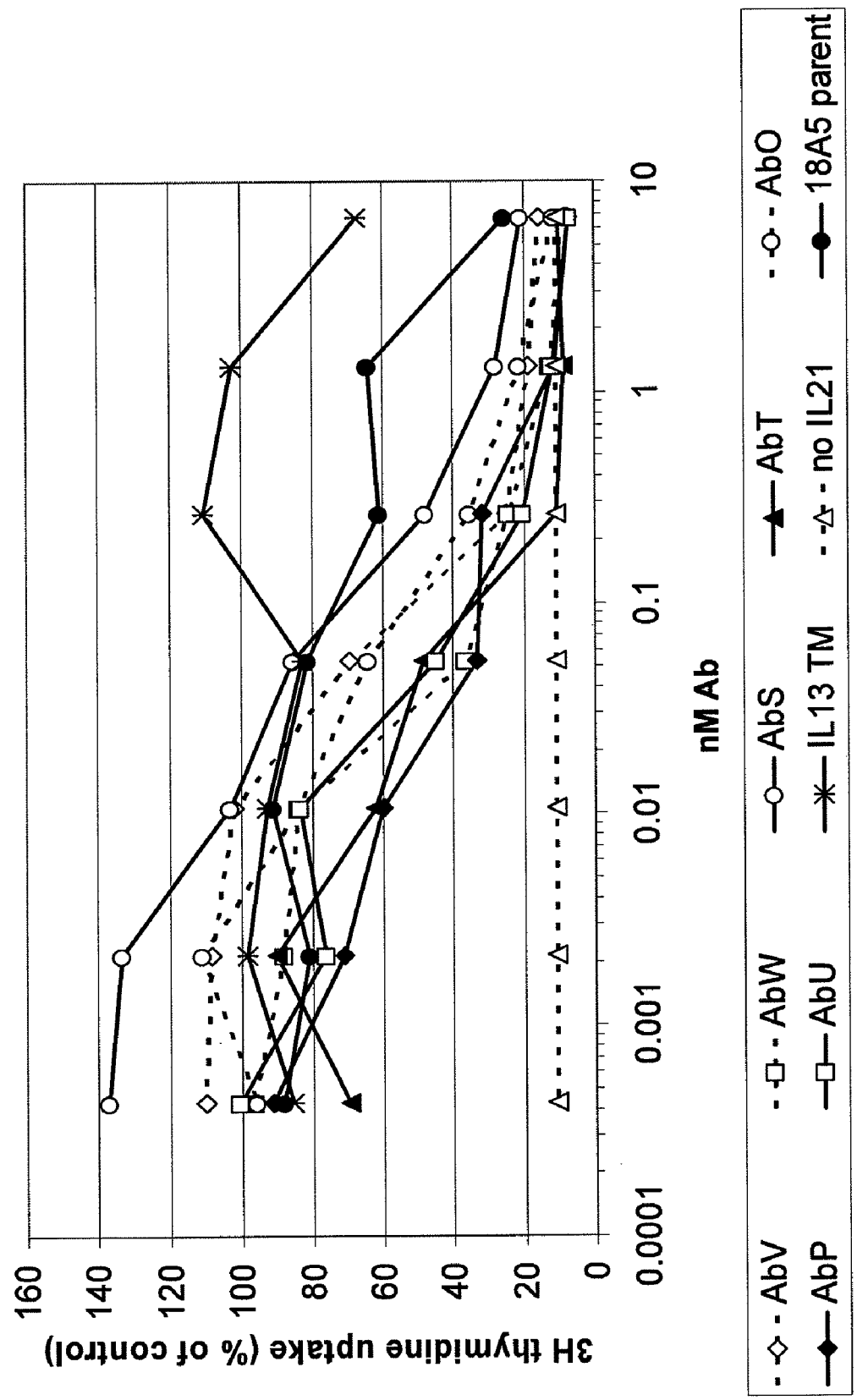
FIG. 13 depicts the neutralization of IL-21-dependent proliferation of human primary CD4$^+$ T cells. The indicated antibodies were added to activated primary human CD4$^+$ T cells along with human IL-21, and incorporation of $^3$H-thymidine was measured after three days.
Figure 26F:
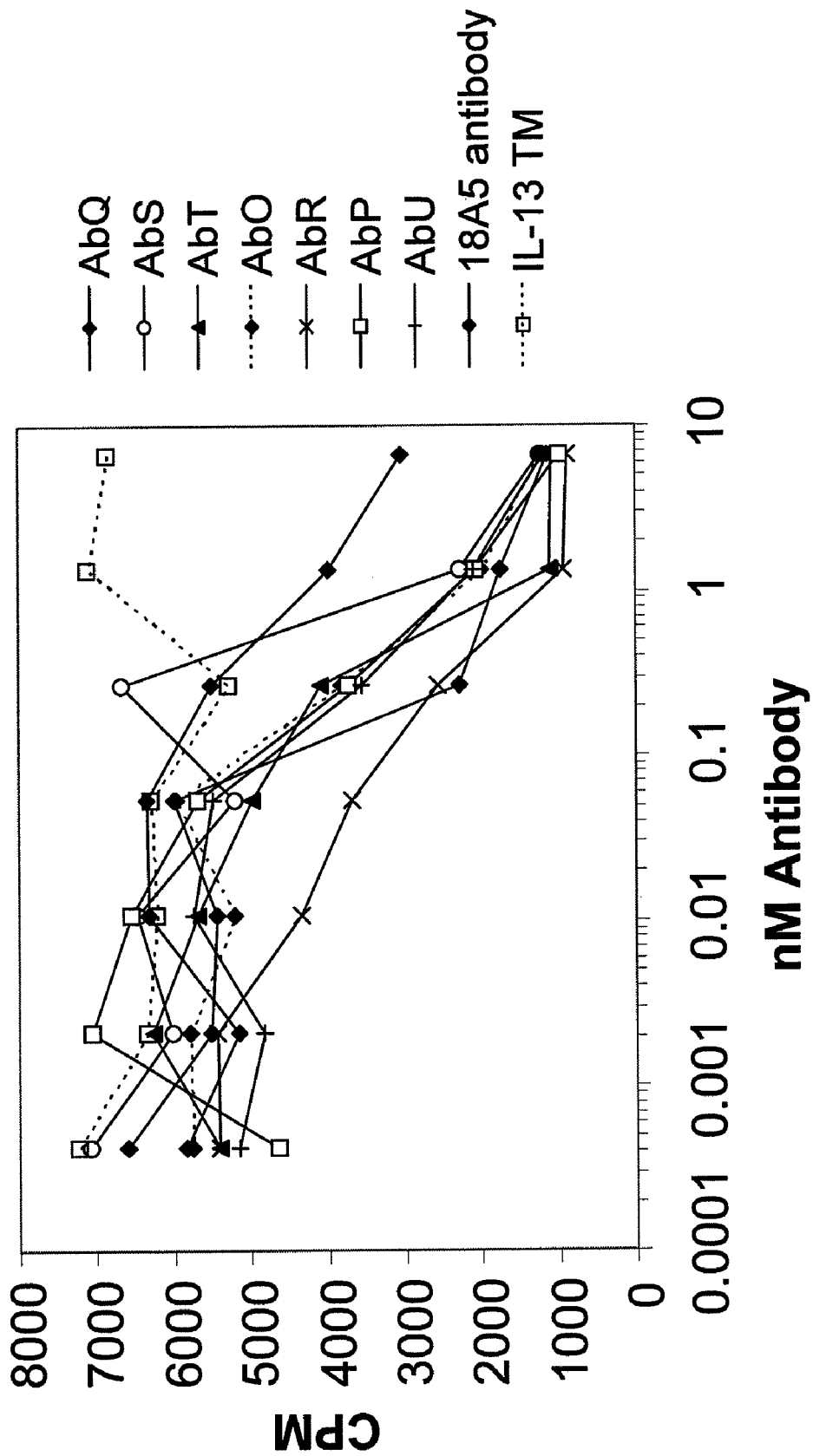

Anti-IL-21R antibodies were tested for their ability to inhibit IL-21-dependent proliferation of primary human $CD4^+$ T cells. Buffy coat cells from healthy human donors were obtained from Massachusetts General Hospital. $CD4^+$ T cells were isolated by negative selection using ROSETTE- SEP™ CD4+ T cell enrichment cocktail (StemCell Technologies), according to the manufacturer's instructions. The resulting population was ~80-90% CD4+/CD3+ T cells. Enriched human CD4+ T cells were activated for 3 days with anti-CD3/anti-CD28-coated microspheres in RPMI containing 10% FBS, 100 U/ml penicillin, 100 µg/ml streptomycin, 2 mM L-glutamine, and HEPES in a 37° C. incubator adjusted to 5% $CO_2$. After activation, the microspheres were removed and the cells were washed and rested overnight at approximately $1 \times 10^6$ cells/ml in culture medium. The rested cells were then washed again before addition to the assay plates. Serial dilutions of anti-human IL-21 receptor antibodies were made in culture medium in flat-bottomed 96-well plates, followed by the sequential addition of human IL-21 (20 ng/ml final concentration) and the activated and rested CD4+ T cells ($10^5$ cells/well). The plates were then incubated for an additional 3 days and pulsed with 1 µCi/well 3H-thymidine (Perkin Elmer (NEN)) during the final 6 hr of the assay. Cells were harvested onto glass fiber filter mats and $^3$H-thymidine incorporation was determined by liquid scintillation counting. All of the improved antibodies neutralized IL-21-dependent proliferation with greater potency than the parental 18A5 antibody (FIG. 13, Table 10A; also see FIG. 26f).

TABLE 10A

Neutralization of Human Primary T Cell Proliferation

| Antibody | Neutralization of T cell Proliferation $IC_{50}$ (nM) |
|---|---|
| AbO | 0.06 |
| AbP | 0.02 |
| AbQ | 0.08 |
| AbR | 0.04 |
| AbS | 0.06 |
| AbT | 0.03 |
| AbU | 0.03 |
| 18A5 antibody | 1.42 |

Example 9.11

Primary Murine T Cell Proliferation Assays

Figure 14:
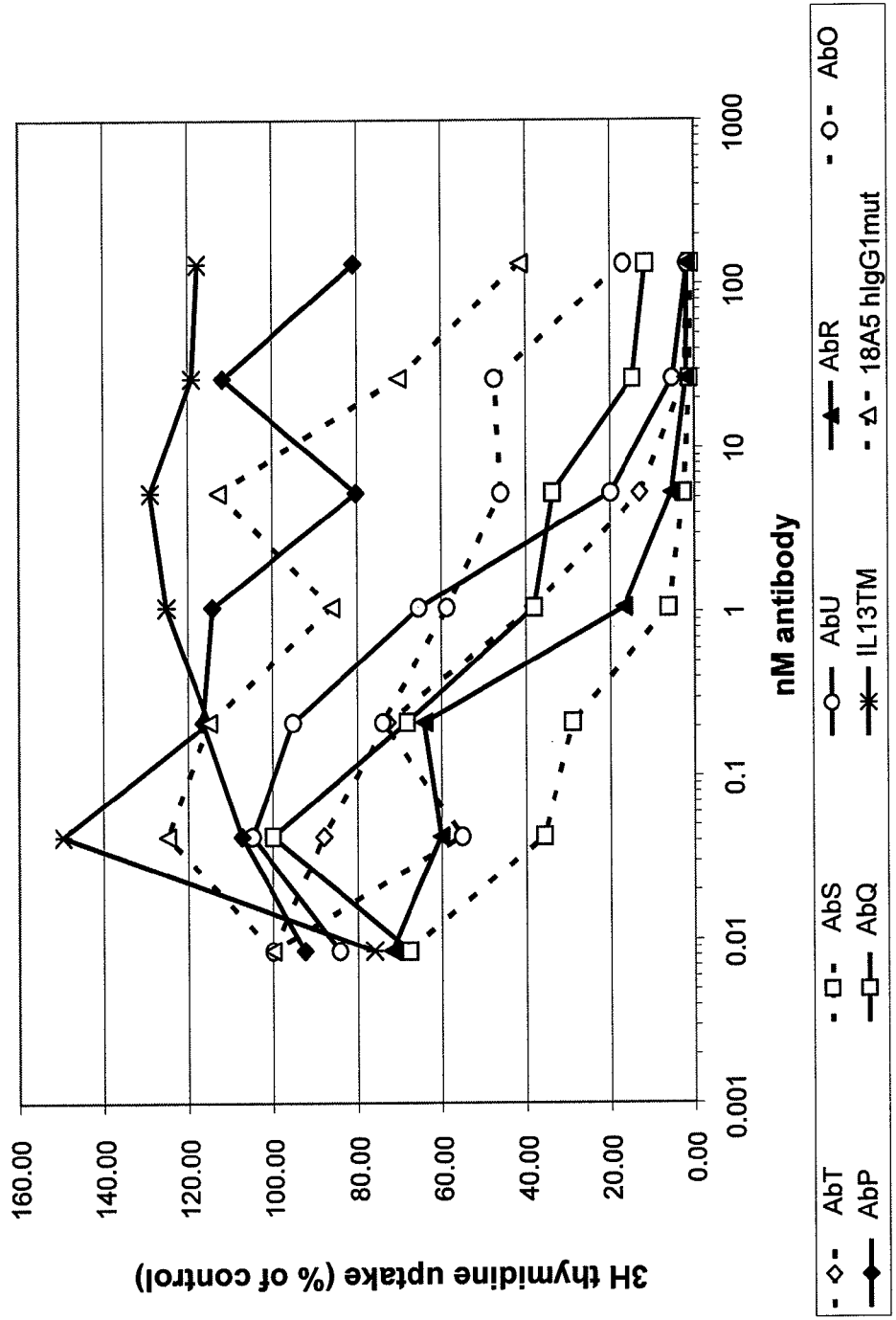
FIG. 14 depicts the neutralization of IL-21-dependent proliferation of murine primary CD8$^+$ T cells. The indicated antibodies were added to activated primary murine CD8$^+$ T cells along with human IL-21, and incorporation of $^3$H-thymidine was measured after three days.
Figure 26G:
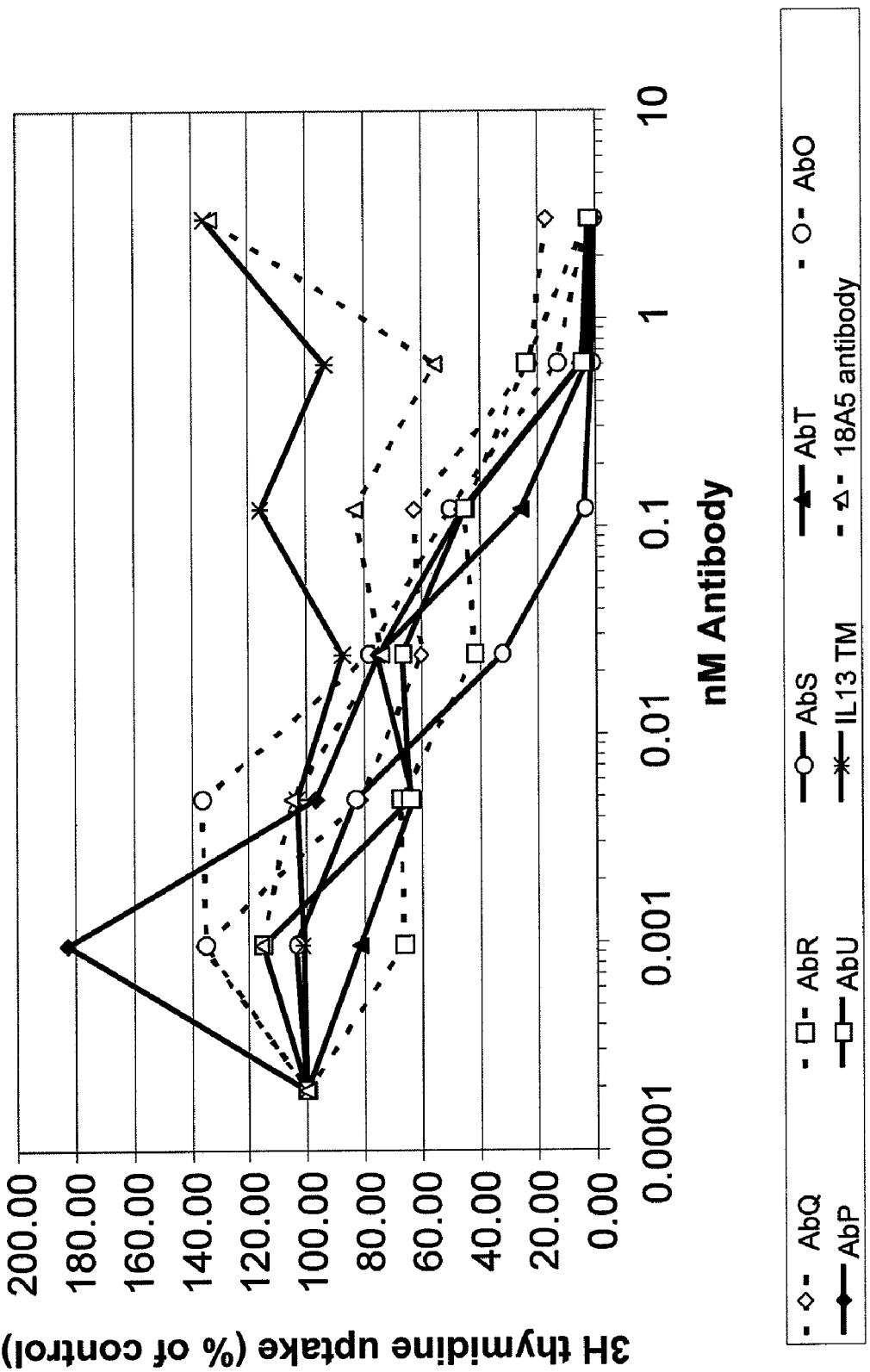

Anti-IL-21R antibodies were tested for their ability to inhibit IL-21-dependent proliferation of primary murine CD8+ T cells. Popliteal, axillary, brachial, and inguinal lymph nodes and spleens from 12-week-old female BALB/C mice were collected. A single-cell suspension of the spleen cells was depleted of red blood cells using 0.16 M $NH_4Cl$ in 0.017 M Tris (pH 7.4). The spleen and lymph node cells were pooled and enriched for CD8+ cells using a murine T cell CD8 Subset Column Kit (R&D Systems). Murine CD8+ cells ($3 \times 10^4$; suspended in DMEM containing 10% fetal calf serum and supplemented with 0.05 mM β-mercaptoethanol, 2 mM L-glutamine, 0.1 mM nonessential amino acids, 1 mM sodium pyruvate, 100 U/ml penicillin, 100 µg/ml streptomycin and 50 µg/ml gentamicin) were plated in 96-well, anti-mCD3 activation plates (BD Biosciences); mIL-21 (50 ng/ml) was added to all the wells. The test antibodies were titered in triplicate beginning at 20 µg/ml. Cells were grown for 3 days in a 37° C./10% $CO_2$ incubator. During the last 5 hr of culture, cells were labeled with 0.5 µCi methyl-3H-thymidine/well (GE Healthcare). The cells were harvested using a Mach III cell harvester (TomTec, Hamden, Conn.) and counted using a Trilux microbeta counter (Perkin Elmer). Aside from AbP, all of the improved antibodies neutralized IL-21-dependent proliferation with greater potency than the parental 18A5 antibody (FIG. 14, Table 10B; also see FIG. 26g).

TABLE 10B

Neutralization of Murine Primary T Cell Proliferation

| Antibody | Neutralization of T cell Proliferation $IC_{50}$ (nM) |
|---|---|
| AbO | 4.92 |
| AbP | no inhibition |
| AbQ | 0.85 |
| AbR | 0.13 |
| AbS | 0.02 |
| AbT | 0.61 |
| AbU | 1.79 |
| 18A5 antibody | >85 |

Example 9.12

ADCC Assay

Figure 15:
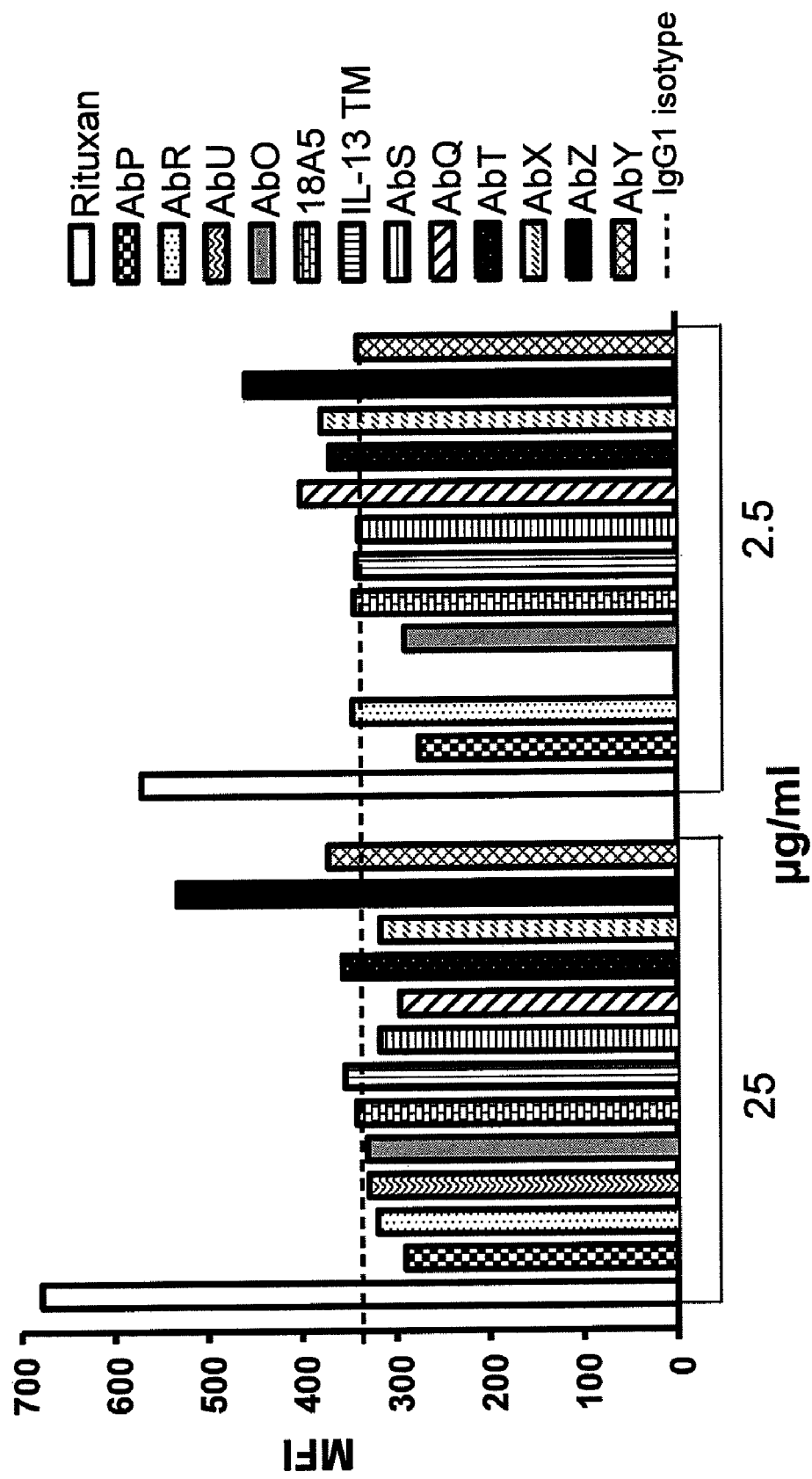
FIG. 15 depicts the measurement of antibody-dependent cellular cytotoxicity (ADCC) induced by anti-IL-21R antibodies. PBMC-dependent killing of CFSE-labeled BJAB cells coated with the indicated anti-IL-21R antibodies was measured by incorporation of propidium iodide. The anti-CD20 antibody rituximab (RITUXAN®, Genentech, Inc., South San Francisco, Calif.) was included as a positive control, and an anti-IL-13 antibody was included as a negative control.

Anti-IL-21R antibodies were tested for their ability to induce antibody-dependent cellular cytotoxicity (ADCC) when bound to target cells. The day before the experiment, PBMC were isolated from buffy coat by diluting the buffy coat 1:1 in PBS, layering it over FICOLL® (GE Healthcare), and centrifuging at 1200 g for 20 min. PBMCs were removed from the top of the FICOLL® layer, washed, and stimulated overnight with 10 ng/ml IL-2 and 10 ng/ml IL-12 (R&D Systems). The day of the experiment, stimulated PBMCs were collected by centrifugation and resuspended in media at $1 \times 10^8$ cells/ml. BJAB cells were labeled with 0.5 µM CFSE (MOLECULAR PROBES®, Invitrogen Corporation) for 10 min at 37° C., and then washed with fetal bovine serum once and PBS twice. Cells were then plated into a 96-well flat-bottom plate at $2 \times 10^5$ cells/well in 100 µl media. Fifty µl of the 4× antibodies were added to the BJAB cells, followed by $5 \times 10^6$ PBMC in 50 µl, giving a final 1:25 target:effector cell ratio. Cells were incubated at 37° C. for 6 hr and stained with propidium iodide (PI) to label dead and dying cells. Killing of target cells (CFSE+) was assessed by measuring PI staining in a FACSCALIBUR™ flow cytometer (BD Biosciences). Only one anti-IL-21R antibody, AbZ, which has a wild-type human IgG1 constant region, showed ADCC above the background level displayed by a control anti-IL-13 antibody that did not bind to the target cells. All antibodies with the same variable domains as AbZ, including forms with human IgG4 (AbY), and those with double-mutant (AbX) and triple-mutant (AbT) forms of human IgG1, showed only background levels of ADCC (FIG. 15). All other anti-IL-21R antibodies tested contained the triple-mutant form of human IgG1 and showed background ADCC. A positive control antibody, rituximab (RITUXAN®), induced ADCC in all experiments.

Example 9.13

C1q ELISA

Figure 16:
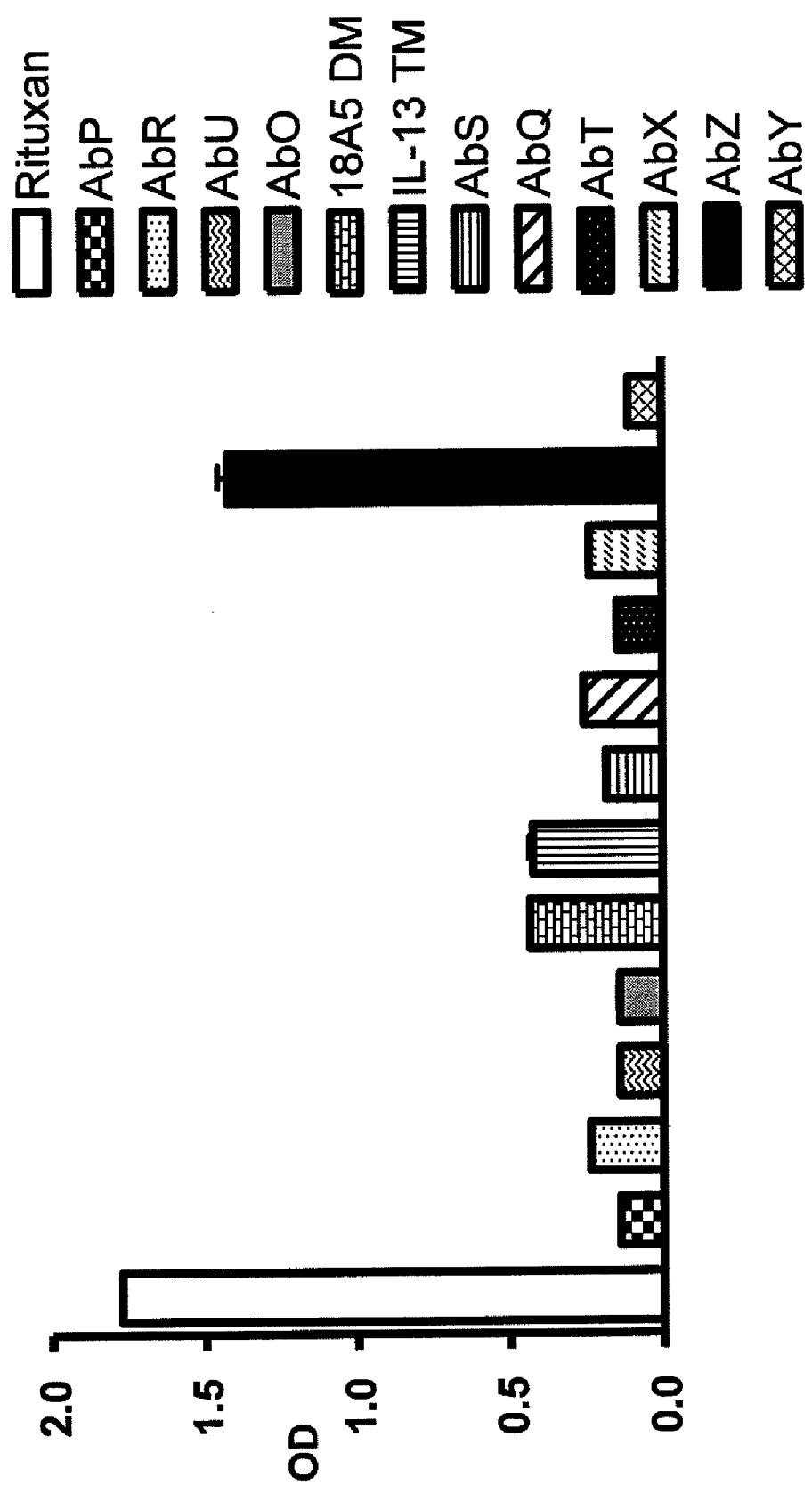
FIG. 16 depicts complement C1q binding by anti-IL-21R antibodies. The indicated anti-IL-21R antibodies were immobilized on an ELISA plate and, following incubation with human serum, C1q binding was measured with chicken anti-human C1q and an HRP-conjugated anti-chicken IgY antibody. The anti-CD20 antibody rituximab (RITUXAN®) was included as a positive control, and an anti-IL-13 antibody was included as a negative control.

In order to determine whether cell-surface binding by anti-IL-21R antibodies is likely to lead to complement-dependent cytotoxicity (CDC), the antibodies were tested for their ability to bind to the complement component C1q in an ELISA. IL-21R antibodies and rituximab (RITUXAN®) were diluted in PBS to 5 µg/ml. Diluted antibodies (100 µl) were coated onto a COSTAR® high-binding ELISA plate (Corning Life Sciences, Lowell, Mass.) overnight at 4° C. Plates were washed 3× with PBS/Tween-20 and blocked with 200 µl of blocking buffer (0.1 M NaPO$_4$, 0.1 M NaCl, 0.1% gelatin, 0.01% Tween) for 1 hr at RT. Human serum previously determined to contain C1q (Quidel, San Diego, Calif.) was diluted 1:50 in PBS. After 1 hr of blocking, plates were washed and 100 µl of diluted serum was added to each well and incubated for 2 hr at RT on a shaker. Following three washes, 100 µl of 0.1 µg/ml chicken polyclonal anti-human C1q antibody (AbCam, Cambridge, Mass.) was added to each well and incubated for 1 hr at RT. Plates were again washed and incubated with 100 µl of a rabbit polyclonal antibody to chicken Ig-Y—HRP diluted 1:4000 (AbCam) for 1 hr at RT. Plates were washed and developed with TMB for 5 min, followed by 50 µl of 1 M H$_2$SO$_4$ to stop the reaction, and then read at 450 nm. Only one anti-IL-21R antibody, AbZ, which has a wild-type human IgG1 constant region, showed C1q binding above the background level displayed by a control antibody with a triple-mutant human IgG1 constant region that had previously been shown to lack C1q binding. All antibodies with the same variable domains as AbZ, including forms with human IgG4 (AbY), and those with double-mutant (AbX) and triple-mutant (AbT) forms of human IgG1, showed only background levels of C1q binding (FIG. 16). All other anti-IL-21R antibodies tested contained the triple-mutant form of human IgG1 and showed background C1q binding.

Example 9.14

Cytokine Competition Assay

Figure 27A:
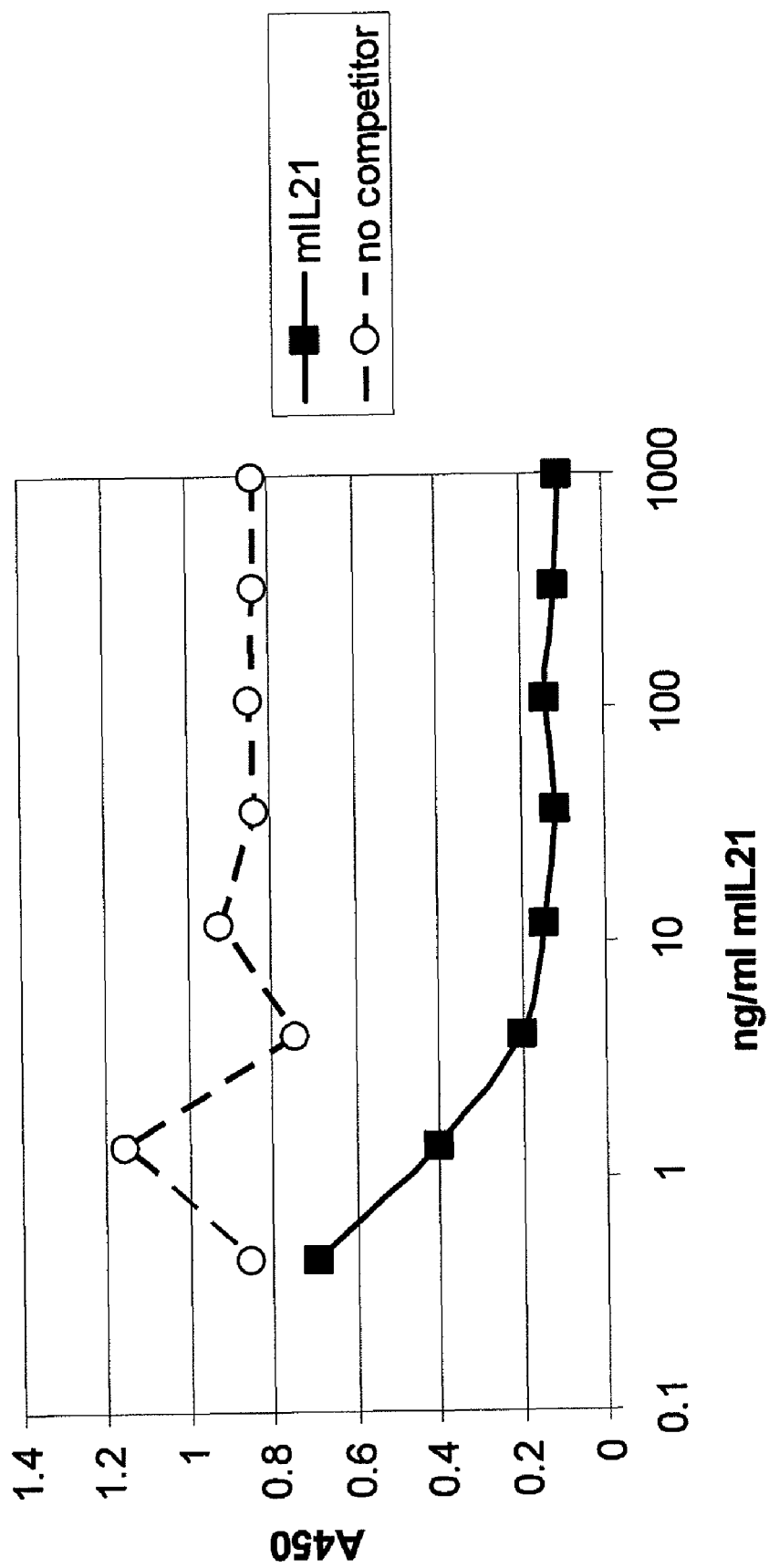
FIG. 27a depicts IL-21 cytokine competition with antibody AbT for binding to murine IL-21R. Vehicle, or increasing amounts of IL-21, was mixed with biotinylated murine IL-21R-His/FLAG, and the mixtures were added to AbT immobilized on an ELISA plate. Capture of mIL-21R was detected with HRP-streptavidin, and competition for binding to mIL-21R was indicated by a reduction in the A450 signal.

In order to demonstrate that antibody AbT binds to the murine IL-21R in a manner that competes with the IL-21 cytokine, a cytokine competition assay was performed. Antibody AbT was coated at 1 µg/ml onto ELISA plates, which were then blocked with 1% BSA in PBS/0.05% Tween. Biotinylated murine IL-21R-His/FLAG (1.5 ng/ml) was added to the wells, either alone or in the presence of increasing concentrations of murine IL-21, and the binding of the receptor to the immobilized antibody was detected with HRP-conjugated streptavidin and subsequent incubation with TMB detection reagent. Mouse IL-21 was able to block the binding of mIL-21R to AbT nearly completely above 4 ng/ml, indicating that the antibody and the cytokine compete for binding to murine IL-21R (FIG. 27a).

Figure 27B:
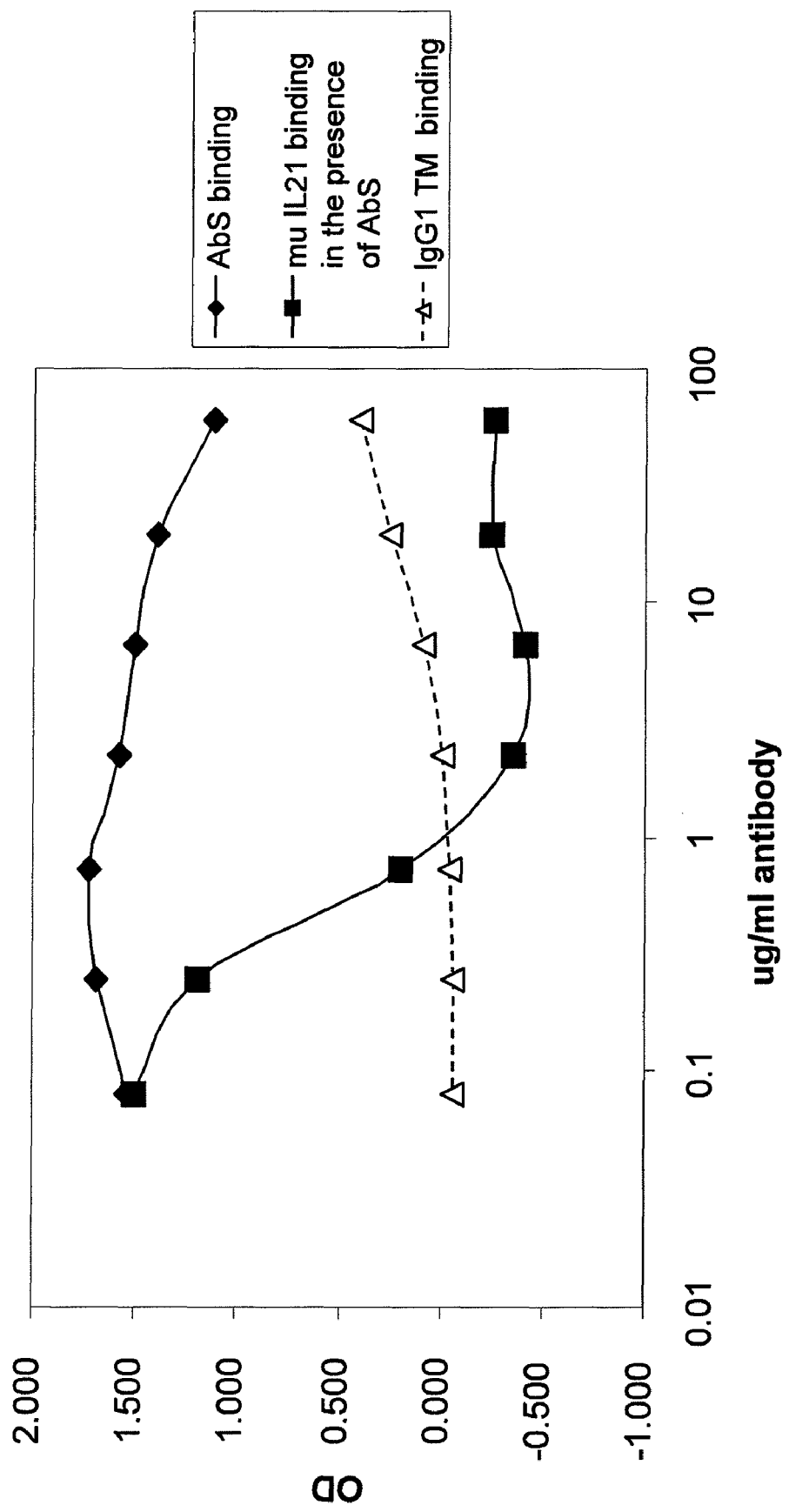
FIG. 27b depicts the competition of AbS and IL-21 for binding to murine IL-21R. AbS and mIL-21 were mixed and applied to immobilized mIL-21R-Fc in ELISA plates, and the binding of AbS (filled diamonds), isotype control antibody (open triangles), or mIL-21 (squares) was monitored.

A second assay was performed to demonstrate that antibody AbS binds to the murine IL-21R in a manner that competes with the IL-21 cytokine. Murine IL-21R-Fc was captured on ELISA plates coated with an anti-mouse IgG2a antibody. Plates were blocked with 1% BSA in PBS and washed, and varying concentrations of AbS were added to the plate in the presence of 10 µg/ml mIL-21. The binding of mIL-21 to the receptor was detected by an HRP-conjugated anti-His$_6$ antibody, and the binding of AbS to the receptor was detected by an anti-human Ig antibody. Concentrations of AbS above approximately 2 µg/ml completely prevented binding of mIL-21 to mIL-21R-Fc, indicating that the antibody and the cytokine compete for binding to murine IL-21R (FIG. 27b).

Example 9.15

Inhibition of Rat T Cell Proliferation by Anti-IL-21R Antibodies

Lewis female rat splenic T cells were purified to 95% CD3$^+$ using Rat T cell Enrichment Columns (RTCC-25; R&D Systems) according to the manufacturer's instructions. Serial dilutions of the anti-human IL-21R antibodies and isotype control protein were made in culture medium (Dulbecco's Modified Eagle Medium containing 10% FCS, L-glutamine, beta-mercaptoethanol, nonessential amino acids, sodium pyruvate, penicillin, streptomycin, and gentamycin) in flat-bottomed 96-well tissue culture plates which had been pre-coated with 1 µg of anti-rat CD3 antibody (BD Pharmingen Cat#554829), followed by the addition of 5 ng/ml rat IL-21 and 20,000 CD3 T cells per well. The cells were grown for 3 days in a 10% CO$_2$, 37° C., humidified incubator. For the last 5 hr of culture, cells were labeled with 0.5 µCi of $^3$H-thymidine (GE Amersham Cat# TRA-120). The plates were harvested onto glass fiber filter mats by a Tomtec Mach III plate harvester and were counted on a Perkin Elmer 1450 Microbeta Counter.

Figure 28:
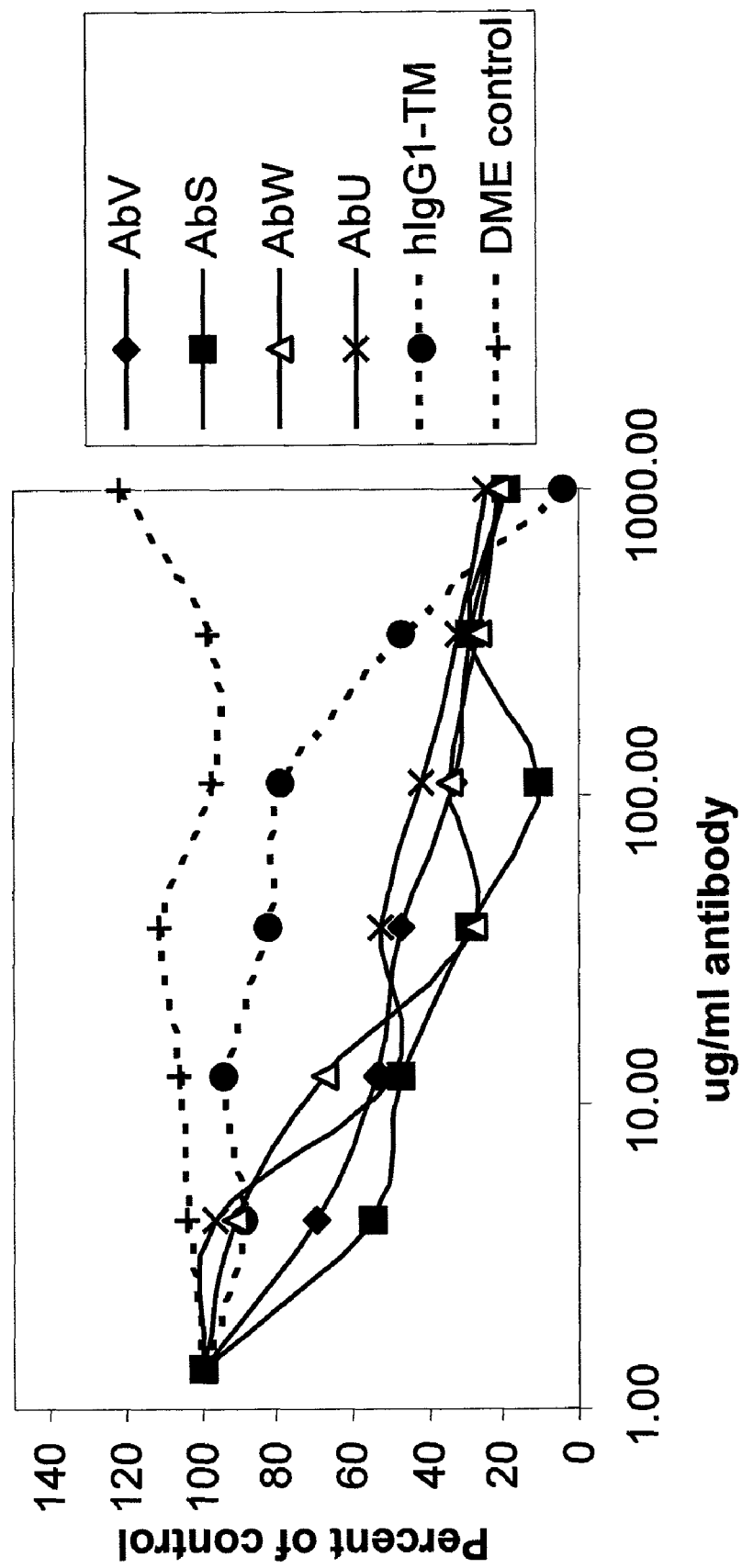
FIG. 28 depicts IL-21-dependent $^3$H thymidine incorporation into rat CD3 T cells in the presence of anti-IL-21R antibodies AbS, AbU, AbV, or AbW, or an isotype control antibody, hIgG1-TM.

The response of the rat T cells to 5 ng/ml rat IL-21 was 6-fold above the background response to 1 µg of anti-CD3 alone. Antibodies AbS, AbU, AbV, and AbW were able to inhibit the $^3$H thymidine incorporation stimulated by 5 ng/ml rat IL-21 (57,000 cpm in the absence of antibody treatment; FIG. 28). IC$_{50}$ values for neutralization in two independent experiments are shown in Table 11.

TABLE 11

Blockade of IL-21-dependent Rat T cell Proliferation by Anti-IL-21R Antibodies.

| Antibody | IC50 (nM) experiment 1 | IC50 (nM) experiment 2 |
|---|---|---|
| AbS | 35.98 | 27.07 |
| AbU | 172.79 | 105.46 |
| AbV | 70.55 | 59.23 |
| AbW | 159.06 | 94.74 |

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated binding protein or antigen-binding fragment thereof that binds to interleukin-21 receptor ("IL-21R"), wherein the binding protein or antigen-binding fragment thereof comprises the CDR sequences set forth in SEQ ID NOs:163, 164, 169, 194, 195, and 176.

2. The isolated binding protein or antigen-binding fragment of claim 1, wherein the binding protein or antigen-binding fragment is an antibody.

3. The isolated binding protein or antigen-binding fragment of claim 1, wherein the binding protein or antigen-binding fragment is an scFv.

4. An isolated binding protein or antigen-binding fragment thereof that binds to IL-21R, wherein the binding protein or antigen-binding fragment thereof comprises the CDR sequences encoded by the nucleotide sequences of:
   (a) nucleotide 148 to 165 of SEQ ID NO:239;
   (b) nucleotide 208 to 255 of SEQ ID NO:239;
   (c) nucleotide 352 to 378 of SEQ ID NO:239;
   (d) nucleotide 124 to 156 of SEQ ID NO:97;
   (e) nucleotide 202 to 222 of SEQ ID NO:97; and
   (f) nucleotide 319 to 354 of SEQ ID NO:97.

5. The isolated binding protein or antigen-binding fragment of claim 4, wherein the binding protein or antigen-binding fragment is an antibody.

6. The isolated binding protein or antigen-binding fragment of claim 4, wherein the binding protein or antigen-binding fragment is an scFv.

7. An isolated binding protein or antigen-binding fragment thereof that binds to IL-21R, wherein the binding protein or antigen-binding fragment thereof comprises a $V_L$ domain and a $V_H$ domain, and wherein the $V_L$ domain comprises SEQ ID NO:221, and the $V_H$ domain comprises amino acid 1 to 118 of SEQ ID NO:219.

8. The binding protein or antigen-binding fragment of any one of claim 1, 2, 4, or 5, wherein the association constant of the binding protein or antigen-binding fragment for human IL-21R is at least about $10^5$ $M^{-1}s^{-1}$.

9. The binding protein or antigen-binding fragment of any one of claim 1, 2, 4, or 5, wherein the binding protein or antigen-binding fragment inhibits interleukin-21 ("IL-21")-mediated proliferation of BaF3 cells with an $IC_{50}$ of about 1.75 nM or less, and wherein the BaF3 cells comprise a human IL-21R.

10. The binding protein or antigen-binding fragment of any one of claim 1, 2, 4, or 5, wherein the binding protein or antigen-binding fragment inhibits IL-21-mediated proliferation of TF1 cells with an $IC_{50}$ of about 14.0 nM or less, and wherein the TF1 cells comprise a human IL-21R.

11. The binding protein or antigen-binding fragment of any one of claim 1, 2, 4, or 5, wherein the binding protein or antigen-binding fragment inhibits IL-21-mediated proliferation of primary human B cells with an $IC_{50}$ of about 1.9 nM or less, and wherein the B cells comprise a human IL-21R.

12. The binding protein or antigen-binding fragment of any one of claim 1, 2, 4, or 5, wherein the binding protein or antigen-binding fragment inhibits IL-21-mediated proliferation of primary human CD4+cells with an $IC_{50}$ of about 1.5 nM or less, and wherein the CD4+cells comprise a human IL-21R.

13. The binding protein or antigen-binding fragment of any one of claim 1, 2, 4, or 5, wherein the binding protein or antigen-binding fragment specifically binds to an amino acid sequence that is at least about 95% identical to any sequence of at least 100 contiguous amino acids of SEQ ID NO:2.

14. The binding protein or antigen-binding fragment of any one of claim 1, 2, 4, or 5, wherein the binding protein or antigen-binding fragment inhibits the binding of IL-21 to IL-21R.

15. The binding protein or antigen-binding fragment of any one of claim 1, 2, 4, or 5, wherein the binding protein or antigen-binding fragment is IgG1.

16. The binding protein or antigen-binding fragment of any one of claim 1, 2, 4, or 5, wherein the binding protein or antigen-binding fragment is human.

17. A pharmaceutical composition comprising the binding protein or antigen-binding fragment of any one of claim 1, 2, 4, or 5.

18. A diagnostic kit comprising the binding protein or antigen-binding fragment of any one of claim 1, 2, 4, or 5.

19. An isolated binding protein or antigen-binding fragment thereof that binds to IL-21R, wherein the binding protein or antigen-binding fragment thereof comprises a $V_L$ domain and a $V_H$ domain, and wherein the $V_L$ domain comprises the amino acid sequence encoded by nucleotide 58 to 384 of SEQ ID NO:97, and the $V_H$ domain comprises the amino acid sequence encoded by nucleotide 58 to 411 of SEQ ID NO:239.

20. The isolated binding protein or antigen-binding fragment of claim 7 or 19, wherein the binding protein or antigen-binding fragment is an antibody.

21. The isolated binding protein or antigen-binding fragment of claim 7 or 19, wherein the binding protein or antigen-binding fragment is an scFv.

* * * * *

SEQUENCE LISTING

<160> NUMBER OF SEQ ID NOS: 248

<210> SEQ ID NO 1
<211> LENGTH: 2665
<212> TYPE: DNA
<213> ORGANISM: Homo sapiens
<220> FEATURE:

```
<221> NAME/KEY: CDS
<222> LOCATION: (236)..(1849)

<400> SEQUENCE: 1
gtcgactgga ggcccagctg cccgtcatca gagtgacagg tcttatgaca gcctgattgg    60
tgactcgggc tgggtgtgga ttctcacccc aggcctctgc ctgctttctc agaccctcat   120
ctgtcacccc cacgctgaac ccagctgcca cccccagaag cccatcagac tgccccagc    180 acacggaatg gatttctgag aaagaagccg aaacagaagg cccgtgggag tcagc atg    238
                                                              Met
                                                              1 ccg cgt ggc tgg gcc gcc ccc ttg ctc ctg ctg ctg ctc cag gga ggc     286
Pro Arg Gly Trp Ala Ala Pro Leu Leu Leu Leu Leu Leu Gln Gly Gly
         5                  10                 15 tgg ggc tgc ccc gac ctc gtc tgc tac acc gat tac ctc cag acg gtc     334
Trp Gly Cys Pro Asp Leu Val Cys Tyr Thr Asp Tyr Leu Gln Thr Val
     20                  25                  30 atc tgc atc ctg gaa atg tgg aac ctc cac ccc agc acg ctc acc ctt     382
Ile Cys Ile Leu Glu Met Trp Asn Leu His Pro Ser Thr Leu Thr Leu
 35                  40                  45 acc tgg caa gac cag tat gaa gag ctg aag gac gag gcc acc tcc tgc     430
Thr Trp Gln Asp Gln Tyr Glu Glu Leu Lys Asp Glu Ala Thr Ser Cys
 50                  55                  60                  65 agc ctc cac agg tcg gcc cac aat gcc acg cat gcc acc tac acc tgc     478
Ser Leu His Arg Ser Ala His Asn Ala Thr His Ala Thr Tyr Thr Cys
             70                  75                  80 cac atg gat gta ttc cac ttc atg gcc gac gac att ttc agt gtc aac     526
His Met Asp Val Phe His Phe Met Ala Asp Asp Ile Phe Ser Val Asn
         85                  90                  95 atc aca gac cag tct ggc aac tac tcc cag gag tgt ggc agc ttt ctc     574
Ile Thr Asp Gln Ser Gly Asn Tyr Ser Gln Glu Cys Gly Ser Phe Leu
    100                 105                 110 ctg gct gag agc atc aag ccg gct ccc cct ttc aac gtg act gtg acc     622
Leu Ala Glu Ser Ile Lys Pro Ala Pro Pro Phe Asn Val Thr Val Thr
115                 120                 125 ttc tca gga cag tat aat atc tcc tgg cgc tca gat tac gaa gac cct     670
Phe Ser Gly Gln Tyr Asn Ile Ser Trp Arg Ser Asp Tyr Glu Asp Pro
130                 135                 140                 145 gcc ttc tac atg ctg aag ggc aag ctt cag tat gag ctg cag tac agg     718
Ala Phe Tyr Met Leu Lys Gly Lys Leu Gln Tyr Glu Leu Gln Tyr Arg
            150                 155                 160 aac cgg gga gac ccc tgg gct gtg agt ccg agg aga aag ctg atc tca     766
Asn Arg Gly Asp Pro Trp Ala Val Ser Pro Arg Arg Lys Leu Ile Ser
        165                 170                 175 gtg gac tca aga agt gtc tcc ctc ctc ccc ctg gag ttc cgc aaa gac     814
Val Asp Ser Arg Ser Val Ser Leu Leu Pro Leu Glu Phe Arg Lys Asp
    180                 185                 190 tcg agc tat gag ctg cag gtg cgg gca ggg ccc atg cct ggc tcc tcc     862
Ser Ser Tyr Glu Leu Gln Val Arg Ala Gly Pro Met Pro Gly Ser Ser
195                 200                 205 tac cag ggg acc tgg agt gaa tgg agt gac ccg gtc atc ttt cag acc     910
Tyr Gln Gly Thr Trp Ser Glu Trp Ser Asp Pro Val Ile Phe Gln Thr
210                 215                 220                 225 cag tca gag gag tta aag gaa ggc tgg aac cct cac ctg ctg ctt ctc     958
Gln Ser Glu Glu Leu Lys Glu Gly Trp Asn Pro His Leu Leu Leu Leu
            230                 235                 240 ctc ctg ctt gtc ata gtc ttc att cct gcc ttc tgg agc ctg aag acc    1006
Leu Leu Leu Val Ile Val Phe Ile Pro Ala Phe Trp Ser Leu Lys Thr
        245                 250                 255 cat cca ttg tgg agg cta tgg aag aag ata tgg gcc gtc ccc agc cct    1054
```

```
              His Pro Leu Trp Arg Leu Trp Lys Lys Ile Trp Ala Val Pro Ser Pro
                      260                 265                 270 gag cgg ttc ttc atg ccc ctg tac aag ggc tgc agc gga gac ttc aag          1102
Glu Arg Phe Phe Met Pro Leu Tyr Lys Gly Cys Ser Gly Asp Phe Lys
        275                 280                 285 aaa tgg gtg ggt gca ccc ttc act ggc tcc agc ctg gag ctg gga ccc          1150
Lys Trp Val Gly Ala Pro Phe Thr Gly Ser Ser Leu Glu Leu Gly Pro
290                 295                 300                 305 tgg agc cca gag gtg ccc tcc acc ctg gag gtg tac agc tgc cac cca          1198
Trp Ser Pro Glu Val Pro Ser Thr Leu Glu Val Tyr Ser Cys His Pro
                310                 315                 320 cca cgg agc ccg gcc aag agg ctg cag ctc acg gag cta caa gaa cca          1246
Pro Arg Ser Pro Ala Lys Arg Leu Gln Leu Thr Glu Leu Gln Glu Pro
            325                 330                 335 gca gag ctg gtg gag tct gac ggt gtg ccc aag ccc agc ttc tgg ccg          1294
Ala Glu Leu Val Glu Ser Asp Gly Val Pro Lys Pro Ser Phe Trp Pro
        340                 345                 350 aca gcc cag aac tcg ggg ggc tca gct tac agt gag gag agg gat cgg          1342
Thr Ala Gln Asn Ser Gly Gly Ser Ala Tyr Ser Glu Glu Arg Asp Arg
    355                 360                 365 cca tac ggc ctg gtg tcc att gac aca gtg act gtg cta gat gca gag          1390
Pro Tyr Gly Leu Val Ser Ile Asp Thr Val Thr Val Leu Asp Ala Glu
370                 375                 380                 385 ggg cca tgc acc tgg ccc tgc agc tgt gag gat gac ggc tac cca gcc          1438
Gly Pro Cys Thr Trp Pro Cys Ser Cys Glu Asp Asp Gly Tyr Pro Ala
                390                 395                 400 ctg gac ctg gat gct ggc ctg gag ccc agc cca ggc cta gag gac cca          1486
Leu Asp Leu Asp Ala Gly Leu Glu Pro Ser Pro Gly Leu Glu Asp Pro
            405                 410                 415 ctc ttg gat gca ggg acc aca gtc ctg tcc tgt ggc tgt gtc tca gct          1534
Leu Leu Asp Ala Gly Thr Thr Val Leu Ser Cys Gly Cys Val Ser Ala
        420                 425                 430 ggc agc cct ggg cta gga ggg ccc ctg gga agc ctc ctg gac aga cta          1582
Gly Ser Pro Gly Leu Gly Gly Pro Leu Gly Ser Leu Leu Asp Arg Leu
    435                 440                 445 aag cca ccc ctt gca gat ggg gag gac tgg gct ggg gga ctg ccc tgg          1630
Lys Pro Pro Leu Ala Asp Gly Glu Asp Trp Ala Gly Gly Leu Pro Trp
450                 455                 460                 465 ggt ggc cgg tca cct gga ggg gtc tca gag agt gag gcg ggc tca ccc          1678
Gly Gly Arg Ser Pro Gly Gly Val Ser Glu Ser Glu Ala Gly Ser Pro
                470                 475                 480 ctg gcc ggc ctg gat atg gac acg ttt gac agt ggc ttt gtg ggc tct          1726
Leu Ala Gly Leu Asp Met Asp Thr Phe Asp Ser Gly Phe Val Gly Ser
            485                 490                 495 gac tgc agc agc cct gtg gag tgt gac ttc acc agc ccc ggg gac gaa          1774
Asp Cys Ser Ser Pro Val Glu Cys Asp Phe Thr Ser Pro Gly Asp Glu
        500                 505                 510 gga ccc ccc cgg agc tac ctc cgc cag tgg gtg gtc att cct ccg cca          1822
Gly Pro Pro Arg Ser Tyr Leu Arg Gln Trp Val Val Ile Pro Pro Pro
    515                 520                 525 ctt tcg agc cct gga ccc cag gcc agc taatgaggct gactggatgt                1869
Leu Ser Ser Pro Gly Pro Gln Ala Ser
530                 535 ccagagctgg ccaggccact gggccctgag ccagagacaa ggtcacctgg gctgtgatgt        1929
gaagacacct gcagcctttg gtctcctgga tgggcctttg agcctgatgt ttacagtgtc        1989
tgtgtgtgtg tgtgcatatg tgtgtgtgtg catatgcatg tgtgtgtgtg tgtgtgtctt        2049
aggtgcgcag tggcatgtcc acgtgtgtgt gtgattgcac gtgcctgtgg gcctgggata        2109
atgcccatgg tactccatgc attcacctgc cctgtgcatg tctggactca cggagctcac        2169
```

```
ccatgtgcac aagtgtgcac agtaaacgtg tttgtggtca acagatgaca acagccgtcc    2229
tccctcctag ggtcttgtgt tgcaagttgg tccacagcat ctccggggct tgtgggatc     2289 agggcattgc ctgtgactga ggcggagccc agccctccag cgtctgcctc caggagctgc    2349
aagaagtcca tattgttcct tatcacctgc aacaggaag cgaaagggga tggagtgagc     2409
ccatggtgac ctcgggaatg gcaattttt gggcggcccc tggacgaagg tctgaatccc     2469
gactctgata ccttctggct gtgctacctg agccaagtcg cctcccctct ctgggctaga    2529
gtttccttat ccagacagtg gggaaggcat gacacacctg ggggaaattg cgatgtcac     2589 ccgtgtacgg tacgcagccc agagcagacc ctcaataaac gtcagcttcc ttcaaaaaaa    2649
aaaaaaaaaa tctaga                                                    2665

<210> SEQ ID NO 2
<211> LENGTH: 538
<212> TYPE: PRT
<213> ORGANISM: Homo sapiens

<400> SEQUENCE: 2

Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
        50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285
```

```
Lys Lys Trp Val Gly Ala Pro Phe Thr Gly Ser Ser Leu Glu Leu Gly
    290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Pro Leu Gly Ser Leu Leu Asp Arg
        435                 440                 445

Leu Lys Pro Pro Leu Ala Asp Gly Glu Asp Trp Ala Gly Gly Leu Pro
450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535

<210> SEQ ID NO 3
<211> LENGTH: 2628
<212> TYPE: DNA
<213> ORGANISM: Mus musculus
<220> FEATURE:
<221> NAME/KEY: CDS
<222> LOCATION: (407)..(1993)

<400> SEQUENCE: 3
gtcgacgcgg cggtaccagc tgtctgccca cttctcctgt ggtgtgcctc acggtcactt      60
gcttgtctga ccgcaagtct gcccatccct ggggcagcca actggcctca gcccgtgccc     120
caggcgtgcc ctgtctctgt ctggctgccc agcccctact gtcttcctct gtgtaggctc     180
tgcccagatg cccggctggt cctcagcctc aggactatct cagcagtgac tcccctgatt     240
ctggacttgc acctgactga actcctgccc acctcaaacc ttcacctccc accaccacca     300
ctccgagtcc cgctgtgact cccacgccca ggagaccacc caagtgcccc agcctaaaga     360
atggctttct gagaaagacc ctgaaggagt aggtctggga cacagc atg ccc cgg        415
                                               Met Pro Arg
                                                 1 ggc cca gtg gct gcc tta ctc ctg ctg att ctc cat gga gct tgg agc       463
Gly Pro Val Ala Ala Leu Leu Leu Leu Ile Leu His Gly Ala Trp Ser
  5                  10                  15
```

```
tgc ctg gac ctc act tgc tac act gac tac ctc tgg acc atc acc tgt        511
Cys Leu Asp Leu Thr Cys Tyr Thr Asp Tyr Leu Trp Thr Ile Thr Cys
 20              25                  30                  35 gtc ctg gag aca cgg agc ccc aac ccc agc ata ctc agt ctc acc tgg        559
Val Leu Glu Thr Arg Ser Pro Asn Pro Ser Ile Leu Ser Leu Thr Trp
                 40                  45                  50 caa gat gaa tat gag gaa ctt cag gac caa gag acc ttc tgc agc cta        607
Gln Asp Glu Tyr Glu Glu Leu Gln Asp Gln Glu Thr Phe Cys Ser Leu
                     55                  60                  65 cac agg tct ggc cac aac acc aca cat ata tgg tac acg tgc cat atg        655
His Arg Ser Gly His Asn Thr Thr His Ile Trp Tyr Thr Cys His Met
                 70                  75                  80 cgc ttg tct caa ttc ctg tcc gat gaa gtt ttc att gtc aat gtg acg        703
Arg Leu Ser Gln Phe Leu Ser Asp Glu Val Phe Ile Val Asn Val Thr
 85                  90                  95 gac cag tct ggc aac aac tcc caa gag tgt ggc agc ttt gtc ctg gct        751
Asp Gln Ser Gly Asn Asn Ser Gln Glu Cys Gly Ser Phe Val Leu Ala
100                 105                 110                 115 gag agc atc aaa cca gct ccc ccc ttg aac gtg act gtg gcc ttc tca        799
Glu Ser Ile Lys Pro Ala Pro Pro Leu Asn Val Thr Val Ala Phe Ser
                120                 125                 130 gga cgc tat gat atc tcc tgg gac tca gct tat gac gaa ccc tcc aac        847
Gly Arg Tyr Asp Ile Ser Trp Asp Ser Ala Tyr Asp Glu Pro Ser Asn
                    135                 140                 145 tac gtg ctg agg ggc aag cta caa tat gag ctg cag tat cgg aac ctc        895
Tyr Val Leu Arg Gly Lys Leu Gln Tyr Glu Leu Gln Tyr Arg Asn Leu
                150                 155                 160 aga gac ccc tat gct gtg agg ccg gtg acc aag ctg atc tca gtg gac        943
Arg Asp Pro Tyr Ala Val Arg Pro Val Thr Lys Leu Ile Ser Val Asp
            165                 170                 175 tca aga aac gtc tct ctt ctc cct gaa gag ttc cac aaa gat tct agc        991
Ser Arg Asn Val Ser Leu Leu Pro Glu Glu Phe His Lys Asp Ser Ser
180                 185                 190                 195 tac cag ctg cag gtg cgg gca gcg cct cag cca ggc act tca ttc agg       1039
Tyr Gln Leu Gln Val Arg Ala Ala Pro Gln Pro Gly Thr Ser Phe Arg
                200                 205                 210 ggg acc tgg agt gag tgg agt gac ccc gtc atc ttt cag acc cag gct       1087
Gly Thr Trp Ser Glu Trp Ser Asp Pro Val Ile Phe Gln Thr Gln Ala
                    215                 220                 225 ggg gag ccc gag gca ggc tgg gac cct cac atg ctg ctg ctc ctg gct       1135
Gly Glu Pro Glu Ala Gly Trp Asp Pro His Met Leu Leu Leu Leu Ala
                230                 235                 240 gtc ttg atc att gtc ctg gtt ttc atg ggt ctg aag atc cac ctg cct       1183
Val Leu Ile Ile Val Leu Val Phe Met Gly Leu Lys Ile His Leu Pro
                    245                 250                 255 tgg agg cta tgg aaa aag ata tgg gca cca gtg ccc acc cct gag agt       1231
Trp Arg Leu Trp Lys Lys Ile Trp Ala Pro Val Pro Thr Pro Glu Ser
260                 265                 270                 275 ttc ttc cag ccc ctg tac agg gag cac agc ggg aac ttc aag aaa tgg       1279
Phe Phe Gln Pro Leu Tyr Arg Glu His Ser Gly Asn Phe Lys Lys Trp
                280                 285                 290 gtt aat acc cct ttc acg gcc tcc agc ata gag ttg gtg cca cag agt       1327
Val Asn Thr Pro Phe Thr Ala Ser Ser Ile Glu Leu Val Pro Gln Ser
                    295                 300                 305 tcc aca aca aca tca gcc tta cat ctg tca ttg tat cca gcc aag gag       1375
Ser Thr Thr Thr Ser Ala Leu His Leu Ser Leu Tyr Pro Ala Lys Glu
                310                 315                 320 aag aag ttc ccg ggg ctg ccg ggt ctg gaa gag caa ctg gag tgt gat       1423
Lys Lys Phe Pro Gly Leu Pro Gly Leu Glu Glu Gln Leu Glu Cys Asp
325                 330                 335
```

-continued

| | | | | | | | | | | | | | | | |
|---|---|---|---|---|---|---|---|---|---|---|---|---|---|---|---|
| gga | atg | tct | gag | cct | ggt | cac | tgg | tgc | ata | atc | ccc | ttg | gca | gct | ggc | 1471 |
| Gly | Met | Ser | Glu | Pro | Gly | His | Trp | Cys | Ile | Ile | Pro | Leu | Ala | Ala | Gly |
| 340 | | | | | 345 | | | | | 350 | | | | | 355 |

| caa | gcg | gtc | tca | gcc | tac | agt | gag | gag | aga | gac | cgg | cca | tat | ggt | ctg | 1519 |
| Gln | Ala | Val | Ser | Ala | Tyr | Ser | Glu | Glu | Arg | Asp | Arg | Pro | Tyr | Gly | Leu |
|  |  |  | 360 |  |  |  |  | 365 |  |  |  |  | 370 |  |  |

| gtg | tcc | att | gac | aca | gtg | act | gtg | gga | gat | gca | gag | ggc | ctg | tgt | gtc | 1567 |
| Val | Ser | Ile | Asp | Thr | Val | Thr | Val | Gly | Asp | Ala | Glu | Gly | Leu | Cys | Val |
|  |  | 375 |  |  |  |  | 380 |  |  |  |  | 385 |  |  |  |

| tgg | ccc | tgt | agc | tgt | gag | gat | gat | ggc | tat | cca | gcc | atg | aac | ctg | gat | 1615 |
| Trp | Pro | Cys | Ser | Cys | Glu | Asp | Asp | Gly | Tyr | Pro | Ala | Met | Asn | Leu | Asp |
| | | 390 | | | | | 395 | | | | | 400 | | | |

| gct | ggc | cga | gag | tct | ggc | cct | aat | tca | gag | gat | ctg | ctc | ttg | gtc | aca | 1663 |
| Ala | Gly | Arg | Glu | Ser | Gly | Pro | Asn | Ser | Glu | Asp | Leu | Leu | Leu | Val | Thr |
| 405 | | | | | 410 | | | | | 415 | | | | | |

| gac | cct | gct | ttt | ctg | tct | tgc | ggc | tgt | gtc | tca | ggt | agt | ggt | ctc | agg | 1711 |
| Asp | Pro | Ala | Phe | Leu | Ser | Cys | Gly | Cys | Val | Ser | Gly | Ser | Gly | Leu | Arg |
| 420 | | | | 425 | | | | | 430 | | | | | 435 | |

| ctt | gga | ggc | tcc | cca | ggc | agc | cta | ctg | gac | agg | ttg | agg | ctg | tca | ttt | 1759 |
| Leu | Gly | Gly | Ser | Pro | Gly | Ser | Leu | Leu | Asp | Arg | Leu | Arg | Leu | Ser | Phe |
| | | | 440 | | | | | 445 | | | | | 450 | | |

| gca | aag | gaa | ggg | gac | tgg | aca | gca | gac | cca | acc | tgg | aga | act | ggg | tcc | 1807 |
| Ala | Lys | Glu | Gly | Asp | Trp | Thr | Ala | Asp | Pro | Thr | Trp | Arg | Thr | Gly | Ser |
| | | | 455 | | | | | 460 | | | | | 465 | | |

| cca | gga | ggg | ggc | tct | gag | agt | gaa | gca | ggt | tcc | ccc | cct | ggt | ctg | gac | 1855 |
| Pro | Gly | Gly | Gly | Ser | Glu | Ser | Glu | Ala | Gly | Ser | Pro | Pro | Gly | Leu | Asp |
| | | 470 | | | | | 475 | | | | | 480 | | | |

| atg | gac | aca | ttt | gac | agt | ggc | ttt | gca | ggt | tca | gac | tgt | ggc | agc | ccc | 1903 |
| Met | Asp | Thr | Phe | Asp | Ser | Gly | Phe | Ala | Gly | Ser | Asp | Cys | Gly | Ser | Pro |
| | 485 | | | | | 490 | | | | | 495 | | | | |

| gtg | gag | act | gat | gaa | gga | ccc | cct | cga | agc | tat | ctc | cgc | cag | tgg | gtg | 1951 |
| Val | Glu | Thr | Asp | Glu | Gly | Pro | Pro | Arg | Ser | Tyr | Leu | Arg | Gln | Trp | Val |
| 500 | | | | | 505 | | | | | 510 | | | | | 515 |

| gtc | agg | acc | cct | cca | cct | gtg | gac | agt | gga | gcc | cag | agc | agc | | | 1993 |
| Val | Arg | Thr | Pro | Pro | Pro | Val | Asp | Ser | Gly | Ala | Gln | Ser | Ser | | | |
| | | | 520 | | | | | 525 | | | | | | | | | tagcatataa taaccagcta tagtgagaag aggcctctga gcctggcatt tacagtgtga   2053 acatgtaggg gtgtgtgtgt gtgtgtgtgt gtgtgtgtgt gtgtgtgtgt gtgtgtgtgt   2113 gtgtgtgtgt cttgggttgt gtgttagcac atccatgttg ggatttggtc tgttgctatg   2173 tattgtaatg ctaaattctc tacccaaagt tctaggccta cgagtgaatt ctcatgttta   2233 caaacttgct gtgtaaacct tgttccttaa tttaatacca ttggttaaat aaaattggct   2293 gcaaccaatt actggaggga ttagaggtag ggggcttttg agttacctgt ttggagatgg   2353 agaaggagag aggagagacc aagaggagaa ggaggaagga gaggagagga gaggagagga   2413 gaggagagga gaggagagga gaggagagga gaggagaggc tgccgtgagg ggagagggac   2473 catgagcctg tggccaggag aaacagcaag tatctggggt acactggtga ggaggtggcc   2533 aggccagcag ttagaagagt agattagggg tgacctccag tatttgtcaa agccaattaa   2593 aataacaaaa aaaaaaaaaa agcggccgct ctaga   2628

<210> SEQ ID NO 4
<211> LENGTH: 529
<212> TYPE: PRT
<213> ORGANISM: Mus musculus

<400> SEQUENCE: 4

Met Pro Arg Gly Pro Val Ala Ala Leu Leu Leu Leu Ile Leu His Gly
1               5                   10                  15

```
Ala Trp Ser Cys Leu Asp Leu Thr Cys Tyr Thr Asp Tyr Leu Trp Thr
             20                  25                  30
Ile Thr Cys Val Leu Glu Thr Arg Ser Pro Asn Pro Ser Ile Leu Ser
             35                  40                  45
Leu Thr Trp Gln Asp Glu Tyr Glu Glu Leu Gln Asp Gln Glu Thr Phe
     50                  55                  60
Cys Ser Leu His Arg Ser Gly His Asn Thr Thr His Ile Trp Tyr Thr
65                  70                  75                  80
Cys His Met Arg Leu Ser Gln Phe Leu Ser Asp Glu Val Phe Ile Val
                 85                  90                  95
Asn Val Thr Asp Gln Ser Gly Asn Asn Ser Gln Glu Cys Gly Ser Phe
             100                 105                 110
Val Leu Ala Glu Ser Ile Lys Pro Ala Pro Pro Leu Asn Val Thr Val
             115                 120                 125
Ala Phe Ser Gly Arg Tyr Asp Ile Ser Trp Asp Ser Ala Tyr Asp Glu
         130                 135                 140
Pro Ser Asn Tyr Val Leu Arg Gly Lys Leu Gln Tyr Glu Leu Gln Tyr
145                 150                 155                 160
Arg Asn Leu Arg Asp Pro Tyr Ala Val Arg Pro Val Thr Lys Leu Ile
                 165                 170                 175
Ser Val Asp Ser Arg Asn Val Ser Leu Leu Pro Glu Glu Phe His Lys
             180                 185                 190
Asp Ser Ser Tyr Gln Leu Gln Val Arg Ala Ala Pro Gln Pro Gly Thr
         195                 200                 205
Ser Phe Arg Gly Thr Trp Ser Glu Trp Ser Asp Pro Val Ile Phe Gln
210                 215                 220
Thr Gln Ala Gly Glu Pro Glu Ala Gly Trp Asp Pro His Met Leu Leu
225                 230                 235                 240
Leu Leu Ala Val Leu Ile Ile Val Leu Val Phe Met Gly Leu Lys Ile
             245                 250                 255
His Leu Pro Trp Arg Leu Trp Lys Lys Ile Trp Ala Pro Val Pro Thr
                 260                 265                 270
Pro Glu Ser Phe Phe Gln Pro Leu Tyr Arg Glu His Ser Gly Asn Phe
             275                 280                 285
Lys Lys Trp Val Asn Thr Pro Phe Thr Ala Ser Ser Ile Glu Leu Val
         290                 295                 300
Pro Gln Ser Ser Thr Thr Thr Ser Ala Leu His Leu Ser Leu Tyr Pro
305                 310                 315                 320
Ala Lys Glu Lys Lys Phe Pro Gly Leu Pro Gly Leu Glu Glu Gln Leu
                 325                 330                 335
Glu Cys Asp Gly Met Ser Glu Pro Gly His Trp Cys Ile Ile Pro Leu
             340                 345                 350
Ala Ala Gly Gln Ala Val Ser Ala Tyr Ser Glu Glu Arg Asp Arg Pro
         355                 360                 365
Tyr Gly Leu Val Ser Ile Asp Thr Val Thr Val Gly Asp Ala Glu Gly
     370                 375                 380
Leu Cys Val Trp Pro Cys Ser Cys Glu Asp Asp Gly Tyr Pro Ala Met
385                 390                 395                 400
Asn Leu Asp Ala Gly Arg Glu Ser Gly Pro Asn Ser Glu Asp Leu Leu
                 405                 410                 415
Leu Val Thr Asp Pro Ala Phe Leu Ser Cys Gly Cys Val Ser Gly Ser
             420                 425                 430
Gly Leu Arg Leu Gly Gly Ser Pro Gly Ser Leu Leu Asp Arg Leu Arg
```

Leu Ser Phe Ala Lys Glu Gly Asp Trp Thr Ala Asp Pro Thr Trp Arg
                450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                    485                 490                 495

Gly Ser Pro Val Glu Thr Asp Glu Gly Pro Pro Arg Ser Tyr Leu Arg
                500                 505                 510

Gln Trp Val Val Arg Thr Pro Pro Val Asp Ser Gly Ala Gln Ser
            515                 520                 525

Ser

<210> SEQ ID NO 5
<211> LENGTH: 354
<212> TYPE: DNA
<213> ORGANISM: Homo sapiens

<400> SEQUENCE: 5
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagt           354

<210> SEQ ID NO 6
<211> LENGTH: 118
<212> TYPE: PRT
<213> ORGANISM: Homo sapiens

<400> SEQUENCE: 6

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser
        115

<210> SEQ ID NO 7
<211> LENGTH: 354
<212> TYPE: DNA
<213> ORGANISM: Homo sapiens

<400> SEQUENCE: 7
caggtgcagc tgcaggagtc tggccctggc ctggtgaagc cttccgagac cctgtctctg      60

```
acctgtgccg tgtccggcta ctccatctcc tccggctact actggggctg gatcagacag    120
cctcctggca agggcctgga gtggatcggc tccatctctc acaccggcaa cacctactac    180 aaccccctc tgaagtccag agtgaccatc tccgtggaca cctccaagaa ccagttctcc     240
ctgaagctgt cctctgtgac cgctgccgat accgccgtgt actactgtgc cagaggcggc   300
ggaatctcca gacctgagta ctggggccag ggcaccctgg tgaccgtgtc ctct          354
```

<210> SEQ ID NO 8
<211> LENGTH: 118
<212> TYPE: PRT
<213> ORGANISM: Homo sapiens

<400> SEQUENCE: 8

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Gln Gly Thr
            100                 105                 110

Leu Val Thr Val Ser Ser
        115
```

<210> SEQ ID NO 9
<211> LENGTH: 327
<212> TYPE: DNA
<213> ORGANISM: Homo sapiens

<400> SEQUENCE: 9

```
tcttctgagc tgactcagga ccctcctgtg tctgtggcct tgggacagac agtcacgctc    60
acatgccaag agacagcct cagaacctat tatgcaagct ggtaccagca gaagtcagga    120
caggccccta tacttctcct ctatggtaaa cacaaacggc cctcagggat cccagaccgc    180
ttctctggct ccacctcagg agacacagct tccttgacca tcactggggc tcaggcggaa    240
gacgaggctg actattactg taactcccgg gactccagtg caaccccca tgttctgttc    300 ggcggaggga cccagctcac cgtttta                                       327
```

<210> SEQ ID NO 10
<211> LENGTH: 109
<212> TYPE: PRT
<213> ORGANISM: Homo sapiens

<400> SEQUENCE: 10

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45
```

```
Gly Lys His Lys Arg Pro Ser Gly Ile Pro Asp Arg Phe Ser Gly Ser
        50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                 85                  90                  95

His Val Leu Phe Gly Gly Gly Thr Gln Leu Thr Val Leu
            100                 105

<210> SEQ ID NO 11
<211> LENGTH: 327
<212> TYPE: DNA
<213> ORGANISM: Homo sapiens

<400> SEQUENCE: 11
tcctctgagc tgacccagga tcctgctgtg tctgtggccc tgggccagac cgtcaggatc    60
acctgccagg gcgatagcct gagaacctac tacgcctcct ggtatcagca gaagcctgga   120
caggcccctg tgctggtgat ctacggcaag acaagaggc catccggcat ccctgacaga   180
ttctccggct cctcctctgg caataccgcc tccctgacca tcaccggcgc tcaggccgag   240
gacgaggccg actactactg taactcccgg gactcttccg gcaaccctca cgtgctgttt   300
ggcggcggaa cccagctgac cgtgcta                                       327

<210> SEQ ID NO 12
<211> LENGTH: 109
<212> TYPE: PRT
<213> ORGANISM: Homo sapiens

<400> SEQUENCE: 12

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Thr Tyr Tyr Ala
                 20                  25                  30

Ser Trp Tyr Gln Gln Lys Pro Gly Gln Ala Pro Val Leu Val Ile Tyr
             35                  40                  45

Gly Lys His Lys Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Pro
                 85                  90                  95

His Val Leu Phe Gly Gly Gly Thr Gln Leu Thr Val Leu
            100                 105

<210> SEQ ID NO 13
<211> LENGTH: 354
<212> TYPE: DNA
<213> ORGANISM: artificial
<220> FEATURE:
<223> OTHER INFORMATION: H3 VH

<400> SEQUENCE: 13
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgattcatg   300
```
gggttcggcc gcccggagta ctggggcaaa ggcaccctgg tcaccgtctc gagt 354

<210> SEQ ID NO 14
<211> LENGTH: 118
<212> TYPE: PRT
<213> ORGANISM: artificial
<220> FEATURE:
<223> OTHER INFORMATION: H3 VH

<400> SEQUENCE: 14

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Met Gly Phe Gly Arg Pro Glu Tyr Trp Gly Lys Gly Thr
            100                 105                 110

Leu Val Thr Val Ser Ser
        115

<210> SEQ ID NO 15
<211> LENGTH: 354
<212> TYPE: DNA
<213> ORGANISM: artificial
<220> FEATURE:
<223> OTHER INFORMATION: H4 VH

<400> SEQUENCE: 15
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga agggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgatggctc     300
gggttcggcc gcccggagta ctggggcaaa ggcaccctgg tcaccgtctc gagt            354

<210> SEQ ID NO 16
<211> LENGTH: 118
<212> TYPE: PRT
<213> ORGANISM: artificial
<220> FEATURE:
<223> OTHER INFORMATION: H4 VH

<400> SEQUENCE: 16

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

-continued

```
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Trp Leu Gly Phe Gly Arg Pro Glu Tyr Trp Gly Lys Gly Thr
            100                 105                 110

Leu Val Thr Val Ser Ser
        115

<210> SEQ ID NO 17
<211> LENGTH: 354
<212> TYPE: DNA
<213> ORGANISM: artificial
<220> FEATURE:
<223> OTHER INFORMATION: H5 VH

<400> SEQUENCE: 17
caggtgcagc tgcaggagtc gggcccagga ctggtgaaga cttcggagac cctgtccctc      60
acctgcgctg tctctggtta ctccatcagc agtggttact actggggctg atccggcag     120 cccccaggga agggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgattcttg     300
ggcttcggcc ggccggagta ctggggcaaa ggcaccctgg tcaccgtctc gagt           354

<210> SEQ ID NO 18
<211> LENGTH: 118
<212> TYPE: PRT
<213> ORGANISM: artificial
<220> FEATURE:
<223> OTHER INFORMATION: H5 VH

<400> SEQUENCE: 18

Gln Val Gln Leu Gln Glu Ser Gly Pro Gly Leu Val Lys Thr Ser Glu
 1               5                  10                  15

Thr Leu Ser Leu Thr Cys Ala Val Ser Gly Tyr Ser Ile Ser Ser Gly
                 20                  25                  30

Tyr Tyr Trp Gly Trp Ile Arg Gln Pro Pro Gly Lys Gly Leu Glu Trp
             35                  40                  45

Ile Gly Ser Ile Ser His Thr Gly Asn Thr Tyr Tyr Asn Pro Pro Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Phe Leu Gly Phe Gly Arg Pro Glu Tyr Trp Gly Lys Gly Thr
            100                 105                 110

Leu Val Thr Val Ser Ser
        115

<210> SEQ ID NO 19
<211> LENGTH: 354
<212> TYPE: DNA
<213> ORGANISM: artificial
<220> FEATURE:
<223> OTHER INFORMATION: H6 VH

<400> SEQUENCE: 19
caggtgcagc tgcaggagtc gggcccagga ctggtgaaga cttcggagac cctgtccctc      60
```

```
acctgcgctg tctctggtta ctccatcagc agtggttact actggggctg gatccggcag    120
cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgattcttc    300
ggcttcggcc gcccggagta ctggggcaaa ggcaccctgg tcaccgtctc gagt           354
```

<210> SEQ ID NO 20
<211> LENGTH: 118
<212> TYPE: PRT
<213> ORGANISM: artificial
<220> FEATURE:
<223> OTHER INFORMATION: H6 VH

<400> SEQUENCE: 20

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Phe Gly Phe Gly Arg Pro Glu Tyr Trp Gly Lys Gly Thr
            100                 105                 110

Leu Val Thr Val Ser Ser
        115
```

<210> SEQ ID NO 21
<211> LENGTH: 327
<212> TYPE: DNA
<213> ORGANISM: artificial
<220> FEATURE:
<223> OTHER INFORMATION: L1 VL

<400> SEQUENCE: 21

```
tcttctgagc tgactcagga ccctcctgtg tctgtggcct tgggacagac agtcacgctc     60
acatgccaag agacagcct cagaacctat tatgcaagct ggtaccagca gaagtcagga    120
caggccccta tacttctcct ctatggtaaa cacaaacggc cctcaggat cccagaccgc    180 ttctctggct ccacctcagg agacacagct tccttgacca tcactgggc tcaggcggaa    240 gacgaggctg actattactg tgcgtcccgg tcggtgagcg gcaaccccca tgttctgttc    300
ggcggaggga cccagctcac cgttttta                                        327
```

<210> SEQ ID NO 22
<211> LENGTH: 109
<212> TYPE: PRT
<213> ORGANISM: artificial
<220> FEATURE:
<223> OTHER INFORMATION: L1 VL

<400> SEQUENCE: 22

```
Ser Ser Glu Leu Thr Gln Asp Pro Pro Val Ser Val Ala Leu Gly Gln
1               5                   10                  15
```

```
Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ala Ser Arg Ser Val Ser Gly Asn Pro
                85                  90                  95

His Val Leu Phe Gly Gly Gly Thr Gln Leu Thr Val Leu
            100                 105
```

```
<210> SEQ ID NO 23
<211> LENGTH: 327
<212> TYPE: DNA
<213> ORGANISM: artificial
<220> FEATURE:
<223> OTHER INFORMATION: L2 VL

<400> SEQUENCE: 23
tcttctgagc tgactcagga ccctcctgtg tctgtggcct tgggacagac agtcacgctc    60
acatgccaag agacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tgtcgcccgg tcggtggtgg caaccccca tgttctgttc   300 ggcggaggga cccagctcac cgttttta                                     327
```

```
<210> SEQ ID NO 24
<211> LENGTH: 109
<212> TYPE: PRT
<213> ORGANISM: artificial
<220> FEATURE:
<223> OTHER INFORMATION: L2 VL

<400> SEQUENCE: 24

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Ala Arg Ser Val Val Gly Asn Pro
                85                  90                  95

His Val Leu Phe Gly Gly Gly Thr Gln Leu Thr Val Leu
            100                 105
```

```
<210> SEQ ID NO 25
<211> LENGTH: 327
<212> TYPE: DNA
<213> ORGANISM: artificial
<220> FEATURE:
<223> OTHER INFORMATION: L3 VL

<400> SEQUENCE: 25
```

```
tcttctgagc tgactcagga ccctcctgtg tctgtggcct tgggacagac agtcacgctc      60
acatgccaag agacagcct cagaacctat tatgcaagct ggtaccagca gaagtcagga      120
caggccccta cttctcct ctatggtaaa cacaaacggc cctcaggat cccagaccgc       180 ttctctggct ccacctcagg agacacagct tccttgacca tcactggggc tcaggcggaa   240
gacgaggctg actattactg tgtcagcagg gcggtggtgg gcaaccccca tgttctgttc   300
ggcggaggga cccagctcac cgtttta                                         327
```

<210> SEQ ID NO 26
<211> LENGTH: 109
<212> TYPE: PRT
<213> ORGANISM: artificial
<220> FEATURE:
<223> OTHER INFORMATION: L3 VL

<400> SEQUENCE: 26

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Ser Arg Ala Val Val Gly Asn Pro
                85                  90                  95

His Val Leu Phe Gly Gly Gly Thr Gln Leu Thr Val Leu
            100                 105

<210> SEQ ID NO 27
<211> LENGTH: 327
<212> TYPE: DNA
<213> ORGANISM: Artificial
<220> FEATURE:
<223> OTHER INFORMATION: L4 VL

<400> SEQUENCE: 27

```
tcttctgagc tgactcagga ccctcctgtg tctgtggcct tgggacagac agtcacgctc      60
acatgccaag agacagcct cagaacctat tatgcaagct ggtaccagca gaagtcagga      120
caggccccta cttctcct ctatggtaaa cacaaacggc cctcaggat cccagaccgc       180 ttctctggct ccacctcagg agacacagct tccttgacca tcactggggc tcaggcggaa   240
gacgaggctg actattactg tagcacccgc agcagcaagg gcaaccccca tgttctgttc   300
ggcggaggga cccagctcac cgtttta                                         327
```

<210> SEQ ID NO 28
<211> LENGTH: 109
<212> TYPE: PRT
<213> ORGANISM: artificial
<220> FEATURE:
<223> OTHER INFORMATION: L4 VL

<400> SEQUENCE: 28

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala

```
                        20                  25                  30
Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
        50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ser Thr Arg Ser Ser Lys Gly Asn Pro
                85                  90                  95

His Val Leu Phe Gly Gly Gly Thr Gln Leu Thr Val Leu
                100                 105
```

<210> SEQ ID NO 29
<211> LENGTH: 327
<212> TYPE: DNA
<213> ORGANISM: artificial
<220> FEATURE:
<223> OTHER INFORMATION: L5 VL

<400> SEQUENCE: 29

```
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta cttctcct ctatggtaaa cacaaacggc cctcaggat cccgaccgc       180 ttctctggct ccacctcagg agacacagct tccttgacca tcactggggc tcaggcggaa    240
gacgaggctg actattactg tgccagcagg tcctccaagg gcaaccccca tgttctgttc    300
ggcggaggga cccagctcac cgttttta                                        327
```

<210> SEQ ID NO 30
<211> LENGTH: 109
<212> TYPE: PRT
<213> ORGANISM: artificial
<220> FEATURE:
<223> OTHER INFORMATION: L5 VL

<400> SEQUENCE: 30

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
        50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ala Ser Arg Ser Ser Lys Gly Asn Pro
                85                  90                  95

His Val Leu Phe Gly Gly Gly Thr Gln Leu Thr Val Leu
                100                 105
```

<210> SEQ ID NO 31
<211> LENGTH: 327
<212> TYPE: DNA
<213> ORGANISM: artificial
<220> FEATURE:
<223> OTHER INFORMATION: L6 VL

<400> SEQUENCE: 31

```
tcttctgagc tgactcagga ccctcctgtg tctgtggcct tgggacagac agtcacgctc    60
acatgccaag gagacagcct cagaacctat tatgcaagct ggtaccagca gaagtcagga   120 caggcccta tacttctcct ctatggtaaa cacaaacggc cctcagggat cccagaccgc    180
ttctctggct ccacctcagg agacacagct tccttgacca tcactgggc tcaggcggaa    240 gacgaggctg actattactg tatgagcagg agcatctggg caacccca tgttctgttc     300 ggcggaggga cccagctcac cgtttta                                        327

<210> SEQ ID NO 32
<211> LENGTH: 109
<212> TYPE: PRT
<213> ORGANISM: artificial
<220> FEATURE:
<223> OTHER INFORMATION: L6 VL

<400> SEQUENCE: 32

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Met Ser Arg Ser Ile Trp Gly Asn Pro
                85                  90                  95

His Val Leu Phe Gly Gly Gly Thr Gln Leu Thr Val Leu
            100                 105

<210> SEQ ID NO 33
<211> LENGTH: 327
<212> TYPE: DNA
<213> ORGANISM: artificial
<220> FEATURE:
<223> OTHER INFORMATION: L8 VL

<400> SEQUENCE: 33
tcttctgagc tgactcagga ccctcctgtg tctgtggcct tgggacagac agtcacgctc    60
acatgccaag gagacagcct cagaacctat tatgcaagct ggtaccagca gaagtcagga   120 caggcccta tacttctcct ctatggtaaa cacaaacggc cctcagggat cccagaccgc    180
ttctctggct ccacctcagg agacacagct tccttgacca tcactgggc tcaggcggaa    240 gacgaggctg actattactg taccacgcgc tccacccagg caacccca tgttctgttc    300 ggcggaggga cccagctcac cgtttta                                        327

<210> SEQ ID NO 34
<211> LENGTH: 109
<212> TYPE: PRT
<213> ORGANISM: artificial
<220> FEATURE:
<223> OTHER INFORMATION: L8 VL

<400> SEQUENCE: 34

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30
```

Ser Trp Tyr Gln Gln Lys Ser Gly Gln Ala Pro Ile Leu Leu Leu Tyr
                35                  40                  45

Gly Lys His Lys Arg Pro Ser Gly Ile Pro Asp Arg Phe Ser Gly Ser
         50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Thr Thr Arg Ser Thr Gln Gly Asn Pro
                 85                  90                  95

His Val Leu Phe Gly Gly Gly Thr Gln Leu Thr Val Leu
                100                 105

<210> SEQ ID NO 35
<211> LENGTH: 327
<212> TYPE: DNA
<213> ORGANISM: artificial
<220> FEATURE:
<223> OTHER INFORMATION: L9 VL

<400> SEQUENCE: 35
tcttctgagc tgactcagga ccctcctgtg tctgtggcct tgggacagac agtcacgctc     60
acatgccaag agacagcct cagaacctat tatgcaagct ggtaccagca gaagtcagga    120
caggccccta tacttctcct ctatggtaaa cacaaacggc cctcaggat cccagaccgc    180 ttctctggct ccacctcagg agacacagct ccttgacca tcactggggc tcaggcggaa    240
gacgaggctg actattactg tgtcgccagg tccaacaagg caaccccca tgttctgttc    300 ggcggaggga cccagctcac cgttttta                                       327

<210> SEQ ID NO 36
<211> LENGTH: 109
<212> TYPE: PRT
<213> ORGANISM: artificial
<220> FEATURE:
<223> OTHER INFORMATION: L9 VL

<400> SEQUENCE: 36

Ser Ser Glu Leu Thr Gln Asp Pro Pro Val Ser Val Ala Leu Gly Gln
 1               5                  10                  15

Thr Val Thr Leu Thr Cys Gln Gly Asp Ser Leu Arg Thr Tyr Tyr Ala
                20                  25                  30

Ser Trp Tyr Gln Gln Lys Ser Gly Gln Ala Pro Ile Leu Leu Leu Tyr
                35                  40                  45

Gly Lys His Lys Arg Pro Ser Gly Ile Pro Asp Arg Phe Ser Gly Ser
         50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Val Ala Arg Ser Asn Lys Gly Asn Pro
                 85                  90                  95

His Val Leu Phe Gly Gly Gly Thr Gln Leu Thr Val Leu
                100                 105

<210> SEQ ID NO 37
<211> LENGTH: 327
<212> TYPE: DNA
<213> ORGANISM: artificial
<220> FEATURE:
<223> OTHER INFORMATION: L10 VL

<400> SEQUENCE: 37
tcttctgagc tgactcagga ccctcctgtg tctgtggcct tgggacagac agtcacgctc     60

```
acatgccaag gagacagcct cagaacctat tatgcaagct ggtaccagca gaagtcagga    120 caggcccta  tacttctcct ctatggtaaa cacaaacggc cctcagggat cccagaccgc    180
ttctctggct ccacctcagg agacacagct tccttgacca tcactggggc tcaggcggaa    240
gacgaggctg actattactg tatcagccgg tcgatctacg gcaaccccca tgttctgttc    300
ggcggaggga cccagctcac cgtttta                                        327
```

<210> SEQ ID NO 38
<211> LENGTH: 109
<212> TYPE: PRT
<213> ORGANISM: artificial
<220> FEATURE:
<223> OTHER INFORMATION: L10 VL

<400> SEQUENCE: 38

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ile Ser Arg Ser Ile Tyr Gly Asn Pro
                85                  90                  95

His Val Leu Phe Gly Gly Gly Thr Gln Leu Thr Val Leu
            100                 105
```

<210> SEQ ID NO 39
<211> LENGTH: 327
<212> TYPE: DNA
<213> ORGANISM: artificial
<220> FEATURE:
<223> OTHER INFORMATION: L11 VL

<400> SEQUENCE: 39

```
tcttctgagc tgactcagga ccctcctgtg tctgtggcct tgggacagac agtcacgctc    60
acatgccaag gagacagcct cagaacctat tatgcaagct ggtaccagca gaagtcagga    120 caggcccta  tacttctcct ctatggtaaa cacaaacggc cctcagggat cccagaccgc    180
ttctctggct ccacctcagg agacacagct tccttgacca tcactggggc tcaggcggaa    240
gacgaggctg actattactg ttcctcccgc tcccgccacg gcaaccccca tgttctgttc    300
ggcggaggga cccagctcac cgtttta                                        327
```

<210> SEQ ID NO 40
<211> LENGTH: 109
<212> TYPE: PRT
<213> ORGANISM: artificial
<220> FEATURE:
<223> OTHER INFORMATION: L11 VL

<400> SEQUENCE: 40

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30
```

```
Ser Trp Tyr Gln Gln Lys Ser Gly Gln Ala Pro Ile Leu Leu Leu Tyr
         35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ser Ser Arg Ser Arg His Gly Asn Pro
                 85                  90                  95

His Val Leu Phe Gly Gly Gly Thr Gln Leu Thr Val Leu
            100                 105
```

```
<210> SEQ ID NO 41
<211> LENGTH: 327
<212> TYPE: DNA
<213> ORGANISM: artificial
<220> FEATURE:
<223> OTHER INFORMATION: L12 VL

<400> SEQUENCE: 41
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta tacttctcct ctatggtaaa cacaaacggc cctcagggat cccagaccgc    180
ttctctggct ccacctcagg agacacagct tccttgacca tcactgggc tcaggcggaa     240 gacgaggctg actattactg tcgcgagggg ggacgagggg caacccccca tgttctgttc    300
ggcggaggga cccagctcac cgtttta                                        327
```

```
<210> SEQ ID NO 42
<211> LENGTH: 109
<212> TYPE: PRT
<213> ORGANISM: artificial
<220> FEATURE:
<223> OTHER INFORMATION: L12 VL

<400> SEQUENCE: 42

Ser Ser Glu Leu Thr Gln Asp Pro Pro Val Ser Val Ala Leu Gly Gln
  1               5                  10                  15

Thr Val Thr Leu Thr Cys Gln Gly Asp Ser Leu Arg Thr Tyr Tyr Ala
             20                  25                  30

Ser Trp Tyr Gln Gln Lys Ser Gly Gln Ala Pro Ile Leu Leu Leu Tyr
         35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Val Ala Arg Gly Thr Arg Gly Asn Pro
                 85                  90                  95

His Val Leu Phe Gly Gly Gly Thr Gln Leu Thr Val Leu
            100                 105
```

```
<210> SEQ ID NO 43
<211> LENGTH: 327
<212> TYPE: DNA
<213> ORGANISM: artificial
<220> FEATURE:
<223> OTHER INFORMATION: L13 VL

<400> SEQUENCE: 43
tcttctgagc tgactcagga ccctcctgtg tctgtggcct tgggacagac agtcacgctc      60
```

```
acatgccaag gagacagcct cagaacctat tatgcaagct ggtaccagca gaagtcagga   120
caggccccta tacttctcct ctatggtaaa cacaaacggc cctcaggat cccagaccgc    180 ttctctggct ccacctcagg agacacagct tccttgacca tcactggggc tcaggcggaa   240
gacgaggctg actattactg tgtcacccgc aaccgctacg gcaaccccca tgttctgttc   300
ggcggaggga cccagctcac cgttttta                                      327
```

<210> SEQ ID NO 44
<211> LENGTH: 109
<212> TYPE: PRT
<213> ORGANISM: artificial
<220> FEATURE:
<223> OTHER INFORMATION: L13 VL

<400> SEQUENCE: 44

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
                20                  25                  30

Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
        50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Thr Arg Asn Arg Tyr Gly Asn Pro
                85                  90                  95

His Val Leu Phe Gly Gly Gly Thr Gln Leu Thr Val Leu
            100                 105
```

<210> SEQ ID NO 45
<211> LENGTH: 327
<212> TYPE: DNA
<213> ORGANISM: artificial
<220> FEATURE:
<223> OTHER INFORMATION: L14 VL

<400> SEQUENCE: 45

```
tcttctgagc tgactcagga ccctcctgtg tctgtggcct tgggacagac agtcacgctc   60
acatgccaag gagacagcct cagaacctat tatgcaagct ggtaccagca gaagtcagga   120
caggccccta tacttctcct ctatggtaaa cacaaacggc cctcaggat cccagaccgc    180 ttctctggct ccacctcagg agacacagct tccttgacca tcactggggc tcaggcggaa   240
gacgaggctg actattactg tatggcgagg tcgaggaagg caaccccca tgttctgttc    300 ggcggaggga cccagctcac cgttttta                                      327
```

<210> SEQ ID NO 46
<211> LENGTH: 109
<212> TYPE: PRT
<213> ORGANISM: artificial
<220> FEATURE:
<223> OTHER INFORMATION: L14 VL

<400> SEQUENCE: 46

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
                20                  25                  30

Ser Trp Tyr Gln Gln Lys Ser Gly Gln Ala Pro Ile Leu Leu Leu Tyr
```

```
                35                  40                  45
Gly Lys His Lys Arg Pro Ser Gly Ile Pro Asp Arg Phe Ser Gly Ser
 50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Met Ala Arg Ser Arg Lys Gly Asn Pro
                 85                  90                  95

His Val Leu Phe Gly Gly Gly Thr Gln Leu Thr Val Leu
            100                 105

<210> SEQ ID NO 47
<211> LENGTH: 327
<212> TYPE: DNA
<213> ORGANISM: artificial
<220> FEATURE:
<223> OTHER INFORMATION: L15 VL

<400> SEQUENCE: 47
tcttctgagc tgactcagga ccctcctgtg tctgtggcct tgggacagac agtcacgctc      60
acatgccaag gagacagcct cagaacctat tatgcaagct ggtaccagca gaagtcagga    120
caggccccta tacttctcct ctatggtaaa cacaaacggc cctcagggat cccagaccgc    180
ttctctggct ccacctcagg agacacagct tccttgacca tcactgggsc tcaggcggaa    240
gacgaggctg actattactg ttccacccgc gccatccacg gcaaccccca tgttctgttc    300
ggcggaggga cccagctcac cgttttta                                        327

<210> SEQ ID NO 48
<211> LENGTH: 109
<212> TYPE: PRT
<213> ORGANISM: artificial
<220> FEATURE:
<223> OTHER INFORMATION: L15 VL

<400> SEQUENCE: 48

Ser Ser Glu Leu Thr Gln Asp Pro Pro Val Ser Val Ala Leu Gly Gln
 1               5                  10                  15

Thr Val Thr Leu Thr Cys Gln Gly Asp Ser Leu Arg Thr Tyr Tyr Ala
                 20                  25                  30

Ser Trp Tyr Gln Gln Lys Ser Gly Gln Ala Pro Ile Leu Leu Leu Tyr
             35                  40                  45

Gly Lys His Lys Arg Pro Ser Gly Ile Pro Asp Arg Phe Ser Gly Ser
 50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ser Thr Arg Ala Ile His Gly Asn Pro
                 85                  90                  95

His Val Leu Phe Gly Gly Gly Thr Gln Leu Thr Val Leu
            100                 105

<210> SEQ ID NO 49
<211> LENGTH: 327
<212> TYPE: DNA
<213> ORGANISM: artificial
<220> FEATURE:
<223> OTHER INFORMATION: L16 VL

<400> SEQUENCE: 49
tcttctgagc tgactcagga ccctcctgtg tctgtggcct tgggacagac agtcacgctc      60
acatgccaag gagacagcct cagaacctat tatgcaagct ggtaccagca gaagtcagga    120
```

```
caggcccta tacttctcct ctatggtaaa cacaaacggc cctcagggat cccagaccgc        180
ttctctggct ccacctcagg agacacagct tccttgacca tcactgggc tcaggcggaa         240 gacgaggctg actattactg tgtgacgagg agcgcgaagg caaccccca tgttctgttc         300 ggcggaggga cccagctcac cgtttta                                           327
```

<210> SEQ ID NO 50
<211> LENGTH: 109
<212> TYPE: PRT
<213> ORGANISM: artificial
<220> FEATURE:
<223> OTHER INFORMATION: L16 VL

<400> SEQUENCE: 50

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Thr Arg Ser Ala Lys Gly Asn Pro
                85                  90                  95

His Val Leu Phe Gly Gly Gly Thr Gln Leu Thr Val Leu
            100                 105
```

<210> SEQ ID NO 51
<211> LENGTH: 327
<212> TYPE: DNA
<213> ORGANISM: artificial
<220> FEATURE:
<223> OTHER INFORMATION: L17 VL

<400> SEQUENCE: 51

```
tcttctgagc tgactcagga ccctcctgtg tctgtggcct tgggacagac agtcacgctc        60
acatgccaag agacagcct cagaacctat tatgcaagct ggtaccagca aaagtcagga         120 caggcccta tacttctcct ctatggtaaa cacaaacggc cctcagggat cccagaccgc        180
ttctctggct ccacctcagg agacacagct tccttgacca tcactgggc tcaggcggaa         240 gacgaggctg actattactg tagcacgagg tcgaggaagg caaccccca tgttctgttc         300 ggcggaggga cccagctcac cgtttta                                           327
```

<210> SEQ ID NO 52
<211> LENGTH: 109
<212> TYPE: PRT
<213> ORGANISM: artificial
<220> FEATURE:
<223> OTHER INFORMATION: L17 VL

<400> SEQUENCE: 52

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45
```

```
Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ser Thr Arg Ser Arg Lys Gly Asn Pro
                 85                  90                  95

His Val Leu Phe Gly Gly Gly Thr Gln Leu Thr Val Leu
            100                 105

<210> SEQ ID NO 53
<211> LENGTH: 327
<212> TYPE: DNA
<213> ORGANISM: artificial
<220> FEATURE:
<223> OTHER INFORMATION: L18 VL

<400> SEQUENCE: 53
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta cttctcct ctatggtaaa cacaaacggc cctcaggat ccagaccgc       180 ttctctggct ccacctcagg agacacagct tccttgacca tcactggggc tcaggcggaa    240
gacgaggctg actattactg tgtcacgagg agcgtgaagg gcaaccccca tgttctgttc    300
ggcggaggga cccagctcac cgtttta                                        327

<210> SEQ ID NO 54
<211> LENGTH: 109
<212> TYPE: PRT
<213> ORGANISM: artificial
<220> FEATURE:
<223> OTHER INFORMATION: L18 VL

<400> SEQUENCE: 54

Ser Ser Glu Leu Thr Gln Asp Pro Pro Val Ser Val Ala Leu Gly Gln
 1               5                  10                  15

Thr Val Thr Leu Thr Cys Gln Gly Asp Ser Leu Arg Thr Tyr Tyr Ala
             20                  25                  30

Ser Trp Tyr Gln Gln Lys Ser Gly Gln Ala Pro Ile Leu Leu Leu Tyr
         35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Val Thr Arg Ser Val Lys Gly Asn Pro
                 85                  90                  95

His Val Leu Phe Gly Gly Gly Thr Gln Leu Thr Val Leu
            100                 105

<210> SEQ ID NO 55
<211> LENGTH: 327
<212> TYPE: DNA
<213> ORGANISM: artificial
<220> FEATURE:
<223> OTHER INFORMATION: L19 VL

<400> SEQUENCE: 55
tcttctgagc tgactcagga ccctcctgtg tctgtggcct tgggacagac agtcacgctc      60
acatgccaag agacagcct cagaacctat tatgcaagct ggtaccagca gaagtcagga     120
```

```
caggcccta tacttctcct ctatggtaaa cacaaacggc cctcagggat cccagaccgc      180
ttctctggct ccacctcagg agacacagct tccttgacca tcactgggc tcaggcggaa      240 gacgaggctg actattactg tgtcgcgcgg gcggtgaggg gcaaccccca tgttctgttc      300
ggcggaggga cccagctcac cgtttta                                         327
```

<210> SEQ ID NO 56
<211> LENGTH: 109
<212> TYPE: PRT
<213> ORGANISM: artificial
<220> FEATURE:
<223> OTHER INFORMATION: L19 VL

<400> SEQUENCE: 56

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Ala Arg Ala Val Arg Gly Asn Pro
                85                  90                  95

His Val Leu Phe Gly Gly Gly Thr Gln Leu Thr Val Leu
            100                 105
```

<210> SEQ ID NO 57
<211> LENGTH: 327
<212> TYPE: DNA
<213> ORGANISM: artificial
<220> FEATURE:
<223> OTHER INFORMATION: L20 VL

<400> SEQUENCE: 57

```
tcttctgagc tgactcagga ccctcctgtg tctgtggcct tgggacagac agtcacgctc      60
acatgccaag agacagcct cagaacctat tatgcaagct ggtaccagca gaagtcagga     120 caggcccta tacttctcct ctatggtaaa cacaaacggc cctcagggat cccagaccgc      180
ttctctggct ccacctcagg agacacagct tccttgacca tcactgggc tcaggcggaa      240 gacgaggctg actattactg tctccccgc agcgcgaagg gcaaccccca tgttctgttc      300
ggcggaggga cccagctcac cgtttta                                         327
```

<210> SEQ ID NO 58
<211> LENGTH: 109
<212> TYPE: PRT
<213> ORGANISM: artificial
<220> FEATURE:
<223> OTHER INFORMATION: L20 VL

<400> SEQUENCE: 58

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45
```

```
Gly Lys His Lys Arg Pro Ser Gly Ile Pro Asp Arg Phe Ser Gly Ser
         50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Val Ser Arg Ser Ala Lys Gly Asn Pro
                     85                  90                  95

His Val Leu Phe Gly Gly Gly Thr Gln Leu Thr Val Leu
                100                 105
```

<210> SEQ ID NO 59
<211> LENGTH: 327
<212> TYPE: DNA
<213> ORGANISM: artificial
<220> FEATURE:
<223> OTHER INFORMATION: L21 VL

<400> SEQUENCE: 59

```
tcttctgagc tgactcagga ccctcctgtg tctgtggcct tgggacagac agtcacgctc    60
acatgccaag agacagcct cagaacctat tatgcaagct ggtaccagca gaagtcagga    120
caggccccta acttctcct ctatggtaaa cacaaacggc cctcagggat cccagaccgc    180
ttctctggct ccacctcagg agacacagct tccttgacca tcactggggc tcaggcggaa    240
gacgaggctg actattactg tgccacccgg gcggtccggg caaccccca tgttctgttc    300 ggcggaggga cccagctcac cgtttta                                       327
```

<210> SEQ ID NO 60
<211> LENGTH: 109
<212> TYPE: PRT
<213> ORGANISM: artificial
<220> FEATURE:
<223> OTHER INFORMATION: L21 VL

<400> SEQUENCE: 60

```
Ser Ser Glu Leu Thr Gln Asp Pro Pro Val Ser Val Ala Leu Gly Gln
  1               5                  10                  15

Thr Val Thr Leu Thr Cys Gln Gly Asp Ser Leu Arg Thr Tyr Tyr Ala
                 20                  25                  30

Ser Trp Tyr Gln Gln Lys Ser Gly Gln Ala Pro Ile Leu Leu Leu Tyr
             35                  40                  45

Gly Lys His Lys Arg Pro Ser Gly Ile Pro Asp Arg Phe Ser Gly Ser
         50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ala Thr Arg Ala Val Arg Gly Asn Pro
                     85                  90                  95

His Val Leu Phe Gly Gly Gly Thr Gln Leu Thr Val Leu
                100                 105
```

<210> SEQ ID NO 61
<211> LENGTH: 327
<212> TYPE: DNA
<213> ORGANISM: artificial
<220> FEATURE:
<223> OTHER INFORMATION: L23 VL

<400> SEQUENCE: 61

```
tcttctgagc tgactcagga ccctcctgtg tctgtggcct tgggacagac agtcacgctc    60
acatgccaag agacagcct cagaacctat tatgcaagct ggtaccagca gaagtcagga    120
caggccccta acttctcct ctatggtaaa cacaaacggc cctcagggat cccagaccgc    180
```

```
ttctctggct ccacctcagg agacacagct tccttgacca tcactggggc tcaggcggaa    240
gacgaggctg actattactg ttcggcgcgg tcggtgaggg gcaaccccca tgttctgttc    300
ggcggaggga cccagctcac cgtttta                                        327
```

```
<210> SEQ ID NO 62
<211> LENGTH: 109
<212> TYPE: PRT
<213> ORGANISM: artificial
<220> FEATURE:
<223> OTHER INFORMATION: L23 VL

<400> SEQUENCE: 62
```

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ser Ala Arg Ser Val Arg Gly Asn Pro
                85                  90                  95

His Val Leu Phe Gly Gly Gly Thr Gln Leu Thr Val Leu
            100                 105

```
<210> SEQ ID NO 63
<211> LENGTH: 327
<212> TYPE: DNA
<213> ORGANISM: artificial
<220> FEATURE:
<223> OTHER INFORMATION: L24 VL

<400> SEQUENCE: 63
tcttctgagc tgactcagga ccctcctgtg tctgtggcct tgggacagac agtcacgctc     60
acatgccaag agacagcct cagaacctat tatgcaagct ggtaccagca gaagtcagga    120
caggccccta tacttctcct ctatggtaaa cacaaacggc cctcaggat cccagaccgc     180 ttctctggct ccacctcagg agacacagct tccttgacca tcactggggc tcaggcggaa    240
gacgaggctg actattactg tatcgccagg agcaacaagg gcaaccccca tgttctgttc    300
ggcggaggga cccagctcac cgtttta                                        327
```

```
<210> SEQ ID NO 64
<211> LENGTH: 109
<212> TYPE: PRT
<213> ORGANISM: artificial
<220> FEATURE:
<223> OTHER INFORMATION: L24 VL

<400> SEQUENCE: 64
```

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser

```
                    50                  55                  60
Thr Ser Gly Asp Thr Ala Ser Leu Thr Ile Thr Gly Ala Gln Ala Glu
 65                  70                  75                  80

Asp Glu Ala Asp Tyr Tyr Cys Ile Ala Arg Ser Asn Lys Gly Asn Pro
                 85                  90                  95

His Val Leu Phe Gly Gly Gly Thr Gln Leu Thr Val Leu
            100                 105

<210> SEQ ID NO 65
<211> LENGTH: 327
<212> TYPE: DNA
<213> ORGANISM: artificial
<220> FEATURE:
<223> OTHER INFORMATION: L25 VL

<400> SEQUENCE: 65
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta tacttctcct ctatggtaaa cacaaacggc cctcagggat cccagaccgc    180
ttctctggct ccacctcagg agacacagct tccttgacca tcactgggc tcaggcggaa    240 gacgaggctg actattactg tacgacgcgg agcaacaagg caaccccca tgttctgttc    300 ggcggaggga cccagctcac cgtttta                                        327

<210> SEQ ID NO 66
<211> LENGTH: 109
<212> TYPE: PRT
<213> ORGANISM: artificial
<220> FEATURE:
<223> OTHER INFORMATION: L25 VL

<400> SEQUENCE: 66

Ser Ser Glu Leu Thr Gln Asp Pro Pro Val Ser Val Ala Leu Gly Gln
 1               5                  10                  15

Thr Val Thr Leu Thr Cys Gln Gly Asp Ser Leu Arg Thr Tyr Tyr Ala
                20                  25                  30

Ser Trp Tyr Gln Gln Lys Ser Gly Gln Ala Pro Ile Leu Leu Leu Tyr
             35                  40                  45

Gly Lys His Lys Arg Pro Ser Gly Ile Pro Asp Arg Phe Ser Gly Ser
         50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Thr Thr Arg Ser Asn Lys Gly Asn Pro
                 85                  90                  95

His Val Leu Phe Gly Gly Gly Thr Gln Leu Thr Val Leu
            100                 105

<210> SEQ ID NO 67
<211> LENGTH: 1401
<212> TYPE: DNA
<213> ORGANISM: artificial
<220> FEATURE:
<223> OTHER INFORMATION: VH4 heavy chain

<400> SEQUENCE: 67
atgggatgga gctgtatcat cctcttcttg gtagcaacag ctacaggcgc gcactctcag      60
gtgcagctgc aggagtctgg ccctggcctg gtgaagcctt cgagaccct gtctctgacc     120 tgtgccgtgt ccggctactc catctcctcc ggctactact ggggctggat cagacagcct    180
```

```
cctggcaagg gcctggagtg gatcggctcc atctctcaca ccggcaacac ctactacaac    240
ccccctctga agtccagagt gaccatctcc gtggacacct ccaagaacca gttctccctg    300
aagctgtcct ctgtgaccgc tgccgatacc gccgtgtact actgtgccag atggctcggg    360
ttcggccgcc cggagtactg gggcaaaggc accctggtga ccgtgtcctc tgcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagccc aaatcttgt    720 gacaaaactc acacatgccc accgtgccca gcacctgaag ccgcggggc accgtcagtc    780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                             1401
```

<210> SEQ ID NO 68
<211> LENGTH: 467
<212> TYPE: PRT
<213> ORGANISM: artificial
<220> FEATURE:
<223> OTHER INFORMATION: VH4 heavy chain

<400> SEQUENCE: 68

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Trp Leu Gly Phe Gly Arg Pro Glu Tyr Trp Gly
        115                 120                 125

Lys Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
```

```
                    145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Leu Gly Thr Gln Thr Tyr Ile Cys Asn Val Asn His
    210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Ala Ala Gly
                245                 250                 255
Ala Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 69
<211> LENGTH: 1401
<212> TYPE: DNA
<213> ORGANISM: artificial
<220> FEATURE:
<223> OTHER INFORMATION: VH5 heavy chain

<400> SEQUENCE: 69
atgggatgga gctgtatcat cctcttcttg gtagcaacag ctacaggcgc gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240
```

-continued

```
cccctctga agtccagagt gaccatctcc gtggacacct ccaagaacca gttctccctg    300
aagctgtcct ctgtgaccgc tgccgatacc gccgtgtact actgtgccag attcttgggc    360
ttcggccggc cggagtactg gggcaaaggc accctggtga ccgtgtcctc tgcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaag ccgcggggc accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc ccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca gagcaggtg gcagcagggg   1320
aacgtcttct catgctccgt gatgcatgag gctctgcaca accactacac gcagaagagc   1380
ctctccctgt ccccgggtaa a                                             1401
```

<210> SEQ ID NO 70
<211> LENGTH: 467
<212> TYPE: PRT
<213> ORGANISM: artificial
<220> FEATURE:
<223> OTHER INFORMATION: VH5 heavy chain

<400> SEQUENCE: 70

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Leu Gly Phe Gly Arg Pro Glu Tyr Trp Gly
        115                 120                 125

Lys Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160
```

```
Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
    195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
            245                 250                 255

Ala Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 71
<211> LENGTH: 1401
<212> TYPE: DNA
<213> ORGANISM: artificial
<220> FEATURE:
<223> OTHER INFORMATION: VH6 heavy chain

<400> SEQUENCE: 71
atgggatgga gctgtatcat cctcttcttg gtagcaacag ctacaggcgc gcactctcag      60
gtgcagctgc aggagtctgg ccctggcctg gtgaagcctt cgagaccct gtctctgacc     120 tgtgccgtgt ccggctactc catctcctcc ggctactact ggggctggat cagacagcct     180
cctggcaagg gctggagtg gatcggctcc atctctcaca ccggcaacac ctactacaac     240
ccccctctga agtccagagt gaccatctcc gtggacacct ccaagaacca gttctccctg     300
```

```
aagctgtcct ctgtgaccgc tgccgatacc gccgtgtact actgtgccag attcttcggc    360
ttcggccgcc cggagtactg gggcaaaggc accctggtga ccgtgtcctc tgcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720 gacaaaactc acacatgccc accgtgccca gcacctgaag ccgcggggc accgtcagtc      780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
ggtcagcccc gagaaccaca ggtgtacacc ctgcccccat cccgggagga tgaccaag     1140 aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ccccgggtaa a                                              1401
```

<210> SEQ ID NO 72
<211> LENGTH: 467
<212> TYPE: PRT
<213> ORGANISM: artificial
<220> FEATURE:
<223> OTHER INFORMATION: VH6 heavy chain

<400> SEQUENCE: 72

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Phe Gly Phe Gly Arg Pro Glu Tyr Trp Gly
        115                 120                 125

Lys Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
            210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
            245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 73
<211> LENGTH: 702
<212> TYPE: DNA
<213> ORGANISM: artificial
<220> FEATURE:
<223> OTHER INFORMATION: VL3 light chain

<400> SEQUENCE: 73
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cagcagggcg gtggtgggca ccccacatgt tctgttcggc     360

| | |
|---|---|
| ggagggaccc agctcaccgt tttaggtcag cccaaggctg ccccctcggt cactctgttc | 420 |
| ccgcccctcct ctgaggagct tcaagccaac aaggccacac tggtgtgtct cataagtgac | 480 |
| ttctacccgg agccgtgac agtggcctgg aaggcagata gcagccccgt caaggcggga | 540 |
| gtggagacca ccacaccctc caaacaaagc aacaacaagt acgcggccag cagctatctg | 600 |
| agcctgacgc ctgagcagtg gaagtcccac agaagctaca gctgccaggt cacgcatgaa | 660 |
| gggagcaccg tggagaagac agtggcccct acagaatgtt ca | 702 |

<210> SEQ ID NO 74
<211> LENGTH: 234
<212> TYPE: PRT
<213> ORGANISM: artificial
<220> FEATURE:
<223> OTHER INFORMATION: VL3 light chain

<400> SEQUENCE: 74

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Ser Arg Ala Val Val
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 75
<211> LENGTH: 702
<212> TYPE: DNA
<213> ORGANISM: artificial
<220> FEATURE:
<223> OTHER INFORMATION: VL11 light chain

<400> SEQUENCE: 75

| | |
|---|---|
| atgggatgga gctgtatcat cctcttcttg gtagcaacag ctacaggcgc gcactcttcc | 60 |
| tctgagctga cccaggatcc tgctgtgtct gtggccctgg gccagaccgt caggatcacc | 120 |

```
tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgttc ctcccgctcc cgccacggca accccatgt tctgttcggc     360 ggagggaccc agctcaccgt tttaggtcag cccaaggctg cccctcggt cactctgttc     420 ccgcccctcct ctgaggagct tcaagccaac aaggccacac tggtgtgtct cataagtgac    480
ttctacccgg agccgtgac agtggcctgg aaggcagata gcagcccgt caaggcggga      540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggccct acagaatgtt ca                        702
```

<210> SEQ ID NO 76
<211> LENGTH: 234
<212> TYPE: PRT
<213> ORGANISM: artificial
<220> FEATURE:
<223> OTHER INFORMATION: VL11 light chain

<400> SEQUENCE: 76

```
Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ser Ser Arg Ser Arg His
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 77
<211> LENGTH: 702
<212> TYPE: DNA

<213> ORGANISM: artificial
<220> FEATURE:
<223> OTHER INFORMATION: VL13 light chain

<400> SEQUENCE: 77

```
atgggatgga gctgtatcat cctcttcttg gtagcaacag ctacaggcgc gcactcttcc      60
tctgagctga cccaggatcc tgctgtgtct gtggccctgg ccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cacccgcaac cgctacggca ccccatgt ctgttcggc      360
ggagggaccc agctcaccgt tttaggtcag cccaaggctg cccctcggt cactctgttc     420
ccgccctcct ctgaggagct tcaagccaac aaggccacac tggtgtgtct cataagtgac     480
ttctaccccgg agccgtgac agtggcctgg aaggcagata gcagcccgt caaggcggga     540
gtggagacca ccacacccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggccccct acagaatgtt ca                      702
```

<210> SEQ ID NO 78
<211> LENGTH: 234
<212> TYPE: PRT
<213> ORGANISM: artificial
<220> FEATURE:
<223> OTHER INFORMATION: VL13 light chain

<400> SEQUENCE: 78

Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Asn Arg Tyr
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val

Glu Lys Thr Val Ala Pro Thr Glu Cys Ser
225                 230

<210> SEQ ID NO 79
<211> LENGTH: 702
<212> TYPE: DNA
<213> ORGANISM: artificial
<220> FEATURE:
<223> OTHER INFORMATION: VL14 light chain

<400> SEQUENCE: 79

```
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtat ggcgaggtcg aggaagggca ccccatgt tctgttcggc      360
ggagggaccc agctcaccgt tttaggtcag cccaaggctg ccccctcggt cactctgttc     420
ccgccctcct ctgaggagct tcaagccaac aaggccacac tggtgtgtct cataagtgac     480
ttctacccgg gagccgtgac agtggcctgg aaggcagata gcagcccgt caaggcggga     540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702
```

<210> SEQ ID NO 80
<211> LENGTH: 234
<212> TYPE: PRT
<213> ORGANISM: artificial
<220> FEATURE:
<223> OTHER INFORMATION: VL14 light chain

<400> SEQUENCE: 80

Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Met Ala Arg Ser Arg Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro

```
                   165                 170                 175
Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

```
<210> SEQ ID NO 81
<211> LENGTH: 702
<212> TYPE: DNA
<213> ORGANISM: artificial
<220> FEATURE:
<223> OTHER INFORMATION: VL17 light chain

<400> SEQUENCE: 81
atgggatgga gctgtatcat cctcttcttg gtagcaacag ctacaggcgc gcactcttcc    60
tctgagctga cccaggatcc tgctgtgtct gtggccctgg ccagaccag aatcctgacc    120 tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgtag cacgaggtcg aggaagggca ccccatgt tctgttcggc    360 ggagggaccc agctcaccgt tttaggtcag cccaaggctg ccccctcggt cactctgttc    420
ccgccctcct ctgaggagct tcaagccaac aaggccacac tggtgtgtct cataagtgac    480
ttctacccgg agccgtgac agtggcctgg aaggcagata gcagcccgt caaggcggga    540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca    702
```

```
<210> SEQ ID NO 82
<211> LENGTH: 234
<212> TYPE: PRT
<213> ORGANISM: artificial
<220> FEATURE:
<223> OTHER INFORMATION: VL17 light chain

<400> SEQUENCE: 82

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
                20                  25                  30

Leu Gly Gln Thr Arg Ile Leu Thr Cys Gln Gly Asp Ser Leu Arg Thr
            35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ser Thr Arg Ser Arg Lys
                100                 105                 110

Gly Asn Pro His Val Leu Phe Gly Gly Gly Thr Gln Leu Thr Val Leu
```

```
              115                 120                 125
Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 83
<211> LENGTH: 702
<212> TYPE: DNA
<213> ORGANISM: artificial
<220> FEATURE:
<223> OTHER INFORMATION: VL23 light chain

<400> SEQUENCE: 83
atgggatgga gctgtatcat cctcttcttg gtagcaacag ctacaggcgc gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgttc ggcgcggtcg gtgaggggca ccccatgt tctgttcggc      360 ggagggaccc agctcaccgt tttaggtcag cccaaggctg ccccctcggt cactctgttc    420
ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacccctc aaacaaagc aacaacaagt acgcggccag cagctatctg      600
agcctgacgc ctgagcagtg gaagtcccac agaagctaca gctgccaggt cacgcatgaa    660
gggagcaccg tggagaagac agtggcccct acagaatgtt ca                       702

<210> SEQ ID NO 84
<211> LENGTH: 234
<212> TYPE: PRT
<213> ORGANISM: artificial
<220> FEATURE:
<223> OTHER INFORMATION: VL23 light chain

<400> SEQUENCE: 84

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
```

```
                65                  70                  75                  80
Ser Gly Ser Ser Ser Gly Asn Thr Ala Ser Leu Thr Ile Thr Gly Ala
                        85                  90                  95

Gln Ala Glu Asp Glu Ala Asp Tyr Tyr Cys Ser Ala Arg Ser Val Arg
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 85
<211> LENGTH: 702
<212> TYPE: DNA
<213> ORGANISM: artificial
<220> FEATURE:
<223> OTHER INFORMATION: VL24 light chain

<400> SEQUENCE: 85
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctgggctca ggcggaagac     300 gaggctgact attactgtat cgccaggagc aacaagggca ccccatgt tctgttcggc      360 ggagggaccc agctcaccgt tttaggtcag cccaaggctg cccctcggt cactctgttc     420 ccgcccctcc ctgaggagct tcaagccaac aaggccacac tggtgtgtct cataagtgac     480
ttctacccgg gagccgtgac agtggcctgg aaggcagata gcagccccgt caaggcggga     540
gtggagacca ccacccctc aaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702

<210> SEQ ID NO 86
<211> LENGTH: 234
<212> TYPE: PRT
<213> ORGANISM: artificial
<220> FEATURE:
<223> OTHER INFORMATION: VL24 light chain

<400> SEQUENCE: 86

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
```

```
                    20                  25                  30
Leu Gly Gln Thr Val Arg Ile Thr Cys Gln Gly Asp Ser Leu Arg Thr
                35                  40                  45

Tyr Tyr Ala Ser Trp Tyr Gln Gln Lys Pro Gly Gln Ala Pro Val Leu
50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ile Ala Arg Ser Asn Lys
            100                 105                 110

Gly Asn Pro His Val Leu Phe Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 87
<211> LENGTH: 1401
<212> TYPE: DNA
<213> ORGANISM: artificial
<220> FEATURE:
<223> OTHER INFORMATION: VHPTM heavy chain with signal sequence

<400> SEQUENCE: 87

```
atgggatgga gctgtatcat cctcttcttg gtagcaacag ctacaggcgc gcactctcag    60
gtgcagctgc aggagtctgg ccctggcctg gtgaagcctt ccgagaccct gtctctgacc   120
tgtgccgtgt ccggctactc catctcctcc ggctactact ggggctggat cagacagcct   180
cctggcaagg gcctggagtg gatcggctcc atctctcaca ccggcaacac ctactacaac   240
cccccctctga agtccagagt gaccatctcc gtggacacct ccaagaacca gttctccctg   300
aagctgtcct ctgtgaccgc tgccgatacc gccgtgtact actgtgccag aggcggcgga   360
atctccagac tgagtactg gggccagggc accctggtga ccgtgtcctc tgcctccacc   420
aagggcccat cggtcttccc cctggcaccc tcctccaaga gcacctctgg gggcacagcg   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacccagac ctacatctgc   660
aacgtgaatc acaagcccag caacaccaag gtggacaaga agttgagcc caaatcttgt   720
gacaaaactc acacatgccc accgtgccca gcacctgaag ccgcgggggc accgtcagtc   780
ttcctcttcc ccccaaaacc caaggacacc ctcatgatct cccggacccc tgaggtcaca   840
tgcgtggtgg tggacgtgag ccacgaagac cctgaggtca agttcaactg gtacgtggac   900
```

-continued

```
ggcgtggagg tgcataatgc aagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                             1401
```

<210> SEQ ID NO 88
<211> LENGTH: 467
<212> TYPE: PRT
<213> ORGANISM: artificial
<220> FEATURE:
<223> OTHER INFORMATION: VHPTM heavy chain with signal sequence

<400> SEQUENCE: 88

```
Met Gly Trp Ser Cys Ile Ile Leu Phe Leu Val Ala Thr Ala Thr Gly
1               5                  10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Gly Ile Ser Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
        290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
450                 455                 460
Pro Gly Lys
465

<210> SEQ ID NO 89
<211> LENGTH: 1401
<212> TYPE: DNA
<213> ORGANISM: artificial
<220> FEATURE:
<223> OTHER INFORMATION: VHPDM heavy chain with signal sequence

<400> SEQUENCE: 89
atgggatgga gctgtatcat cctcttcttg gtagcaacag ctacaggcgc gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240 cccccttctga agtccagagt gaccatctcc gtggacacct ccaagaacca gttctccctg     300
aagctgtcct ctgtgaccgc tgccgatacc gccgtgtact actgtgccag aggcggcgga     360
atctccagac tgagtactg gggccagggc accctggtga ccgtgtcctc tgcctccacc     420
aagggcccat cggtcttccc cctggcaccc tcctccaaga gcacctctgg ggcacagcg     480 gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga aagttgagcc caaatcttgt     720
gacaaaactc acacatgccc accgtgccca gcacctgaag ccctggggggc accgtcagtc     780 ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
```

-continued

```
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                             1401
```

<210> SEQ ID NO 90
<211> LENGTH: 467
<212> TYPE: PRT
<213> ORGANISM: artificial
<220> FEATURE:
<223> OTHER INFORMATION: VHPDM heavy chain with signal sequence

<400> SEQUENCE: 90

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Gly Ile Ser Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Leu Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 91
<211> LENGTH: 1401
<212> TYPE: DNA
<213> ORGANISM: artificial
<220> FEATURE:
<223> OTHER INFORMATION: VH3TM heavy chain with signal sequence

<400> SEQUENCE: 91
atgggatgga gctgtatcat cctcttcttg gtagcaacag ctacaggcgc gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240 cccccctctga agtccagagt gaccatctcc gtggacacct ccaagaacca gttctccctg     300
aagctgtcct ctgtgaccgc tgccgatacc gccgtgtact actgtgccag attcatgggg     360
ttcggccgcc cggagtactg gggccagggc accctggtga ccgtgtcctc tgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720 gacaaaactc acacatgccc accgtgccca gcacctgaag ccgcggggggc accgtcagtc     780 ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
```

```
tgcaaggtct ccaacaaagc cctcccagcc cccatcgaga aaaccatctc caaagccaaa      1080
ggtcagcccc gagaaccaca ggtgtacacc ctgcccccat cccgggagga gatgaccaag      1140
aaccaggtca gcctgacctg cctggtcaaa ggcttctatc ccagcgacat cgccgtggag      1200
tgggagagca atgggcagcc ggagaacaac tacaagacca cgcctcccgt gctggactcc      1260
gacggctcct tcttcctcta tagcaagctc accgtggaca agagcaggtg gcagcagggg      1320
aacgtcttct catgctccgt gatgcatgag gctctgcaca accactacac gcagaagagc      1380 ctctcccctgt ccccgggtaa a      1401

<210> SEQ ID NO 92
<211> LENGTH: 467
<212> TYPE: PRT
<213> ORGANISM: artificial
<220> FEATURE:
<223> OTHER INFORMATION: VH3DM heavy chain with signal sequence

<400> SEQUENCE: 92

Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Met Gly Phe Gly Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Leu Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

|     |     |     |     | 290 |     |     |     | 295 |     |     |     | 300 |     |     |
| --- | --- | --- | --- | --- | --- | --- | --- | --- | --- | --- | --- | --- | --- | --- |

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 93
<211> LENGTH: 1401
<212> TYPE: DNA
<213> ORGANISM: artificial
<220> FEATURE:
<223> OTHER INFORMATION: VH3DM heavy chain with signal sequence

<400> SEQUENCE: 93

```
atgggatgga gctgtatcat cctcttcttg gtagcaacag ctacaggcgc gcactctcag      60
gtgcagctgc aggagtctgg ccctggcctg gtgaagcctt cgagaccct gtctctgacc     120
tgtgccgtgt ccggctactc catctcctcc ggctactact ggggctggat cagacagcct     180
cctggcaagg gctggagtg atcggctcc atctctcaca ccggcaacac ctactacaac     240
ccccctctga agtccagagt gaccatctcc gtggacacct ccaagaacca gttctccctg     300
aagctgtcct ctgtgaccgc tgccgatacc gccgtgtact actgtgccag attcatgggg     360
tcggccgcc cggagtactg gggccagggc accctggtga ccgtgtcctc tgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc cggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
gacaaaactc acacatgccc accgtgccca gcacctgaag ccctggggc accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
```

```
ggtcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ccccgggtaa a                                              1401
```

<210> SEQ ID NO 94
<211> LENGTH: 467
<212> TYPE: PRT
<213> ORGANISM: artificial
<220> FEATURE:
<223> OTHER INFORMATION: VH3TM heavy chain with signal sequence

<400> SEQUENCE: 94

Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Met Gly Phe Gly Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

-continued

```
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 95
<211> LENGTH: 702
<212> TYPE: DNA
<213> ORGANISM: artificial
<220> FEATURE:
<223> OTHER INFORMATION: VL2 light chain with signal sequence

<400> SEQUENCE: 95
atgggatgga gctgtatcat cctcttcttg gtagcaacag ctacaggcgc gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cgcccggtcg gtggtgggca accccatgt tctgttcggc     360 ggagggaccc agctcaccgt tttaggtcag cccaaggctg ccccctcggt cactctgttc     420
ccgccctcct ctgaggagct tcaagccaac aaggccacac tggtgtgtct cataagtgac     480
ttctacccgg gagccgtgac agtggcctgg aaggcagata gcagcccgt caaggcggga     540 gtggagacca ccacaccctc caaacaaagc aacaacaagt acgcggccag cagctatctg     600
agcctgacgc ctgagcagtg gaagtccac agaagctaca gctgccaggt cacgcatgaa     660
gggagcaccg tggagaagac agtggcccct acagaatgtt ca                       702

<210> SEQ ID NO 96
<211> LENGTH: 234
<212> TYPE: PRT
<213> ORGANISM: artificial
<220> FEATURE:
<223> OTHER INFORMATION: VL2 light chain with signal sequence

<400> SEQUENCE: 96

Met Gly Trp Ser Cys Ile Ile Leu Phe Leu Val Ala Thr Ala Thr Gly
1               5                   10                  15
```

| Ala | His | Ser | Ser | Ser | Glu | Leu | Thr | Gln | Asp | Pro | Ala | Val | Ser | Val | Ala |
|---|---|---|---|---|---|---|---|---|---|---|---|---|---|---|---|
| | | | 20 | | | | 25 | | | | 30 | | | | |

Leu Gly Gln Thr Val Arg Ile Thr Cys Gln Gly Asp Ser Leu Arg Thr
    35                  40                  45

Tyr Tyr Ala Ser Trp Tyr Gln Gln Lys Pro Gly Gln Ala Pro Val Leu
 50                  55                  60

Val Ile Tyr Gly Lys His Lys Arg Pro Ser Gly Ile Pro Asp Arg Phe
 65                  70                  75                  80

Ser Gly Ser Ser Ser Gly Asn Thr Ala Ser Leu Thr Ile Thr Gly Ala
                 85                  90                  95

Gln Ala Glu Asp Glu Ala Asp Tyr Tyr Cys Val Ala Arg Ser Val Val
            100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 97
<211> LENGTH: 702
<212> TYPE: DNA
<213> ORGANISM: artificial
<220> FEATURE:
<223> OTHER INFORMATION: VL6 light chain with signal sequence

<400> SEQUENCE: 97

```
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt agcaggagc atctggggca accccatgt tctgttcggc     360
ggagggaccc agctcaccgt tttaggtcag cccaaggctg cccctcggt cactctgttc     420
ccgccctcct ctgaggagct tcaagccaac aaggccacac tggtgtgtct cataagtgac     480
ttctacccgg agccgtgac agtggcctgg aaggcagata gcagcccgt caaggcggga     540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                         702
```

<210> SEQ ID NO 98
<211> LENGTH: 234
<212> TYPE: PRT

-continued

<213> ORGANISM: artificial
<220> FEATURE:
<223> OTHER INFORMATION: VL6 light chain with signal sequence

<400> SEQUENCE: 98

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Met Ser Arg Ser Ile Trp
            100                 105                 110

Gly Asn Pro His Val Leu Phe Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 99
<211> LENGTH: 702
<212> TYPE: DNA
<213> ORGANISM: artificial
<220> FEATURE:
<223> OTHER INFORMATION: VL9 light chain with signal sequence

<400> SEQUENCE: 99
atgggatgga gctgtatcat cctcttcttg gtagcaacag ctacaggcgc gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cgccaggtcc aacaagggca accccatgt tctgttcggc     360 ggagggaccc agctcaccgt tttaggtcag cccaaggctg ccccctcggt cactctgttc     420
ccgccctcct ctgaggagct tcaagccaac aaggccacac tggtgtgtct cataagtgac     480
ttctacccgg gagccgtgac agtggcctgg aaggcagata gcagcccgt caaggcggga     540 gtggagacca ccacaccctc caaacaaagc aacaacaagt acgcggccag cagctatctg     600

```
agcctgacgc ctgagcagtg gaagtcccac agaagctaca gctgccaggt cacgcatgaa      660
gggagcaccg tggagaagac agtggcccct acagaatgtt ca                        702
```

<210> SEQ ID NO 100
<211> LENGTH: 234
<212> TYPE: PRT
<213> ORGANISM: artificial
<220> FEATURE:
<223> OTHER INFORMATION: VL9 light chain with signal sequence

<400> SEQUENCE: 100

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65              70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Ala Arg Ser Asn Lys
            100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 101
<211> LENGTH: 702
<212> TYPE: DNA
<213> ORGANISM: artificial
<220> FEATURE:
<223> OTHER INFORMATION: VL16 light chain  with signal sequence

<400> SEQUENCE: 101

```
atgggatgga gctgtatcat cctcttcttg gtagcaacag ctacaggcgc gcactcttcc      60
tctgagctga cccaggatcc tgctgtgtct gtggccctgg ccagaccgt caggatcacc      120 tgccagggcg atagcctgag aacctactac gcctcctggt atcagcagaa gcctggacag      180
gcccctgtgc tggtgatcta cggcaagcac aagaggccat ccggcatccc tgacagattc      240
tccggctcct cctctggcaa taccgcctcc ctgaccatca ctggggctca ggcggaagac      300
```

```
gaggctgact attactgtgt gacgaggagc gcgaagggca accccatgt tctgttcggc    360 ggagggaccc agctcaccgt tttaggtcag cccaaggctg cccctcggt cactctgttc    420 ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc tgagcagtg gaagtcccac agaagctaca gctgccaggt cacgcatgaa    660
gggagcaccg tggagaagac agtggcccct acagaatgtt ca                      702
```

```
<210> SEQ ID NO 102
<211> LENGTH: 234
<212> TYPE: PRT
<213> ORGANISM: artificial
<220> FEATURE:
<223> OTHER INFORMATION: VL16 light chain with signal sequence

<400> SEQUENCE: 102
```

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Ser Ala Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

```
<210> SEQ ID NO 103
<211> LENGTH: 702
<212> TYPE: DNA
<213> ORGANISM: artificial
<220> FEATURE:
<223> OTHER INFORMATION: VL18 light chain with signal sequence

<400> SEQUENCE: 103
atgggatgga gctgtatcat cctcttcttg gtagcaacag ctacaggcgc gcactcttcc    60
```

-continued

```
tctgagctga cccaggatcc tgctgtgtct gtggccctgg gccagaccgt caggatcacc    120
tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgtgt cacgaggagc gtgaagggca accccatgt tctgttcggc     360 ggagggaccc agctcaccgt tttaggtcag cccaaggctg cccctcggt cactctgttc      420 ccgcccctcct ctgaggagct tcaagccaac aaggccacac tggtgtgtct cataagtgac   480
ttctacccgg agccgtgac agtggcctgg aaggcagata gcagcccgt caaggcggga      540 gtggagacca ccacaccctc caaacaaagc aacaacaagt acgcggccag cagctatctg    600
agcctgacgc tgagcagtg gaagtccac agaagctaca gctgccaggt cacgcatgaa      660
gggagcaccg tggagaagac agtggcccct acagaatgtt ca                        702
```

<210> SEQ ID NO 104
<211> LENGTH: 234
<212> TYPE: PRT
<213> ORGANISM: artificial
<220> FEATURE:
<223> OTHER INFORMATION: VL18 light chain with signal sequence

<400> SEQUENCE: 104

```
Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Ser Val Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 105

<211> LENGTH: 702
<212> TYPE: DNA
<213> ORGANISM: artificial
<220> FEATURE:
<223> OTHER INFORMATION: VL20 light chain with signal sequence

<400> SEQUENCE: 105

```
atgggatgga gctgtatcat cctcttcttg gtagcaacag ctacaggcgc gcactcttcc      60
tctgagctga cccaggatcc tgctgtgtct gtggccctgg ccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt ctcccgcagc gcgaagggca accccatgt tctgttcggc     360
ggagggaccc agctcaccgt tttaggtcag cccaaggctg cccctcggt cactctgttc     420
ccgcccctcct ctgaggagct tcaagccaac aaggccacac tggtgtgtct cataagtgac     480
ttctacccgg gagccgtgac agtggcctgg aaggcagata gcagcccgt caaggcggga     540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                        702
```

<210> SEQ ID NO 106
<211> LENGTH: 234
<212> TYPE: PRT
<213> ORGANISM: artificial
<220> FEATURE:
<223> OTHER INFORMATION: VL20 light chain with signal sequence

<400> SEQUENCE: 106

```
Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Ser Arg Ser Ala Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205
```

```
Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 107
<211> LENGTH: 702
<212> TYPE: DNA
<213> ORGANISM: artificial
<220> FEATURE:
<223> OTHER INFORMATION: VL25 light chain with signal sequence

<400> SEQUENCE: 107

```
atgggatgga gctgtatcat cctcttcttg gtagcaacag ctacaggcgc gcactcttcc      60
tctgagctga cccaggatcc tgctgtgtct gtggccctgg ccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctgggctca ggcggaagac     300
gaggctgact attactgtac gacgcggagc aacaagggca ccccccatgt tctgttcggc     360
ggagggaccc agctcaccgt tttaggtcag cccaaggctg cccctcggt cactctgttc     420
ccgccctcct ctgaggagct tcaagccaac aaggccacac tggtgtgtct cataagtgac     480
ttctacccgg agccgtgac agtggcctgg aaggcagata gcagccccgt caaggcggga     540
gtggagacca ccacccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702
```

<210> SEQ ID NO 108
<211> LENGTH: 234
<212> TYPE: PRT
<213> ORGANISM: artificial
<220> FEATURE:
<223> OTHER INFORMATION: VL25 light chain with signal sequence

<400> SEQUENCE: 108

```
Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Thr Thr Arg Ser Asn Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160
```

```
Phe Tyr Pro Gly Ala Val Thr Val Ala Trp Lys Ala Asp Ser Ser Pro
            165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230
```

```
<210> SEQ ID NO 109
<211> LENGTH: 732
<212> TYPE: DNA
<213> ORGANISM: artificial
<220> FEATURE:
<223> OTHER INFORMATION: H3 scFV

<400> SEQUENCE: 109
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgattcatg     300
gggttcggcc gcccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc cctatactt      540
ctcctctatg gtaaacacaa acggccctca gggatcccag accgcttctc tggctccacc     600
tcaggagaca cagcttcctt gaccatcact ggggctcagg cggaagacga ggctgactat     660
tactgtaact cccgggactc cagtggcaac ccccatgttc tgttcggcgg agggacccag     720
ctcaccgttt ta                                                          732
```

```
<210> SEQ ID NO 110
<211> LENGTH: 244
<212> TYPE: PRT
<213> ORGANISM: artificial
<220> FEATURE:
<223> OTHER INFORMATION: H3 scFV

<400> SEQUENCE: 110

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
            35                  40                  45

Ile Gly Ser Ile Ser His Thr Gly Asn Thr Tyr Tyr Asn Pro Pro Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Phe Met Gly Phe Gly Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn Pro His Val Leu Phe Gly Gly Gly Thr Gln
225                 230                 235                 240

Leu Thr Val Leu

<210> SEQ ID NO 111
<211> LENGTH: 732
<212> TYPE: DNA
<213> ORGANISM: artificial
<220> FEATURE:
<223> OTHER INFORMATION: H4 scFV

<400> SEQUENCE: 111
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgatggctc   300
gggttcggcc gcccggagta ctggggcaaa ggcaccctgg tcaccgtctc gagtggaggc   360
ggcggttcag gcgaggtgg ctctggcggt ggcggaagtg cactttcttc tgagctgact   420
caggaccctc ctgtgtctgt ggccttggga cagacagtca cgctcacatg ccaaggagac   480
agcctcagaa cctattatgc aagctggtac cagcagaagt caggacaggc ccctatactt   540
ctcctctatg gtaaacacaa acggccctca gggatcccag accgcttctc tggctccacc   600
tcaggagaca cagcttcctt gaccatcact ggggctcagg cggaagacga ggctgactat   660
tactgtaact cccgggactc cagtggcaac ccccatgttc tgttcggcgg agggacccag   720
ctcaccgttt ta                                                       732

<210> SEQ ID NO 112
<211> LENGTH: 244
<212> TYPE: PRT
<213> ORGANISM: artificial
<220> FEATURE:
<223> OTHER INFORMATION: H4 scFV

<400> SEQUENCE: 112

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30
```

```
Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Leu Gly Phe Gly Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn Pro His Val Leu Phe Gly Gly Gly Thr Gln
225                 230                 235                 240

Leu Thr Val Leu
```

<210> SEQ ID NO 113
<211> LENGTH: 732
<212> TYPE: DNA
<213> ORGANISM: artificial
<220> FEATURE:
<223> OTHER INFORMATION: H5 scFV

<400> SEQUENCE: 113

```
caggtgcagc tgcaggagtc gggcccagga ctggtgaaga cttcggagac cctgtccctc     60
acctgcgctg tctctggtta ctccatcagc agtggttact actggggctg gatccggcag    120
cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgattcttg    300
ggcttcggcc ggccggagta ctggggcaaa ggcaccctgg tcaccgtctc gagtggaggc    360
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtaact cccgggactc cagtggcaac ccccatgttc tgttcggcgg agggacccag    720
ctcaccgttt ta                                                        732
```

<210> SEQ ID NO 114

<211> LENGTH: 244
<212> TYPE: PRT
<213> ORGANISM: artificial
<220> FEATURE:
<223> OTHER INFORMATION: H5 scFV

<400> SEQUENCE: 114

```
Gln Val Gln Leu Gln Glu Ser Gly Pro Gly Leu Val Lys Thr Ser Glu
1               5                   10                  15
Thr Leu Ser Leu Thr Cys Ala Val Ser Gly Tyr Ser Ile Ser Ser Gly
            20                  25                  30
Tyr Tyr Trp Gly Trp Ile Arg Gln Pro Pro Gly Lys Gly Leu Glu Trp
        35                  40                  45
Ile Gly Ser Ile Ser His Thr Gly Asn Thr Tyr Tyr Asn Pro Pro Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Phe Leu Gly Phe Gly Arg Pro Glu Tyr Trp Gly Lys Gly Thr
            100                 105                 110
Leu Val Thr Val Ser Ser Gly Gly Gly Gly Ser Gly Gly Gly Gly Ser
        115                 120                 125
Gly Gly Gly Gly Ser Ala Leu Ser Ser Glu Leu Thr Gln Asp Pro Pro
    130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
            180                 185                 190
Pro Asp Arg Phe Ser Gly Ser Ser Ser Gly Asp Thr Ala Ser Leu Thr
        195                 200                 205
Ile Thr Gly Ala Gln Ala Glu Asp Glu Ala Asp Tyr Tyr Cys Asn Ser
    210                 215                 220
Arg Asp Ser Ser Gly Asn Pro His Val Leu Phe Gly Gly Gly Thr Gln
225                 230                 235                 240
Leu Thr Val Leu
```

<210> SEQ ID NO 115
<211> LENGTH: 732
<212> TYPE: DNA
<213> ORGANISM: artificial
<220> FEATURE:
<223> OTHER INFORMATION: H6 scFv

<400> SEQUENCE: 115

```
caggtgcagc tgcaggagtc gggcccagga ctggtgaaga cttcggagac cctgtccctc      60
acctgcgctg tctctggtta ctccatcagc agtggttact actggggctg atccggcag     120 cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgattcttc     300
ggcttcggcc gccggagta ctggggcaaa ggcaccctgg tcaccgtctc gagtggaggc     360
ggcggttcag gcggaggtgg ctctggcggt ggcggaagtg cactttcttc tgagctgact     420
caggacccct ctgtgtctgt ggccttggga cagacagtca cgctcacatg ccaaggagac     480
```

```
agcctcagaa cctattatgc aagctggtac cagcagaagt caggacaggc ccctatactt      540
ctcctctatg gtaaacacaa acggccctca gggatcccag accgcttctc tggctccacc      600
tcaggagaca cagcttcctt gaccatcact ggggctcagg cggaagacga ggctgactat      660
tactgtaact cccgggactc cagtggcaac ccccatgttc tgttcggcgg agggacccag      720
ctcaccgttt ta                                                          732
```

<210> SEQ ID NO 116
<211> LENGTH: 244
<212> TYPE: PRT
<213> ORGANISM: artificial
<220> FEATURE:
<223> OTHER INFORMATION: H6 scFv

<400> SEQUENCE: 116

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Phe Gly Phe Gly Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn Pro His Val Leu Phe Gly Gly Thr Gln
225                 230                 235                 240

Leu Thr Val Leu
```

<210> SEQ ID NO 117
<211> LENGTH: 732
<212> TYPE: DNA
<213> ORGANISM: artificial
<220> FEATURE:
<223> OTHER INFORMATION: L1 scFv

<400> SEQUENCE: 117

```
caggtgcagc tgcaggagtc gggcccagga ctggtgaaga cttcggagac cctgtccctc       60
```

```
acctgcgctg tctctggtta ctccatcagc agtggttact actggggctg atccggcag      120 ccccaggga aggggttgga gtggattggg agtatctctc atactgggaa cacctactac      180
aacccgcccc tcaagagtcg cgtcaccata tcagtagaca cgtccaagaa ccagttctcc      240
ctgaaactga gctctgtgac cgccgcagac acggccgtgt attactgtgc gcgaggtggg      300
ggaattagca ggccggagta ctggggcaaa ggcaccctgg tcaccgtctc gagtggaggc      360
ggcggttcag gcggaggtgg ctctggcggt ggcggaagtg cacttttctc tgagctgact      420
caggaccctc ctgtgtctgt ggccttggga cagacagtca cgctcacatg ccaaggagac      480
agcctcagaa cctattatgc aagctggtac cagcagaagt caggacaggc ccctatactt      540
ctcctctatg gtaaacacaa acggccctca gggatcccag accgcttctc tggctccacc      600
tcaggagaca cagcttcctt gaccatcact ggggctcagg cggaagacga ggctgactat      660
tactgtgcgt cccggtcggt gagcggcaac ccccatgttc tgttcggcgg agggacccag      720
ctcaccgttt ta                                                         732
```

<210> SEQ ID NO 118
<211> LENGTH: 244
<212> TYPE: PRT
<213> ORGANISM: artificial
<220> FEATURE:
<223> OTHER INFORMATION: L1 scFv

<400> SEQUENCE: 118

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ala Ser
    210                 215                 220

Arg Ser Val Ser Gly Asn Pro His Val Leu Phe Gly Gly Gly Thr Gln
225                 230                 235                 240

Leu Thr Val Leu

<210> SEQ ID NO 119
<211> LENGTH: 732
<212> TYPE: DNA
<213> ORGANISM: artificial
<220> FEATURE:
<223> OTHER INFORMATION: L2 scFv

<400> SEQUENCE: 119

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggacccct ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtcg cccggtcggt ggtgggcaac cccatgttc tgttcggcgg agggacccag      720
ctcaccgttt ta                                                         732
```

<210> SEQ ID NO 120
<211> LENGTH: 244
<212> TYPE: PRT
<213> ORGANISM: artificial
<220> FEATURE:
<223> OTHER INFORMATION: L2 scFv

<400> SEQUENCE: 120

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175
```

```
Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ala
    210                 215                 220

Arg Ser Val Val Gly Asn Pro His Val Leu Phe Gly Gly Gly Thr Gln
225                 230                 235                 240

Leu Thr Val Leu

<210> SEQ ID NO 121
<211> LENGTH: 732
<212> TYPE: DNA
<213> ORGANISM: artificial
<220> FEATURE:
<223> OTHER INFORMATION: L3 scFV

<400> SEQUENCE: 121
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420 caggacccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtca gcagggcggt ggtgggcaac ccccatgttc tgttcggcgg agggacccag     720
ctcaccgttt ta                                                         732

<210> SEQ ID NO 122
<211> LENGTH: 244
<212> TYPE: PRT
<213> ORGANISM: artificial
<220> FEATURE:
<223> OTHER INFORMATION: L3 scFv

<400> SEQUENCE: 122

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Gly Ile Ser Arg Pro Glu Tyr Trp Gly Lys Gly Thr
        100                 105                 110
```

```
Leu Val Thr Val Ser Ser Gly Gly Gly Ser Gly Gly Gly Ser
            115                 120                 125

Gly Gly Gly Gly Ser Ala Leu Ser Ser Glu Leu Thr Gln Asp Pro Pro
            130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
            195                 200                 205

Ile Thr Gly Ala Gln Ala Glu Asp Glu Ala Asp Tyr Tyr Cys Val Ser
            210                 215                 220

Arg Ala Val Val Gly Asn Pro His Val Leu Phe Gly Gly Gly Thr Gln
225                 230                 235                 240

Leu Thr Val Leu
```

```
<210> SEQ ID NO 123
<211> LENGTH: 732
<212> TYPE: DNA
<213> ORGANISM: artificial
<220> FEATURE:
<223> OTHER INFORMATION: L4 scFv

<400> SEQUENCE: 123
caggtgcagc tgcaggagtc gggcccagga ctggtgaaga cttcggagac cctgtccctc      60
acctgcgctg tctctggtta ctccatcagc agtggttact actggggctg gatccggcag    120
cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtagca cccgcagcag caagggcaac ccccatgttc tgttcggcgg agggacccag    720
ctcaccgttt ta                                                        732
```

```
<210> SEQ ID NO 124
<211> LENGTH: 244
<212> TYPE: PRT
<213> ORGANISM: artificial
<220> FEATURE:
<223> OTHER INFORMATION: L4 scFv

<400> SEQUENCE: 124

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
```

```
                35                  40                  45
Ile Gly Ser Ile Ser His Thr Gly Asn Thr Tyr Tyr Asn Pro Pro Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ser Thr
210                 215                 220

Arg Ser Ser Lys Gly Asn Pro His Val Leu Phe Gly Gly Gly Thr Gln
225                 230                 235                 240

Leu Thr Val Leu

<210> SEQ ID NO 125
<211> LENGTH: 732
<212> TYPE: DNA
<213> ORGANISM: artificial
<220> FEATURE:
<223> OTHER INFORMATION: L5 scFv

<400> SEQUENCE: 125
caggtgcagc tgcaggagtc gggcccagga ctggtgaaga cttcggagac cctgtccctc      60
acctgcgctg tctctggtta ctccatcagc agtggttact actggggctg atccggcag     120
ccccagggaa aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc     360
ggcggttcag gcggaggtgg ctctggcggt ggcggaagtg cactttcttc tgagctgact     420
caggacccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgcca gcaggtcctc caagggcaac ccccatgttc tgttcggcgg agggacccag     720
ctcaccgttt ta                                                         732

<210> SEQ ID NO 126
<211> LENGTH: 244
<212> TYPE: PRT
```

```
<213> ORGANISM: artificial
<220> FEATURE:
<223> OTHER INFORMATION: L5 scFv

<400> SEQUENCE: 126

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ala Ser
    210                 215                 220

Arg Ser Ser Lys Gly Asn Pro His Val Leu Phe Gly Gly Gly Thr Gln
225                 230                 235                 240

Leu Thr Val Leu

<210> SEQ ID NO 127
<211> LENGTH: 732
<212> TYPE: DNA
<213> ORGANISM: artificial
<220> FEATURE:
<223> OTHER INFORMATION: L6 scFv

<400> SEQUENCE: 127
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc      360
ggcggttcag gcggaggtgg ctctggcggt ggcggaagtg cactttcttc tgagctgact     420 caggacccctc ctgtgtctgt ggccttggga cagacagtca cgctcacatg ccaaggagac    480
agcctcagaa cctattatgc aagctggtac cagcagaagt caggacaggc ccctatactt     540
```

```
ctcctctatg gtaaacacaa acggccctca gggatcccag accgcttctc tggctccacc      600
tcaggagaca cagcttcctt gaccatcact ggggctcagg cggaagacga ggctgactat      660
tactgtatga gcaggagcat ctggggcaac ccccatgttc tgttcggcgg agggacccag      720
ctcaccgttt ta                                                          732
```

<210> SEQ ID NO 128
<211> LENGTH: 244
<212> TYPE: PRT
<213> ORGANISM: artificial
<220> FEATURE:
<223> OTHER INFORMATION: L6 scFv

<400> SEQUENCE: 128

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Met Ser
    210                 215                 220

Arg Ser Ile Trp Gly Asn Pro His Val Leu Phe Gly Gly Gly Thr Gln
225                 230                 235                 240

Leu Thr Val Leu

<210> SEQ ID NO 129
<211> LENGTH: 732
<212> TYPE: DNA
<213> ORGANISM: artificial
<220> FEATURE:
<223> OTHER INFORMATION: L8 scFv

<400> SEQUENCE: 129

```
caggtgcagc tgcaggagtc gggcccagga ctggtgaaga cttcggagac cctgtccctc      60
acctgcgctg tctctggtta ctccatcagc agtggttact actggggctg gatccggcag      120
```

```
cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc cctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtacca cgcgctccac ccagggcaac cccatgttc tgttcggcgg agggacccag    720
ctcaccgttt ta                                                        732
```

<210> SEQ ID NO 130
<211> LENGTH: 244
<212> TYPE: PRT
<213> ORGANISM: artificial
<220> FEATURE:
<223> OTHER INFORMATION: L8 scFv

<400> SEQUENCE: 130

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Thr Thr
    210                 215                 220

Arg Ser Thr Gln Gly Asn Pro His Val Leu Phe Gly Gly Gly Thr Gln
225                 230                 235                 240

Leu Thr Val Leu

<210> SEQ ID NO 131
<211> LENGTH: 732
<212> TYPE: DNA
<213> ORGANISM: artificial
<220> FEATURE:
<223> OTHER INFORMATION: L9 scFv

<400> SEQUENCE: 131

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc      360
ggcggttcag gcggaggtgg ctctggcggt ggcggaagtg cactttcttc tgagctgact     420 caggacccctc ctgtgtctgt ggccttggga cagacagtca cgctcacatg ccaaggagac    480
agcctcagaa cctattatgc aagctggtac cagcagaagt caggacaggc ccctatactt     540
ctcctctatg gtaaacacaa acggccctca gggatcccag accgcttctc tggctccacc    600
tcaggagaca cagcttcctt gaccatcact ggggctcagg cggaagacga ggctgactat     660
tactgtgtcg ccaggtccaa caagggcaac cccatgttc tgttcggcgg agggacccag     720
ctcaccgttt ta                                                         732
```

<210> SEQ ID NO 132
<211> LENGTH: 244
<212> TYPE: PRT
<213> ORGANISM: artificial
<220> FEATURE:
<223> OTHER INFORMATION: L9 scFv

<400> SEQUENCE: 132

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190
```

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ala
        210                 215                 220

Arg Ser Asn Lys Gly Asn Pro His Val Leu Phe Gly Gly Gly Thr Gln
225                 230                 235                 240

Leu Thr Val Leu

<210> SEQ ID NO 133
<211> LENGTH: 732
<212> TYPE: DNA
<213> ORGANISM: artificial
<220> FEATURE:
<223> OTHER INFORMATION: L10 scFv

<400> SEQUENCE: 133
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtatca gccggtcgat ctacggcaac cccatgttc tgttcggcgg agggacccag     720
ctcaccgttt ta                                                         732

<210> SEQ ID NO 134
<211> LENGTH: 244
<212> TYPE: PRT
<213> ORGANISM: artificial
<220> FEATURE:
<223> OTHER INFORMATION: L10 scFv

<400> SEQUENCE: 134

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser

|  |  |  |  |  | 115 |  |  |  |  | 120 |  |  |  |  | 125 |
| Gly | Gly | Gly | Gly | Ser | Ala | Leu | Ser | Ser | Glu | Leu | Thr | Gln | Asp | Pro | Pro |
|  |  |  |  |  | 130 |  |  |  |  | 135 |  |  |  |  | 140 |

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
              165                 170                 175

Ala Pro Ile Leu Leu Leu Tyr Gly Lys His Lys Arg Pro Ser Gly Ile
              180                 185                 190

Pro Asp Arg Phe Ser Gly Ser Thr Ser Gly Asp Thr Ala Ser Leu Thr
              195                 200                 205

Ile Thr Gly Ala Gln Ala Glu Asp Glu Ala Asp Tyr Tyr Cys Ile Ser
    210                 215                 220

Arg Ser Ile Tyr Gly Asn Pro His Val Leu Phe Gly Gly Gly Thr Gln
225                 230                 235                 240

Leu Thr Val Leu

<210> SEQ ID NO 135
<211> LENGTH: 732
<212> TYPE: DNA
<213> ORGANISM: artificial
<220> FEATURE:
<223> OTHER INFORMATION: L11 scFv

<400> SEQUENCE: 135

```
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgaggtggg   300
ggaattagca ggccggagta ctggggcaaa ggcaccctgg tcaccgtctc gagtggaggc   360
ggcggttcag gcgaggtgg ctctggcggt ggcggaagtg cactttcttc tgagctgact   420
caggaccctc ctgtgtctgt ggccttggga cagacagtca cgctcacatg ccaaggagac   480
agcctcagaa cctattatgc aagctggtac cagcagaagt caggacaggc ccctatactt   540
ctcctctatg gtaaacacaa acggccctca gggatcccag accgcttctc tggctccacc   600
tcaggagaca cagcttcctt gaccatcact ggggctcagg cggaagacga ggctgactat   660
tactgttcct cccgctcccg ccacggcaac cccatgttc tgttcggcgg agggacccag   720
ctcaccgttt ta                                                       732
```

<210> SEQ ID NO 136
<211> LENGTH: 244
<212> TYPE: PRT
<213> ORGANISM: artificial
<220> FEATURE:
<223> OTHER INFORMATION: L11 scFv

<400> SEQUENCE: 136

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
 50                  55                  60
Lys Ser Arg Val Thr Ile Ser Val Asp Thr Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Gly Gly Gly Ile Ser Arg Pro Glu Tyr Trp Gly Lys Gly Thr
            100                 105                 110
Leu Val Thr Val Ser Ser Gly Gly Gly Gly Ser Gly Gly Gly Gly Ser
        115                 120                 125
Gly Gly Gly Gly Ser Ala Leu Ser Ser Glu Leu Thr Gln Asp Pro Pro
    130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
            180                 185                 190
Pro Asp Arg Phe Ser Gly Ser Ser Ser Gly Asp Thr Ala Ser Leu Thr
        195                 200                 205
Ile Thr Gly Ala Gln Ala Glu Asp Glu Ala Asp Tyr Tyr Cys Ser Ser
    210                 215                 220
Arg Ser Arg His Gly Asn Pro His Val Leu Phe Gly Gly Gly Thr Gln
225                 230                 235                 240
Leu Thr Val Leu

<210> SEQ ID NO 137
<211> LENGTH: 732
<212> TYPE: DNA
<213> ORGANISM: artificial
<220> FEATURE:
<223> OTHER INFORMATION: L12 scFv

<400> SEQUENCE: 137
caggtgcagc tgcaggagtc gggcccagga ctggtgaaga cttcggagac cctgtccctc      60
acctgcgctg tctctggtta ctccatcagc agtggttact actggggctg atccggcag     120 cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420 caggacccte ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtcg cgagggggac gagggcaac cccatgttc tgttcggcgg agggacccag     720
ctcaccgttt ta                                                        732

<210> SEQ ID NO 138
<211> LENGTH: 244
<212> TYPE: PRT
<213> ORGANISM: artificial
<220> FEATURE:

<223> OTHER INFORMATION: L12 scFv

<400> SEQUENCE: 138

```
Gln Val Gln Leu Gln Glu Ser Gly Pro Gly Leu Val Lys Thr Ser Glu
1               5                   10                  15

Thr Leu Ser Leu Thr Cys Ala Val Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Ser Ala Leu Ser Ser Glu Leu Thr Gln Asp Pro Pro
130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Ser Gly Asp Thr Ala Ser Leu Thr
        195                 200                 205

Ile Thr Gly Ala Gln Ala Glu Asp Glu Ala Asp Tyr Tyr Cys Val Ala
    210                 215                 220

Arg Gly Thr Arg Gly Asn Pro His Val Leu Phe Gly Gly Gly Thr Gln
225                 230                 235                 240

Leu Thr Val Leu
```

<210> SEQ ID NO 139
<211> LENGTH: 732
<212> TYPE: DNA
<213> ORGANISM: artificial
<220> FEATURE:
<223> OTHER INFORMATION: L13 scFv

<400> SEQUENCE: 139

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
```
tcaggagaca cagcttcctt gaccatcact ggggctcagg cggaagacga ggctgactat    660
tactgtgtca cccgcaaccg ctacggcaac ccccatgttc tgttcggcgg agggacccag    720
ctcaccgttt ta                                                        732

<210> SEQ ID NO 140
<211> LENGTH: 244
<212> TYPE: PRT
<213> ORGANISM: artificial
<220> FEATURE:
<223> OTHER INFORMATION: L13 scFv

<400> SEQUENCE: 140

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Thr
    210                 215                 220

Arg Asn Arg Tyr Gly Asn Pro His Val Leu Phe Gly Gly Gly Thr Gln
225                 230                 235                 240

Leu Thr Val Leu

<210> SEQ ID NO 141
<211> LENGTH: 732
<212> TYPE: DNA
<213> ORGANISM: artificial
<220> FEATURE:
<223> OTHER INFORMATION: L14 scFv

<400> SEQUENCE: 141
caggtgcagc tgcaggagtc gggcccagga ctggtgaaga cttcggagac cctgtccctc     60
acctgcgctg tctctggtta ctccatcagc agtggttact actggggctg gatccggcag    120
cccccaggga aggggttgga gtggattggg agtatctctc atactgggaa cacctactac    180

```
aacccgcccc tcaagagtcg cgtcaccata tcagtagaca cgtccaagaa ccagttctcc    240
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtatgg cgaggtcgag gaagggcaac ccccatgttc tgttcggcgg agggacccag    720
ctcaccgttt ta                                                        732
```

<210> SEQ ID NO 142
<211> LENGTH: 244
<212> TYPE: PRT
<213> ORGANISM: artificial
<220> FEATURE:
<223> OTHER INFORMATION: L14 scFv

<400> SEQUENCE: 142

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Met Ala
    210                 215                 220

Arg Ser Arg Lys Gly Asn Pro His Val Leu Phe Gly Gly Gly Thr Gln
225                 230                 235                 240

Leu Thr Val Leu
```

<210> SEQ ID NO 143
<211> LENGTH: 732

```
<212> TYPE: DNA
<213> ORGANISM: artificial
<220> FEATURE:
<223> OTHER INFORMATION: L15 scFv

<400> SEQUENCE: 143
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgaggtggg   300
ggaattagca ggccggagta ctggggcaaa ggcaccctgg tcaccgtctc gagtggaggc   360
ggcggttcag gcggaggtgg ctctggcggt ggcggaagtg cacttttctt tgagctgact   420
caggacccctc ctgtgtctgt ggccttggga cagacagtca cgctcacatg ccaaggagac   480
agcctcagaa cctattatgc aagctggtac cagcagaagt caggacaggc ccctatactt   540
ctcctctatg gtaaacacaa acggccctca gggatcccag accgcttctc tggctccacc   600
tcaggagaca cagcttcctt gaccatcact ggggctcagg cggaagacga ggctgactat   660
tactgttcca cccgcgccat ccacggcaac ccccatgttc tgttcggcgg agggacccag   720
ctcaccgttt ta                                                       732

<210> SEQ ID NO 144
<211> LENGTH: 244
<212> TYPE: PRT
<213> ORGANISM: artificial
<220> FEATURE:
<223> OTHER INFORMATION: L15 scFv

<400> SEQUENCE: 144

Gln Val Gln Leu Gln Glu Ser Gly Pro Gly Leu Val Lys Thr Ser Glu
  1               5                  10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
         35                  40                  45

Ile Gly Ser Ile Ser His Thr Gly Asn Thr Tyr Tyr Asn Pro Pro Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
```

```
                195                 200                 205
Ile Thr Gly Ala Gln Ala Glu Asp Glu Ala Asp Tyr Tyr Cys Ser Thr
    210                 215                 220

Arg Ala Ile His Gly Asn Pro His Val Leu Phe Gly Gly Gly Thr Gln
225                 230                 235                 240

Leu Thr Val Leu

<210> SEQ ID NO 145
<211> LENGTH: 732
<212> TYPE: DNA
<213> ORGANISM: artificial
<220> FEATURE:
<223> OTHER INFORMATION: L16 scFv

<400> SEQUENCE: 145
caggtgcagc tgcaggagtc gggcccagga ctggtgaaga cttcggagac cctgtccctc        60
acctgcgctg tctctggtta ctccatcagc agtggttact actggggctg atccggcag       120 cccccaggga aggggttgga gtggattggg agtatctctc atactgggaa cacctactac       180
aacccgcccc tcaagagtcg cgtcaccata tcagtagaca cgtccaagaa ccagttctcc       240
ctgaaactga gctctgtgac cgccgcagac acggccgtgt attactgtgc gcgaggtggg       300
ggaattagca ggccggagta ctggggcaaa ggcaccctgg tcaccgtctc gagtggaggc       360
ggcggttcag gcggaggtgg ctctggcggt ggcggaagtg cactttcttc tgagctgact       420
caggaccctc ctgtgtctgt ggccttggga cagacagtca cgctcacatg ccaaggagac       480
agcctcagaa cctattatgc aagctggtac cagcagaagt caggacaggc cctatactt       540 ctcctctatg gtaaacacaa acggccctca gggatcccag accgcttctc tggctccacc       600
tcaggagaca cagcttcctt gaccatcact ggggctcagg cggaagacga ggctgactat       660
tactgtgtga cgaggagcgc gaagggcaac cccatgttc tgttcggcgg agggacccag       720
ctcaccgttt ta                                                           732

<210> SEQ ID NO 146
<211> LENGTH: 244
<212> TYPE: PRT
<213> ORGANISM: artificial
<220> FEATURE:
<223> OTHER INFORMATION: L16 scFv

<400> SEQUENCE: 146

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Ser
        115                 120                 125
```

```
Gly Gly Gly Gly Ser Ala Leu Ser Ser Glu Leu Thr Gln Asp Pro Pro
            130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
                180                 185                 190

Pro Asp Arg Phe Ser Gly Ser Thr Ser Gly Asp Thr Ala Ser Leu Thr
                195                 200                 205

Ile Thr Gly Ala Gln Ala Glu Asp Glu Ala Asp Tyr Tyr Cys Val Thr
            210                 215                 220

Arg Ser Ala Lys Gly Asn Pro His Val Leu Phe Gly Gly Gly Thr Gln
225                 230                 235                 240

Leu Thr Val Leu
```

```
<210> SEQ ID NO 147
<211> LENGTH: 732
<212> TYPE: DNA
<213> ORGANISM: artificial
<220> FEATURE:
<223> OTHER INFORMATION: L17 scFv

<400> SEQUENCE: 147
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtagca cgaggtcgag gaagggcaac ccccatgttc tgttcggcgg agggacccag     720
ctcaccgttt ta                                                         732
```

```
<210> SEQ ID NO 148
<211> LENGTH: 244
<212> TYPE: PRT
<213> ORGANISM: artificial
<220> FEATURE:
<223> OTHER INFORMATION: L17 scFv

<400> SEQUENCE: 148

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60
```

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Gly Gly Gly Ile Ser Arg Pro Glu Tyr Trp Gly Lys Gly Thr
        100                 105                 110

Leu Val Thr Val Ser Ser Gly Gly Gly Gly Ser Gly Gly Gly Gly Ser
            115                 120                 125

Gly Gly Gly Gly Ser Ala Leu Ser Ser Glu Leu Thr Gln Asp Pro Pro
        130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ser Thr
            210                 215                 220

Arg Ser Arg Lys Gly Asn Pro His Val Leu Phe Gly Gly Gly Thr Gln
225                 230                 235                 240

Leu Thr Val Leu

<210> SEQ ID NO 149
<211> LENGTH: 732
<212> TYPE: DNA
<213> ORGANISM: artificial
<220> FEATURE:
<223> OTHER INFORMATION: L18 scFv

<400> SEQUENCE: 149
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc      360
ggcggttcag gcggaggtgg ctctggcggt ggcggaagtg cactttcttc tgagctgact     420
caggacccc tctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtca cgaggagcgt gaagggcaac ccccatgttc tgttcggcgg agggacccag     720
ctcaccgttt ta                                                          732

<210> SEQ ID NO 150
<211> LENGTH: 244
<212> TYPE: PRT
<213> ORGANISM: artificial
<220> FEATURE:
<223> OTHER INFORMATION: L18 scFv

<400> SEQUENCE: 150

| Gln | Val | Gln | Leu | Gln | Glu | Ser | Gly | Pro | Gly | Leu | Val | Lys | Thr | Ser | Glu |
|---|---|---|---|---|---|---|---|---|---|---|---|---|---|---|---|
| 1 | | | | 5 | | | | | 10 | | | | | 15 | |

Thr Leu Ser Leu Thr Cys Ala Val Ser Gly Tyr Ser Ile Ser Ser Gly
    20        25        30

Tyr Tyr Trp Gly Trp Ile Arg Gln Pro Pro Gly Lys Gly Leu Glu Trp
     35        40        45

Ile Gly Ser Ile Ser His Thr Gly Asn Thr Tyr Tyr Asn Pro Pro Leu
   50        55        60

Lys Ser Arg Val Thr Ile Ser Val Asp Thr Ser Lys Asn Gln Phe Ser
65        70        75        80

Leu Lys Leu Ser Ser Val Thr Ala Ala Asp Thr Ala Val Tyr Tyr Cys
     85        90        95

Ala Arg Gly Gly Gly Ile Ser Arg Pro Glu Tyr Trp Gly Lys Gly Thr
    100        105        110

Leu Val Thr Val Ser Ser Gly Gly Gly Ser Gly Gly Gly Ser
     115        120        125

Gly Gly Gly Gly Ser Ala Leu Ser Ser Glu Leu Thr Gln Asp Pro Pro
   130        135        140

Val Ser Val Ala Leu Gly Gln Thr Val Thr Leu Thr Cys Gln Gly Asp
145        150        155       160

Ser Leu Arg Thr Tyr Tyr Ala Ser Trp Tyr Gln Gln Lys Ser Gly Gln
     165        170        175

Ala Pro Ile Leu Leu Leu Tyr Gly Lys His Lys Arg Pro Ser Gly Ile
     180        185        190

Pro Asp Arg Phe Ser Gly Ser Thr Ser Gly Asp Thr Ala Ser Leu Thr
     195        200        205

Ile Thr Gly Ala Gln Ala Glu Asp Glu Ala Asp Tyr Tyr Cys Val Thr
   210        215        220

Arg Ser Val Lys Gly Asn Pro His Val Leu Phe Gly Gly Gly Thr Gln
225        230        235       240

Leu Thr Val Leu

<210> SEQ ID NO 151
<211> LENGTH: 732
<212> TYPE: DNA
<213> ORGANISM: artificial
<220> FEATURE:
<223> OTHER INFORMATION: L19 scFv

<400> SEQUENCE: 151

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc     360
ggcggttcag gcggaggtgg ctctggcggt ggcggaagtg cactttcttc tgagctgact     420
caggacccct ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
```

```
tactgtgtcg cgcgggcggt gaggggcaac ccccatgttc tgttcggcgg agggacccag    720
ctcaccgttt ta                                                        732
```

<210> SEQ ID NO 152
<211> LENGTH: 244
<212> TYPE: PRT
<213> ORGANISM: artificial
<220> FEATURE:
<223> OTHER INFORMATION: L19 scFv

<400> SEQUENCE: 152

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ala
    210                 215                 220

Arg Ala Val Arg Gly Asn Pro His Val Leu Phe Gly Gly Gly Thr Gln
225                 230                 235                 240

Leu Thr Val Leu

<210> SEQ ID NO 153
<211> LENGTH: 732
<212> TYPE: DNA
<213> ORGANISM: artificial
<220> FEATURE:
<223> OTHER INFORMATION: L20 scFv

<400> SEQUENCE: 153

```
caggtgcagc tgcaggagtc gggcccagga ctggtgaaga cttcggagac cctgtccctc    60
acctgcgctg tctctggtta ctccatcagc agtggttact actgggctg gatccggcag    120 cccccaggga aggggttgga gtggattggg agtatctctc atactgggaa cacctactac    180
aacccgcccc tcaagagtcg cgtcaccata tcagtagaca cgtccaagaa ccagttctcc    240
```

```
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtgtct cccgcagcgc gaagggcaac ccccatgttc tgttcggcgg agggacccag    720
ctcaccgttt ta                                                        732
```

<210> SEQ ID NO 154
<211> LENGTH: 244
<212> TYPE: PRT
<213> ORGANISM: artificial
<220> FEATURE:
<223> OTHER INFORMATION: L20 scFv

<400> SEQUENCE: 154

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ser
    210                 215                 220

Arg Ser Ala Lys Gly Asn Pro His Val Leu Phe Gly Gly Gly Thr Gln
225                 230                 235                 240

Leu Thr Val Leu
```

<210> SEQ ID NO 155
<211> LENGTH: 732
<212> TYPE: DNA
<213> ORGANISM: artificial

```
<220> FEATURE:
<223> OTHER INFORMATION: L21 scFv

<400> SEQUENCE: 155
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc      360
ggcggttcag gcggaggtgg ctctggcggt ggcggaagtg cactttcttc tgagctgact     420
caggacccctc ctgtgtctgt ggccttggga cagacagtca cgctcacatg ccaaggagac    480
agcctcagaa cctattatgc aagctggtac cagcagaagt caggacaggc ccctatactt     540
ctcctctatg gtaaacacaa acggccctca gggatcccag accgcttctc tggctccacc    600
tcaggagaca cagcttcctt gaccatcact ggggctcagg cggaagacga ggctgactat    660
tactgtgcca cccgggcggt ccggggcaac cccatgttc tgttcggcgg agggacccag     720
ctcaccgttt ta                                                          732

<210> SEQ ID NO 156
<211> LENGTH: 244
<212> TYPE: PRT
<213> ORGANISM: artificial
<220> FEATURE:
<223> OTHER INFORMATION: L21 scFv

<400> SEQUENCE: 156

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205
```

```
Ile Thr Gly Ala Gln Ala Glu Asp Glu Ala Asp Tyr Tyr Cys Ala Thr
        210                 215                 220

Arg Ala Val Arg Gly Asn Pro His Val Leu Phe Gly Gly Gly Thr Gln
225                 230                 235                 240

Leu Thr Val Leu

<210> SEQ ID NO 157
<211> LENGTH: 732
<212> TYPE: DNA
<213> ORGANISM: artificial
<220> FEATURE:
<223> OTHER INFORMATION: L23 scFv

<400> SEQUENCE: 157
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420 caggacccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgttcgg cgcggtcggt gagggcaac ccccatgttc tgttcggcgg agggaccccag     720 ctcaccgttt ta                                                          732

<210> SEQ ID NO 158
<211> LENGTH: 244
<212> TYPE: PRT
<213> ORGANISM: artificial
<220> FEATURE:
<223> OTHER INFORMATION: L23 scFv

<400> SEQUENCE: 158

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Leu Ser Glu Leu Thr Gln Asp Pro Pro
    130                 135                 140
```

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ser Ala
    210                 215                 220

Arg Ser Val Arg Gly Asn Pro His Val Leu Phe Gly Gly Gly Thr Gln
225                 230                 235                 240

Leu Thr Val Leu

<210> SEQ ID NO 159
<211> LENGTH: 732
<212> TYPE: DNA
<213> ORGANISM: artificial
<220> FEATURE:
<223> OTHER INFORMATION: L24 scFv

<400> SEQUENCE: 159

| | | | | | |
|---|---|---|---|---|---|
| caggtgcagc | tgcaggagtc | gggcccagga | ctggtgaaga | cttcggagac | cctgtccctc | 60 |
| acctgcgctg | tctctggtta | ctccatcagc | agtggttact | actggggctg | gatccggcag | 120 |
| cccccaggga | aggggttgga | gtggattggg | agtatctctc | atactgggaa | cacctactac | 180 |
| aacccgcccc | tcaagagtcg | cgtcaccata | tcagtagaca | cgtccaagaa | ccagttctcc | 240 |
| ctgaaactga | gctctgtgac | cgccgcagac | acggccgtgt | attactgtgc | gcgaggtggg | 300 |
| ggaattagca | ggccggagta | ctgggcaaa | ggcaccctgg | tcaccgtctc | gagtggaggc | 360 |
| ggcggttcag | gcggaggtgg | ctctggcggt | ggcggaagtg | cactttcttc | tgagctgact | 420 |
| caggaccctc | ctgtgtctgt | ggccttggga | cagacagtca | cgctcacatg | ccaaggagac | 480 |
| agcctcagaa | cctattatgc | aagctggtac | cagcagaagt | caggacaggc | ccctatactt | 540 |
| ctcctctatg | gtaaacacaa | acggccctca | gggatcccag | accgcttctc | tggctccacc | 600 |
| tcaggagaca | cagcttcctt | gaccatcact | ggggctcagg | cggaagacga | ggctgactat | 660 |
| tactgtatcg | ccaggagcaa | caagggcaac | ccccatgttc | tgttcggcgg | agggacccag | 720 |
| ctcaccgttt | ta | | | | | 732 |

<210> SEQ ID NO 160
<211> LENGTH: 244
<212> TYPE: PRT
<213> ORGANISM: artificial
<220> FEATURE:
<223> OTHER INFORMATION: L24 scFv

<400> SEQUENCE: 160

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser

```
                65                  70                  75                  80
Leu Lys Leu Ser Ser Val Thr Ala Ala Asp Thr Ala Val Tyr Tyr Cys
                    85                  90                  95

Ala Arg Gly Gly Gly Ile Ser Arg Pro Glu Tyr Trp Gly Lys Gly Thr
                100                 105                 110

Leu Val Thr Val Ser Ser Gly Gly Gly Gly Ser Gly Gly Gly Gly Ser
                115                 120                 125

Gly Gly Gly Gly Ser Ala Leu Ser Ser Glu Leu Thr Gln Asp Pro Pro
                130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
                180                 185                 190

Pro Asp Arg Phe Ser Gly Ser Ser Ser Gly Asp Thr Ala Ser Leu Thr
                195                 200                 205

Ile Thr Gly Ala Gln Ala Glu Asp Glu Ala Asp Tyr Tyr Cys Ile Ala
                210                 215                 220

Arg Ser Asn Lys Gly Asn Pro His Val Leu Phe Gly Gly Gly Thr Gln
225                 230                 235                 240

Leu Thr Val Leu

<210> SEQ ID NO 161
<211> LENGTH: 732
<212> TYPE: DNA
<213> ORGANISM: artificial
<220> FEATURE:
<223> OTHER INFORMATION: L25 scFv

<400> SEQUENCE: 161
caggtgcagc tgcaggagtc gggcccagga ctggtgaaga cttcggagac cctgtccctc     60
acctgcgctg tctctggtta ctccatcagc agtggttact actggggctg atccggcag    120 cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtacga cgcggagcaa caagggcaac ccccatgttc tgttcggcgg agggacccag    720
ctcaccgttt ta                                                         732

<210> SEQ ID NO 162
<211> LENGTH: 244
<212> TYPE: PRT
<213> ORGANISM: artificial
<220> FEATURE:
<223> OTHER INFORMATION: L25 scFv

<400> SEQUENCE: 162
```

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
            115                 120                 125

Gly Gly Gly Gly Ser Ala Leu Ser Ser Glu Leu Thr Gln Asp Pro Pro
        130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Ser Gly Asp Thr Ala Ser Leu Thr
            195                 200                 205

Ile Thr Gly Ala Gln Ala Glu Asp Glu Ala Asp Tyr Tyr Cys Thr Thr
210                 215                 220

Arg Ser Asn Lys Gly Asn Pro His Val Leu Phe Gly Gly Thr Gln
225                 230                 235                 240

Leu Thr Val Leu

<210> SEQ ID NO 163
<211> LENGTH: 6
<212> TYPE: PRT
<213> ORGANISM: Homo sapiens

<400> SEQUENCE: 163

Ser Gly Tyr Tyr Trp Gly
1               5

<210> SEQ ID NO 164
<211> LENGTH: 16
<212> TYPE: PRT
<213> ORGANISM: Homo sapiens

<400> SEQUENCE: 164

Ser Ile Ser His Thr Gly Asn Thr Tyr Tyr Asn Pro Pro Leu Lys Ser
1               5                   10                  15

<210> SEQ ID NO 165
<211> LENGTH: 9
<212> TYPE: PRT
<213> ORGANISM: artificial
<220> FEATURE:
<223> OTHER INFORMATION: H3 heavy chain CDR3

<400> SEQUENCE: 165

Phe Met Gly Phe Gly Arg Pro Glu Tyr
```

```
1               5

<210> SEQ ID NO 166
<211> LENGTH: 9
<212> TYPE: PRT
<213> ORGANISM: artificial
<220> FEATURE:
<223> OTHER INFORMATION: H4 heavy chain CDR3

<400> SEQUENCE: 166

Trp Leu Gly Phe Gly Arg Pro Glu Tyr
1               5

<210> SEQ ID NO 167
<211> LENGTH: 9
<212> TYPE: PRT
<213> ORGANISM: artificial
<220> FEATURE:
<223> OTHER INFORMATION: H5 heavy chain CDR3

<400> SEQUENCE: 167

Phe Leu Gly Phe Gly Arg Pro Glu Tyr
1               5

<210> SEQ ID NO 168
<211> LENGTH: 9
<212> TYPE: PRT
<213> ORGANISM: artificial
<220> FEATURE:
<223> OTHER INFORMATION: H6 heavy chain CDR3

<400> SEQUENCE: 168

Phe Phe Gly Phe Gly Arg Pro Glu Tyr
1               5

<210> SEQ ID NO 169
<211> LENGTH: 9
<212> TYPE: PRT
<213> ORGANISM: Homo sapiens

<400> SEQUENCE: 169

Gly Gly Gly Ile Ser Arg Pro Glu Tyr
1               5

<210> SEQ ID NO 170
<211> LENGTH: 12
<212> TYPE: PRT
<213> ORGANISM: Homo sapiens

<400> SEQUENCE: 170

Asn Ser Arg Asp Ser Ser Gly Asn Pro His Val Leu
1               5                   10

<210> SEQ ID NO 171
<211> LENGTH: 12
<212> TYPE: PRT
<213> ORGANISM: artificial
<220> FEATURE:
<223> OTHER INFORMATION: L1 light chain CDR3

<400> SEQUENCE: 171

Ala Ser Arg Ser Val Ser Gly Asn Pro His Val Leu
1               5                   10

<210> SEQ ID NO 172
<211> LENGTH: 12
<212> TYPE: PRT
```

```
<213> ORGANISM: artificial
<220> FEATURE:
<223> OTHER INFORMATION: L2 light chain CDR3

<400> SEQUENCE: 172

Val Ala Arg Ser Val Val Gly Asn Pro His Val Leu
1               5                   10

<210> SEQ ID NO 173
<211> LENGTH: 12
<212> TYPE: PRT
<213> ORGANISM: artificial
<220> FEATURE:
<223> OTHER INFORMATION: L3 light chain CDR3

<400> SEQUENCE: 173

Val Ser Arg Ala Val Val Gly Asn Pro His Val Leu
1               5                   10

<210> SEQ ID NO 174
<211> LENGTH: 12
<212> TYPE: PRT
<213> ORGANISM: artificial
<220> FEATURE:
<223> OTHER INFORMATION: L4 light chain CDR3

<400> SEQUENCE: 174

Ser Thr Arg Ser Ser Lys Gly Asn Pro His Val Leu
1               5                   10

<210> SEQ ID NO 175
<211> LENGTH: 12
<212> TYPE: PRT
<213> ORGANISM: artificial
<220> FEATURE:
<223> OTHER INFORMATION: L5 light chain CDR3

<400> SEQUENCE: 175

Ala Ser Arg Ser Ser Lys Gly Asn Pro His Val Leu
1               5                   10

<210> SEQ ID NO 176
<211> LENGTH: 12
<212> TYPE: PRT
<213> ORGANISM: artificial
<220> FEATURE:
<223> OTHER INFORMATION: L6 light chain CDR3

<400> SEQUENCE: 176

Met Ser Arg Ser Ile Trp Gly Asn Pro His Val Leu
1               5                   10

<210> SEQ ID NO 177
<211> LENGTH: 12
<212> TYPE: PRT
<213> ORGANISM: artificial
<220> FEATURE:
<223> OTHER INFORMATION: L8 light chain CDR3

<400> SEQUENCE: 177

Thr Thr Arg Ser Thr Gln Gly Asn Pro His Val Leu
1               5                   10

<210> SEQ ID NO 178
<211> LENGTH: 12
<212> TYPE: PRT
<213> ORGANISM: artificial
<220> FEATURE:
```

<223> OTHER INFORMATION: L9 light chain CDR3

<400> SEQUENCE: 178

Val Ala Arg Ser Asn Lys Gly Asn Pro His Val Leu
1               5                   10

<210> SEQ ID NO 179
<211> LENGTH: 12
<212> TYPE: PRT
<213> ORGANISM: artificial
<220> FEATURE:
<223> OTHER INFORMATION: L10 light chain CDR3

<400> SEQUENCE: 179

Ile Ser Arg Ser Ile Tyr Gly Asn Pro His Val Leu
1               5                   10

<210> SEQ ID NO 180
<211> LENGTH: 12
<212> TYPE: PRT
<213> ORGANISM: artificial
<220> FEATURE:
<223> OTHER INFORMATION: L11 light chain CDR3

<400> SEQUENCE: 180

Ser Ser Arg Ser Arg His Gly Asn Pro His Val Leu
1               5                   10

<210> SEQ ID NO 181
<211> LENGTH: 12
<212> TYPE: PRT
<213> ORGANISM: artificial
<220> FEATURE:
<223> OTHER INFORMATION: L12 light chain CDR3

<400> SEQUENCE: 181

Val Ala Arg Gly Thr Arg Gly Asn Pro His Val Leu
1               5                   10

<210> SEQ ID NO 182
<211> LENGTH: 12
<212> TYPE: PRT
<213> ORGANISM: artificial
<220> FEATURE:
<223> OTHER INFORMATION: L13 light chain CDR3

<400> SEQUENCE: 182

Val Thr Arg Asn Arg Tyr Gly Asn Pro His Val Leu
1               5                   10

<210> SEQ ID NO 183
<211> LENGTH: 12
<212> TYPE: PRT
<213> ORGANISM: artificial
<220> FEATURE:
<223> OTHER INFORMATION: L14 light chain CDR3

<400> SEQUENCE: 183

Met Ala Arg Ser Arg Lys Gly Asn Pro His Val Leu
1               5                   10

<210> SEQ ID NO 184
<211> LENGTH: 12
<212> TYPE: PRT
<213> ORGANISM: artificial
<220> FEATURE:
<223> OTHER INFORMATION: L15 light chain CDR3

<400> SEQUENCE: 184

Ser Thr Arg Ala Ile His Gly Asn Pro His Val Leu
1               5                   10

<210> SEQ ID NO 185
<211> LENGTH: 12
<212> TYPE: PRT
<213> ORGANISM: artificial
<220> FEATURE:
<223> OTHER INFORMATION: L16 light chain CDR3

<400> SEQUENCE: 185

Val Thr Arg Ser Ala Lys Gly Asn Pro His Val Leu
1               5                   10

<210> SEQ ID NO 186
<211> LENGTH: 12
<212> TYPE: PRT
<213> ORGANISM: artificial
<220> FEATURE:
<223> OTHER INFORMATION: L17 light chain CDR3

<400> SEQUENCE: 186

Ser Thr Arg Ser Arg Lys Gly Asn Pro His Val Leu
1               5                   10

<210> SEQ ID NO 187
<211> LENGTH: 12
<212> TYPE: PRT
<213> ORGANISM: artificial
<220> FEATURE:
<223> OTHER INFORMATION: L18 light chain CDR3

<400> SEQUENCE: 187

Val Thr Arg Ser Val Lys Gly Asn Pro His Val Leu
1               5                   10

<210> SEQ ID NO 188
<211> LENGTH: 12
<212> TYPE: PRT
<213> ORGANISM: artificial
<220> FEATURE:
<223> OTHER INFORMATION: L19 light chain CDR3

<400> SEQUENCE: 188

Val Ala Arg Ala Val Arg Gly Asn Pro His Val Leu
1               5                   10

<210> SEQ ID NO 189
<211> LENGTH: 12
<212> TYPE: PRT
<213> ORGANISM: artificial
<220> FEATURE:
<223> OTHER INFORMATION: L20 light chain CDR3

<400> SEQUENCE: 189

Val Ser Arg Ser Ala Lys Gly Asn Pro His Val Leu
1               5                   10

<210> SEQ ID NO 190
<211> LENGTH: 12
<212> TYPE: PRT
<213> ORGANISM: artificial
<220> FEATURE:
<223> OTHER INFORMATION: L21 light chain CDR3

<400> SEQUENCE: 190

Ala Thr Arg Ala Val Arg Gly Asn Pro His Val Leu
1               5                   10

<210> SEQ ID NO 191
<211> LENGTH: 12
<212> TYPE: PRT
<213> ORGANISM: artificial
<220> FEATURE:
<223> OTHER INFORMATION: L23 light chain CDR3

<400> SEQUENCE: 191

Ser Ala Arg Ser Val Arg Gly Asn Pro His Val Leu
1               5                   10

<210> SEQ ID NO 192
<211> LENGTH: 12
<212> TYPE: PRT
<213> ORGANISM: artificial
<220> FEATURE:
<223> OTHER INFORMATION: L24 light chain CDR3

<400> SEQUENCE: 192

Ile Ala Arg Ser Asn Lys Gly Asn Pro His Val Leu
1               5                   10

<210> SEQ ID NO 193
<211> LENGTH: 12
<212> TYPE: PRT
<213> ORGANISM: artificial
<220> FEATURE:
<223> OTHER INFORMATION: L25 light chain CDR3

<400> SEQUENCE: 193

Thr Thr Arg Ser Asn Lys Gly Asn Pro His Val Leu
1               5                   10

<210> SEQ ID NO 194
<211> LENGTH: 11
<212> TYPE: PRT
<213> ORGANISM: Homo sapiens

<400> SEQUENCE: 194

Gln Gly Asp Ser Leu Arg Thr Tyr Tyr Ala Ser
1               5                   10

<210> SEQ ID NO 195
<211> LENGTH: 7
<212> TYPE: PRT
<213> ORGANISM: Homo sapiens

<400> SEQUENCE: 195

Gly Lys His Lys Arg Pro Ser
1               5

<210> SEQ ID NO 196
<211> LENGTH: 330
<212> TYPE: PRT
<213> ORGANISM: artificial
<220> FEATURE:
<223> OTHER INFORMATION: human IgG constant region TM

<400> SEQUENCE: 196

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 197
<211> LENGTH: 330
<212> TYPE: PRT
<213> ORGANISM: artificial
<220> FEATURE:
<223> OTHER INFORMATION: human IgG constant region DM

<400> SEQUENCE: 197

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Ala Leu Gly Ala Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 198
<211> LENGTH: 106
<212> TYPE: PRT
<213> ORGANISM: Homo sapiens

<400> SEQUENCE: 198

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105
```

<210> SEQ ID NO 199
<211> LENGTH: 100
<212> TYPE: DNA
<213> ORGANISM: Homo sapiens

<400> SEQUENCE: 199
gctctgtgac cgccgcagac acggccgtgt attactgtgc gcgaggtggg ggaattagca    60
ggccggagta ctggggcaaa ggcaccctgg tcaccgtctc                          100

<210> SEQ ID NO 200
<211> LENGTH: 34
<212> TYPE: PRT
<213> ORGANISM: Homo sapiens

<400> SEQUENCE: 200

Ser Ser Val Thr Ala Ala Asp Thr Ala Val Tyr Tyr Cys Ala Arg Gly
1               5                   10                  15

Gly Gly Ile Ser Arg Pro Glu Tyr Trp Gly Lys Gly Thr Leu Val Thr
            20                  25                  30

Val Ser

<210> SEQ ID NO 201
<211> LENGTH: 60
<212> TYPE: DNA
<213> ORGANISM: artificial
<220> FEATURE:
<223> OTHER INFORMATION: H3B1 VH library
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 201
cacataatga cacgcgctnn snnsnnsnns nnsnnsggcc tcatgacccc gtttccgtgg    60

<210> SEQ ID NO 202
<211> LENGTH: 20
<212> TYPE: PRT
<213> ORGANISM: artificial
<220> FEATURE:
<223> OTHER INFORMATION: H3B1 VH library

<400> SEQUENCE: 202

Val Tyr Tyr Cys Ala Arg Gly Gly Gly Ile Ser Arg Pro Glu Tyr Trp
1               5                   10                  15

Gly Lys Gly Thr
            20

```
<210> SEQ ID NO 203
<211> LENGTH: 56
<212> TYPE: DNA
<213> ORGANISM: artificial
<220> FEATURE:
<223> OTHER INFORMATION: H3B2 VH library
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 203
gacacgcgct ccaccccctn nsnnsnnsnn snnsnnsacc ccgtttccgt gggacc      56

<210> SEQ ID NO 204
<211> LENGTH: 18
<212> TYPE: PRT
<213> ORGANISM: artificial
<220> FEATURE:
<223> OTHER INFORMATION: H3B2 VH library

<400> SEQUENCE: 204

Cys Ala Arg Gly Gly Gly Ile Ser Arg Pro Glu Tyr Trp Gly Lys Gly
 1               5                  10                  15

Thr Leu

<210> SEQ ID NO 205
<211> LENGTH: 85
<212> TYPE: DNA
<213> ORGANISM: Homo sapiens

<400> SEQUENCE: 205
ggctgactat tactgtaact cccgggactc cagtggcaac ccccatgttc tgttcggcgg    60
agggacccag ctcaccgttt taagt                                          85

<210> SEQ ID NO 206
<211> LENGTH: 28
<212> TYPE: PRT
<213> ORGANISM: Homo sapiens

<400> SEQUENCE: 206

Ala Asp Tyr Tyr Cys Asn Ser Arg Asp Ser Ser Gly Asn Pro His Val
 1               5                  10                  15

Leu Phe Gly Gly Gly Thr Gln Leu Thr Val Leu Ser
                 20                  25

<210> SEQ ID NO 207
<211> LENGTH: 55
<212> TYPE: DNA
```

```
<213> ORGANISM: artificial
<220> FEATURE:
<223> OTHER INFORMATION: L3B1 VL library
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 207
ccgactgata atgacannsn nsnnsnnsnn snnsccgttg ggggtacaag acaag            55

<210> SEQ ID NO 208
<211> LENGTH: 18
<212> TYPE: PRT
<213> ORGANISM: artificial
<220> FEATURE:
<223> OTHER INFORMATION: L3B1 VL library

<400> SEQUENCE: 208

Ala Asp Tyr Tyr Cys Asn Ser Arg Asp Ser Ser Gly Asn Pro His Val
 1               5                  10                  15

Leu Phe

<210> SEQ ID NO 209
<211> LENGTH: 59
<212> TYPE: DNA
<213> ORGANISM: artificial
<220> FEATURE:
<223> OTHER INFORMATION: L3B2 VL library
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 209
```

```
gacattgagg gccctgaggt cannsnnsnn snnsnnsnns aagccgcctc cctgggtcg      59
```

<210> SEQ ID NO 210
<211> LENGTH: 19
<212> TYPE: PRT
<213> ORGANISM: artificial
<220> FEATURE:
<223> OTHER INFORMATION: L3B2 VL library

<400> SEQUENCE: 210

```
Cys Asn Ser Arg Asp Ser Ser Gly Asn Pro His Val Leu Phe Gly Gly
1               5                   10                  15

Gly Thr Gln
```

<210> SEQ ID NO 211
<211> LENGTH: 617
<212> TYPE: DNA
<213> ORGANISM: Homo sapiens
<220> FEATURE:
<221> NAME/KEY: CDS
<222> LOCATION: (47)..(532)

<400> SEQUENCE: 211

```
gctgaagtga aaacgagacc aaggtctagc tctactgttg gtactt atg aga tcc       55
                                                Met Arg Ser
                                                1 agt cct ggc aac atg gag agg att gtc atc tgt ctg atg gtc atc ttc     103
Ser Pro Gly Asn Met Glu Arg Ile Val Ile Cys Leu Met Val Ile Phe
    5               10                  15 ttg ggg aca ctg gtc cac aaa tca agc tcc caa ggt caa gat cgc cac    151
Leu Gly Thr Leu Val His Lys Ser Ser Ser Gln Gly Gln Asp Arg His
20                  25                  30                  35 atg att aga atg cgt caa ctt ata gat att gtt gat cag ctg aaa aat   199
Met Ile Arg Met Arg Gln Leu Ile Asp Ile Val Asp Gln Leu Lys Asn
                40                  45                  50 tat gtg aat gac ttg gtc cct gaa ttt ctg cca gct cca gaa gat gta   247
Tyr Val Asn Asp Leu Val Pro Glu Phe Leu Pro Ala Pro Glu Asp Val
            55                  60                  65 gag aca aac tgt gag tgg tca gct ttt tcc tgc ttt cag aag gcc caa   295
Glu Thr Asn Cys Glu Trp Ser Ala Phe Ser Cys Phe Gln Lys Ala Gln
        70                  75                  80 cta aag tca gca aat aca gga aac aat gaa agg ata atc aat gta tca   343
Leu Lys Ser Ala Asn Thr Gly Asn Asn Glu Arg Ile Ile Asn Val Ser
    85                  90                  95 att aaa aag ctg aag agg aaa cca cct tcc aca aat gca ggg aga aga   391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa   439
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg   487
Pro Pro Lys Glu Phe Leu Glu Arg Phe Lys Ser Leu Leu Gln Lys Met
            135                 140                 145 att cat cag cat ctg tcc tct aga aca cac gga agt gaa gat tcc       532
Ile His Gln His Leu Ser Ser Arg Thr His Gly Ser Glu Asp Ser
        150                 155                 160 tgaggatcta acttgcagtt ggacactatg ttcatactc taatatagta gtgaaagtca   592
tttctttgta ttccaagtgg aggag                                        617
```

<210> SEQ ID NO 212
<211> LENGTH: 162

```
<212> TYPE: PRT
<213> ORGANISM: Homo sapiens

<400> SEQUENCE: 212

Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 213
<211> LENGTH: 448
<212> TYPE: PRT
<213> ORGANISM: artificial
<220> FEATURE:
<223> OTHER INFORMATION: VH3DM heavy chain

<400> SEQUENCE: 213

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Met Gly Phe Gly Arg Pro Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Leu Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 214
<211> LENGTH: 215
<212> TYPE: PRT
<213> ORGANISM: artificial
<220> FEATURE:
<223> OTHER INFORMATION: VL2 light chain

<400> SEQUENCE: 214

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
            35                  40                  45

Gly Lys His Lys Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ala Arg Ser Val Val Gly Asn Pro
            85                  90                  95

His Val Leu Phe Gly Gly Gly Thr Gln Leu Thr Val Leu Gly Gln Pro
```

```
                    100                 105                 110
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
            210                 215

<210> SEQ ID NO 215
<211> LENGTH: 109
<212> TYPE: PRT
<213> ORGANISM: artificial
<220> FEATURE:
<223> OTHER INFORMATION: variable region of VL2 light chain

<400> SEQUENCE: 215

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ala Arg Ser Val Val Gly Asn Pro
                85                  90                  95

His Val Leu Phe Gly Gly Gly Thr Gln Leu Thr Val Leu
            100                 105

<210> SEQ ID NO 216
<211> LENGTH: 215
<212> TYPE: PRT
<213> ORGANISM: artificial
<220> FEATURE:
<223> OTHER INFORMATION: VL18 light chain

<400> SEQUENCE: 216

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Val Lys Gly Asn Pro
```

-continued

```
                        85                  90                  95
His Val Leu Phe Gly Gly Gly Thr Gln Leu Thr Val Leu Gly Gln Pro
                    100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 217
<211> LENGTH: 109
<212> TYPE: PRT
<213> ORGANISM: artificial
<220> FEATURE:
<223> OTHER INFORMATION: variable region of VL18 light chain

<400> SEQUENCE: 217

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Val Lys Gly Asn Pro
                85                  90                  95

His Val Leu Phe Gly Gly Gly Thr Gln Leu Thr Val Leu
                    100                 105

<210> SEQ ID NO 218
<211> LENGTH: 448
<212> TYPE: PRT
<213> ORGANISM: artificial
<220> FEATURE:
<223> OTHER INFORMATION: VH3TM heavy chain

<400> SEQUENCE: 218

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
```

|   |   |   |   |   |   |   |   |   |   |   |   |
|---|---|---|---|---|---|---|---|---|---|---|---|
| 65 | | | | 70 | | | | 75 | | | 80 |
| Leu | Lys | Leu | Ser | Ser | Val | Thr | Ala | Ala | Asp | Thr | Ala | Val | Tyr | Tyr | Cys |

Leu Lys Leu Ser Ser Val Thr Ala Ala Asp Thr Ala Val Tyr Tyr Cys
                85                  90                  95

Ala Arg Phe Met Gly Phe Gly Arg Pro Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 219
<211> LENGTH: 448
<212> TYPE: PRT
<213> ORGANISM: artificial
<220> FEATURE:
<223> OTHER INFORMATION: VHPTM heavy chain

<400> SEQUENCE: 219

```
Gln Val Gln Leu Gln Glu Ser Gly Pro Gly Leu Val Lys Pro Ser Glu
  1               5                   10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
             35                  40                  45

Ile Gly Ser Ile Ser His Thr Gly Asn Thr Tyr Tyr Asn Pro Pro Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Gly Ile Ser Arg Pro Glu Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

-continued

```
                420            425                430
Leu His Asn His Tyr Thr Gln Lys Ser Leu Ser Leu Ser Pro Gly Lys
            435                440                445

<210> SEQ ID NO 220
<211> LENGTH: 215
<212> TYPE: PRT
<213> ORGANISM: artificial
<220> FEATURE:
<223> OTHER INFORMATION: VL6 light chain

<400> SEQUENCE: 220

Ser Ser Glu Leu Thr Gln Asp Pro Ala Val Ser Val Ala Leu Gly Gln
1               5                  10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Met Ser Arg Ser Ile Trp Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 221
<211> LENGTH: 109
<212> TYPE: PRT
<213> ORGANISM: artificial
<220> FEATURE:
<223> OTHER INFORMATION: variable region of VL6 light chain

<400> SEQUENCE: 221

Ser Ser Glu Leu Thr Gln Asp Pro Ala Val Ser Val Ala Leu Gly Gln
1               5                  10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
```

```
                 65                  70                  75                  80
Asp Glu Ala Asp Tyr Tyr Cys Met Ser Arg Ser Ile Trp Gly Asn Pro
                    85                  90                  95
His Val Leu Phe Gly Gly Gly Thr Gln Leu Thr Val Leu
                100                 105

<210> SEQ ID NO 222
<211> LENGTH: 215
<212> TYPE: PRT
<213> ORGANISM: artificial
<220> FEATURE:
<223> OTHER INFORMATION: VL9 light chain

<400> SEQUENCE: 222

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
                20                  25                  30

Ser Trp Tyr Gln Gln Lys Pro Gly Gln Ala Pro Val Leu Val Ile Tyr
                35                  40                  45

Gly Lys His Lys Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ala Arg Ser Asn Lys Gly Asn Pro
                    85                  90                  95

His Val Leu Phe Gly Gly Gly Thr Gln Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
        210                 215

<210> SEQ ID NO 223
<211> LENGTH: 109
<212> TYPE: PRT
<213> ORGANISM: artificial
<220> FEATURE:
<223> OTHER INFORMATION: variable region of VL9 light chain

<400> SEQUENCE: 223

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
                20                  25                  30

Ser Trp Tyr Gln Gln Lys Pro Gly Gln Ala Pro Val Leu Val Ile Tyr
                35                  40                  45

Gly Lys His Lys Arg Pro Ser Gly Ile Pro Asp Arg Phe Ser Gly Ser
```

```
                50                  55                  60
Ser Ser Gly Asn Thr Ala Ser Leu Thr Ile Thr Gly Ala Gln Ala Glu
65                  70                  75                  80

Asp Glu Ala Asp Tyr Tyr Cys Val Ala Arg Ser Asn Lys Gly Asn Pro
                85                  90                  95

His Val Leu Phe Gly Gly Gly Thr Gln Leu Thr Val Leu
            100                 105

<210> SEQ ID NO 224
<211> LENGTH: 215
<212> TYPE: PRT
<213> ORGANISM: artificial
<220> FEATURE:
<223> OTHER INFORMATION: VL16 light chain

<400> SEQUENCE: 224

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
                20                  25                  30

Ser Trp Tyr Gln Gln Lys Pro Gly Gln Ala Pro Val Leu Val Ile Tyr
            35                  40                  45

Gly Lys His Lys Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Ala Lys Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 225
<211> LENGTH: 109
<212> TYPE: PRT
<213> ORGANISM: artificial
<220> FEATURE:
<223> OTHER INFORMATION: variable region of VL16 light chain

<400> SEQUENCE: 225

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
                20                  25                  30

Ser Trp Tyr Gln Gln Lys Pro Gly Gln Ala Pro Val Leu Val Ile Tyr
```

```
                35                  40                  45
Gly Lys His Lys Arg Pro Ser Gly Ile Pro Asp Arg Phe Ser Gly Ser
         50                  55                  60
Ser Ser Gly Asn Thr Ala Ser Leu Thr Ile Thr Gly Ala Gln Ala Glu
 65                  70                  75                  80
Asp Glu Ala Asp Tyr Tyr Cys Val Thr Arg Ser Ala Lys Gly Asn Pro
                 85                  90                  95
His Val Leu Phe Gly Gly Thr Gln Leu Thr Val Leu
            100                 105

<210> SEQ ID NO 226
<211> LENGTH: 215
<212> TYPE: PRT
<213> ORGANISM: artificial
<220> FEATURE:
<223> OTHER INFORMATION: VL20 light chain

<400> SEQUENCE: 226

Ser Ser Glu Leu Thr Gln Asp Pro Ala Val Ser Val Ala Leu Gly Gln
 1               5                  10                  15
Thr Val Arg Ile Thr Cys Gln Gly Asp Ser Leu Arg Thr Tyr Tyr Ala
             20                  25                  30
Ser Trp Tyr Gln Gln Lys Pro Gly Gln Ala Pro Val Leu Val Ile Tyr
         35                  40                  45
Gly Lys His Lys Arg Pro Ser Gly Ile Pro Asp Arg Phe Ser Gly Ser
     50                  55                  60
Ser Ser Gly Asn Thr Ala Ser Leu Thr Ile Thr Gly Ala Gln Ala Glu
 65                  70                  75                  80
Asp Glu Ala Asp Tyr Tyr Cys Val Ser Arg Ser Ala Lys Gly Asn Pro
                 85                  90                  95
His Val Leu Phe Gly Gly Thr Gln Leu Thr Val Leu Gly Gln Pro
            100                 105                 110
Lys Ala Ala Pro Ser Val Thr Leu Phe Pro Pro Ser Ser Glu Glu Leu
        115                 120                 125
Gln Ala Asn Lys Ala Thr Leu Val Cys Leu Ile Ser Asp Phe Tyr Pro
    130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Val Ala Pro Thr Glu Cys Ser
    210                 215

<210> SEQ ID NO 227
<211> LENGTH: 109
<212> TYPE: PRT
<213> ORGANISM: artificial
<220> FEATURE:
<223> OTHER INFORMATION: variable region of VL20 light chain

<400> SEQUENCE: 227

Ser Ser Glu Leu Thr Gln Asp Pro Ala Val Ser Val Ala Leu Gly Gln
 1               5                  10                  15
Thr Val Arg Ile Thr Cys Gln Gly Asp Ser Leu Arg Thr Tyr Tyr Ala
```

```
                    20                  25                  30
Ser Trp Tyr Gln Gln Lys Pro Gly Gln Ala Pro Val Leu Val Ile Tyr
            35                  40                  45

Gly Lys His Lys Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ser Arg Ser Ala Lys Gly Asn Pro
                85                  90                  95

His Val Leu Phe Gly Gly Gly Thr Gln Leu Thr Val Leu
            100                 105

<210> SEQ ID NO 228
<211> LENGTH: 215
<212> TYPE: PRT
<213> ORGANISM: artificial
<220> FEATURE:
<223> OTHER INFORMATION: VL25 light chain

<400> SEQUENCE: 228

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
            35                  40                  45

Gly Lys His Lys Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Thr Thr Arg Ser Asn Lys Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 229
<211> LENGTH: 109
<212> TYPE: PRT
<213> ORGANISM: artificial
<220> FEATURE:
<223> OTHER INFORMATION: variable region of VL25 light chain

<400> SEQUENCE: 229

Ser Ser Glu Leu Thr Gln Asp Pro Ala Val Ser Val Ala Leu Gly Gln
```

```
                1               5                  10                  15
              Thr Val Arg Ile Thr Cys Gln Gly Asp Ser Leu Arg Tyr Tyr Ala
                             20                  25                  30

Ser Trp Tyr Gln Gln Lys Pro Gly Gln Ala Pro Val Leu Val Ile Tyr
                         35                  40                  45

Gly Lys His Lys Arg Pro Ser Gly Ile Pro Asp Arg Phe Ser Gly Ser
                     50                  55                  60

Ser Ser Gly Asn Thr Ala Ser Leu Thr Ile Thr Gly Ala Gln Ala Glu
                 65                  70                  75                  80

Asp Glu Ala Asp Tyr Tyr Cys Thr Thr Arg Ser Asn Lys Gly Asn Pro
                             85                  90                  95

His Val Leu Phe Gly Gly Gly Thr Gln Leu Thr Val Leu
                             100                 105
```

<210> SEQ ID NO 230
<211> LENGTH: 34
<212> TYPE: DNA
<213> ORGANISM: Artificial Sequence
<220> FEATURE:
<223> OTHER INFORMATION: Primer BssHII_II_VH_F

<400> SEQUENCE: 230
gcttggcgcg cactctcagg tgcagctgca ggag                                   34

<210> SEQ ID NO 231
<211> LENGTH: 21
<212> TYPE: DNA
<213> ORGANISM: Artificial Sequence
<220> FEATURE:
<223> OTHER INFORMATION: Primer GVH_R_for_BssHII

<400> SEQUENCE: 231
tcagggagaa ctggttcttg g                                                 21

<210> SEQ ID NO 232
<211> LENGTH: 21
<212> TYPE: DNA
<213> ORGANISM: Artificial Sequence
<220> FEATURE:
<223> OTHER INFORMATION: Primer G_VH_F_for_SalI

<400> SEQUENCE: 232
tccaagaacc agttctccct g                                                 21

<210> SEQ ID NO 233
<211> LENGTH: 45
<212> TYPE: DNA
<213> ORGANISM: Artificial Sequence
<220> FEATURE:
<223> OTHER INFORMATION: Primer scFv_SalI_VH_R

<400> SEQUENCE: 233
gcgacgtcga caggactcac cactcgagac ggtgaccagg gtgcc                       45

<210> SEQ ID NO 234
<211> LENGTH: 32
<212> TYPE: DNA
<213> ORGANISM: Artificial Sequence
<220> FEATURE:
<223> OTHER INFORMATION: Primer Sal_VH_R_RJ

<400> SEQUENCE: 234
gcgacgtcga caggactcac cactcgagac gg                                     32

<210> SEQ ID NO 235
<211> LENGTH: 34
<212> TYPE: DNA
<213> ORGANISM: Artificial Sequence
<220> FEATURE:
<223> OTHER INFORMATION: Primer BssHII_II_VL_F

<400> SEQUENCE: 235

| gcttggcgcg cactcttcct ctgagctgac ccag | 34 |
|---|---|

<210> SEQ ID NO 236
<211> LENGTH: 22
<212> TYPE: DNA
<213> ORGANISM: Artificial Sequence
<220> FEATURE:
<223> OTHER INFORMATION: Primer scFv_VL_R_for_BssHII

<400> SEQUENCE: 236

| gcctgagccc cagtgatggt ca | 22 |
|---|---|

<210> SEQ ID NO 237
<211> LENGTH: 20
<212> TYPE: DNA
<213> ORGANISM: Artificial Sequence
<220> FEATURE:
<223> OTHER INFORMATION: Primer GVL_F_for_XbaI

<400> SEQUENCE: 237

| accgcctccc tgaccatcac | 20 |
|---|---|

<210> SEQ ID NO 238
<211> LENGTH: 50
<212> TYPE: DNA
<213> ORGANISM: Artificial Sequence
<220> FEATURE:
<223> OTHER INFORMATION: Primer scFv_XbaI_VL_R

<400> SEQUENCE: 238

| gcgccgtcta gagttattct actcacctaa aacggtgagc tgggtccctc | 50 |
|---|---|

<210> SEQ ID NO 239
<211> LENGTH: 1401
<212> TYPE: DNA
<213> ORGANISM: artificial
<220> FEATURE:
<223> OTHER INFORMATION: VHPTM heavy chain with signal sequence

<400> SEQUENCE: 239

| atgggatgga gctgtatcat cctcttcttg gtggcaacag ctacaggcgt gcactctcag | 60 |
|---|---|
| gtgcagctgc aggagtctgg ccctggcctg gtgaagcctt ccgagaccct gtctctgacc | 120 |
| tgtgccgtgt ccggctactc catctcctcc ggctactact ggggctggat cagacagcct | 180 |
| cctggcaagg gctggagtg gatcggctcc atctctcaca ccggcaacac ctactacaac | 240 |
| cccccctctga agtccagagt gaccatctcc gtggacacct ccaagaacca gttctccctg | 300 |
| aagctgtcct ctgtgaccgc tgccgatacc gccgtgtact actgtgccag aggcggcgga | 360 |
| atctccagac ctgagtactg ggccagggc accctggtga ccgtgtcctc tgcctccacc | 420 |
| aagggcccat cggtcttccc cctggcaccc tcctccaaga gcacctctgg ggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tcccctcagca gcgtggtgac cgtgccctcc agcagcttgg gcacccagac ctacatctgc | 660 |

-continued

```
aacgtgaatc acaagcccag caacaccaag gtggacaaga agttgagcc caaatcttgt    720
gacaaaactc acacatgccc accgtgccca gcacctgaag ccgcgggggc accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                             1401
```

<210> SEQ ID NO 240
<211> LENGTH: 467
<212> TYPE: PRT
<213> ORGANISM: artificial
<220> FEATURE:
<223> OTHER INFORMATION: VHPTM heavy chain with signal sequence

<400> SEQUENCE: 240

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Gly Ile Ser Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240
```

```
Asp Lys Thr His Thr Cys Pro Pro Cys Pro Ala Pro Glu Ala Ala Gly
            245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 241
<211> LENGTH: 1401
<212> TYPE: DNA
<213> ORGANISM: artificial
<220> FEATURE:
<223> OTHER INFORMATION: VH3TM heavy chain with signal sequence

<400> SEQUENCE: 241
atgggatgga gctgtatcat cctcttcttg gtggcaacag ctacaggcgt gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240 cccccctctga agtccagagt gaccatctcc gtggacacct ccaagaacca gttctccctg     300
aagctgtcct ctgtgaccgc tgccgatacc gccgtgtact actgtgccag attcatgggg     360
ttcggccgcc cggagtactg gggccagggc accctggtga ccgtgtcctc tgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
```

```
gacaaaactc acacatgccc accgtgccca gcacctgaag ccgcgggggc accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga tgaccaag     1140 aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                             1401

<210> SEQ ID NO 242
<211> LENGTH: 467
<212> TYPE: PRT
<213> ORGANISM: artificial
<220> FEATURE:
<223> OTHER INFORMATION: VH3TM heavy chain with signal sequence

<400> SEQUENCE: 242

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
                20                  25                  30

Pro Ser Glu Thr Leu Ser Leu Thr Cys Ala Val Ser Gly Tyr Ser Ile
            35                  40                  45

Ser Ser Gly Tyr Tyr Trp Gly Trp Ile Arg Gln Pro Pro Gly Lys Gly
        50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Met Gly Phe Gly Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
```

```
         245                 250                 255
Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 243
<211> LENGTH: 703
<212> TYPE: DNA
<213> ORGANISM: artificial
<220> FEATURE:
<223> OTHER INFORMATION: VL2 light chain with signal sequence

<400> SEQUENCE: 243
atgggatgga gctgtatcat cctcttcttg gtggcaacag ctacaggcgt gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cgcccggtcg gtggtgggca accccatgt tctgttcggc     360 ggagggaccc agctcaccgt tttaggtcag cccaaggctg ccccctcggt cactctgttc     420 ccgcccctcct ctgaggagct tcaagccaac aaggccacac tggtgtgtct cataagtgac     480
ttctacccgg agccgtgaca gtggcctgg aaggcagata gcagcccgt caaggcggga     540 gtggagacca ccacccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt cat                       703

<210> SEQ ID NO 244
```

```
<211> LENGTH: 234
<212> TYPE: PRT
<213> ORGANISM: artificial
<220> FEATURE:
<223> OTHER INFORMATION: VL2 light chain with signal sequence

<400> SEQUENCE: 244
```

Met Gly Trp Ser Cys Ile Ile Leu Phe Leu Val Ala Thr Ala Thr Gly
1               5                   10                  15

Val His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Ala Arg Ser Val Val
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

```
<210> SEQ ID NO 245
<211> LENGTH: 703
<212> TYPE: DNA
<213> ORGANISM: artificial
<220> FEATURE:
<223> OTHER INFORMATION: VL18 light chain with signal sequence

<400> SEQUENCE: 245
```

| | | | | | |
|---|---|---|---|---|---|
| atgggatgga | gctgtatcat | cctcttcttg | gtggcaacag | ctacaggcgt | gcactcttcc | 60 |
| tctgagctga | cccaggatcc | tgctgtgtct | gtggccctgg | ccagaccgt | caggatcacc | 120 |
| tgccagggcg | atagcctgag | aacctactac | gcctcctggt | atcagcagaa | gcctggacag | 180 |
| gcccctgtgc | tggtgatcta | cggcaagcac | aagaggccat | ccggcatccc | tgacagattc | 240 |
| tccggctcct | cctctggcaa | taccgcctcc | ctgaccatca | ctgggctca | ggcggaagac | 300 |
| gaggctgact | attactgtgt | cacgaggagc | gtgaagggca | accccatgt | tctgttcggc | 360 |
| ggagggaccc | agctcaccgt | tttaggtcag | cccaaggctg | ccccctcggt | cactctgttc | 420 |
| ccgcccctcct | ctgaggagct | tcaagccaac | aaggccacac | tggtgtgtct | cataagtgac | 480 |
| ttctacccgg | gagccgtgac | agtggcctgg | aaggcagata | gcagccccgt | caaggcggga | 540 |

```
gtggagacca ccacaccctc caaacaaagc aacaacaagt acgcggccag cagctatctg    600
agcctgacgc ctgagcagtg aagtccac agaagctaca gctgccaggt cacgcatgaa     660
gggagcaccg tggagaagac agtggcccct acagaatgtt cat                    703
```

<210> SEQ ID NO 246
<211> LENGTH: 234
<212> TYPE: PRT
<213> ORGANISM: artificial
<220> FEATURE:
<223> OTHER INFORMATION: VL18 light chain with signal sequence

<400> SEQUENCE: 246

```
Met Gly Trp Ser Cys Ile Ile Leu Phe Leu Val Ala Thr Ala Thr Gly
 1               5                  10                  15

Val His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Ser Val Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 247
<211> LENGTH: 703
<212> TYPE: DNA
<213> ORGANISM: artificial
<220> FEATURE:
<223> OTHER INFORMATION: VL25 light chain with signal sequence

<400> SEQUENCE: 247

```
atgggatgga gctgtatcat cctcttcttg gtggcaacag ctacaggcgt gcactcttcc    60
tctgagctga cccaggatcc tgctgtgtct gtggccctgg gccagaccgt caggatcacc   120
tgccagggcg atagcctgag aacctactac gcctcctggt atcagcagaa gcctggacag   180
gcccctgtgc tggtgatcta cggcaagcac aagaggccat ccggcatccc tgacagattc   240
```

```
tccggctcct cctctggcaa taccgcctcc ctgaccatca ctggggctca ggcggaagac    300
gaggctgact attactgtac gacgcggagc aacaagggca accccatgt tctgttcggc    360 ggagggaccc agctcaccgt tttaggtcag cccaaggctg cccctcggt cactctgttc    420 ccgcctcct ctgaggagct tcaagccaac aaggccacac tggtgtgtct cataagtgac    480
ttctacccgg gagccgtgac agtggcctgg aaggcagata gcagccccgt caaggcggga    540
gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt cat                     703
```

```
<210> SEQ ID NO 248
<211> LENGTH: 234
<212> TYPE: PRT
<213> ORGANISM: artificial
<220> FEATURE:
<223> OTHER INFORMATION: VL25 light chain with signal sequence

<400> SEQUENCE: 248

Met Gly Trp Ser Cys Ile Ile Leu Phe Leu Val Ala Thr Ala Thr Gly
1               5                   10                  15

Val His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Thr Thr Arg Ser Asn Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```